US010077461B2

(12) United States Patent
Beaulieu et al.

(10) Patent No.: US 10,077,461 B2
(45) Date of Patent: Sep. 18, 2018

(54) METHOD FOR CHARACTERIZING AT LEAST ONE MICROORGANISM BY MEANS OF MASS SPECTROMETRY

(75) Inventors: Corinne Beaulieu, Rillieux la Pape (FR); Yannick Charretier, Courzieu (FR); Jean-Philippe Charrier, Tassin la Demi-lune (FR); Sonia Chatellier, Amberieu en Bugey (FR); Philippe Dufour, Caluire et Cuire (FR); Christine Franceschi, Meximieux (FR); Victoria Girard, Lyons (FR); Sylvie Pons, Saint Genis les Ollieres (FR)

(73) Assignee: BIOMERIEUX S.A., Marcy l'Etoile (FR)

( * ) Notice: Subject to any disclaimer, the term of this patent is extended or adjusted under 35 U.S.C. 154(b) by 208 days.

(21) Appl. No.: 13/502,020

(22) PCT Filed: Oct. 14, 2010

(86) PCT No.: PCT/FR2010/052181
§ 371 (c)(1),
(2), (4) Date: Jun. 29, 2012

(87) PCT Pub. No.: WO2011/045544
PCT Pub. Date: Apr. 21, 2011

(65) Prior Publication Data
US 2012/0264156 A1 Oct. 18, 2012

(30) Foreign Application Priority Data
Oct. 15, 2009 (FR) ...................... 09 57218

(51) Int. Cl.
| C12Q 1/28 | (2006.01) |
| C12Q 1/04 | (2006.01) |
| C12Q 1/14 | (2006.01) |
| C12Q 1/18 | (2006.01) |
| G01N 33/68 | (2006.01) |

(52) U.S. Cl.
CPC ............. *C12Q 1/04* (2013.01); *C12Q 1/14* (2013.01); *C12Q 1/18* (2013.01); *G01N 33/6851* (2013.01); *G01N 2333/245* (2013.01); *G01N 2333/31* (2013.01); *G01N 2333/40* (2013.01)

(58) Field of Classification Search
None
See application file for complete search history.

(56) References Cited

U.S. PATENT DOCUMENTS

| 8,735,091 B2 * | 5/2014 | Hyman | ................ | G01N 1/4077 |
| | | | | 435/253.1 |
| 2007/0006950 A1 | 1/2007 | Okada et al. | | |
| 2007/0269814 A1 | 11/2007 | Wilkes et al. | | |

FOREIGN PATENT DOCUMENTS

| WO | WO 2006128492 | 12/2006 |
| WO | WO 2005098071 | 1/2007 |
| WO | WO 2008066629 | 6/2008 |
| WO | WO 20080145763 | 12/2008 |

OTHER PUBLICATIONS

Zheng et al. (Rapid Commun. in Mass Spect., vol. 14, pp. 261-269, 2000).*
Sauer et al. (Jul. 2008, PLOS ONE, vol. 3, issue 7, 1-10).*
Becerril et al. (Anal. Bioanl. Chem., 2007, vol. 388, pp. 1003-1011).*
Kuhn et al. (Proteomics, vol. 4, 2004, pp. 1175-1186).*
Keller et al. (Mol. Systems Biol. vol. 1, 2005, pp. 1-8).*
Dubois et al.*
Fox (J of. Chrom. A, vol. 843, 1999, pp. 287-300).*
Rashed et al. (J. of Chromatography B., vol. 758, 2001, pp. 27-48).*
Anderson, et al., "Quantitative Mass Spectrometric Multiple Reaction Monitoring Assays for Major Plasma Proteins" Mol. Cell Proteomics, pp. 573-588 (2006).
Anhalt, J., et al, "Identification of bacteria using mass spectrometry", Anal. Chem., pp. 219-225, 47(2) (1975).
Bernardo et al, "Identification and discrimination of *Staphylococcus aureus* strains using matrix-assisted laser desorption/ionization-time of flight mass spectrometry", Protemics, pp. 747-753, 2(6) (2002).
Bernardo et al, "Identification of *Staphylococcus aureus* exotoxins by combined sodium dodecyl sulfate gel electrophoresis and matrix-assisted laser desorption/ionization-time of flight mass spectrometry", Proteomics, pp. 740-746, 2(6) (2002).
Brun, V., et al., "Isotope-labeled Protein Standards", Mol. Cell Proteomics, pp. 2139-2149 (2007).
Bundy, J., et al., "Lectin-Based Affinity Capture for MALDI-MS Analysis of Bacteria", Anal. Chem., pp. 1460-1463, 71 (1999).
Camara et al, "Discrimination between wild-type and ampicillin-resistant *Escherichia coli* by matrix-assisted laser desorption/ionization time-of flight mass spectrometry", Analytical and Bioanal. Chemistry, pp. 1633-1638, 389(5) (2007).
Carbonnelle et al, "Rapid identification of Staphylococci isolated in clinical microbiology laboratories by matrix-assisted laser desorption ionization-time of flight mass spectrometry", Journal of Clinical Microbio., pp. 2156-2161, 45(7) (2007).

(Continued)

*Primary Examiner* — Hope Robinson
(74) *Attorney, Agent, or Firm* — Oliff PLC

(57) ABSTRACT

A method for characterizing at least one microorganism from a sample includes identifying the at least one microorganism and determining the properties of typing, potential resistance to at least one antimicrobial, and virulence factor. The properties of typing, resistance to at least one antimicrobial, and virulence factor for the at least one microorganism are determined by implementing mass spectrometry using proteins, peptides and/or metabolites as markers of the properties of typing, resistance to at least one antimicrobial, and virulence factor.

20 Claims, No Drawings

Specification includes a Sequence Listing.

(56) References Cited

OTHER PUBLICATIONS

Chen, W-J, "Functional Nanoparticle-Based Proteomic Strategies for Characterization of Pathogenic Bacteria" et al., Anal. Chem., pp. 9612-9621, 80 (2008).
Claydon, et al., "The rapid identification of intact microorganisms using mass spectrometry" Nature Biotech, pp. 1584-1586, 14 (1996).
Dare et al, "Staphylococci speciation and Panton-Valentine leukocidin detection by matrix-assisted laser desorption ionisation time-of-flight mass spectrometry", Intern. Journal of Antimicrobial Agents, pp. 103-104, 29(2) (2007).
Desiere, et al., "The PeptideAtlas project", Nucleic Acids Res., pp. D655-D658, 34 (2006).
Ding, et al., "Identification of protein components and quantitative immunoassay for SEC2 in staphylococcin injection" J. Pharm. Biomed. Anal., pp. 79-85, 50 (2009).
Ecker, et al., "Ibis T5000: a universal biosensor approach for microbiology", Nat. Rev. Microbiol., pp. 553-558, 6(7) (2008).
Everley, et al., "Characterization of Clostridium species utilizing liquid chromatography/mass spectrometry of intact proteins", J. Microbiol. Methods, pp. 152-158, 77 (2009).
Fenselau., et al., "Identification of β-Lactamase in Antibiotic-Resistant Bacillus cereus Spores", Appl. Environ. Microbiol., pp. 904-906, 74(3) (2008).
Fortin, et al., "Clinical Quantitation of Prostate-specific Antigen Biomarker in the Low Nanogram/Milliliter Range by Conventional Bore Liquid Chromatography-Tandem Mass Spectrometry (Multiple Reaction Monitoring) Coupling and Correlation with ELISA Tests", Mol. Cell Proteomics, pp. 1006-1015, 8(5) (2009).
Fusaro, et al., "Prediction of high-responding peptides for targeted protein assays by mass spectrometry", Nature Biotech., pp. 190-198, 27(2) (2009).
Gaskell, S., "Electrospray: Principles and Practise", J. Mass Spectrom., pp. 677-688, 32 (1997).
Han, B., et al., "Proteomics: from hypothesis to quantitative assay on a single platform. Guidelines for developing MRM assays using ion trap mass spectrometers", Brief Funct Genomic Proteomic, pp. 340-354, 7(5) (2008).
Hernychova, L., et al., "Detection and Identification of Coxiella burnetii Based on the Mass Sprectrometric Analyses of the Extracted Proteins", Anal. Chem, pp. 7097-7104, 80 (2008).
Ho, K., et al., "Using Biofunctionalized Nanoparticles to Probe Pathogenic Bacteria", Anal. Chem, pp. 7162-7168, 76 (2004).
Hofstadler, et al., "TIGER: the universal biosensor", Int. J. Mass Spectrom., pp. 23-41, 242 (2005).
Keshishian, H., et al., "Quantitative, Multiplexed Assays for Low Abundance Proteins in Plasma by Targeted Mass Spectrometry and Stable Isotope Dilution", Mol. Cell Proteomics, pp. 2212-2229 (2007).
Kondo, F., et al, "Identification of Shiga toxins in Shiga toxin-producing *Escherichia coli* using immunoprecipitation and high-performance liquid chromatography-electrospray ionization mass spectrometry", The Analyst, pp. 1360-1364, 128(11) (2003).
Krishnamurthy, et al., "Rapid identification of bacteria by direct matrix-assisted laser desorption/ionization mass spectrometric analysis of whole cells" Rapid Com. Mass Spec, pp. 1992-1996, 10 (1996).
Li, M., et al, "Comparative proteomic analysis to identification of extracellular virulence factors of enterohemorrhagic *Escherichia coli* (EHEC) and enteropathogenic *Escherichia coli* (EPEC)", Faseb Journal, A1388, 19(5) (2005).
Lin, Y.S., et al., "Affinity Capture Using Vancomycin-Bound Magnetic Nanoparticles for the MALDI-MS Analysis of Bacteria", Anal. Chem, pp. 1753-1760, 77 (2005).
Lopez-Ferrer, D., et al., "On-line Digestion System for Protein Characterization and Proteome Analysis", Anal. Chem., 2008, 8930-8936, 80 (2008).
Lopez-Ferrer, D., et al., "Ultra Fast Trypsin Digestion of Proteins by High Intensity Focused Ultrasound", J. Proteome Res., pp. 1569-1574, 4(5).
Majcherczyk P., et al, "The discriminatory power of MALDI-TOF mass spectrometry to differentiate between isogenic teicoplanin-susceptible and teicoplanin-resistant strains of methicillin-resistant *Staphylococcus aureus*", Fems Microbiol Letters, pp. 233-239, 255(2) (2006).
Manes, N., et al., "Targeted Protein Degradation by Salmonella under Phagosome-mimicking Culture Conditions Investigated Using Comparative Peptidomics", Mol. & Cell. Proteomics, pp. 717-727, 6(4) (2007).
Marinach, C. et al, "MALDI-TOF MS-based drug susceptibility testing of pathogens: The example of Candida albicans and fluconazole", Proteomics, pp. 4627-4631, 9(20) (2009).
Mazzeo, M., et al, "Matrix-assisted laser desorption ionization-time of flight mass spectrometry for the discrimination of food-borne microorganisms", Applied and Env. Microbio., pp. 1180-1189, 72(2) (2006).
Mead, J., et al., "MRMaid, the Web-based Tool for Designing Multiple Reaction Monitoring (MRM) Transitions", Mol. Cell Proteomics, pp. 696-705, 8(4) (2009).
Melanson, J., et al, "Targeted comparative proteomics by liquid chromatography/matrix-assi sted laser desorption/ionization triple-quadrupole mass spectrometry", Rapid Communications in Mass Sprectrometry, pp. 904-910, 20(5) (2006).
Nandakumar, R., et al., "Proteomic analysis of endodontic infections by liquid chromatography-tandem mass sprectrometry", Oral Microbiology Immunology, pp. 347-352, 24 (2009).
Pratt, J., et al., "Multiplexed absolute quantification for proteomics using concatenated signature peptides encoded by QconCAT genes", Nature Protocols, pp. 1029-1043, 1(2) (2006).
Qian, J., et al, "MALDI-TOF mass signatures for differentiation of yeast species, strain grouping and monitoring of morphogenesis markers", Analytical and Bioanaly Chemistry, pp. 439-449, 392(3) (2008).
Seng, P., et al, "Ongoing Revolution in Bacteriology: Routine Identification of Bacteria by Matrix-Assisted Laser Desorption Ionization Time-of-Flight Mass Spectrometry", Clinical Infectious Diseases, pp. 543-551, 49(4) (2009).
Stahl-Zeng, et al., "High Sensitivity Detection of Plasma Proteins by Multiple Reaction Monitoring of N-Glycosites", Mol. Cell Proteomics, pp. 1809-1817, 6(10) (2007).
Takao, T., et al, "Identity of molecular structure of Shiga-like toxin I (VT1) from *Escherichia coli* O157 : H7 with that of Shiga toxin", Microbial Pathogenesis, pp. 357-369, 5(5) (1988).
Vaidyanathan, S., et al., "Discrimination of Aerobic Endospore-forming Bacteria via Electrospray-Ionization Mass Spectrometry of Whole Cell Suspensions", Anal. Chem, pp. 4134-4144, 73 (2001).
Wang, et al, "Multiplexed Immunoassay: Quantitation and Profiling of Serum Biomarkers Using Magnetic Nanoprobes and MALDI-TOF MS", Anal. Chem, pp. 6159-6167, 80(16) (2008).
The English Translation of the International Search Report for PCT/FR2010/052181.
The English Translation of the Written Opinion for PCT/FR2010/052181.
Fortin et al., Clinical quantitation of prostate-specific antigen biomarker in the low nanogram/milliliter range by conventional bore liquid chromatography-tandem mass spectrometry (multiple reaction monitoring) coupling and correlation with ELISA tests, Molecular & Cellular Proteomics, 2009, vol. 8.5, pp. 1006-1015.
Lange et al., Targeted quantitative analysis of *Streptococcus pyogenes* virulence factors by multiple reaction monitoring, Molecular & Cellular Proteomics, 2008, vol. 7.8, pp. 1489-1500.
Vaezzadeh et al., Imaging mass spectrometry using peptide isoelectric focusing, Rapid Communications in Mass Spectrometry, 2008, vol. 22, p. 2667-2676.
Leitner, et al., Determination of metabolites of nitrofuran antibiotics in animal tissue by high-performance liquid chromatography—tandem mass spectrometry, Journal of Chromatography A, vol. 939, pp. 49-58 (2001).

* cited by examiner

METHOD FOR CHARACTERIZING AT LEAST ONE MICROORGANISM BY MEANS OF MASS SPECTROMETRY

The present invention relates to the field of microbiology. More specifically, the invention relates to the characterization of microorganisms from a sample using mass spectrometry.

Since the discovery of microbes by Pasteur, microorganisms have been studied by microscopy and biochemical analyses. These conventional methods are often long and laborious and analytical alternatives were very soon sought. Thus, the analysis of bacteria by mass spectrometry was initiated as early as 1975 by J. Anhalt and C. Fenselau [1].

These preliminary studies were followed by the study, by gas chromatography coupled to mass spectrometry (GC-MS), of microorganism wall fatty acids [2]. This method was popularized under the name FAME for Fatty Acid Methyl Ester. It currently constitutes a reference method for taxonomic studies. However, its use remains limited to certain specialist laboratories which master the treatment of the sample by saponification, hydrolysis and derivation.

In 1996, the work of M. Claydon et al. [3] and also of T. Krishnamurthy and P. Ross [4] showed the possibility of identifying various bacterial species with a mass spectrometer of MALDI-TOF (Matrix Assisted Laser Desorption Ionization—Time Of Flight) type. The analysis combines the acquisition of a mass spectrum and the interpretation by expert software. It is extremely simple and can be carried out in a few minutes. However, it has only very recently become to spread among medical test laboratories [5]. Its clinical use is currently limited to the identification of species of bacteria and yeasts. It is used neither for typing nor for identifying resistances to antimicrobials, nor for analyzing virulence.

However, the characterization of microorganisms is fundamental both in the clinical field and in the industrial field. Thus, for example, the identification of resistances to antimicrobials such as antibiotics, and the detection of virulence factors are essential elements for ensuring optimum treatment of patients. Likewise, typing is crucial for epidemiological studies and for combating nosocomial diseases.

Other methods of mass spectrometry, in particular tandem mass spectrometry, have been proposed in order to meet these needs. By way of example, mention may be made of the work of C. Fenselau et al. for identifying β-lactamase with a quadrupole-TOF (Q-TOF) [6], the work of D. Ding et al. for the detection of staphylococcal enterotoxin C2 (virulence factor SEC2) with a triple quadrupole [7], or else the work of R. Everley et al. for the typing of *Clostridium* with a Q-TOF [8].

However, these research results are not applicable to routine clinical use. They were obtained with research instruments requiring highly qualified personnel. The analysis times, which are often more than one hour per sample, are incompatible with the workload of a microbiological test laboratory. Finally, the data obtained by the various teams reply to a specific question, but not simultaneously to all the clinical needs.

More recently, S. Hofstadler et al. have proposed a method which meets all the clinical needs [9]. They have combined amplification of the microbial genome by PCR with detection of the PCR products by electrospray-TOF (ESI-TOF). This method is now completely automated [10]. However, it requires a PCR amplification with the deficiencies inherent in molecular biology, namely cost of probes, extraction yield, etc.

In this context, the objective of the present invention is to propose a method for characterizing microorganisms, namely identifying and determining the properties of typing, resistance to at least one antimicrobial, and virulence factor, which makes it possible to overcome the drawbacks of the prior art methods, namely to provide a method which is inexpensive, without reagents specific to each species, in particular compared with the molecular biology methods, which gives a result in a short time, less than one hour, and which can be routinely used clinically, without requiring highly qualified personnel. Furthermore, the entire method for characterizing microorganisms can be advantageously carried out with the same mass spectrometer, thereby simplifying the instrumentation of the microbiological test laboratory.

To this end, the invention proposes a novel method for characterizing at least one microorganism from a sample, which comprises identifying said at least one microorganism and determining the properties of typing, potential resistance to at least one antimicrobial, and virulence factor, characterized in that the determining of the properties of typing, resistance to at least one antimicrobial, and virulence factor for said at least one microorganism is implemented by means of mass spectrometry using proteins, peptides and/or metabolites as markers of said properties of typing, resistance to at least one antimicrobial, and virulence factor.

Thus, the method of the invention is such that at least three of the properties for characterizing a microorganism are made use of by means of the mass spectrometry technique using, as markers, proteins, peptides or metabolites representative of the microorganisms to be characterized.

The microorganisms that can be characterized by means of the method of the invention are all pathogenic or non-pathogenic microorganisms encountered both industrially and clinically. They may be bacteria, viruses, protozoa or yeasts.

The expression "markers of the properties of typing, resistance to at least one antimicrobial, and virulence factor" is intended to mean molecules, of protein or metabolic origin, which are characteristic of said properties.

The expression "typing a microorganism" is intended to mean the differentiation of several strains within the same species. Typing has an epidemiological value; the clinician knows whether the strain isolated from the patient comes from the same source as other strains that are apparently identical and isolated from other patients or from the environment. This thus makes it possible to reveal a seat of infection in a hospital or at the time of food poisoning. By way of nonlimiting examples of markers of typing properties in bacteria, mention may be made of peptides having characteristic mutations, such as the transcription products of the adk, fumC, gyrB, icd, mdh, purA and recA genes of *Escherichia coli*, and those of the arc, aroE, glpF, gmk, pta, tpi and yqiL genes of *Staphylococcus aureus*. By way of nonlimiting examples of markers of typing properties in protozoa, mention may be made of the products of the chitinase gene of *Entamoeba histolytica* and *E. dispar*. By way of nonlimiting examples of markers of typing properties in viruses, mention may be made of the products of the polymerase gene of the human immunodeficiency virus. Finally, by way of nonlimiting examples of markers of typing properties in yeasts, mention may be made of the products of transcription of the aat1a, acc1, adp1, mpib, sya1, vps13 and zwf1b gene fragments of *Candida albicans*.

The expression "determining the resistance to at least one antimicrobial" is intended to mean determining a microorganism's susceptibility to being destroyed by an antimicrobial. Thus, if the microorganism is a bacterium, the antimicrobial against which it may develop a resistance is an antibiotic, if it is a protozoan, the antimicrobial is an antiparasitic, if it is a virus, the antimicrobial is an antiviral, and if it is a yeast, the antimicrobial is an antifungal. The proteins involved in the resistance mechanisms will differ according to the family and the species. By way of nonlimiting examples of markers of resistance to at least one antibiotic that are of use in bacteria, mention may be made of the transcription products of the mecA gene of *Staphylococcus aureus*, conferring resistance to methicillin, and making it possible to indicate whether strains are methicillin-resistant (MRSA strains) or else methicillin-sensitive (MSSA strains). Mention may also be made of the TEM-2 protein which makes it possible to indicate whether *Escherichia coli* strains are resistant to penicillins but sensitive to other classes of antibiotics such as cephalosporins or carbapenems. Another marker is the enzyme called KPC (for *Klebsiella pneumoniae* carbapenemase) which confers resistance to carbapenems. Another example of a resistance marker for *Staphylococcus aureus* is the metabolic profile representative of the resistance to vancomycin as described by E. Alexander et al., in the poster "Metabolomics-based approach to antibiotic resistance in *Staphylococcus aureus*" presented at the ASMS conference, 2009. By way of non-limiting example of markers of resistance to at least one antiparasitic of use in protozoa, mention may be made of iron-containing superoxide dismutase (Fe-SOD) and peroxyredoxin, the increased expression of which confers resistance to metronidazole. By way of nonlimiting example of a marker of resistance to at least one antiviral of use in viruses, mention may be made of mutations of the human immunodeficiency virus reverse transcriptase enzyme, conferring decreased sensitivity to reverse-transcriptase nucleoside inhibitors. Finally, by way of nonlimiting example of markers of resistance to at least one antifungal of use in yeasts, mention may be made of the mutation of the *Candida albicans* 1,3-b-D-glucan synthase enzyme, which confers decreased sensitivity to echinocandins. For another example, mention may be made of resistance to azole antifungals in *Candida albicans*, in particular resistance to fluconazole. The target of fluconazole is an enzyme, lanosterol demethylase, involved in the synthesis of ergosterol, a main constituent of the fungal wall. The resistance to fluconazole may be associated with the appearance of point mutations in the erg11 gene encoding lanosterol demethylase.

It should be noted that the resistance-specific markers can also be used as typing markers, as demonstrated by the applicant.

The expression "determining the virulence of a microorganism" is intended to mean evaluating the pathogenic, harmful and violent nature of the microorganism. By way of nonlimiting examples of a virulence marker in bacteria, mention may be made of PVL (Panton-Valentine Leukocidin), a cytolytic toxin with two synergistic components (LukFet LukS), present in *Staphylococcus aureus*, which is one of the most virulent toxins causing skin conditions, extensive cellulitis, osteomyelitis and necrotizing pneumonia, and is involved in viral superinfections. Other examples comprise autolysin and pneumolysin present in *Streptococcus pneumoniae*, a species responsible for respiratory tract infections, meningitis and bacteriemia, and also toxins A and B of *Clostridium difficile*, a commensal bacterium of the intestine, which toxins either cause a modification of the permeability of the intestinal epithelium (toxin A), or directly attack the cells of the epithelium (toxin B), or decrease intestinal transit and intestinal absorption over time, causing diarrhoea (combined action of toxins A and B). Mention may also be made, as an example, of the Shiga toxins Stx1 and Stx2 present in *Escherichia coli*. These two cytotoxins are considered to be important virulence factors of enterohemorrhagic *Escherichia coli*. They are responsible for complications such as ulcerative colitis or hemolytic-uremic syndrome. By way of nonlimiting example of a virulence marker in protozoa, mention may be made of antioxidants (Fe-hydrogenase 2, peroxiredoxin, superoxide dismutase) present in *Entamoeba histolytica*, a species responsible for dysentery and hepatic abscesses. By way of nonlimiting example of a virulence marker in viruses, mention may be made of the Nef protein variant in the human immunodeficiency virus type 1, the more pathogenic type in humans. Finally, by way of nonlimiting example of a virulence marker in yeasts, mention may be made of lipase 8 in *Candida albicans*, a species responsible for superficial candidiasis, but also septicemic and disseminated candidiasis.

It should be noted that the virulence-specific markers can also be used as a typing marker, as demonstrated by the applicant.

The method of the invention can be implemented for characterizing bacteria, said antimicrobial then being an antibiotic, which constitutes an embodiment of the invention. Thus, for example, by way of bacteria that can be characterized according to the method of the invention, mention may be made of:

*Escherichia coli* using TEM-2 as resistance and typing marker, and also Shiga toxins, OmpA as virulence and typing marker.

*Enterococcus faecalis* and *faecium* using VanA and VanB for resistance and typing, and also ESP (Enterococcal Surface Protein) for virulence and typing, or else

*Staphylococcus aureus* using the protein known as Immunoglobulin G-binding protein A (also known as protein A) for typing, the PBP2a protein for resistance, or even typing, and also the PVL protein for virulence, or even also typing.

By way of other microorganisms that can be characterized according to the method of the invention, mention may be made of:

*Candida albicans* using the 1,3-b-D-glucan synthase enzyme or else the lanosterol demethylase enzyme as resistance and typing marker, and also lipase 8 as virulence and typing marker.

The sample on which the method of the invention can be implemented is any sample capable of containing a target microorganism. The sample may be of biological origin, that is to say animal, vegetable or human origin. It may then correspond to a specimen of biological fluid (whole blood, serum, plasma, urine, cerebro-spinal fluid, organic secretion, for example), a tissue specimen or isolated cells. This specimen can be used as it is insofar as the markers for characterizing the microorganisms are available in the tested specimen, or else it can undergo, prior to the analysis, a preparation of enrichment, extraction, concentration, purification and/or culturing type, according to methods known to those skilled in the art.

The sample may be of industrial origin, i.e., according to a nonexhaustive list, a specimen of air, a specimen of water, a specimen taken from a surface, an object or a manufactured product, or a product of food origin. Among the samples of food origin, mention may be made, nonexhaustively, of a sample of a milk product (yoghurt, cheeses), of meat, of fish, of egg, of fruit, of a vegetable, of water or of a beverage (milk, fruit juice, soda, etc.). These samples of food origin may also come from sauces or prepared dishes. Finally, a food sample may be derived from an animal feed, such as in particular animal meals.

When the markers for characterizing microorganisms are of protein origin, upstream of the detection by mass spectrometry, the sample to be analyzed is preferentially pretreated in order to generate peptides from all the proteins present in the sample so as to fragment these proteins into peptides, for example by digestion with a proteolytic enzyme (protease), or via the action of a chemical reagent. Indeed, proteins can be cleaved by means of a physicochemical treatment, by means of a biological treatment or by means of a combination of the two treatments. Among the treatments that can be used, mention may be made of treatment with hydroxyl radicals, in particular with $H_2O_2$. Treatment with hydroxyl radicals causes cleavage of the peptide bonds, which takes place randomly on any peptide bond of the protein. The concentration of hydroxyl radicals conditions the number of cleavages made and therefore the length of the peptide fragments obtained. Other chemical treatments can also be used, for instance treatment with cyanogen bromide (CNBr) which specifically breaks the peptide bonds at the level of the carboxyl group of methionyl residues. It is also possible to carry out a partial acid cleavage at the aspartyl residues by heating at 1000° C. a solution of proteins in trifluoroacetic acid.

Treatment of the proteins by enzymatic digestion is nevertheless preferred compared with physicochemical treatments since it more extensively preserves the structure of the proteins, and is easier to control. The term "enzymatic digestion" is intended to mean the single or combined action of one or more enzymes under appropriate reaction conditions. The enzymes which carry out proteolysis, called proteases, cleave proteins at specific sites. Each protease generally recognizes a sequence of amino acids within which it always performs the same cleavage. Certain proteases recognize a single amino acid or a sequence of two amino acids between which they perform a cleavage, other proteases recognize only longer sequences. These proteases may be endoproteases or exoproteases. Among the known proteases, mention may be made, as described in WO2005/098071, of:

specific enzymes, such as trypsin which splits the peptide bond at the level of the carboxylic group of Arg and Lys residues, endolysin which cleaves the peptide bond of the —CO group of lysines, chymotrypsin which hydrolyzes the peptide bond at the level of the carboxylic group of aromatic residues (Phe, Tyr and Trp), pepsin which cleaves at the level of the $NH_2$ group of aromatic residues (Phe, Tyr and Trp), the V8 protease of the V8 strain of *Staphylococcus aureus*, which cleaves the peptide bond at the level of the carboxylic group of the Glu residue;

nonspecific enzymes, such as thermolysin originating from the *Bacillus thermoproteolyticus* bacterium, which hydrolyzes the peptide bond of the $NH_2$ group of hydrophobic amino acids (Xaa-Leu, Xaa-Ile, Xaa-Phe), subtilisin and pronase which are bacterial proteases that hydrolyze virtually all the bonds and can convert proteins into oligopeptides under controlled reaction conditions (enzyme concentration and reaction time).

Several proteases can be used simultaneously, if their methods of action are compatible, or they can be used successively. In the context of the invention, the digestion of the sample is preferably carried out via the action of a protease enzyme, for example trypsin.

The generation of peptides using a chemical reagent or a protease can be obtained by simple reaction in solution. It can also be carried out with a microwave oven [11], or under pressure [12], or alternatively with an ultrasonic device [13]. In the latter three cases, the protocol will be much faster.

Among the peptides thus obtained, the peptides specific for the protein are called proteotypic peptides. It is these which will be assayed by mass spectrometry.

According to one embodiment of the invention, the characterization markers are proteins of the microorganism to be characterized. In particular, said proteins are digested into peptides, preferably with an enzyme, more preferably with trypsin.

Similarly, the sample containing characterization markers of protein origin can also be pretreated for purification purposes. When the markers are of protein origin, this purification pretreatment can be carried out before or after the step of generating peptides as described above.

The sample purification pretreatment is widely known to those skilled in the art and may in particular implement centrifugation, filtration, electrophoresis or chromatography techniques. These separating techniques can be used alone or combined with one another in order to obtain a multidimensional separation. For example, a multidimensional chromatography can be used by combining a separation by ion exchange chromatography with a reverse-phase chromatography, as described by T. Fortin et al. [14], or H. Keshishian et al. [15]. In these publications, the chromatographic medium may be in a column or a cartridge (solid-phase extraction).

The electrophoretic or chromatographic fraction (or the retention time in monodimensional or multidimensional chromatography) of the proteotypic peptides is characteristic of each peptide and the implementation of these techniques therefore makes it possible to select the proteotypic peptide(s) to be assayed. Such a fractionation of the peptides generated makes it possible to increase the specificity of the subsequent assay by mass spectrometry.

An alternative to electrophoresis or chromatography techniques, for the peptide fractionation, consists in specifically purifying the N-glycopeptides ([16] and patent application WO 2008/066629). Nevertheless, such a purification only allows the quantification of peptides having undergone a post-translation modification of N-glycosylation type. However, not all proteins are glycosylated, which therefore limits its use.

The mass spectrometry to be implemented in the method of the invention is widely known to those skilled in the art as a powerful tool for analyzing and detecting various types of molecules. Generally, any type of molecule that can be ionized can be detected as a function of its molecular weight using a mass spectrometer. Depending on the nature of the molecule to be detected, of protein or metabolic origin, certain mass spectrometry techniques may be more suitable. Nevertheless, whatever the mass spectrometry method used for the detection, the latter comprises a step of ionization of the target molecule into ions termed molecular ions, in the present case a step of ionization of the characterization markers, and a step of separation of the molecular ions obtained as a function of their weight.

All mass spectrometers therefore comprise:

i) an ionization source intended to ionize the markers present in the sample to be analyzed, i.e. to give these markers a positive or negative charge;

ii) a mass analyzer intended to separate the ionized markers, or molecular ions, according to their mass to charge ratio (m/z);

iii) a detector intended to measure the signal produced either directly by the molecular ions, or by ions produced from the molecular ions, as detailed hereinafter.

The ionization step necessary for implementing mass spectrometry can be carried out by any method known to those skilled in the art. The ionization source makes it possible to bring the molecules to be assayed into an ionized and gaseous state. An ionization source can be used either in positive mode for studying positive ions, or in negative mode for studying negative ions. Several types of sources exist and will be used depending on the desired result and the molecules analyzed. Mention may in particular be made of:

electron ionization (EI), chemical ionization (CI) and desorption-chemical ionization (DCI),
fast atom bombardment (FAB), metastable atom bombardment (MAB) or ion bombardment (SIMS, LSIMS),
inductively coupled plasma (ICP),
atmospheric pressure chemical ionization (APCI) and atmospheric pressure photoionization (APPI),
electrospray ionization (ESI),
matrix assisted laser desorption ionization (MALDI), surface enhanced laser desorption ionization (SELDI) or desorption/ionization on silicon (DIOS),
ionization-desorption by interaction with metastable species (DART).

In particular, the ionization can be carried out as follows: the sample containing the target molecules is introduced into an ionization source, where the molecules are ionized in the gas state and thus converted into molecular ions which correspond to the initial molecules. An ionization source of electrospray type (ESI for ElectroSpray Ionisation) makes it possible to ionize a molecule while at the same time causing it to pass from a liquid state to a gas state. The molecular ions obtained then correspond to the molecules present in the liquid state, with, in the positive mode, one, two or even three additional protons or more, and therefore carry one, two or even three charges or more. For example, when the target molecule is a protein, ionization of the proteotypic peptides obtained after fractionation of the target protein, by virtue of a source of electrospray type operating in the positive mode, results in polypeptide ions in the gas state, with one, two or even three additional protons or more and which therefore carry one, two or even three charges or more, and allows change from a liquid state to a gas state [17]. This type of source is particularly suitable when the target molecules or proteotypic peptides obtained are separated beforehand by reverse-phase liquid chromatography. Nevertheless, the yield from ionization of the molecules present in the sample can vary according to the concentration and the nature of the various species present. This phenomenon results in a matrix effect known to those skilled in the art.

A MALDI ionization source will make it possible to ionize molecules from a sample in the solid state.

The mass analyzer in which the step of separating the ionized markers as a function of their mass/charge ratio (m/z) is carried out is any mass analyzer known to those skilled in the art. Mention may be made of low-resolution analyzers, of the quadrupole (Q), 3D ion trap (IT) or linear ion trap (LIT) type, also called ion trap, and high-resolution analyzers, for measuring the exact mass of the analytes and which use in particular the magnetic sector coupled to an electrical sector, the time of flight (TOF).

The separation of the molecular ions according to their m/z ratio can be implemented a single time (single mass spectrometry or MS), or else several successive MS separations can be carried out. When two successive MS separations are carried out, the analysis is called MS/MS or $MS^2$. When three successive MS separations are carried out, the analysis is called MS/MS/MS or $MS^3$ and more generally, when n successive MS separations are carried out, the analysis is called $MS^n$.

Among the techniques implementing several successive separations, the SRM (Selected Reaction Monitoring) mode in the case of detection or assaying of a single target molecule, or else the MRM (Multiple Reaction Monitoring) mode in the case of detection or assaying of several target molecules, are particularly uses of $MS^2$ separation. Similarly, the $MRM^3$ mode is a particular use of separation by MS/MS/MS. The term targeted mass spectrometry is then used.

In the case of a detection in single MS mode, it is the mass/charge ratio of the molecular ions obtained which is correlated with the target molecule to be detected.

In the case of a detection in the MS/MS mode, essentially two steps are added, compared with an MS assay, which are:

i) a fragmentation of the molecular ions, then called precursor ions, to give ions termed 1st-generation fragment ions, and ii) a separation of the ions termed 1st-generation fragment ions according to their mass $(m/z)_2$, the ratio $(m/z)_1$ corresponding to the ratio (m/z) of the precursor ions.

It is then the mass/charge ratio of the 1 st-generation fragment ions thus obtained which is correlated with the target molecule to be detected. The term "first-generation fragment ion" is intended to mean an ion resulting from the precursor ion, following a fragmentation step and the mass to charge ratio m/z of which is different than the precursor ion.

The pairs $(m/z)_1$ and $(m/z)_2$ are named transitions and are representative of the characteristic ions to be detected.

The choice of the characteristic ions that are detected in order to be correlated with the target molecule is made by those skilled in the art according to standard methods. Their selection will advantageously result in assays which are as sensitive as possible, as specific as possible and as robust as possible, in terms of reproducibility and reliability. In the methods developed for the selection of proteotypic peptides $(m/z)_1$, and of a first-generation fragment $(m/z)_2$, the choice is essentially based on the intensity of the response. For further details, reference may be made to V. Fusaro et al. [18]. Commercial software, such as the MIDAS software and the MRM Pilot software from Applied Biosystems or else MRMaid [19], may be used by those skilled in the art to allow them to predict all the possible transition pairs. Use may also be made of a database called PeptideAtlas, constructed by F. Desiere et al. [20] in order to compile all the peptide MRM transitions described by the scientific community. This PeptideAtlas database is freely available on the Internet. For nonprotein molecules, it is also possible to use databases, such as, for example, the one accessible through the Cliquid software from the company Applied Biosystems (United States of America).

An alternative approach for selecting the proteotypic peptides, $(m/z)_1$ and $(m/z)_2$, consists in using the MS/MS fragmentation spectra obtained on the occasion of other studies. These studies may be, for example, the phases of discovery and identification of biomarkers by proteomic analysis. This approach was proposed by Thermo Scientific during a meeting of users [19]. It makes it possible to generate a list of candidate transitions from the peptides identified experimentally by the SIEVE software (Thermo Scientific). Certain criteria have been detailed by J. Mead et al. [19] for the choice of the $(m/z)_1$ and $(m/z)_2$ ions and are detailed hereinafter:

Peptides with internal cleavage sites, i.e. with internal lysine or arginine, should be avoided, unless the lysine or the arginine is followed by proline.

Peptides with asparagine or glutamine should be avoided because they can deaminate.

Peptides with N-terminal glutamine or glutamic acid should be avoided because they can spontaneously cyclize.

Peptides with methionine should be avoided because they can be oxidized.

Peptides with cysteine should be avoided because they can be nonreproducibly modified during a possible step of denaturation, reduction and blocking of the thiol functions.

Peptides with proline can be considered to be favorable because they generally produce intense fragments in MS/MS with a single very predominant peak. However, a single very predominant fragment does not make it possible to validate the identity of the transition in a complex mixture. Indeed, only the simultaneous presence of several characteristic fragments makes it possible to verify that the desired precursor ion is indeed detected.

Peptides having a proline adjacent to the C-terminal (position n−1) or in the second position relative to the C-terminal (position n−2) are to be avoided because, in this case, the size of the first-generation fragment peptide is generally considered to be too small to be sufficiently specific.

The selection of fragments having a mass greater than the precursor is to be preferred in order to promote the specificity. For this, it is necessary to select a doubly-charged precursor ion and to select the most intense first-generation fragment ion having a mass greater than the precursor, i.e. a singly-charged first-generation fragment ion.

The fragmentation of the precursor ions selected is carried out in a fragmentation cell such as the models of triple quadrupole type [21], or of ion trap type [22], or else of time of flight (TOF) type [23], which also make it possible to separate the ions. The fragmentation(s) will be conventionally carried out by collision with an inert gas such as argon or nitrogen, in an electrical field, by photoexcitation or photodissociation using an intense light source, collision with electrons or radical species, by application of a potential difference, for example in a time of flight tube, or by any other activation mode. The characteristics of the electrical field condition the intensity and the nature of the fragmentation. Thus, the electrical field applied in the presence of an inert gas, for example in a quadrupole, conditions the collision energy supplied to the ions. This collision energy will be optimized, by those skilled in the art, in order to increase the sensitivity of the transition to be assayed. By way of example, it is possible to vary the collision energy between 5 and 180 e⁻V in q2 in an AB SCIEX QTRAP® 5500 mass spectrometer from the company Applied Biosystems (Foster City, United States of America). Similarly, the duration of the collision step and the excitation energy within, for example, an ion trap will be optimized, by those skilled in the art, in order to produce the most sensitive assay. By way of example, it is possible to vary this duration, called excitation time, between 0.010 and 50 ms and the excitation energy between 0 and 1 (arbitrary unit) in Q3 in an AB SCIEX QTRAP® 5500 mass spectrometer from the company Applied Biosystems.

Finally, the detection of the characteristic ions selected is carried out conventionally, in particular by means of a detector and a processing system. The detector collects the ions and produces an electrical signal, the intensity of which depends on the amount of ions collected. The signal obtained is then amplified so that it can be processed by computer. A data-processing computer assembly makes it possible to convert the information received by the detector into a mass spectrum.

The principle of the SRM mode, or else of the MRM mode, is to specifically select a precursor ion, to fragment it, and then to specifically select one of its fragment ions. For such applications, devices of the triple quadrupole type or triple quadrupole-ion trap hybrids are generally used.

In the case of a triple quadrupole device (Q1q2Q3) used in $MS^2$ mode, for the purpose of assaying or detecting a target protein, the first quadrupole (Q1) makes it possible to filter the molecular ions, corresponding to the proteotypic peptides characteristic of the protein to be assayed and obtained during a prior digestion step, according to their mass to charge ratio (m/z). Only the peptides having the mass/charge ratio of the proteotypic peptide being sought, ratio called $(m/z)_1$, are transmitted to the second quadrupole (q2) and play the role of precursor ions for the subsequent fragmentation. The q2 analyzer makes it possible to fragment the peptides of mass/charge ratio $(m/z)_1$ into first-generation fragment ions. The fragmentation is generally obtained by collision of the precursor peptides with an inert gas, for instance nitrogen or argon in q2. The first-generation fragment ions are transmitted to a third quadrupole (Q3) which filters the first-generation fragment ions according to a specific mass to charge ratio, which ratio is called $(m/z)_2$. Only the first-generation fragment ions having the mass/charge ratio of a characteristic fragment of the proteotypic peptide sought $(m/z)_2$ are transmitted to the detector in order to be detected, or even quantified.

This operating mode has a double selectivity, in relation to the selection of, on the one hand, the precursor ion and the selection of, on the other hand, the first-generation fragment ion. Mass spectrometry in SRM or MRM mode is therefore advantageous for the quantification.

When the mass spectrometry implemented in the method of the invention is tandem mass spectrometry ($MS^2$, $MS^3$, $MS^4$ or $MS^5$), several mass analyzers can be coupled together. For example, a first analyzer separates the ions, a collision cell makes it possible to fragment the ions, and a second analyzer separates the fragment ions. Some analyzers, such as ion traps or FT-ICR, constitute several analyzers in one and make it possible to fragment the ions and to analyze the fragments directly.

According to preferred embodiments of the invention, the method of the invention comprises one or more of the following characteristics:

the mass spectrometry, implemented for the properties of typing, potential resistance to at least one antimicrobial, and virulence factor, is a spectrometry of MS/MS type, which has the advantage of generating a fragment specific to the molecule to be detected or to be quantified, and thus of providing the assay method with great specificity;

the MS/MS spectrometry is MRM, which has the advantage of using an analysis cycle time in the mass spectrometer of a few tens of milliseconds, which makes it possible to detect or quantify with great sensitivity, and in a multiplexed manner, a large number of different molecules;

the determination of the properties of typing, resistance to an antimicrobial, and virulence factor is carried out in the same mass spectrometry apparatus, preferably simultaneously, which has the advantage of reducing the analysis time and the cost of the instrument; this also facilitates the processing and reporting of the results.

In addition to determining the properties of typing, resistance to an antimicrobial and virulence factor, it is advisable to identify the microorganism(s) present in the sample to be tested.

The methods for identifying microorganisms are widely known to those skilled in the art, as described, for example, by P. R. Murray el al., in Manual of Clinical Microbiology, 2007, 9th edition, and in particular in Vol. I, Section III, chapters 15 and 16 for bacteria and yeasts, Vol. II, Section VI, chapter 82 for viruses, and Vol. II, Section X, chapter 135 for protozoa. By way of example of conventional identification methods, mention may be made of the determination of the biological profile, using for example Vitek 2 identification cards (bioMérieux), or alternatively using molecular biology techniques with identification criteria based on studying the presence of certain genes, and on studying the sequence thereof.

The identification can be carried out directly from the sample in which the identification is performed, or else the microorganisms contained in the sample can be cultured by methods well known to those skilled in the art with culture media and optimum culture conditions adapted according to the species of microorganisms to be sought, as described by P. R. Murray et al., in Manual of Clinical Microbiology, 2007, 9th edition, Vol. I, Section III, chapter 14, in particular in Vol. I, Section IV, chapter 21 for bacteria, Vol. II, Section VI, chapter 81 for viruses, Vol. II, Section VIII, chapter 117 for yeasts, and Vol. II, Section X, chapter 134 for protozoa.

Thus, in general, in the case of an identification, by means of a biochemical method, of a bacterium in a specimen, it is first necessary to obtain it in pure culture, for example after inoculation on agar. The molecular biology (PCR) can in certain cases be applied directly to the sample to be analyzed.

Instead of culturing the microorganisms, the latter can be concentrated by capture directly in the sample by means of active surfaces. Such a method has been described by W.-J. Chen et al. [11], who captured various bacterial species by means of magnetic beads with an $Fe_3O_4/TiO_2$-activated surface. Capture by other means is also possible, such as capture by means of lectins [24], or by means of antibodies [25], or else by means of vancomycin [26]. The capture makes it possible to concentrate the microorganisms and thus to reduce or even eliminate the culture step. This results in a considerable time saving.

The identification can also be carried out by mass spectrometry, according to the techniques previously described, preferably by MS, by MS/MS, or else by MS followed by spectrometry of MS/MS type, which constitutes an embodiment of the invention. In this case also, the sample can be subjected beforehand to a culture step such as inoculation on agar.

The use of a method of identification by MS is advantageous since it can be carried out in a few minutes and it requires a mass spectrometer with a single analyzer, i.e. an instrument that is less complex than a tandem mass spectrometer used in MS/MS.

The use of a method of identification by MS followed by spectrometry of MS/MS type is also advantageous. It makes it possible to be sure of the identity of the ions observed in MS, which increases the specificity of the analysis.

The use of a method of identification by MS/MS of MRM type has the advantage of being more sensitive and simpler than the conventional approaches of MS then MS/MS. This method requires neither effective software for processing the information between the acquisition of the MS spectrum and of the MS/MS spectrum, nor any change in regulation of the machine parameters for linking MS and MS/MS spectra.

The method of identification by MS can be carried out with an electrospray source on a crude sample, as described by S. Vaidyanathan et al. [27] or else by R. Everley et al. [8] after chromatographic separation. Various ranges of m/z then make it possible to identify the microorganisms. S. Vaidyanathan et al. have used a window between 200 and 2000 Th, and R. Everley et al. a window between 620 and 2450 Th. The mass spectra can also be deconvoluted in order to access the mass of the proteins independently of their charge state. R. Everley et al. have thus exploited the masses between approximately 5 000 and 50 000 Da. Alternatively, the method of identification by MS can also be carried out by means of MALDI-TOF, as described by Claydon et al. [3] and T. Krishnamurthy and P. Ross [4]. The analysis combines the acquisition of a mass spectrum and interpretation by expert software. It is extremely simple and can be performed in a few minutes. This method of identification is currently spreading through medical test laboratories [28].

The identification of bacteria by MS then MS/MS via their proteins present in the sample has been widely applied by many teams. By way of example, mention may be made of the recent studies by N. Manes et al. [29] who have studied the peptidome of *Salmonella enterica*, or the studies by R. Nandakumar et al. [30] or by L. Hernychova et al. [31] who have studied the proteome of bacteria after digestion of the proteins with trypsin. The conventional approach consists in i) acquiring an MS spectrum, ii) successively selecting each precursor ion observed on the MS spectrum with an intense signal, iii) successively fragmenting each precursor ion and acquiring its MS/MS spectrum, iv) searching protein databases such as SWISS-PROT or NCBI, through software such as Mascot (Matrix Science, London, United Kingdom) or SEQUEST (Thermo Scientific, Waltham, United States of America), in order to identify the peptide having a strong probability of corresponding to the MS/MS spectrum observed. This method can result in the identification of a microorganism if a protein or a peptide characteristic of the species is identified.

According to yet another embodiment, the identification of said at least one microorganism is carried out by means of a conventional identification method and the method of the invention comprises an additional step of confirming the identification of said at least one microorganism, which confirmation step is carried out by mass spectrometry, according to the techniques previously described for the identification of microorganisms.

According to one particular embodiment, the mass spectrometry of the confirmation step is mass spectrometry of MS/MS type, preferably an MRM.

One of the advantages of the use of mass spectrometry lies in the fact that it is particularly useful to quantify molecules, in the present case the markers of the properties of typing and resistance to at least one antimicrobial. To do this, the current intensity detected, which is proportional to the amount of target molecule, is used. The current intensity thus measured may serve as a quantitative measurement for determining the amount of target molecule present, which is characterized by its expression in International System (SI) units of mol/m³ or kg/m³ type, or by multiples or submultiples of these units, or by the usual derivatives of SI units, including multiples or submultiples thereof. By way of nonlimiting example, units such as ng/ml or fmol/l are units characterizing a quantitative measurement.

A calibration is nevertheless necessary in order to be able to correlate the area of the peak measured, corresponding to the intensity of current induced by the ions detected, with the amount of target molecule to be assayed. For this, the calibrations conventionally used in mass spectrometry may be implemented, in the context of the invention. MRM assays are conventionally calibrated using external standards or, preferably, using internal standards as described by T. Fortin et al. [14]. When the target molecule is a proteotypic peptide, making it possible to assay a protein of interest, the correlation between the quantitative measurement and the amount of target proteotypic peptide, and consequently of protein of interest, is obtained by calibrating the signal measured relative to a standard signal for which the amount to be assayed is known. The calibration can be carried out by means of a calibration curve, for example obtained by successive injections of standard proteotypic peptide at various concentrations (external calibration) or, preferentially, by internal calibration using a heavy peptide, as internal standard, for example in accordance with the AQUA, QconCAT or PSAQ methods detailed hereinafter. The term "heavy peptide" is intended to mean a peptide corresponding to the proteotypic peptide, but in which one or more carbon 12 ($^{12}$C) atoms is (are) replaced with carbon 13 ($^{13}$C), and/or one or more nitrogen 14 ($^{14}$N) atoms is (are) replaced with nitrogen 15 ($^{15}$N).

The use of heavy peptides, as internal standards (AQUA), has also been proposed in patent application US 2004/0229283. The principle is to artificially synthesize proteotypic peptides with amino acids comprising isotopes that are heavier than the usual natural isotopes. Such amino acids are obtained, for example, by replacing some of the carbon 12 ($^{12}$C) atoms with carbon 13 ($^{13}$C), or by replacing some of the nitrogen 14 ($^{14}$N) atoms with nitrogen 15 ($^{15}$N). The artificial peptide (AQUA) thus synthesized has rigorously the same physicochemical properties as the natural peptide (with the exception of a higher mass). It is generally added, at a given concentration, to the sample, upstream of the assay by mass spectrometry, for example between the treatment leading to the cleavage of the proteins of the sample of interest and the fractionation of the peptides obtained after the treatment step. As a result, the AQUA peptide is copurified with the natural peptide to be assayed, during the fractionation of the peptides. The two peptides are therefore injected simultaneously into the mass spectrometer, for the assay. They then undergo the same ionization yields in the source. Comparison of the areas of the peak for the natural and AQUA peptides, the concentration of which is known, makes it possible to calculate the concentration of the natural peptide and to thus work back to the concentration of the protein to be assayed. A variant of the AQUA technique has been proposed by J.-M. Pratt et al. [32] under the name QconCat. This variant is also described in patent application WO 2006/128492. It consists in concatenating various AQUA peptides and in producing the artificial polypeptide in the form of a heavy recombinant protein. The recombinant protein is synthesized with amino acids comprising heavy isotopes. In this way, it is possible to obtain a standard for calibrating the simultaneous assaying of several proteins at a lower cost. The QconCAT standard is added from the beginning, upstream of the treatment leading to the cleavage of the proteins and before the steps of protein fractionation, denaturation, reduction and then blocking of the thiol functions of the proteins, if these are present. The QconCAT standard therefore undergoes the same cycle of treatment leading to cleavage of the proteins as the natural protein, thereby making it possible to take into account the yield from the treatment step leading to the cleavage of the proteins. This is because the treatment, in particular by digestion, of the natural protein may not be complete. In this case, the use of an AQUA standard would result in the amount of natural protein being underestimated. For an absolute assay, it may therefore be important to take into account the yields from treatment leading to cleavage of the proteins. However, V. Brun et al. [33] have shown that, sometimes, the QconCAT standards do not reproduce exactly the yield from treatment, in particular by digestion, of the natural protein, doubtless owing to a different three-dimensional conformation of the QconCAT protein.

V. Brun et al. [33] have therefore proposed using a method called PSAQ which is described in patent application WO 2008/145763. In this case, the internal standard is a recombinant protein, which has the same sequence as the natural protein but has been synthesized with heavy amino acids. The synthesis is carried out ex-vivo with heavy amino acids. This standard has rigorously the same physicochemical properties as the natural protein (with the exception of a higher mass). It is added from the beginning, before the protein fractionation step, when said step is present. It is therefore copurified with the native protein, during the protein fractionation step. It exhibits the same yield from treatment, in particular by digestion, as the native protein. The heavy peptide obtained after cleavage is also copurified with the natural peptide, if a peptide fractionation step is carried out. The two peptides are therefore injected simultaneously into the mass spectrometer, so as to be quantitatively assayed. They therefore undergo the same ionization yields in the source. Comparison of the areas of the peak of the natural peptides and of the reference peptides in the PSAQ method makes it possible to calculate the concentration of the protein to be assayed while taking into account all the steps of the assay method.

All these techniques, namely AQUA, QconCAT or PSAQ or any other calibration technique, used in assays by mass spectrometry and in particular in MRM or MS assays, may be implemented for carrying out the calibration, in the context of the invention.

According to one preferred embodiment, the method of the invention allows the characterization of *Staphylococcus aureus*.

In particular, the characterization of *Staphylococcus aureus* uses at least one peptide as follows:

1. for the typing:
   at least one peptide belonging to protein A having the following sequence SEQ ID NO: 1:

MKKKNIYSIRKLGVGIASVTLGTLLISGGVTPAANAAQHDEAQQNAFYQV

LNMPNLNADQRNGFIQSLKDDPSQSANVLGEAQKLNDSQAPKADAQQNKF

NKDQQSAFYEILNMPNLNEEQRNGFIQSLKDDPSQSTNVLGEAKKLNESQ

APKADNNFNKEQQNAFYEILNMPNLNEEQRNGFIQSLKDDPSQSANLLAE

AKKLNESQAPKADNKFNKEQQNAFYEILHLPNLNEEQRNGFIQSLKDDPS

QSANLLAEAKKLNDAQAPKADNKFNKEQQNAFYEILHLPNLTEEQRNGFI

-continued

QSLKDDPSVSKEILAEAKKLNDAQAPKEEDNNKPGKEDGNKPGKEDGNKP
GKEDNKKPGKEDGNKPGKEDNKKPGKEDGNKPGKEDGNKPGKEDGNKPGK
EDGNKPGKEDGNGVHVVKPGDTVNDIAKANGTTADKIAADNKLADKNMIK
PGQELVVDKKQPANHADANKAQALPETGEENPFIGTTVFGGLSLALGAAL
LAGRRREL said peptides being chosen, preferably, from the peptides having the sequence SEQ ID NO: 2, 3, 4, 5, 6, 7 and 8 as defined hereinafter:

| Peptide SEQ ID NO: | Amino acid sequence | Location in SEQ ID NO: 1 |
|---|---|---|
| 2 | DDPSQSANVLGEAQK | 70-84 |
| 3 | DQQSAFYEILNMPNLNEEQR | 103-122 |
| 4 | DDPSQSTNVLGEAK | 131-144 |
| 5 | EQQNAFYEILNMPNLNEEQR | 161-180 |
| 6 | DDPSQSANLLAEAK | 189-202 |
| 7 | DDPSVSK | 305-311 |
| 8 | IAADNK | 437-442 |

2. For the potential resistance to at least one antibiotic
at least one peptide belonging to the PBP2a protein having the following sequence SEQ ID NO: 9:

MKKIKIVPLILIVVVVGFGIYFYASKDKEINNTIDAIEDKNFKQVYKDSS
YISKSDNGEVEMTERPIKIYNSLGVKDINIQDRKIKKVSKNKKRVDAQYK
IKTNYGNIDRNVQFNFVKEDGMWKLDWDHSVIIPGMQKDQSIHIENLKSE
RGKILDRNNVELANTGTAYEIGIVPKNVSKKDYKAIAKELSISEDYIKQQ
MDQNWVQDDTFVPLKTVKKMDEYLSDFAKKFHLTTNETESRNYPLEKATS
HLLGYVGPINSEELKQKEYKGYKDDAVIGKKGLEKLYDKKLQHEDGYRVT
IVDDNSNTIAHTLIEKKKKDGKDIQLTIDAKVQKSIYNNMKNDYGSGTAI
HPQTGELLALVSTPSYDVYPFMYGMSNEEYNKLTEDKKEPLLNKFQITTS
PGSTQKILTAMIGLNNKTLDDKTSYKIDGKGWQKDKSWGGYNVTRYEVVN
GNIDLKQAIESSDNIFFARVALELGSKKFEKGMKKLGVGEDIPSDYPFYN
AQISNKNLDNEILLADSGYGQEILINPVQILSIYSALENNGNINAPHLL
KDTKNKVWKKNIISKENINLLTDGMQQVVNKTHKEDIYRSYANLIGKSGT
AELKMKQGETGRQIGWFISYDKDNPNMMMAINVKDVQDKGMASYNAKISG
KVYDELYENGNK said peptides being chosen, preferably, from the peptides having the sequence SEQ ID NO: 10 to 17 as defined hereinafter:

| Peptide SEQ ID NO: | Amino acid sequence | Location in SEQ ID NO: 9 |
|---|---|---|
| 10 | IYNSLGVK | 69-76 |
| 11 | DINIQDR | 77-83 |
| 12 | ELSISEDYIK | 189-198 |
| 13 | FQITTSPGSTQK | 395-406 |
| 14 | ILTAMIGLNNK | 407-417 |
| 15 | YEVVNGNIDLK | 446-456 |
| 16 | VALELGSK | 470-477 |
| 17 | SYANLIGK | 590-597 |

3. For the virulence:
at least one peptide belonging to the PVL protein, subunits LukS and LukF, having the following sequences SEQ ID NO: 18 and 22, respectively:

SEQ ID NO: 18:
MIFMVKKRLLAATLSLGIITPIATSFHESKADNNIENIGDGAEVVKRTED
TSSDKWGVTQNIQVDFVKDKKYNKDALILKMQGFINSKTTYYNYKNTDHI
KAMRWPFQYNIGLKTNDPNVDLINYLPKNKIDSVNVSQTLGYNIGGNFNS
GPSTGGNGSFNYSKTISYNQQNYISEVERQNSKSVQWGIKANSFITSLGK
MSGHDPNLFVGYKPYSQNPRDYFVPDNELPPLVHSGFNPSFIATVSHEKG
SGDTSEFEITYGRNMDVTHATRRTTHYGNSYLEGSRIHNAFVNRNYTVKY
EVNWKTHEIKVKGHN

SEQ ID NO: 22:
MKKIVKSSVVTSIALLLLSNTVDAAQHITPVSEKKVDDKITLYKTTATSD
SDKLKISQILTFNFIKDKSYDKDTLILKAAGNIYSGYTKPNPKDTISSQF
YWGSKYNISINSDSNDSVNVVVDYAPKNQNEEFQVQQTVGYSYGGDINISN
GLSGGGNGSKSFSETINYKQESYRTSLDKRTNFKKIGWDVEAHKIMNNGW
GPYGRDSYHSTYGNEMFLGSRQSNLNAGQNFLEYHKMPVLSRGNFNPEFI
GVLSRKQNAAKKSKITVTYQREMDRYTNFWNQLHWIGNNYKDENRATHTS
IYEVDWENHTVKLIDTQSKEKNPMS said peptides being chosen, preferably, from the peptides having the sequences SEQ ID NO: 19, 20, 21, 23 and 24 as defined hereinafter:

| Peptide SEQ ID NO: | Amino acid sequence | |
|---|---|---|
| | | Location in SEQ ID NO: 18 |
| 19 | TNDPNVDLINYLPK | 115-128 |
| 20 | SVQWGIK | 184-190 |
| 21 | ANSFITSLGK | 191-200 |
| | | Location in SEQ ID NO: 22 |
| 23 | MPVLSR | 237-242 |
| 24 | GNFNPEFIGVLSR | 243-255 |

4. For the identification:
   at least one peptide belonging to the 50S ribosomal protein L30 (RL30), 50S ribosomal protein L331 (RL331), staphylococcal secretory antigen ssaA2 (SSAA2), UPF0337 protein SA0772 (Y772), bifunctional autolysin (ATL), elongation factor Tu (EFTU), probable transglycolase isaA (ISAA) and UPF0457 protein SA1975.1 (Y197A), having the following sequences SEQ ID NO: 25, 28, 31, 33, 36, 39, 41 and 43, respectively:

SEQ ID NO: 25:
MAKLQITLTRSVIGRPETQRKTVEALGLKKTNSSVVVEDNPAIRGQINKV
KHLVTVEEK

SEQ ID NO: 28:
MRVNVTLACTECGDRNYITTKNKRNNPERVEMKKFCSRENKQTLHRETK

SEQ ID NO: 31:
MKKIATATIATAGFATIAIASGNQAHASEQDNYGYNPNDPTSYSYTYTID
AQGNYHYTWKGNWHPSQLNQDNGYYSYYYYNGYNNYNNYNNGYSYNNYSR
YNNYSNNNQSYNYNNYNSYNTNSYRTGGLGASYSTSSNNVQVTTTMAPSS
NGRSISSGYTSGRNLYTSGQCTYYVFDRVGGKIGSTWGNASNWANAAARA
GYTVNNTPKAGAIMQTTQGAYGHVAYVESVNSNGSVRVSEMNYGYGPGVV
TSRTISASQAAGYNFIH

SEQ ID NO: 33:
MADESKFEQAKGNVKETVGNVTDNKNLENEGKEDKASGKAKEFVENAKEK
ATDFIDKVKGNKGE

SEQ ID NO: 36:
MAKKFNYKLPSMVALTLVGSAVTAHQVQAAETTQDQTTNKNVLDSNKVKA
TTEQAKAEVKNPTQNISGTQVYQDPAIVQPKTANNKTGNAQVSQKVDTAQ
VNGDTRANQSATTNNTQPVAKSTSTTAPKTNTNVTNAGYSLVDDEDDNSE
HQINPELIKSAAKPAALETQYKAAAPKAKTEATPKVTTFSASAQPRSVAA
TPKTSLPKYKPQVNSSINDYIRKNNLKAPKIEEDYTSYFPKYAYRNGVGR
PEGIVVHDTANDRSTINGEISYMKNNYQNAFVHAFVDGDRIIETAPTDYL
SWGVGAVGNPRFINVEIVHTHDYASFARSMNNYADYAATQLQYYGLKPDS
AEYDGNGTVWTHYAVSKYLGGTDHADPHGYLRSHNYSYDQLYDLINEKYL
IKMGKVAPWGTQFTTTPTTPSKPTTPSKPSTGKLTVAANNGVAQIKPTNS
GLYTTVYDKTGKATNEVQKTFAVSKTATLGNQKFYLVQDYNSGNKFGWVK
EGDVVYNTAKSPVNVNQSYSIKSGTKLYTVPWGTSKQVAGSVSGSGNQTF
KASKQQQIDKSIYLYGSVNGKSGWVSKAYLVDTAKPTPTPIPKPSTPTTN
NKLTVSSLNGVAQINAKNNGLFTTVYDKTGKPTKEVQKTFAVTKEASLGG
NKFYLVKDYNSPTLIGWVKQGDVIYNNAKSPVNVMQTYTVKPGTKLYSVP
WGTYKQEAGAVSGTGNQTFKATKQQQIDKSIYLFGTVNGKSGWVSKAYLA
VPAAPKKAVAQPKTAVKAYTVTKPQTTQTVSKIAQVKPNNTGIRASVYEK
TAKNGAKYADRTFYVTKERAHGNETYVLLNNTSHNIPLGWFNVKDLNVQN
LGKEVKTTQKYTVNKSNNGLSMVPWGTKNQVILTGNNIAQGTFNATKQVS
VGKDVYLYGTINNRTGWVNAKDLTAPTAVKPTTSAAKDYNYTYVIKNGNG
YYYVTPNSDTAKYSLKAFNEQPPFAVVKEQVINGQTWYYGKLSNGKLAWIK

STDLAKELIKYNQTGMTLNQVAQIQAGLQYKPQVQRVPGKWTDANFNDVK
HAMDTKRLAQDPALKYQFLRLDQPQNISIDKINQFLKGKGVLENQGAAFN
KAAQMYGINEVYLISHALLETGNGTSQLAKGADVVNNKVVTNSNTKYHNV
FGIAAYDNDPLREGIKYAKQAGWDTVSKAIVGGAKFIGNSYVKAGQNTLY
KMRWNPAHPGTHQYATDVDWANINAKIIKGYYDKIGEVGKYFDIPQYK

SEQ ID NO: 39:
MAKEKFDRSKEHANIGTIGHVDHGKTTLTAAIATVLAKNGDSVAQSYDMI
DNAPEEKERGITINTSHIEYQTDKRHYAHVDCPGHADYVKNMITGAAQMD
GGILVVSAADGPMPQTREHILLSRNVGVPALVVFLNKVDMVDDEELLELV
EMEVRDLLSEYDFPGDDVPVIAGSALKALEGDAQYEEKILELMEAVDTYI
PTPERDSDKPFMMPVEDVFSITGRGTVATGRVERGQIKVGEEVEIIGLHD
TSKTTVTGVEMFRKLLDYAEAGDNIGALLRGVAREDVQRGQVLAAPGSIT
PHTEFKAEVYVLSKDEGGRHTPFFSNYRPQFYFRTTDVTGVVHLPEGTEM
VMPGDNVEMTVELIAPIAIEDGTRFSIREGGRTVGSGVVTEIIK

SEQ ID NO: 41:
MKKTIMASSLAVALGVTGYAAGTGHQAHAAEVNVDQAHLVDLAHNHQDQL
NAAPIKDGAYDIHFVKDGFQYNFTSNGTTWSWSYEAANGQTAGFSNVAGA
DYTTSYNQGSNVQSVSYNAQSSNSNVEAVSAPTYHNYSTSTTSSSVRLSN
GNTAGATGSSAAQIMAQRTGVSASTWAAIIARESNGQVNAYNPSGASGLF
QTMPGWGPTNTVDQQINAAVKAYKAQGLGAWGF

SEQ ID NO: 43:
MAMTVKKDNNEVRIQWRVADIKIPTSEIKNITQDQDIHAVPKLDSKDVSR
IGSTFGKTNRVIIDTEDHEYIIYTQNDQKVYNELTK said peptides being chosen, preferably, from the peptides having the sequences SEQ ID NO: 26, 27, 29, 30, 32, 34, 35, 37, 38, 40, 42, 44 and 45 as defined hereinafter:

| Peptide SEQ ID NO: | Amino acid sequence | |
|---|---|---|
| | | Location in SEQ ID NO: 25 |
| 26 | LQITLTR | 4-10 |
| 27 | TNSSVVVEDNPAIR | 31-34 |
| | | Location in SEQ ID NO: 28 |
| 29 | VNVTLACTECGDR | 3-15 |
| 30 | NYITTK | 16-21 |
| | | Location in SEQ ID NO: 31 |
| 32 | AGYTVNNTPK | 200-209 |
| | | Location in SEQ ID NO: 33 |
| 34 | EFVENAKEK | 42-50 |
| 35 | ATDFIDKVK | 51-59 |

-continued

| Peptide SEQ ID NO: | Amino acid sequence | |
|---|---|---|
| | | Location in SEQ ID NO: 36 |
| 37 | LYSVPWGTYK | 696-705 |
| 38 | AYLAVPAAPK | 747-756 |
| | | Location in SEQ ID NO: 39 |
| 40 | TVGSGVVTEIIK | 383-394 |
| | | Location in SEQ ID NO: 41 |
| 42 | LSNGNTAGATGSSAAQ-IMAQR | 148-168 |
| | | Location in SEQ ID NO: 43 |
| 44 | NITQDQDIHAVPK | 30-42 |
| 45 | LDSKDVSR | 43-50 |

It should be noted, as previously indicated, that, for the typing, the method of the invention can also use at least one peptide having the sequence SEQ ID NO: 10, 11, 12, 13, 14, 15, 16, 17, 19, 20, 21, 23, 24, 26, 27, 29, 30, 32, 34, 35, 37, 38, 40, 42, 44 and 45, which are of use for determining the potential resistance to at least one antibiotic, or the virulence, as previously indicated.

Of course, the term "at least one peptide" is intended to mean at least one, at least two, at least three, at least four, at least five, at least six or more peptides representative of the marker that it is desired to detect. Preferably, at least two, or even at least three, or even at least four, peptides per characteristic will be used.

According to another preferred embodiment, the method of the invention allows the characterization of *Escherichia coli*.

In particular, the characterization of *Escherichia coli* uses at least one peptide as follows:

1. for the typing:
   at least one peptide belonging to the aspartate ammonia-lyase protein (ASPA), the ATP synthase alpha subunit (ATPA), 10 kDa chaperonin (CH10), 60 kDa chaperonin (CH60), the DNA-binding protein HU-beta (DBHB), glutamate decarboxylase (DCEB), succinate dehydrogenase flavoprotein subunit (DHSA), the DNA protection during starvation protein (DPS), the DNA-binding protein H—NS (HNS), malate dehydrogenase (MDH), phosphoglycerate kinase (PGK), phosphoribosylaminoimidazole-succinocarboxamide synthase (PUR7), the 50S ribosomal protein L4 (RL4), the 30S ribosomal protein S1 (RS1), the UPF0076 protein yjgF (YJGF), having the following sequences SEQ ID NO: 138 to 152, respectively:

SEQ ID NO: 138
MSNNIRIEEDLLGTREVPADAYYGVHTLRAIENFYISNNKISDIPEFVRG
MVMVKKAAAMANKELQTIPKSVANAIIAACDEVLNNGKCMDQFPVDVYQG
GAGTSVNMNTNEVLANIGLELMGHQKGEYQYLNPNDHVNKCQSTNDAYPT
GFRIAVYSSLIKLVDAINQLREGFERKAVEFQDILKMGRTQLQDAVPMTL
GQEFRAFSILLKEEVKNIQRTAELLLEVNLGATAIGTGLNTPKEYSPLAV
KKLAEVTGFPCVPAEDLIEATSDCGAYVMVHGALKRLAVKMSKICNDLRL
LSSGPRAGLNEINLPELQAGSSIMPAKVNPVVPEVVNQVCFKVIGNDTTV
TMAAEAGQLQLNVMEPVIGQAMFESVHILTNACYNLLEKCINGITANKEV
CEGYVYNSIGIVTYLNPFIGHHNGDIVGKICAETGKSVREVVLERGLLTE
AELDDIFSVQNLMHPAYKAKRYTDESEQ

SEQ ID NO: 139
MQLNSTEISELIKQRIAQFNVVSEAHNEGTIVSVSDGVIRIHGLADCMQG
EMISLPGNRYAIALNLERDSVGAVVMGPYADLAEGMKVKCTGRILEVPVG
RGLLGRVVNTLGAPIDGKGPLDHDGFSAVEAIAPGVIERQSVDQPVQTGY
KAVDSMIPIGRGQRELIIGDRQTGKTALAIDAIINQRDSGIKCIYVAIGQ
KASTISNVVRKLEEHGALANTIVVVATASESAALQYLAPYAGCAMGEYFR
DRGEDALIIYDDLSKQAVAYRQISLLLRRPPGREAFPGDVFYLHSRLLER
AARVNAEYVEAFTKGEVKGKTGSLTALPIIETQAGDVSAFVPTNVISITD
GQIFLETNLFNAGIRPAVNPGISVSRVGGAAQTKIMKKLSGGIRTALAQY
RELAAFSQFASDLDDATRKQLDHGQKVTELLKQKQYAPMSVAQQSLVLFA
AERGYLADVELSKIGSFEAALLAYVDRDHAPLMQEINQTGGYNDEIEGKL
KGILDSFKATQSW

SEQ ID NO: 140
MNIRPLHDRVIVKRKEVETKSAGGIVLTGSAAAKSTRGEVLAVGNGRILE
NGEVKPLDVKVGDIVIFNDGYGVKSEKIDNEEVLIMSESDILAIVEA

SEQ ID NO: 141
MAAKDVKFGNDARVKMLRGVNVLADAVKVTLGPKGRNVVLDKSFGAPTIT
KDGVSVAREIELEDKFENMGAQMVKEVASKANDAAGDGTTTATVLAQAII
TEGLKAVAAGMNPMDLKRGIDKAVTAAVEELKALSVPCSDSKAIAQVGTI
SANSDETVGKLIAEAMDKVGKEGVITVEDGTGLQDELDVVEGMQFDRGYL
SPYFINKPETGAVELESPFILLADKKISNIREMLPVLEAVAKAGKPLLII
AEDVEGEALATLVVNTMRGIVKVAAVKAPGFGDRRKAMLQDIATLTGGTV
ISEEIGMELEKATLEDLGQAKRVVINKDTTTIIDGVGEEAAIQGRVAQIR
QQIEEATSDYDREKLQERVAKLAGGVAVIKVGAATEVEMKEKKARVEDAL
HATRAAVEEGVVAGGGVALIRVASKLADLRGQNEDQNVGIKVALRAMEAP
LRQIVLNCGEEPSVVANTVKGGDGNYGYNAATEEYGNMIDMGILDPTKVT
RSALQYAASVAGLMITTECMVTDLPKNDAADLGAAGGMGGMGGMGGMM

SEQ ID NO: 142
MNKSQLIDKIAAGADISKAAAGRALDAIIASVTESLKEGDDVALVGFGTF
AVKERAARTGRNPQTGKEITIAAAKVPSFRAGKALKDAVN

SEQ ID NO: 143
MDKKQVTDLRSELLDSRFGAKSISTIAESKRFPLHEMRDDVAFQIINDEL
YLDGNARQNLATFCQTWDDENVHKLMDLSINKNWIDKEEYPQSAAIDLRC
VNMVADLWHAPAPKNGQAVGTNTIGSSEACMLGGMAMKWRWRKRMEAAGK
PTDKPNLVCGPVQICWHKFARYWDVELREIPMRPGQLFMDPKRMIEACDE

-continued

NTIGVVPTFGVTYTGNYEFPQPLHDALDKFQADTGIDIDMHIDAASGGFL
APFVAPDIVWDFRLPRVKSISASGHKFGLAPLGCGWVIWRDEEALPQELV
FNVDYLGGQIGTFAINFSRPAGQVIAQYYEFLRLGREGYTKVQNASYQVA
AYLADEIAKLGPYEFICTGRPDEGIPAVCFKLKDGEDPGYTLYDLSERLR
LRGWQVPAFTLGGEATDIVVMRIMCRRGFEMDFAELLLEDYKASLKYLSD
HPKLQGIAQQNSFKHT

SEQ ID NO: 144
MKLPVREFDAVVIGAGGAGMRAALQISQSGQTCALLSKVFPTRSHTVSAQ
GGITVALGNTHEDNWEWHMYDTVKGSDYIGDQDAIEYMCKTGPEAILELE
HMGLPFSRLDDGRIYQRPFGGQSKNFGGEQAARTAAAADRTGHALLHTLY
QQNLKNHTTIFSEWYALDLVKNQDGAVVGCTALCIETGEVVYFKARATVL
ATGGAGRIYQSTTNAHINTGDGVGMAIRAGVPVQDMEMWQFHPTGIAGAG
VLVTEGCRGEGGYLLNKHGERFMERYAPNAKDLAGRDVVARSIMIEIREG
RGCDGPWGPHAKLKLDHLGKEVLESRLPGILELSRTFAHVDPVKEPIPVI
PTCHYMMGGIPTKVTGQALTVNEKGEDVVVPGLFAVGEIACVSVHGANRL
GGNSLLDLVVFGRAAGLHLQESIAEQGALRDASESDVEASLDRLNRWNNN
RNGEDPVAIRKALQECMQHNFSVFREGDAMAKGLEQLKVIRERLKNARLD
DTSSEFNTQRVECLELDNLMETAYATAVSANFRTESRGAHSRFDFPDRDD
ENWLCHSLYLPESESMTRRSVNMEPKLRPAFPPKIRTY

SEQ ID NO: 145
MSTAKLVKSKATNLLYTRNDVSDSEKKATVELLNRQVIQFIDLSLITKQA
HWNMRGANFIAVHEMLDGFRTALIDHLDTMAERAVQLGGVALGTTQVINS
KTPLKSYPLDIHNVQDHLKELADRYAIVANDVRKAIGEAKDDDTADILTA
ASRDLDKFLWFIESNIE

SEQ ID NO: 146
MSEALKILNNIRTLRAQARECTLETLEEMLEKLEVVVNERREEESAAAAE
VEERTRKLQQYREMLIADGIDPNELLNSLAAVKSGTKAKRAQRPAKYSYV
DENGETKTWTGQGRTPAVIKKAMDEQGKSLDDFLIKQ

SEQ ID NO: 147
MKVAVLGAAGGIGQALALLLKTQLPSGSELSLYDIAPVTPGVAVDLSHIP
TAVKIKGFSGEDATPALEGANVVLISAGVARKPGMDRSDLFNVNAGIVKN
LVQQVAKTCPKACIGIITNPVNTTVAIAAEVLKKAGVYDKNKLFGVTTLD
IIRSNTFVAELKGKQPGEVEVPVIGGHSGVTILPLLSQVPGVSFTEQEVA
DLTKRIQNAGTEVVEAKAGGGSATLSMGQAAARFGLSLVRALQGEQGVVE
CAYVEGDGQYARFFSQPLLLGKNGVEERKSIGTLSAFEKNALEGMLDTLK
KDIALGEEFVNK

SEQ ID NO: 148
MSVIKMTDLDLAGKRVFIRADLNVPVKDGKVTSDARIRASLPTIELALKQ
GAKVMVTSHLGRPTEGEYNEEFSLLPVVNYLKDKLSNPVRLVKDYLDGVD
VAEGELVVLENVRFNKGEKKDDETLSKKYAALCDVFVMDAFGTAHRAQAS
THGIGKFADVACAGPLLAAELDALGKALKEPARPMVAIVGGSKVSTKLTV
LDSLSKIADQLIVGGGIANTFIAAQGHDVGKSLYEADLVDEAKRLLSTCN
IPVPSDVRVATEFSETAPATLKSVNDVKADEQILDIGDASAQELAEILKN

AKTILWNGPVGVFEFPNFRKGTEIVANAIADSEAFSIAGGGDTLAAIDLF
GIADKISYISTGGGAFLEFVEGKVLPAVAMLEERAKK

SEQ ID NO: 149
MQKQAELYRGKAKTVYSTENPDLLVLEFRNDTSAGDGARIEQFDRKGMVN
NKFNYFIMSKLAEAGIPTQMERLLSDTECLVKKLDMVPVECVVRNRAAGS
LVKRLGIEEGIELNPPLFDLFLKNDAMHDPMVNESYCETFGWVSKENLAR
MKELTYKANDVLKKLFDDAGLILVDFKLEFGLYKGEVVLGDEFSPDGSRL
WDKETLEKMDKDRFRQSLGGLIEAYEAVARRLGVQLD

SEQ ID NO: 150
MELVLKDAQSALTVSETTFGRDFNEALVHQVVVAYAAGARQGTRAQKTRA
EVTGSGKKPWRQKGTGRARSGSIKSPIWRSGGVTFAARPQDHSQKVNKKM
YRGALKSILSELVRQDRLIVVEKFSVEAPKTKLLAQKLKDMALEDVLIIT
GELDENLFLAARNLHKVDVRDATGIDPVSLIAFDKVVMTADAVKQVEEML
A

SEQ ID NO: 151
MTESFAQLFEESLKEIETRPGSIVRGVVVAIDKDVVLVDAGLKSESAIPA
EQFKNAQGELEIQVGDEVDVALDAVEDGFGETLLSREKAKRHEAWITLEK
AYEDAETVTGVINGKVKGGFTVELNGIRAFLPGSLVDVRPVRDTLHLEGK
ELEFKVIKLDQKRNNVVVSRRAVIESENSAERDQLLENLQEGMEVKGIVK
NLTDYGAFVDLGGVDGLLHITDMAWKRVKHPSEIVNVGDEITVKVLKFDR
ERTRVSLGLKQLGEDPWVAIAKRYPEGTKLTGRVTNLTDYGCFVEIEEGV
EGLVHVSEMDWTNKNIHPSKVVNVGDVVEVMVLDIDEERRRISLGLKQCK
ANPWQQFAETHNKGDRVEGKIKSITDFGIFIGLDGGIDGLVHLSDISWNV
AGEEAVREYKKGDEIAAVVLQVDAERERISLGVKQLAEDPFNNWVALNKK
GAIVTGKVTAVDAKGATVELADGVEGYLRASEASRDRVEDATLVLSVGDE
VEAKFTGVDRKNRAISLSVRAKDEADEKDAIATVNKQEDANFSNNAMAEA
FKAAKGE

SEQ ID NO: 152
MSKTIATENAPAAIGPYVQGVDLGNMIITSGQIPVNPKTGEVPADVAAQA
RQSLDNVKAIVEAAGLKVGDIVKTTVFVKDLNDFATVNATYEAFFTEHNA
TFPARSCVEVARLPKDVKIEIEAIAVRR said peptides being chosen, preferably, from the peptides having the sequence SEQ ID NO: 67 to 84 as defined hereinafter:

| Peptide SEQ ID NO: | Amino acid sequence | Location in SEQ ID NO: 138 |
|---|---|---|
| 67 | ISDIPEFVR | 41-49 |
| 68 | IEEDLLGTR | 7-15 |
| 69 | LVDAINQLR | 163-171 |

-continued

| Peptide SEQ ID NO: | Amino acid sequence | |
|---|---|---|
| | | Location in SEQ ID NO: 139 |
| 70 | TALAIDAIINQR | 176-187 |
| 71 | VVNTLGAPIDGK | 107-118 |
| | | Location in SEQ ID NO: 140 |
| 72 | SAGGIVLTGSAAAK | 21-34 |
| | | Location in SEQ ID NO: 141 |
| 73 | AVTAAVEELK | 123-132 |
| | | Location in SEQ ID NO: 142 |
| 74 | ALDAIIASVTESLK | 24-37 |
| | | Location in SEQ ID NO: 143 |
| 75 | YWDVELR | 172-178 |
| | | Location in SEQ ID NO: 144 |
| 76 | LPGILELSR | 327-335 |

HPETLVKVKDAEDKLGARVGYIELDLNSGKILESFRPEERFPMMSTFKVL
LCGAVLSRVDAGQEQLGRRIHYSQNDLVEYSPVTEKHLTDGMTVRELCSA
AITMSDNTAANLLLTTIGGPKELTAFLHNMGDHVTRLDRWEPELNEAIPN
DERDTTMPAAMATTLRKLLTGELLTLASRQQLIDWMEADKVAGPLLRSAL
PAGWFIADKSGVGERGSRGIIAALGPDGKPSRIVVIYTTGSQATMDERNR
QIAEIGASLIKHW

-continued

| Peptide SEQ ID NO: | Amino acid sequence | |
|---|---|---|
| | | Location in SEQ ID NO: 145 |
| 77 | SKATNLLYTR | 9-18 |
| | | Location in SEQ ID NO: 146 |
| 78 | SEALKILNNIR | 2-12 |
| | | Location in SEQ ID NO: 147 |
| 79 | LFGVTTLDIIR | 145-155 |
| | | Location in SEQ ID NO: 148 |
| 80 | ASLPTIELALK | 39-49 |

-continued

| Peptide SEQ ID NO: | Amino acid sequence | |
|---|---|---|
| | | Location in SEQ ID NO: 149 |
| 81 | LLSDTECLVK | 73-82 |
| | | Location in SEQ ID NO: 150 |
| 82 | SILSELVR | 107-114 |
| | | Location in SEQ ID NO: 151 |
| 83 | GGFTVELNGIR | 118-128 |
| | | Location in SEQ ID NO: 152 |
| 84 | TGEVPADVAAQAR | 39-51 |

2. For the potential resistance to at least one antibiotic
at least one peptide belonging to the TEM-2 beta-lactamase protein (TEM-2) having the following sequence SEQ ID NO: 126:

said peptides being chosen, preferably, from the peptides having the sequence SEQ ID NO: 62 to 66 as defined hereinafter:

| Peptide SEQ ID NO: | Amino acid sequence | Location in SEQ ID NO: 126 |
|---|---|---|
| 62 | LLTGELLTLASR | 168-179 |
| 63 | SALPAGWFIADK | 198-209 |
| 64 | VAGPLLR | 191-197 |
| 65 | VGYIELDLNSGK | 19-30 |
| 66 | VLLCGAVLSR | 49-58 |

3. For the virulence:
at least one peptide belonging to the Shiga toxin 1 subunit A protein (STX1A), the Shiga toxin 2 subunit A protein (STX2A) or to both, having the sequences SEQ ID NO: 153 and 154, respectively:

```
                             SEQ ID NO: 153
MKIIIFRVLTFFFVIFSVNVVAKEFTLDFSTAKTYVDSLNVIRSAIGTPL

QTISSGGTSLLMIDSGTGDNLFAVDVRGIDPEEGRFNNLRLIVERNNLYV

TGFVNRTNNVFYRFADFSHVTFPGTTAVTLSGDSSYTTLQRVAGISRTGM

QINRHSLTTSYLDLMSHSGTSLTQSVARAMLRFVTVTAEALRFRQIQRGF

RTTLDDLSGRSYVMTAEDVDLTLNWGRLSSVLPDYHGQDSVRVGRISFGS

INAILGSVALILNCHHHASRVARMASDEFPSMCPADGRVRGITHNKILWD

SSTLGAILMRRTISS

SEQ ID NO: 154
MKCILFKWVLCLLLGFSSVSHSREFTIDFSTQQSYVSSLNSIRTEISTPL

EHISQGTTSVSVINHTPPGSYFAVDIRGLDVYQARFDHLRLIIEQNNLYV

AGFVNTATNTFYRFSDFTHISVPGVTTVSMTTDSSYTTLQRVAALERSGM

QISRHSLVSSYLALVEFSGNTMTRDASRAVLRFVTVTAEALRFRQIQREF

RQALSETAPVYTMTPGDVDLTLNWGRISNVLPEYRGEDGVRVGRISFNNI

SAILGTVAVILNCHHQGARSVRAVNEDSQPECQITGDRPVIKINNTLWES

NTAAAFLNRKSQFLYTTGK
``` said peptides being chosen, preferably, from the peptides having the sequences SEQ ID NO: 85, 86 and 87 as defined hereinafter:

| Peptide SEQ ID NO: | Amino acid sequence | |
|---|---|---|
| | | Location in SEQ ID NO: 153 |
| 85 | TYVDSLNVIR | 34-43 |
| 86 | FVTVTAEALR | 183-192 |
| | | Location in SEQ ID NO: 154 |
| 86 | FVTVTAEALR | 183-192 |
| 87 | ISNVLPEYR | 227-235 |

4. For the identification:
   at least one peptide belonging to aconitate hydratase 2 (ACON2), L-asparaginase 2 (ASPG2), 3-oxoacyl-[acyl-carrier-protein] synthase 1 (FABB), glutamine-binding periplasmic protein (GLNH), molybdate-binding periplasmic protein (MODA), dihydrolipoyllysine-residue acetyltransferase component of pyruvate dehydrogenase complex (ODP2), outer membrane protein C (OMPC), formate acetyltransferase 1 (PFLB), succinyl-CoA ligase [ADP-forming] subunit alpha (SUCD), transketolase 1 (TKT1), UPF0381 protein yfcZ (YFCZ), uncharacterized protein ygaU (YGAU), having the following sequences SEQ ID NO: 127 to 135, 176, 136 and 137, respectively:

```
                             SEQ ID NO: 127
MLEEYRKHVAERAAEGIAPKPLDANQMAALVELLKNPPAGEEEFLLDLLT

NRVPPGVDEAAYVKAGFLAAIAKGEAKSPLLTPEKAIELLGTMQGGYNIH

PLIDALDDAKLAPIAAKALSHTLLMFDNFYDVEEKAKAGNEYAKQVMQSW

ADAEWFLNRPALAEKLTVTVFKVTGETNTDDLSPAPDAWSRPDIPLHALA

MLKNAREGIEPDQPGVVGPIKQIEALQQKGFPLAYVGDVVGTGSSRKSAT

NSVLWFMGDDIPHVPNKRGGGLCLGGKIAPIFFNTMEDAGALPIEVDVSN

LNMGDVIDVYPYKGEVRNHETGELLATFELKTDVLIDEVRAGGRIPLIIG

RGLTTKAREALGLPHSDVFRQAKDVAESDRGFSLAQKMVGRACGVKGIRP

GAYCEPKMTSVGSQDTTGPMTRDELKDLACLGFSADLVMQSFCHTAAYPK

PVDVNTHHTLPDFIMNRGGVSLRPGDGVIHSWLNRMLLPDTVGTGGDSHT

RFPIGISFPAGSGLVAFAAATGVMPLDMPESVLVRFKGKMQPGITLRDLV

HAIPLYAIKQGLLTVEKKGKKNIFSGRILEIEGLPDLKVEQAFELTDASA

ERSAAGCTIKLNKEPIIEYLNSNIVLLKWMIAEGYGDRRTLERRIQGMEK

WLANPELLEADADAEYAAVIDIDLADIKEPILCAPNDPDDARPLSAVQGE

KIDEVFIGSCMTNIGHFRAAGKLLDAHKGQLPTRLWVAPPTRMDAAQLTE

EGYYSVFGKSGARIEIPGCSLCMGNQARVADGATVVSTSTRNFPNRLGTG

ANVFLASAELAAVAALIGKLPTPEEYQTYVAQVDKTAVDTYRYLNFNQLS

QYTEKADGVIFQTAV

SEQ ID NO: 128
MEFFKKTALAALVMGFSGAALALPNITILATGGTIAGGGDSATKSNYTVG

KVGVENLVNAVPQLKDIANVKGEQVVNIGSQDMNDNVWLTLAKKINTDCD

KTDGFVITHGTDTMEETAYFLDLTVKCDKPVVMVGAMRPSTSMSADGPFN

LYNAVVTAADKASANRGVLVVMNDTVLDGRDVTKTNTTDVATFKSVNYGP

LGYIHNGKIDYQRTPARKHTSDTPFDVSKLNELPKVGIVYNYANASDLPA

KALVDAGYDGIVSAGVGNGNLYKSVFDTLATAAKTGTAVVRSSRVPTGAT

TQDAEVDDAKYGFVASGTLNPQKARVLLQLALTQTKDPQQIQQIFNQY

SEQ ID NO: 129
MKRAVITGLGIVSSIGNNQQEVLASLREGRSGITFSQELKDSGMRSHVWG

NVKLDTTGLIDRKVVRFMSDASIYAFLSMEQAIADAGLSPEAYQNNPRVG

LIAGSGGGSPRFQVFGADAMRGPRGLKAVGPYVVTKAMASGVSACLATPF

KIHGVNYSISSACATSAHCIGNAVEQIQLGKQDIVFAGGGEELCWEMACE

FDAMGALSTKYNDTPEKASRTYDAHRDGFVIAGGGGMVVVEELEHALARG

AHIYAEIVGYGATSDGADMVAPSGEGAVRCMKMAMHGVDTPIDYLNSHGT

STPVGDVKELAAIREVFGDKSPAISATKAMTGHSLGAAGVQEAIYSLLML

EHGFIAPSINIEELDEQAAGLNIVTETTDRELTTVMSNSFGFGGTNATLV

MRKLKD

SEQ ID NO: 130
MKSVLKVSLAALTLAFAVSSHAADKKLVVATDTAFVPFEFKQGDKYVGFD

VDLWAAIAKELKLDYELKPMDFSGIIPALQTKNVDLALAGITITDERKKA

IDFSDGYYKSGLLVMVKANNNDVKSVKDLDGKVVAVKSGTGSVDYAKANI

KTKDLRQFPNIDNAYMELGTNRADAVLHDTPNILYFIKTAGNGQFKAVGD

SLEAQQYGIAFPKGSDELRDKVNGALKTLRENGTYNEIYKKWFGTEPK

SEQ ID NO: 131
MARKWLNLFAGAALSFAVAGNALADEGKITVFAAASLTNAMQDIATQFKK

EKGVDVVSSFASSSTLARQIEAGAPADLFISADQKWMDYAVDKKAIDTAT
```

```
RQTLLGNSLVVVAPKASVQKDFTIDSKTNWTSLLNGGRLAVGDPEHVPAG
IYAKEALQKLGAWDTLSPKLAPAEDVRGALALVERNEAPLGIVYGSDAVA
SKGVKVVATFPEDSHKKVEYPVAVVEGHNNATVKAFYDYLKGPQAAEIFK
RYGFTIK

SEQ ID NO: 132
MAIEIKVPDIGADEVEITEILVKVGDKVEAEQSLITVEGDKASMEVPSPQ
AGIVKEIKVSVGDKTQTGALIMIFDSADGAADAAPAQAEEKKEAAPAAAP
AAAAAKDVNVPDIGSDEVEVTEILVKVGDKVEAEQSLITVEGDKASMEVP
APFAGTVKEIKVNVGDKVSTGSLIMVFEVAGEAGAAAPAAKQEAAPAAAP
APAAGVKEVNVPDIGGDEVEVTEVMVKVGDKVAAEQSLITVEGDKASMEV
PAPFAGVVKELKVNVGDKVKTGSLIMIFEVEGAAPAAAPAKQEAAAPAPA
AKAEAPAAAPAAKAEGKSEFAENDAYVHATPLIRRLAREFGVNLAKVKGT
GRKGRILREDVQAYVKEAIKRAEAAPAATGGGIPGMLPWPKVDFSKFGEI
EEVELGRIQKISGANLSRNWVMIPHVTHFDKTDITELEAFRKQQNEEAAK
RKLDVKITPVVFIMKAVAAALEQMPRFNSSLSEDGQRLTLKKYINIGVAV
DTPNGLVVPVFKDVNKKGIIELSRELMTISKKARDGKLTAGEMQGGCFTI
SSIGGLGTTHFAPIVNAPEVAILGVSKSAMEPVWNGKEFVPRLMLPISLS
FDHRVIDGADGARFITIINNTLSDIRRLVM

SEQ ID NO: 133
MKVKVLSLLVPALLVAGAANAAEVYNKDGNKLDLYGKVDGLHYFSDDKSV
DGDQTYMRLGFKGETQVTDQLTGYGQWEYQIQGNSAENENNSWTRVAFAG
LKFQDVGSFDYGRNYGVVYDVTSWTDVLPEFGGDTYGSDNFMQQRGNGFA
TYRNTDFFGLVDGLNFAVQYQGKNGSVSGEGMTNNGREALRQNGDGVGGS
ITYDYEGFGIGAAVSSSKRTDDQNSPLYIGNGDRAETYTGGLKYDANNIY
LAAQYTQTYNATRVGSLGWANKAQNFEAVAQYQFDFGLRPSLAYLQSKGK
NLGVINGRNYDDEDILKYVDVGATYYFNKNMSTYVDYKINLLDDNQFTRD
AGINTDNIVALGLVYQF

SEQ ID NO: 134
MSELNEKLATAWEGFTKGDWQNEVNVRDFIQKNYTPYEGDESFLAGATEA
TTTLWDKVMEGVKLENRTHAPVDFDTAVASTITSHDAGYINKQLEKIVGL
QTEAPLKRALIPFGGIKMIEGSCKAYNRELDPMIKKIFTEYRKTHNQGVF
DVYTPDILRCRKSGVLTGLPDAYGRGRIIGDYRRVALYGIDYLMKDKLAQ
FTSLQADLENGVNLEQTIRLREEIAEQHRALGQMKEMAAKYGYDISGPAT
NAQEAIQWTYFGYLAAVKSQNGAAMSFGRTSTFLDVYIERDLKAGKITEQ
EAQEMVDHLVMKLRMVRFLRTPEYDELFSGDPIWATESIGGMGLDGRTLV
TKNSFRFLNTLYTMGPSPEPNMTILWSEKLPLNFKKFAAKVSIDTSSLQY
ENDDLMRPDFNNDDYAIACCVSPMIVGKQMQFFGARANLAKTMLYAINGG
VDEKLKMQVGPKSEPIKGDVLNYDEVMERMDHFMDWLAKQYITALNIIHY
MHDKYSYEASLMALHDRDVIRTMACGIAGLSVAADSLSAIKYAKVKPIRD
EDGLAIDFEIEGEYPQFGNNDPRVDDLAVDLVERFMKKIQKLHTYRDAIP
TQSVLTITSNVVYGKKTGNTPDGRRAGAPFGPGANPMHGRDQKGAVASLT
SVAKLPFAYAKDGISYTFSIVPNALGKDDEVRKTNLAGLMDGYFHHEASI
```

```
EGGQHLNVNVMNREMLLDAMENPEKYPQLTIRVSGYAVRFNSLTKEQQQD
VITRTFTQSM

SEQ ID NO: 135
MSILIDKNTKVICQGFTGSQGTFHSEQAIAYGTKMVGGVTPGKGGTTHLG
LPVFNTVREAVAATGATASVIYVPAPFCKDSILEAIDAGIKLIITITEGI
PTLDMLTVKVKLDEAGVRMIGPNCPGVITPGECKIGIQPGHIHKPGKVGI
VSRSGTLTYEAVKQTTDYGFGQSTCVGIGGDPIPGSNFIDILEMFEKDPQ
TEAIVMIGEIGGSAEEEAAAYIKEHVTKPVVGYIAGVTAPKGKRMGHAGA
IIAGGKGTADEKFAALEAAGVKTVRSLADIGEALKTVLK

SEQ ID NO: 176
MSSRKELANAIRALSMDAVQKAKSGHPGAPMGMADIAEVLWRDFLKHNPQ
NPSWADRDRFVLSNGHGSMLIYSLLHLTGYDLPMEELKNFRQLHSKTPGH
PEVGYTAGVETTTGPLGQGIANAVGMAIAEKTLAAQFNRPGHDIVDHYTY
AFMGDGCMMEGISHEVCSLAGTLKLGKLIAFYDDNGISIDGHVEGWFTDD
TAMRFEAYGWHVIRDIDGHDAASIKRAVEEARAVTDKPSLLMCKTIIGFG
SPNKAGTHDSHGAPLGDAEIALTREQLGWKYAPFEIPSEIYAQWDAKEAG
QAKESAWNEKFAAYAKAYPQEAAEFTRRMKGEMPSDFDAKAKEFIAKLQA
NPAKIASRKASQNAIEAFGPLLPEFLGGSADLAPSNLTLWSGSKAINEDA
AGNYIHYGVREFGMTAIANGISLHGGFLPYTSTFLMFVEYARNAVRMAAL
MKQRQVMVYTHDSIGLGEDGPTHQPVEQVASLRVTPNMSTWRPCDQVESA
VAWKYGVERQDGPTALILSRQNLAQQERTEEQLANIARGGYVLKDCAGQP
ELIFIATGSEVELAVAAYEKLTAEGVKARVVSMPSTDAFDKQDAAYRESV
LPKAVTARVAVEAGIADYWYKYVGLNGAIVGMTTFGESAPAELLFEEFGF
TVDNVVAKAKELL

SEQ ID NO: 136
MSKCSADETPVCCCMDVGTIMDNSDCTASYSRVFANRAEAEQTLAALTEK
ARSVESEPCKITPTFTEESDGVRLDIDFTFACEAEMLIFQLGLR

SEQ ID NO: 137
MGLFNFVKDAGEKLWDAVTGQHDKDDQAKKVQEHLNKTGIPDADKVNIQI
ADGKATVTGDGLSQEAKEKILVAVGNISGIASVDDQVKTATPATASQFYT
VKSGDTLSAISKQVYGNANLYNKIFEANKPMLKSPDKIYPGQVLRIPEE
``` said peptides being chosen, preferably, from the peptides having the sequence SEQ ID 46 to 61 as defined hereinafter:

| Peptide SEQ ID NO: | Amino acid sequence | Location in SEQ ID NO: 127 |
|---|---|---|
| 46 | ILEIEGLPDLK | 578-588 |
| 47 | VADGATVVSTSTR | 779-791 |
|  |  | Location in SEQ ID NO: 128 |
| 48 | TNTTDVATFK | 185-194 |

| Peptide SEQ ID NO: | Amino acid sequence | |
|---|---|---|
| | | Location in SEQ ID NO: 129 |
| 49 | LDTTGLIDR | 54-62 |
| 50 | VGLIAGSGGGSPR | 99-111 |
| | | Location in SEQ ID NO: 130 |
| 51 | AIDFSDGYYK | 100-109 |
| | | Location in SEQ ID NO: 131 |
| 52 | LGAWDTLSPK | 160-169 |
| | | Location in SEQ ID NO: 132 |
| 53 | FGEIEEVELGR | 397-407 |
| | | Location in SEQ ID NO: 133 |
| 54 | INLLDDNQFTR | 339-349 |
| | | Location in SEQ ID NO: 134 |
| 55 | LATAWEGFTK | 8-17 |
| | | Location in SEQ ID NO: 135 |
| 56 | DSILEAIDAGIK | 80-91 |
| 57 | FAALEAAGVK | 263-272 |
| 58 | SLADIGEALK | 276-285 |
| | | Location in SEQ ID NO: 176 |
| 59 | TEEQLANIAR | 529-538 |
| | | Location in SEQ ID NO: 136 |
| 60 | AEAEQTLAALTEK | 38-50 |
| | | Location in SEQ ID NO: 137 |
| 61 | SGDTLSAISK | 103-112 |

It should be noted, as previously indicated, that, for the typing, the method of the invention may also use at least one peptide having the sequence SEQ ID NO: 46 to 66 and 85 to 87, which are of use for determining the potential resistance to at least one antibiotic, the identification or the virulence, as previously indicated.

According to another preferred embodiment, the method of the invention allows the characterization of *Candida albicans*.

In particular, the characterization of *Candida albicans* uses at least one peptide as follows:
1. for the typing:
   at least one peptide belonging to the alcohol dehydrogenase 1 protein (ADH1), the fructose-biphosphate aldolase protein (ALF), the lanosterol 14-alpha demethylase protein (CP51), F-box protein COS111 (CS111), elongation factor 1-beta (EF1B), enolase 1 (ENO1), glyceraldehyde-3-phosphate dehydrogenase (G3P), heat shock protein SSA1 (HSP71), heat shock protein SSB1 (HSP75), pyruvate kinase (KPYK), lipase 8 (LIPS), multiprotein-bridging factor 1 (MBF1), nuclear transport factor 2 (NTF2), phosphoglycerate kinase (PGK), peptidyl-prolyl cis-trans isomerase (PPIA), 60S ribosomal protein L13 (RL13), 60S ribosomal protein L28 (RL28), 60S ribosomal protein L36 (RL36), 40S ribosomal protein S22 (RS22), triosephosphate isomerase (TPIS), having the following sequences SEQ ID NO: 155 to 175, respectively:

SEQ ID NO: 155
MSEQIPKTQKAVVFDTNGGQLVYKDYPVPTPKPNELLIHVKYSGVCHTDL

HARKGDWPLATKLPLVGGHEGAGVVVGMGENVKGWKIGDFAGIKWLNGSC

MSCEFCQQGAEPNCGEADLSGYTHDGSFEQYATADAVQAAKIPAGTDLAN

VAPILCAGVTVYKALKTADLAAGQWVAISGAGGGLGSLAVQYARAMGLRV

VAIDGGDEKGEFVKSLGAEAYVDFTKDKDIVEAVKKATDGGPHGAINVSV

SEKAIDQSVEYVRPLGKVVLVGLPAHAKVTAPVFDAVVKSIEIKGSYVGN

RKDTAEAIDFFSRGLIKCPIKIVGLSDLPEVFKLMEEGKILGRYVLDTSK

SEQ ID NO: 156
MAPPAVLSKSGVIYGKDVKDLFDYAQEKGFAIPAINVTSSSTVVAALEAA

RDNKAPIILQTSQGGAAYFAGKGVDNKDQAASIAGSIAAAHYIRAIAPTY

GIPVVLHTDHCAKKLLPWFDGMLKADEEFFAKTGTPLFSSHMLDLSEETD

DENIATCAKYFERMAKMGQWLEMEIGITGGEEDGVNNEHVEKDALYTSPE

TVFAVYESLHKISPNFSIAAAFGNVHGVYKPGNVQLRPEILGDHQVYAKK

QIGTDAKHPLYLVFHGGSGSTQEEFNTAIKNGVVKVNLDTDCQYAYLTGI

RDYVTNKIEYLKAPVGNPEGADKPNKKYFDPRVWVREGEKTMSKRIAEAL

DIFHTKGQL

SEQ ID NO: 157
MAIVETVIDGINYFLSLSVTQQISILLGVPFVYNLVWQYLYSLRKDRAPL

VFYWIPWFGSAASYGQQPYEFFESCRQKYGDVFSFMLLGKIMTVYLGPKG

HEFVFNAKLSDVSAEDAYKHLTTPVFGKGVIYDCPNSRLMEQKKFAKFAL

TTDSFKRYVPKIREEILNYFVTDESFKLKEKTHGVANVMKTQPEITIFTA

SRSLFGDEMRRIFDRSFAQLYSDLDKGFTPINFVFPNLPLPHYWRRDAAQ

KKISATYMKEIKSRRERGDIDPNRDLIDSLLIHSTYKDGVKMTDQEIANL

LIGILMGGQHTSASTSAWFLLHLGEKPHLQDVIYQEVVELLKEKGGDLND

LTYEDLQKLPSVNNTIKETLRMHMPLHSIFRKVTNPLRIPETNYIVPKGH

YVLVSPGYAHTSERYFDNPEDFDPTRWDTAAAKANSVSFNSSDEVDYGFG

KVSKGVSSPYLPFGGGRHRCIGEQFAYVQLGTILTTFVYNLRWTIDGYKV

PDPDYSSMVVLPTEPAEIIWEKRETCMF

SEQ ID NO: 158
MLKTDSLDFHSYLPPYRSLINPNARYDYRTHSLIPLTQNDLNLLRIAFQK

KKEAPPSAFKMKYKSLLSDVSRTISMRLSNSNLLSSSSANNNNVLLSPPP

SSSSTLSTPCGNILNRAGTTSSNISKINNLSQNQTQNQLPLFPAELHIKN

LPVEILDYIFYLVDDNLDYKSCMYTCKLFYFLAKPYYYENLVFTSTYRFA

QFVTYLRVNSEVGQYVQSIDLSGIKPGYDEDEQEEGQEENAENGEEENGG

-continued

GARDPQYLLGEIADNPHHERVDQFPRGKILAGWRDWKFKNNPLYTIHPSP
SLTKIASNSQFSNVSSKSSRSTSSKSSSSTTKKFVKPFRYFKSRKRKMSY
SGTTKLERKSPRLEQLQLDQYSSNWNKRVNSHPLINKFLLHYSTSKDLPI
GYILHMINLCPNIVSLNLGNLSLSTDYEISRSTIHKYQNFDLINNYPKDL
IYKVDNIMRLNDVDDVYSIDGSILRFGNINSGSSGSNWERNGSSSNNRIL
FKSNQSIASTASSVYSVTTFSKPIRKYNSLLPPLPQTVADISYLNKGDGK
VYLSDLNLKEINSAYLKKINEDEILSAIINVHGKRLIEYDTSLYQIPKPL
NVDIAGTLKYINLSSMIWLNRKLIEKFLTRLLTKKSPELDMYGICYTDEF
FDSDEQESDDDYEDSDDEEQRQCPIIYKQNLVIDFTDSGMYKSLPWAKRI
DLNSFEGCQLANKIINNDLMTPQEQALRRERRRRGAIAANYLA

SEQ ID NO: 159
MSFSDFSKVESIKSLNEFLADKSYIDGTTATQADVTVYKAFQKEFPQFTR
WFNHIASFTEEFEDLPAGKAPAASGSAAAAAEEEDDEDVDLFGSDDEVDE
EAEKLKQQRLAEYAAKKAAKGPKPAAKSIVTLDVKPWDDETDLDELLTNV
KAIEMEGLTWGAHQWIPVGFGIKKLQINLVVEDALVSLDDLQAAVEEDED
HVQSTDIAAMQKL

SEQ ID NO: 160
MSYATKIHARYVYDSRGNPTVEVDFTTDKGLFRSIVPSGASTGVHEALEL
RDGDKSKWLGKGVLKAVANVNDIIAPALIKAKIDVVDQAKIDEFLLSLDG
TPNKSKLGANAILGVSLAAANAAAAAQGIPLYKHIANISNAKKGKFVLPV
PFQNVLNGGSHAGGALAFQEFMIAPTGVSTFSEALRIGSEVYHNLKSLTK
KKYGQSAGNVGDEGGVAPDIKTPKEALDLIMDAIDKAGYKGKVGIAMDVA
SSEFYKDGKYDLDFKNPESDPSKWLSGPQLADLYEQLISEYPIVSIEDPF
AEDDWDAWVHFFERVGDKIQIVGDDLTVTNPTRIKTAIEKKAANALLLKV
NQIGTLTESIQAANDSYAAGWGVMVSHRSGETEDTFIADLSVGLRSGQIK
TGAPARSERLAKLNQILRIEEELGSEAIYAGKDFQKASQL

SEQ ID NO: 161
MAIKIGINGFGRIGRLVLRVALGRKDIEVVAVNDPFIAPDYAAYMFKYDS
THGRYKGEVTASGDDLVIDGHKIKVFQERDPANIPWGKSGVDYVIESTGV
FTKVEGAQKHIDAGAKKVIITAPSADAPMFVVGVNEDKYTPDLKIISNAS
CTTNCLAPLAKVVNDTFGIEEGLMTTVHSITATQKTVDGPSHKDWRGGRT
ASGNIIPSSTGAAKAVGKVIPELNGKLTGMSLRLPTTDVSVVDLTVRLKK
AASYEEIAPAIKKASEGPLKGVLGYTEDAVVSTDFLGSSYSSIFDEKAGI
LLSPTFVKLISWYDNEYGYSTKVVDLLEHVA

SEQ ID NO: 162
MSKAVGIDLGTTYSCVAHFANDRVEIIANDQGNRTTPSFVAFTDTERLIG
DAAKNQAAMNPANTVFDAKRLIGRKFDDPEVINDAKHFPPFKVIDKAGKPV
IQVEYKGETKTFSPEEISSMVLTKMKEIAEGYLGSTVKDAVVTPAYFND
SQRQATKDAGTIAGLNVLRIINEPTAAAIAYGLDKKGSRGEHNVLIFDLG
GGTFDVSLLAIDEGIFEVKATAGDTHLGGEDFDNRLVNFFIQEFKRKNKK
DISTNQRALRRLRTACERAKRTLSSSAQTSIEIDSLYEGIDFYTSITRAR
FEELCADLFRSTLDPVGKVLADAKIDKSQVEEIVLVGGSTRIPKIQKLVS

DFFNGKELNKSINPDEAVAYGAAVQAAILTGDTSSKTQDILLLDVAPLSL
GIETAGGIMTKLIPRNSTIPTKKSETFSTYADNQPGVLIQVFEGERAKTK
DNNLLGKFELSGIPPAPRGVPQIEVTFDIDANGILNVSALEKGTGKTQKI
TITNDKGRLSKEEIDKMVSEAEKFKEEDEKEAARVQAKNQLESYAYSLKN
TINDGEMKDKIGADDKEKLTKAIDETISWLDASQAASTEEYEDKRKELES
VANPIISGAYGAAGGAPGGAGGFPGAGGFPGGAPGAGGPGGATGGESSGP
TVEEVD

SEQ ID NO: 163
MADGVFQGAIGIDLGTTYSCVATYDSAVEIIANEQGNRVTPSFVAFTSEE
RLIGDAAKNQAALNPKNTVFDAKRLIGRAFDDESVQKDIKSWPFKVVESN
GQPLIEVEYLDETKTFSPQEISSMVLTKMKEIAEAKIGKKVEKAVVTVPA
YFNDAQRQATKDAGAIAGLNVLRIINEPTAAAIAYGLGAGKSEKERHVLI
FDLGGGTFDVSLLNITGGVFTVKATAGDTHLGGQDFDTNLLEHFKKEFQK
KTGNDISSDARALRRLRTACERAKRSLSSGTQTTVEIDSLFDGEDFSANI
TRARFEDINSALFKSTLEPVEQVLEDAKISKSQVDEVVLVGGSTRIPKVQ
KLLSDFFDGKQLEKSINPDEAVAYGAAVQGAILTGQSTNDDTKDLLLLDV
IPLSLGVAMQGNVLAPVVPRNTTVPTIKRRTFTTVADHQTTVQFPVYQGE
RVNCSENTLLGEFDLKNIPPMQAGEPVLEAIFEVDANGILKVTAVEKSTG
RSANITISNSIGRLSTEEIEKMISDAEKFKSSDDAFAKRHEQKQKLEAYV
ASVESTVTDPVLSAKLKKSAKDKIEAALSDALQTLEIEESSADDYRKAEL
ALKRAVTKGMATR

SEQ ID NO: 164
FTIPPNHEMIFTTDDAYKTKCDDKVMIIDYKNITKVIAPGKIIYVDDGVL
SFEVISVDDQQTLKVRSLNAGMISSHKTANDVLELRVLSTSG

SEQ ID NO: 165
MLFLLFLLITPIYAGLIFPTKPSSDPFYNPPKGFEKAAVGDILQSRETPK
SITGRFAPLKIQNSWQLLVRSEDSFGNPNAIVTTVIEPVNADPSKIASYQ
VFEDAAKADCAPSYALQFGSDLTTFVTQAEMYLMAPLLDQGYYVVSPDYE
GPKSTFTIGKQSGQAVLNSIRATLKSSKITNIKEDAKVVMWGYSGGSLAS
GWAAALQPSYAPELSSSLLGAALGGFVTNITATAQAADGTVFAGIVANAL
GGVANEYPEFKSILQSDTDKKSVFDEFDSHCLADGVIDYINTSFLTGDNK
IFKTGWDILKSPTIAKIVEDNGLVYQKQLVPKIPIFVYHGSIDQIVPIVN
VKKTYQNWCEGGISSLEFAEDGTNGHLTETVVGAPAALTWIIDRFNGKQT
VSGCQHDKRLSNFQYPNISSSILKYFKVALDTMMSNGLGSDIQKDKITPD
DLRKFLLGGW

SEQ ID NO: 166
MSSDWDSVTIIGQKARVGGGGPRENVAKTSSQLNAARRAGLVVGTEKKYG
TANTKSNPEGQRLTKLDATDDVVAVKKVDVSVGKAIQQARQEKKLTQKEL
ATKVNEKPNVINDYEAGRAIPNQQLLAKLERALGVKLRGKNIGEPLFAKK
K

-continued

SEQ ID NO: 167
MSVDFNAVATEFCNFYYNQFDSDRSQLGNLYRNESMLTFETSQLQGARDI
VEKLASLPFQKVAHRISTLDAQPASANGDILVMVTGELLIDEEQNAQRYS
QVFHLIPDNGSYYVFNDIFRLNYS

SEQ ID NO: 168
MSLSNKLSVKDLDVAGKRVFIRVDFNVPLDGKTITNNQRIVAALPTIKYV
EEHKPKYIVLASHLGRPNGERNDKYSLAPVATELEKLLGQKVTFLNDCVG
PEVTKAVENAKDGEIFLLENLRYHIEEEGSSKDKDGKKVKADPEAVKKFR
QELTSLADVYINDAFGTAHRAHSSMVGLEVPQRAAGFLMSKELEYFAKAL
ENPERPFLAILGGAKVSDKIQLIDNLLDKVDMLIVGGGMAFTFKKILNKM
PIGDSLFDEAGAKNVEHLVEKAKKNNVELILPVDFVTADKFDKDAKTSSA
TDAEGIPDNWMGLDCGPKSVELFQQAVAKAKTIVWNGPPGVFEFEKFANG
TKSLLDAAVKSAENGNIVIIGGGDTATVAKKYGVVEKLSHVSTGGGASLE
LLEGKDLPGVVALSNKN

SEQ ID NO: 169
MSTVYFDVSADGQKLGKITFKLYDDVVPKTAENFRALCTGEKGFGYKGSI
FHRVIPQFMLQGGDFTNFNGTGGKSIYGTKFADENFVKRHDRPGLLSMAN
AGPNTNGSQFFITTVPCPWLDGKHVVFGEVTDGLDIVKKIESFGSGSGAT
SKKIVIEESGQL

SEQ ID NO: 170
MAISKNLPLLNNHFRKHWQERVRVHFDQAGKKASRRQSRLRKAAKIAPRP
IDALRPVVRAPTVKYNRKVRAGRGFTLAELKAVGIAPKYARTIGISVDHR
RQNKSQETFDANVARLQEYKSKLVIFDKKTKASEVASFEQVDVSATFPVE
QPAPESGLRAVEVPEQTAYRTLRLARNEKKYKGIREKRAKEKAEAEAEKA
KK

SEQ ID NO: 171
EKKDEYLSKSSASAAPVIDTLAHGYGKVLGKGRLPEVPVIVKARFVSKLA
EEKSESLVVLSN

SEQ ID NO: 172
MAKSGIAAGVNKGRKTTAKEVAPKISYRKGASSQRTVFVRSIVKEVAGLA
PYERRLIELIRNAGEKRAKKLAKKRLGTHKRALRKVEEMTQVIAESRRH

SEQ ID NO: 173
MKYLAAYLLLVQGGNTSPSASDITALLESVGVEAEESRLQALLKDLEGKD
LQELIAEGNTKLASVPSGGAAAGGASASTGAAAGGAAEAEEEKEEEAKEE
SDDDMGFGLFD

SEQ ID NO: 174
MTRTSVLADALNAINNAEKTGKRQVLIRPSSKVIIKFLTVMQKHGYIGEF
EYIDDHRSGKIVVQLNGRLNKCGVIQPRFNVKINDIERWTDNLLPARQFG
YVILTTSAGIMDHEEARRKHVSGKILGFVY

SEQ ID NO: 175
MARQFFVGGNFKANGTKQQITSIIDNLNKADLPKDVEVVICPPALYLGLA
VEQNKQPTVAIGAQNVFDKSCGAFTGETCASQILDVGASWTLTGHSERRT
IIKESDEFIAEKTKFALDTGVKVILCIGETLEERKGGVTLDVCARQLDAV
SKIVSDWSNIVVAYEPVWAIGTGLAATPEDAEETHKGIRAHLAKSIGAEQ
AEKTRILYGGSVNGKNAKDFKDKANVDGFLVGGASLKPEFVDIIKSRL said peptides being chosen from the peptides having the sequence SEQ ID NO: 88 to 125 as defined hereinafter:

| Peptide SEQ ID NO: | Amino acid sequence | Location in SEQ ID NO: 156 |
|---|---|---|
| 88 | ADEEFFAK | 125-132 |
| 97 | IAEALDIFHTK | 346-356 |
| | | Location in SEQ ID NO: 163 |
| 89 | AFDDESVQK | 79-87 |
| | | Location in SEQ ID NO: 160 |
| 90 | AKIDVVDQAK | 81-90 |
| 98 | IDVVDQAK | 83-90 |
| 99 | IEEELGSEAIYAGKDFQK | 419-436 |
| 112 | VGDKIQIVGDDLTVTNPTR | 315-333 |
| | | Location in SEQ ID NO: 170 |
| 91 | AVEVPEQTAYR | 160-170 |
| 107 | SQETFDANVAR | 105-115 |
| | | Location in SEQ ID NO: 174 |
| 92 | CGVIQPR | 72-78 |
| 114 | WTDNLLPAR | 89-97 |
| | | Location in SEQ ID NO: 173 |
| 93 | DLQELIAEGNTK | 50-61 |
| | | Location in SEQ ID NO: 169 |
| 94 | FADENFVKR | 81-89 |
| 100 | IESFGSGSGATSK | 140-152 |
| | | Location in SEQ ID NO: 175 |
| 95 | FALDTGVK | 115-122 |
| | | Location in SEQ ID NO: 171 |
| 96 | GRLPEVPVIVK | 32-42 |
| | | Location in SEQ ID NO: 167 |
| 101 | LASLPFQK | 54-61 |
| | | Location in SEQ ID NO: 166 |
| 102 | LDATDDVVAVK | 66-76 |

-continued

| Peptide SEQ ID NO: | Amino acid sequence |  |
|---|---|---|
|  | | Location in SEQ ID NO: 168 |
| 103 | NVEHLVEK | 264-271 |
| 110 | SVELFQQAVAK | 319-329 |
|  | | Location in SEQ ID NO: 172 |
| 104 | SGIAAGVNK | 4-12 |
|  | | Location in SEQ ID NO: 161 |
| 105 | SGVDYVIESTGVFTK | 89-103 |
| 115 | YKGEVTASGDDLVIDGHK | 55-72 |
|  | | Location in SEQ ID NO: 158 |
| 108 | SSSSTTKK | 326-333 |
|  | | Location in SEQ ID NO: 159 |
| 106 | SLNEFLADK | 14-22 |
|  | | Location in SEQ ID NO: 162 |
| 109 | STLDPVGK | 311-318 |
|  | | Location in SEQ ID NO: 164 |
| 111 | TANDVLELR | 78-86 |
|  | | Location in SEQ ID NO: 155 |
| 113 | VVAIDGGDEK | 200-209 |
| 116 | YVLDTSK | 344-350 |
|  | | Location in SEQ ID NO: 157 |
| 117 | AVIYDCPNSR | 399-414 |
| 177 | GHYVLVFPGYAHTSER | 399-414 |
| 118 | GHYVLVSPGYAHTSER | 399-414 |
| 119 | GVIYDCPNSR | 129-138 |
| 120 | GVSSPYLPFGGGR | 455-467 |
| 121 | GVSSPYLPFSGGK | 455-467 |
| 122 | GVSSPYLPFSGGR | 455-467 |
|  | | Location in SEQ ID NO: 165 |
| 123 | AAVGDILQSR | 37-46 |
| 124 | ITPDDLR | 447-453 |
| 125 | TGWDILK | 304-310 |

2. For the potential resistance to at least one antibiotic
at least one peptide belonging to the lanosterol 14-alpha demethylase protein (CP51), having the sequence SEQ ID NO: 157, said peptides being chosen, preferably, from the peptides having the sequences SEQ ID NO: 117 to 122 and 177, as defined above.

3. For the virulence:
at least one peptide belonging to the lipase 8 protein (LIPS) having the sequence SEQ ID NO: 163, said peptides being chosen, preferably, from the peptides having the sequence SEQ ID NO: 123 to 125, as defined above.

4. For the identification:
at least one peptide belonging to the alcohol dehydrogenase 1 protein (ADH1), the fructose-biphosphate aldolase protein (ALF), F-box protein COS111 (CS111), elongation factor 1-beta (EF1B), enolase 1 (ENO1), glyceraldehyde-3-phosphate dehydrogenase (G3P), heat shock protein SSA1 (HSP71), heat shock protein SSB1 (HSP75), pyruvate kinase (KPYK), multiprotein-bridging factor 1 (MBF1), nuclear transport factor 2 (NTF2), phosphoglycerate kinase (PGK), peptidyl-prolyl cis-trans isomerase (PPIA), 60S ribosomal protein L13 (RL13), 60S ribosomal protein L28 (RL28), 60S ribosomal protein L36 (RL36), 40S ribosomal protein S22 (RS22), triosephosphate isomerase (TPIS), having the sequences SEQ ID NO: 155, 156, 158 to 164, and 166 to 175, said peptides being chosen, preferably, from the peptides having the sequence SEQ ID NO: 88 to 116, as defined above.

The peptides that are of use for the purposes of the invention, having the sequence SEQ ID NO: 2, 3, 4, 5, 6, 7, 8, 10, 11, 12, 13, 14, 15, 16, 17, 19, 20, 21, 23, 24, 26, 27, 29, 30, 32, 34, 35, 37, 38, 40, 42, 44 to 125 and 177 are novel and constitute another subject of the invention.

The method of the invention and its advantages will emerge from the rest of the present description relating various nonlimiting examples of implementation of the method of the invention.

EXAMPLE 1: IDENTIFICATION OF MICROORGANISMS FROM A SAMPLE BY MEANS OF BIOCHEMICAL PROFILE

1. Culturing the Sample on a Culture Medium
The optimum culture media and the optimum culture conditions are different according to the species of microorganism. By default, the sample is inoculated onto various media:
Columbia agar with sheep blood (bioMérieux ref 43041) for 18 to 24 h at 35° C., with or without anaerobic conditions;
TSA agar (bioMérieux reference 43011) for 18 to 24 h at 37° C.

2. Identification of Microorganisms
The identification is implemented as follows:
1. Selection of isolated colonies.
2. While observing aseptic conditions, transfer of 3.0 ml of aqueous sterile saline solution (containing 0.45-0.50% of NaCl, at pH 4.5 to 7.0) into a transparent plastic (polystyrene) test tube.
3. Using a sterile cotton bud or a sterile swab, transfer of a sufficient number of identical colonies into the tube of saline solution prepared in step 2 and adjustment of the bacterial suspension to between 0.50 and 0.63 McFarland with a calibrated VITEK 2 DENSICHEK.
4. Positioning of the tube of bacterial suspension and of a VITEK 2 identification card on a VITEK 2 cassette.
5. Loading of the cassette into the VITEK 2 instrument.

6. The filling, sealing, incubation and reading operations are automatic.
7. Acquisition of a biochemical profile.
8. Identification with the VITEK 2 system, carried out by comparison with biochemical profiles of known strains.

EXAMPLE 2: IDENTIFICATION OF MICROORGANISMS FROM A SAMPLE BY MEANS OF MALDI-TOF

The identification is implemented as follows:
1. Transfer, using a 1 µl loop, of a portion of microorganism colony obtained according to example 1, and uniform deposition on a plate for mass spectrometry by MALDI-TOF.
2. Covering of the deposit with 1 µl of matrix. The matrix used is a saturated solution of HCCA (alpha-cyano-4-hydroxycinnamic acid) in an organic solvent (50% acetonitrile and 2.5% trifluoroacetic acid).
3. Drying at ambient temperature.
4. Introduction of the plate into the mass spectrometer.
5. Acquisition of a mass spectrum.
6. Comparison of the spectrum obtained with the spectra contained in a knowledge base.
7. Identification of the microorganism by comparison of the peaks obtained with those of the knowledge base.

EXAMPLE 3: IDENTIFICATION OF MICROORGANISMS FROM A SAMPLE BY MEANS OF ESI-MS

The identification is implemented as follows:
1. Sampling of a microorganism colony, obtained according to example 1, and suspension in 100 µl of demineralized water.
2. Centrifugation at 3000 g for 5 minutes.
3. Removal of the supernatant.
4. Resuspension in 100 µl of demineralized water.
5. Centrifugation at 3000 g for 5 minutes.
6. Removal of the supernatant.
7. Resuspension in 100 µl of a mixture of acetonitrile, demineralized water and formic acid (50/50/0.1%).
8. Filtration with a filter having a pore size of 0.45 µm.
9. Injection into a mass spectrometer in single MS mode.
10. Acquisition of a mass spectrum.
11. Comparison of the spectrum obtained with the spectra contained in a knowledge base.
12. Identification of the microorganism by reference to reference spectra.

EXAMPLE 4: OBTAINING OF DIGESTED PROTEINS FROM MICROORGANISMS

Conventionally, the following protocol is implemented in 11 steps:
1. Sampling of a microorganism colony, obtained according to example 1, and suspension in 10 to 100 µl of a solution of 6M guanidine hydrochloride, 50 mM Tris-HCl, pH=8.0.
2. Addition of dithiothreitol (DTT) in order to obtain a final concentration of 5 mM.
3. Reduction for 20 minutes at 95° C. in a water bath.
4. Cooling of the tubes to ambient temperature.
5. Addition of iodoacetamide in order to obtain a final concentration of 12.5 mM.
6. Alkylation for 40 minutes at ambient temperature and in the dark.
7. Dilution by a factor of 6 with a 50 mM, $NH_4HCO_3$ solution, pH=8.0 in order to obtain a final guanidine hydrochloride concentration of 1M.
8. Addition of 1 µg of trypsin.
9. Digestion at 37° C. for 6 hours overnight.
10. Addition of formic acid to a pH of less than 4 in order to stop the reaction.
11. Ultracentrifugation at 100 000 g for 30 minutes.

EXAMPLE 5: CHARACTERIZATION OF S. AUREUS SAMPLES

After having established the one or more species of the samples according to any one of the methods described in examples 1 to 3, the species listed below are analyzed.
Thirteen strains of S. aureus are analyzed in order to confirm their identification and to establish their characteristics:

| | |
|---|---|
| ID2 | ID3 |
| ID4 | ID2a |
| ID3a | ID4a |
| AST7 | AST8 |
| AST13 | AST14 |
| VIR5 | VIR6 |
| VIR7 | |

The same method of analysis is applied to species that do not belong to the S. aureus species, in order to serve as a negative control:
E. coli

| | |
|---|---|
| ID7 | AST2 |

S. pneumoniae
VIR21
C. difficile
VIR26

Each sample is treated according to example 4, then a volume of 5 µl of digested proteins is injected and analyzed according to the following conditions:
Agilent 1100 series chromatographic system from the company Agilent Technologies (Massy, France).
Waters Symmetry C18 column, 2.1 mm internal diameter, 100 mm long, particle size 3.5 µm.
Solvent A: $H_2O$+0.1% formic acid.
Solvent B: ACN+0.1% formic acid.
HPLC gradient defined in TABLE 1 hereinafter:

TABLE 1

| Time | Flow rate (µl) | Solvent A (%) | Solvent B (%) |
|---|---|---|---|
| 0 | 300 | 95 | 5 |
| 25 | 300 | 60 | 40 |
| 27 | 300 | 0 | 100 |
| 35 | 300 | 0 | 100 |
| 35.1 | 300 | 95 | 5 |
| 45 | 300 | 95 | 5 |

The eluate at the output of the chromatographic column is directly injected into the ionization source of the QTRAP® 5500 mass spectrometer from the company Applied Biosystems (Foster City, United States of America).

The peptides, resulting from the digestion of the proteins of the microorganism, are analyzed by mass spectrometry in MRM mode. Only the peptides indicated in TABLE 2 are detected. For this, the first-generation fragment(s) indicated in TABLE 2 is (are) detected. The application, to which each transition, i.e. each peptide associated with its first-generation fragment, makes it possible to respond, is specified in the clinical interest column of TABLE 2 with the letters I, T, R and V. I denotes the confirmation of the identification of the microorganism, T the typing, R the resistance to at least one antibiotic and V the detection of virulence factors.

TABLE 2

| Transition number | Protein | Peptide (SEQ ID NO.) | First-generation fragment ion | Clinical interest |
|---|---|---|---|---|
| 1 | protein A | DDPSQSANVLGEAQK (2) | y9 singly charged | T |
| 2 | protein A | DDPSQSANVLGEAQK (2) | y13 singly charged | T |
| 3 | protein A | DQQSAFYEILNMPNLNEEQR (3) | y8 singly charged | T |
| 4 | protein A | DQQSAFYEILNMPNLNEEQR (3) | y8 doubly charged | T |
| 5 | protein A | DDPSQSTNVLGEAK (4) | y9 singly charged | T |
| 6 | protein A | DDPSQSTNVLGEAK (4) | y12 singly charged | T |
| 7 | protein A | EQQNAFYEILNMPNLNEEQR (5) | y8 singly charged | T |
| 8 | protein A | EQQNAFYEILNMPNLNEEQR (5) | y8 doubly charged | T |
| 9 | protein A | DDPSQSANLLAEAK (6) | y9 singly charged | T |
| 10 | protein A | DDPSQSANLLAEAK (6) | y12 singly charged | T |
| 11 | protein A | DDPSVSK (7) | y5 singly charged | T |
| 12 | protein A | DDPSVSK (7) | y4 singly charged | T |
| 13 | protein A | IAADNK (8) | y4 singly charged | T |
| 14 | protein A | IAADNK (8) | y5 singly charged | T |
| 15 | PBP2a | IYNSLGVK (10) | y6 singly charged | R + T |
| 16 | PBP2a | IYNSLGVK (10) | y7 singly charged | R + T |
| 17 | PBP2a | DINIQDR (11) | y5 singly charged | R + T |
| 18 | PBP2a | DINIQDR (11) | y4 singly charged | R + T |
| 19 | PBP2a | ELSISEDYIK (12) | y6 singly charged | R + T |
| 20 | PBP2a | ELSISEDYIK (12) | y8 singly charged | R + T |
| 21 | PBP2a | FQITTSPGSTQK (13) | y9 singly charged | R + T |
| 22 | PBP2a | FQITTSPGSTQK (13) | y6 singly charged | R + T |
| 23 | PBP2a | ILTAMIGLNNK (14) | y8 singly charged | R + T |
| 24 | PBP2a | ILTAMIGLNNK (14) | y9 singly charged | R + T |
| 25 | PBP2a | YEVVNGNIDLK (15) | y8 singly charged | R + T |
| 26 | PBP2a | YEVVNGNIDLK (15) | y9 singly charged | R + T |
| 27 | PBP2a | VALELGSK (16) | y6 singly charged | R + T |
| 28 | PBP2a | VALELGSK (16) | y7 singly charged | R + T |
| 29 | PBP2a | SYANLIGK (17) | y6 singly charged | R + T |
| 30 | LukS | TNDPNVDLINYLPK (19) | y8 singly charged | V + T |
| 31 | LukS | TNDPNVDLINYLPK (19) | y11 singly charged | V + T |
| 32 | LukS | SVQWGIK (20) | y5 singly charged | V + T |
| 33 | LukS | SVQWGIK (20) | y4 singly charged | V + T |
| 34 | LukS | ANSFITSLGK (21) | y8 singly charged | V + T |
| 35 | LukS | ANSFITSLGK (21) | y6 singly charged | V + T |
| 36 | LukF | MPVLSR (23) | y5 singly charged | V + T |
| 37 | LukF | MPVLSR (23) | y3 singly charged | V + T |
| 38 | LukF | GNFNPEFIGVLSR (24) | y8 singly charged | V + T |
| 39 | LukF | GNFNPEFIGVLSR (24) | y9 singly charged | V + T |
| 40 | RL30 | LQITLTR (26) | y5 singly charged | I + T |
| 41 | RL30 | LQITLTR (26) | y6 singly charged | I + T |
| 42 | RL30 | TNSSVVVEDNPAIR (27) | y8 singly charged | I + T |
| 43 | RL30 | TNSSVVVEDNPAIR (27) | y8 singly charged | I + T |
| 44 | RL331 | VNVTLAC[CAM]TEC[CAM]GDR (29) | y8 singly charged | I + T |
| 45 | RL331 | NYITTK (30) | y5 singly charged | I + T |
| 46 | RL331 | NYITTK (30) | y4 singly charged | I + T |
| 47 | SSAA2 | AGYTVNNTPK (32) | y6 singly charged | I + T |
| 48 | SSAA2 | AGYTVNNTPK (32) | y7 singly charged | I + T |
| 49 | SSAA2 | AGYTVNNTPK (32) | y8 singly charged | I + T |
| 50 | SSAA2 | AGYTVNNTPK (32) | y9 singly charged | I + T |
| 51 | Y772 | ATDFIDKVK (35) | y6 singly charged | I + T |
| 52 | Y772 | ATDFIDKVK (35) | y8 singly charged | I + T |
| 53 | ATL | AYLAVPAAPK (38) | y7 singly charged | I + T |
| 54 | ATL | AYLAVPAAPK (38) | y8 singly charged | I + T |
| 55 | EFTU | TVGSGVVTEIIK (40) | y7 singly charged | I + T |
| 56 | EFTU | TVGSGVVTEIIK (40) | y8 singly charged | I + T |
| 57 | EFTU | TVGSGVVTEIIK (40) | y9 singly charged | I + T |
| 58 | Y772 | EFVENAKEK (34) | y6 singly charged | I + T |
| 59 | Y772 | EFVENAKEK (34) | y7 singly charged | I + T |
| 60 | Y772 | EFVENAKEK (34) | y8 singly charged | I + T |
| 61 | ISAA | LSNGNTAGATGSSAAQIMAQR (42) | y7 singly charged | I + T |
| 62 | ISAA | LSNGNTAGATGSSAAQIMAQR (42) | y8 singly charged | I + T |
| 63 | ATL | LYSVPWGTYK (37) | y6 singly charged | I + T |
| 64 | ATL | LYSVPWGTYK (37) | y7 singly charged | I + T |
| 65 | ATL | LYSVPWGTYK (37) | y8 singly charged | I + T |
| 66 | Y197A | NITQDQDIHAVPK (44) | y8 singly charged | I + T |
| 67 | Y197A | NITQDQDIHAVPK (44) | y7 singly charged | I + T |
| 68 | Y197A | NITQDQDIHAVPK (44) | y6 singly charged | I + T |

TABLE 2-continued

| Transition number | Protein | Peptide (SEQ ID NO.) | First-generation fragment ion | Clinical interest |
|---|---|---|---|---|
| 69 | Y197A | LDSKDVSR (45) | y6 singly charged | I + T |
| 70 | Y197A | LDSKDVSR (45) | y7 singly charged | I + T |

The charge state of the precursor peptide, its retention time and the transitions, i.e. the ratios $(m/z)_1$ in Q1 and $(m/z)_2$ in Q3, are indicated in TABLE 3. The collision energy used to fragment the precursor ion is also indicated in TABLE 3.

TABLE 3

| Transition number | Precursor charge state | Retention time | (m/z) filtered in Q1 | (m/z) filtered in Q3 | Collision energy |
|---|---|---|---|---|---|
| 1 | 2 | 8.2 | 779.87 | 929.51 | 39 |
| 2 | 2 | 8.2 | 779.87 | 664.84 | 39 |
| 3 | 3 | 17.9 | 813.71 | 999.49 | 45 |
| 4 | 3 | 17.9 | 813.71 | 500.24 | 45 |
| 5 | 2 | 7.9 | 730.85 | 918.49 | 37 |
| 6 | 2 | 7.9 | 730.85 | 615.82 | 37 |
| 7 | 3 | 16.5 | 827.39 | 999.49 | 45 |
| 8 | 3 | 16.5 | 827.39 | 500.25 | 34 |
| 9 | 2 | 10 | 729.86 | 916.51 | 37 |
| 10 | 2 | 10 | 729.86 | 614.83 | 37 |
| 11 | 2 | 11 | 374.18 | 517.3 | 21 |
| 12 | 2 | 11 | 374.18 | 420.25 | 21 |
| 13 | 2 | 8.9 | 316.17 | 447.22 | 19 |
| 14 | 2 | 8.9 | 316.17 | 518.26 | 19 |
| 15 | 2 | 6.7 | 447.26 | 617.36 | 25 |
| 16 | 2 | 6.7 | 447.26 | 780.43 | 25 |
| 17 | 2 | 6.2 | 437.22 | 645.33 | 24 |
| 18 | 2 | 6.2 | 437.22 | 531.3 | 24 |
| 19 | 2 | 11.1 | 598.81 | 754.36 | 31 |
| 20 | 2 | 11.1 | 598.81 | 954.48 | 31 |
| 21 | 2 | 7.4 | 647.84 | 906.45 | 34 |
| 22 | 2 | 7.4 | 647.84 | 617.3 | 26 |
| 23 | 2 | 11.8 | 594.34 | 860.47 | 31 |
| 24 | 2 | 11.8 | 594.34 | 961.51 | 31 |
| 25 | 2 | 10.1 | 632.33 | 872.48 | 33 |
| 26 | 2 | 10.1 | 632.33 | 971.55 | 33 |
| 27 | 2 | 7.4 | 408.74 | 646.38 | 23 |
| 28 | 2 | 7.4 | 408.74 | 717.41 | 23 |
| 29 | 2 | 8.2 | 433.24 | 615.38 | 24 |
| 30 | 2 | 14.9 | 808.42 | 975.55 | 41 |
| 31 | 2 | 14.9 | 808.42 | 643.4 | 41 |
| 32 | 2 | 8.2 | 409.23 | 631.36 | 23 |
| 33 | 2 | 8.2 | 409.23 | 503.3 | 23 |
| 34 | 2 | 10.3 | 519.28 | 852.48 | 28 |
| 35 | 2 | 10.3 | 519.28 | 618.4 | 28 |
| 36 | 2 | 6.4 | 351.7 | 571.36 | 20 |
| 37 | 2 | 6.4 | 351.7 | 375.24 | 20 |
| 38 | 2 | 14.3 | 725.38 | 920.52 | 37 |
| 39 | 2 | 14.3 | 725.38 | 509.29 | 37 |
| 40 | 2 | 9.2 | 422.77 | 603.38 | 24 |
| 41 | 2 | 9.2 | 422.77 | 731.44 | 24 |
| 42 | 2 | 8 | 750.89 | 913.47 | 38 |
| 43 | 3 | 8 | 500.93 | 913.47 | 29 |
| 44 | 2 | 7.9 | 747.84 | 968.36 | 38 |
| 45 | 2 | 2.8 | 370.2 | 625.36 | 21 |
| 46 | 2 | 2.8 | 370.2 | 462.29 | 21 |
| 47 | 2 | 3.9 | 532.77 | 672.37 | 28 |
| 48 | 2 | 3.9 | 532.77 | 773.42 | 28.442 |
| 49 | 2 | 3.9 | 532.77 | 936.48 | 28.442 |
| 50 | 2 | 3.9 | 532.77 | 993.5 | 28.442 |
| 51 | 2 | 7.2 | 518.79 | 749.46 | 28 |
| 52 | 2 | 7.2 | 518.79 | 965.53 | 27.827 |
| 53 | 2 | 9 | 500.79 | 653.4 | 27 |
| 54 | 2 | 9 | 500.79 | 766.48 | 27.035 |
| 55 | 2 | 11.2 | 601.85 | 801.51 | 31 |
| 56 | 2 | 11.2 | 601.85 | 858.53 | 31.482 |
| 57 | 2 | 11.2 | 601.85 | 945.56 | 31.482 |
| 58 | 2 | 2.3 | 547.28 | 718.37 | 29 |
| 59 | 2 | 2.3 | 547.28 | 817.44 | 29.08 |
| 60 | 2 | 2.3 | 547.28 | 964.51 | 29.08 |
| 61 | 3 | 8.7 | 669.33 | 817.43 | 37 |
| 62 | 3 | 8.7 | 669.33 | 888.47 | 37.466 |
| 63 | 2 | 12.2 | 607.32 | 751.38 | 32 |
| 64 | 2 | 12.2 | 607.32 | 850.45 | 31.722 |
| 65 | 2 | 12.2 | 607.32 | 937.48 | 31.722 |
| 66 | 2 | 6.3 | 739.88 | 907.5 | 38 |
| 67 | 2 | 6.3 | 739.88 | 779.44 | 37.555 |
| 68 | 2 | 6.3 | 739.88 | 664.41 | 37.555 |
| 69 | 2 | 2 | 460.25 | 691.37 | 25.251 |
| 70 | 2 | 2 | 460.25 | 806.4 | 25.251 |

The other machine parameters used are the following:
Scan type: MRM
Polarity: Positive
Ionization source: Turbo V™ (Applied BioSystems)
Q1 setting: Filtering with unit resolution
Q3 setting: Filtering with unit resolution
Inter-scan pause: 5.00 msec
Scan speed: 10 Da/s
Curtain gas: 50.00 psi
Cone voltage: 5500.00 V
Source temperature: 500.00° C.
Nebulizing gas: 50.00 psi
Heating gas: 40.00 psi
Dynamic filling: activated
Declustering potential (DP): 100.00 V
Entry potential before Q0 (EP): 6.00 V
Collision cell exit potential (CXP): 11 V
Total cycle time: 1.6 sec The areas obtained for each of the transitions and for each of the microorganisms studied were measured. All the transitions with an area greater than or equal to 1000 (arbitrary units) are considered to be positive and have been denoted "1" in tables 4A and 4B. All the transitions with an area less than 1000 are considered to be negative and have been denoted 0 in tables 4A and 4B. When no signal peak was observed, the transition was noted as negative.

The positive-transition number is then summed for the applications I, R and V and reported in TABLE 5:

TABLE 4A

| Transition | ID2 S. aureus | ID3 S. aureus | ID4 S. aureus | ID2a S. aureus | ID3a S. aureus | ID4a S. aureus | AST7 S. aureus | AST8 S. aureus |
|---|---|---|---|---|---|---|---|---|
| 1 | 0 | 1 | 1 | 0 | 1 | 1 | 0 | 0 |
| 2 | 0 | 1 | 1 | 0 | 1 | 1 | 0 | 0 |

TABLE 4A-continued

| Transition | ID2 S. aureus | ID3 S. aureus | ID4 S. aureus | ID2a S. aureus | ID3a S. aureus | ID4a S. aureus | AST7 S. aureus | AST8 S. aureus |
|---|---|---|---|---|---|---|---|---|
| 3 | 0 | 1 | 1 | 0 | 1 | 1 | 0 | 0 |
| 4 | 0 | 1 | 1 | 0 | 1 | 1 | 0 | 0 |
| 5 | 1 | 1 | 1 | 1 | 1 | 1 | 0 | 0 |
| 6 | 1 | 1 | 1 | 1 | 1 | 1 | 0 | 1 |
| 7 | 1 | 1 | 1 | 1 | 1 | 1 | 0 | 0 |
| 8 | 1 | 1 | 1 | 1 | 1 | 1 | 0 | 0 |
| 9 | 1 | 1 | 1 | 1 | 1 | 1 | 0 | 0 |
| 10 | 1 | 1 | 1 | 1 | 1 | 1 | 0 | 0 |
| 11 | 0 | 0 | 0 | 0 | 0 | 0 | 1 | 0 |
| 12 | 0 | 0 | 0 | 0 | 0 | 0 | 0 | 0 |
| 13 | 1 | 1 | 1 | 0 | 1 | 1 | 0 | 0 |
| 14 | 1 | 1 | 1 | 1 | 1 | 1 | 1 | 0 |
| 15 | 1 | 0 | 1 | 1 | 0 | 1 | 0 | 0 |
| 16 | 0 | 0 | 1 | 0 | 0 | 1 | 0 | 0 |
| 17 | 1 | 0 | 1 | 1 | 0 | 1 | 0 | 0 |
| 18 | 1 | 0 | 1 | 1 | 0 | 1 | 0 | 0 |
| 19 | 1 | 0 | 1 | 1 | 0 | 1 | 0 | 0 |
| 20 | 1 | 0 | 1 | 1 | 0 | 1 | 0 | 0 |
| 21 | 1 | 0 | 1 | 1 | 0 | 1 | 0 | 0 |
| 22 | 1 | 0 | 1 | 1 | 0 | 1 | 0 | 0 |
| 23 | 1 | 0 | 1 | 1 | 0 | 1 | 0 | 0 |
| 24 | 1 | 0 | 1 | 1 | 0 | 1 | 0 | 0 |
| 25 | 1 | 0 | 1 | 1 | 0 | 1 | 0 | 0 |
| 26 | 1 | 0 | 1 | 1 | 0 | 1 | 0 | 0 |
| 27 | 1 | 1 | 1 | 1 | 1 | 1 | 0 | 0 |
| 28 | 1 | 0 | 1 | 1 | 0 | 1 | 0 | 0 |
| 29 | 1 | 0 | 1 | 1 | 0 | 1 | 0 | 0 |
| 30 | 0 | 0 | 0 | 0 | 0 | 0 | 0 | 0 |
| 31 | 0 | 0 | 0 | 0 | 0 | 0 | 0 | 0 |
| 32 | 0 | 0 | 0 | 0 | 0 | 0 | 0 | 0 |
| 33 | 0 | 0 | 1 | 0 | 0 | 0 | 0 | 0 |
| 34 | 0 | 0 | 0 | 0 | 0 | 0 | 0 | 0 |
| 35 | 0 | 0 | 0 | 0 | 0 | 0 | 0 | 1 |
| 36 | 0 | 0 | 0 | 0 | 0 | 0 | 1 | 1 |
| 37 | 0 | 0 | 0 | 0 | 0 | 1 | 0 | 0 |
| 38 | 0 | 0 | 0 | 0 | 0 | 1 | 0 | 0 |
| 39 | 0 | 0 | 0 | 0 | 0 | 0 | 0 | 0 |
| 40 | 1 | 1 | 1 | 1 | 1 | 1 | 1 | 1 |
| 41 | 1 | 1 | 1 | 1 | 1 | 1 | 1 | 1 |
| 42 | 1 | 1 | 1 | 1 | 1 | 1 | 1 | 1 |
| 43 | 1 | 1 | 1 | 1 | 1 | 1 | 1 | 1 |
| 44 | 1 | 1 | 1 | 1 | 1 | 1 | 1 | 1 |
| 45 | 1 | 1 | 1 | 1 | 1 | 1 | 1 | 1 |
| 46 | 1 | 1 | 1 | 1 | 1 | 1 | 1 | 1 |
| 47 | 1 | 1 | 1 | 1 | 1 | 1 | 1 | 1 |
| 48 | 1 | 1 | 1 | 1 | 1 | 1 | 1 | 1 |
| 49 | 1 | 1 | 1 | 1 | 1 | 1 | 1 | 1 |
| 50 | 1 | 1 | 1 | 1 | 1 | 1 | 1 | 1 |
| 51 | 1 | 1 | 1 | 1 | 1 | 1 | 1 | 1 |
| 52 | 1 | 1 | 1 | 1 | 1 | 1 | 1 | 1 |
| 53 | 1 | 1 | 1 | 1 | 1 | 1 | 1 | 1 |
| 54 | 1 | 1 | 1 | 1 | 1 | 1 | 1 | 1 |
| 55 | 1 | 1 | 1 | 1 | 1 | 1 | 1 | 1 |
| 56 | 1 | 1 | 1 | 1 | 1 | 1 | 1 | 1 |
| 57 | 1 | 1 | 1 | 1 | 1 | 1 | 1 | 1 |
| 58 | 1 | 1 | 1 | 1 | 1 | 1 | 1 | 1 |
| 59 | 1 | 1 | 1 | 1 | 1 | 1 | 1 | 1 |
| 60 | 1 | 1 | 1 | 1 | 1 | 1 | 1 | 1 |
| 61 | 1 | 1 | 1 | 1 | 1 | 1 | 1 | 1 |
| 62 | 1 | 1 | 1 | 1 | 1 | 1 | 1 | 1 |
| 63 | 1 | 1 | 1 | 1 | 1 | 1 | 1 | 1 |
| 64 | 1 | 1 | 1 | 1 | 1 | 1 | 0 | 0 |
| 65 | 1 | 1 | 1 | 1 | 1 | 1 | 1 | 1 |
| 66 | 1 | 1 | 1 | 1 | 1 | 1 | 1 | 1 |
| 67 | 1 | 1 | 1 | 1 | 1 | 1 | 1 | 1 |
| 68 | 1 | 1 | 1 | 1 | 1 | 1 | 1 | 1 |
| 69 | 1 | 1 | 1 | 1 | 1 | 1 | 1 | 1 |
| 70 | 1 | 1 | 1 | 1 | 1 | 1 | 1 | 1 |

TABLE 4B

| Transition | AST13 S. aureus | AST14 S. aureus | VIR5 S. aureus | VIR6 S. aureus | VIR7 S. aureus | ID7 E. coli | AST2 E. coli | VIR21 S. pneumoniae | VIR26 C. difficile |
|---|---|---|---|---|---|---|---|---|---|
| 1 | 0 | 0 | 0 | 0 | 0 | 0 | 0 | 0 | 0 |
| 2 | 0 | 0 | 0 | 1 | 0 | 0 | 0 | 0 | 0 |
| 3 | 0 | 0 | 0 | 0 | 0 | 0 | 0 | 0 | 0 |
| 4 | 0 | 0 | 0 | 0 | 0 | 0 | 0 | 0 | 0 |
| 5 | 0 | 0 | 0 | 1 | 0 | 0 | 0 | 0 | 0 |
| 6 | 1 | 0 | 0 | 1 | 0 | 0 | 0 | 0 | 0 |
| 7 | 0 | 0 | 0 | 1 | 0 | 0 | 0 | 0 | 0 |
| 8 | 0 | 0 | 0 | 1 | 0 | 0 | 0 | 0 | 0 |
| 9 | 0 | 0 | 0 | 1 | 0 | 0 | 0 | 0 | 0 |
| 10 | 0 | 0 | 0 | 1 | 0 | 0 | 0 | 0 | 0 |
| 11 | 0 | 1 | 1 | 1 | 0 | 0 | 0 | 0 | 0 |
| 12 | 0 | 1 | 1 | 0 | 0 | 0 | 0 | 0 | 0 |
| 13 | 0 | 0 | 0 | 0 | 0 | 0 | 0 | 0 | 0 |
| 14 | 1 | 0 | 0 | 1 | 0 | 0 | 0 | 0 | 0 |
| 15 | 1 | 0 | 0 | 0 | 0 | 0 | 0 | 0 | 0 |
| 16 | 1 | 0 | 0 | 0 | 0 | 0 | 0 | 0 | 0 |
| 17 | 1 | 1 | 0 | 0 | 0 | 0 | 0 | 0 | 0 |
| 18 | 1 | 0 | 0 | 0 | 0 | 0 | 1 | 0 | 0 |
| 19 | 1 | 1 | 0 | 0 | 0 | 0 | 0 | 0 | 0 |
| 20 | 1 | 1 | 0 | 0 | 0 | 0 | 0 | 0 | 0 |
| 21 | 1 | 1 | 0 | 0 | 0 | 0 | 0 | 0 | 0 |
| 22 | 1 | 0 | 0 | 0 | 0 | 0 | 0 | 0 | 0 |
| 23 | 1 | 0 | 0 | 0 | 0 | 0 | 1 | 0 | 0 |
| 24 | 1 | 1 | 0 | 1 | 0 | 0 | 0 | 0 | 0 |
| 25 | 1 | 1 | 0 | 0 | 0 | 0 | 0 | 0 | 0 |
| 26 | 1 | 0 | 0 | 0 | 0 | 0 | 0 | 0 | 0 |
| 27 | 1 | 1 | 0 | 0 | 0 | 0 | 0 | 0 | 1 |
| 28 | 1 | 1 | 0 | 0 | 0 | 0 | 0 | 0 | 0 |
| 29 | 1 | 1 | 0 | 0 | 0 | 0 | 0 | 0 | 0 |
| 30 | 0 | 0 | 1 | 0 | 1 | 0 | 0 | 0 | 0 |
| 31 | 0 | 0 | 1 | 0 | 1 | 0 | 0 | 0 | 0 |
| 32 | 0 | 0 | 1 | 0 | 1 | 0 | 0 | 0 | 0 |
| 33 | 0 | 0 | 1 | 0 | 1 | 0 | 0 | 0 | 0 |
| 34 | 0 | 0 | 1 | 0 | 1 | 0 | 0 | 0 | 0 |
| 35 | 0 | 0 | 1 | 0 | 1 | 0 | 0 | 0 | 0 |
| 36 | 1 | 1 | 1 | 1 | 1 | 0 | 0 | 0 | 0 |
| 37 | 0 | 0 | 1 | 0 | 1 | 0 | 0 | 0 | 0 |
| 38 | 0 | 0 | 1 | 0 | 1 | 0 | 0 | 0 | 0 |
| 39 | 0 | 0 | 1 | 0 | 1 | 0 | 0 | 0 | 0 |
| 40 | 1 | 1 | 1 | 1 | 1 | 0 | 0 | 0 | 0 |
| 41 | 1 | 1 | 1 | 1 | 1 | 0 | 0 | 1 | 0 |
| 42 | 1 | 1 | 1 | 1 | 1 | 0 | 0 | 0 | 0 |
| 43 | 0 | 1 | 0 | 1 | 0 | 0 | 0 | 0 | 0 |
| 44 | 1 | 1 | 1 | 1 | 1 | 0 | 0 | 0 | 0 |
| 45 | 1 | 1 | 0 | 1 | 1 | 0 | 0 | 0 | 0 |
| 46 | 1 | 1 | 1 | 1 | 1 | 0 | 0 | 0 | 0 |
| 47 | 1 | 1 | 1 | 1 | 1 | 0 | 0 | 0 | 0 |
| 48 | 1 | 1 | 0 | 1 | 1 | 0 | 0 | 0 | 0 |
| 49 | 1 | 1 | 0 | 1 | 0 | 0 | 0 | 0 | 0 |
| 50 | 1 | 0 | 0 | 1 | 0 | 0 | 0 | 0 | 0 |
| 51 | 1 | 1 | 0 | 1 | 1 | 0 | 0 | 0 | 0 |
| 52 | 1 | 1 | 0 | 1 | 1 | 1 | 0 | 0 | 0 |
| 53 | 1 | 1 | 1 | 1 | 1 | 0 | 0 | 0 | 0 |
| 54 | 1 | 1 | 1 | 1 | 1 | 0 | 0 | 0 | 0 |
| 55 | 1 | 1 | 1 | 1 | 1 | 0 | 0 | 0 | 0 |
| 56 | 1 | 1 | 1 | 1 | 1 | 0 | 0 | 0 | 0 |
| 57 | 1 | 1 | 1 | 1 | 1 | 0 | 0 | 0 | 0 |
| 58 | 1 | 1 | 0 | 1 | 1 | 0 | 0 | 0 | 0 |
| 59 | 1 | 1 | 0 | 1 | 1 | 0 | 0 | 0 | 0 |
| 60 | 1 | 1 | 0 | 1 | 1 | 0 | 0 | 0 | 0 |
| 61 | 1 | 1 | 0 | 1 | 1 | 0 | 0 | 0 | 0 |
| 62 | 1 | 1 | 0 | 1 | 1 | 0 | 0 | 0 | 0 |
| 63 | 1 | 1 | 1 | 1 | 1 | 0 | 0 | 0 | 0 |
| 64 | 1 | 0 | 0 | 0 | 0 | 0 | 0 | 0 | 0 |
| 65 | 1 | 1 | 1 | 1 | 1 | 0 | 0 | 0 | 0 |
| 66 | 1 | 1 | 0 | 1 | 1 | 0 | 0 | 0 | 0 |
| 67 | 0 | 1 | 0 | 1 | 0 | 0 | 0 | 0 | 0 |
| 68 | 1 | 1 | 0 | 1 | 0 | 0 | 0 | 0 | 0 |
| 69 | 1 | 1 | 1 | 1 | 1 | 0 | 0 | 0 | 0 |
| 70 | 1 | 1 | 0 | 1 | 1 | 0 | 0 | 0 | 0 |

TABLE 5

|  |  | I | R | V |
|---|---|---|---|---|
| ID2 | S. aureus | 30 | 14 | 0 |
| ID3 | S. aureus | 30 | 1 | 0 |
| ID4 | S. aureus | 30 | 15 | 1 |
| ID2a | S. aureus | 30 | 14 | 0 |
| ID3a | S. aureus | 30 | 1 | 0 |
| ID4a | S. aureus | 30 | 15 | 2 |
| AST7 | S. aureus | 29 | 0 | 1 |
| AST8 | S. aureus | 29 | 0 | 2 |
| AST13 | S. aureus | 28 | 15 | 1 |
| AST14 | S. aureus | 28 | 9 | 1 |
| VIR5 | S. aureus | 13 | 0 | 10 |
| VIR6 | S. aureus | 29 | 1 | 1 |
| VIR7 | S. aureus | 24 | 0 | 10 |
| ID7 | E. coli | 1 | 0 | 0 |
| AST2 | E. coli | 0 | 2 | 0 |
| VIR21 | S. pneumoniae | 1 | 0 | 0 |
| VIR26 | C. difficile | 0 | 1 | 0 |

All the S. aureus samples exhibit more than 12 positive transitions in the I category. All these samples are therefore confirmed as indeed belonging to the S. aureus species.

On the other hand, the samples ID7, AST2, VIR21 and VIR26 exhibit less than two positive transitions in the I category, these samples are therefore confirmed as not belonging to the S. aureus species.

The ID2, ID4, ID2a, ID4a, AST13 and AST14 strains of S. aureus exhibit more than eight positive transitions for the R category, they therefore express the penicillin binding protein (PBP2a), this being synonymous with a mechanism of resistance to group M penicillins (e.g. methicillin).

On the other hand, the ID3, ID3a, AST7, AST8, VIR5, VIR6 and VIR7 strains of S. aureus exhibit less than three positive transitions for the V category, they therefore do not express PBP2a. These strains are therefore sensitive to an antibiotic such as a group M penicillin The ID7, AST2, VIR21 and VIR26 strains which do not belong to the S. aureus species also exhibit less than three transitions for the R category, they do not therefore express PBP2a, thereby confirming the specificity of the method.

The VIR5 and VIR7 samples of S. aureus exhibit more than nine positive transitions in the V category, they therefore express the Panton-Valentine-Leukocidin (PVL) protein.

On the other hand, the ID2, ID3, ID4, ID2a, ID3a, ID4a, AST7, AST8, AST13, AST14 and VIR6 strains of S. aureus exhibit less than three positive transitions, they do not therefore express PVL. These strains do not therefore have the virulence properties related to PVL.

The ID7, AST2, VIR21 and VIR26 strains which do not belong to the S. aureus species also exhibit less than three transitions for the V category, they do not therefore express PVL, thereby confirming the specificity of the method.

For the typing, the T-category transitions of each strain are compared with the transitions of the other strains considered as reference strains. In practice, a value 0 is assigned when the transitions between the two strains are classified in the same category (positive or negative) and a value 1 is assigned when the transitions between the two strains are classified in different categories (a positive transition and a negative transition). The values are summed for all the T-category transitions of each strain pair in order to establish a score. The scores are shown in TABLE 6:

TABLE 6

|  | ID2 | ID3 | ID4 | ID2a | ID3a | ID4a | AST7 | AST8 | AST13 | AST14 | VIR5 | VIR6 | VIR7 | ID7 | AST2 | VIR21 | VIR26 |
|---|---|---|---|---|---|---|---|---|---|---|---|---|---|---|---|---|---|
| ID2 | 0 | 17 | 6 | 1 | 17 | 7 | 24 | 24 | 10 | 18 | 51 | 18 | 38 | 52 | 51 | 52 | 52 |
| ID3 | 17 | 0 | 15 | 18 | 0 | 16 | 15 | 15 | 27 | 25 | 42 | 9 | 29 | 43 | 46 | 43 | 43 |
| ID4 | 6 | 15 | 0 | 7 | 15 | 3 | 30 | 30 | 14 | 24 | 55 | 22 | 42 | 58 | 57 | 58 | 58 |
| ID2a | 1 | 18 | 7 | 0 | 18 | 8 | 23 | 23 | 9 | 17 | 50 | 17 | 37 | 51 | 50 | 51 | 51 |
| ID3a | 17 | 0 | 15 | 18 | 0 | 16 | 15 | 15 | 27 | 25 | 42 | 9 | 29 | 43 | 46 | 43 | 43 |
| ID4a | 7 | 16 | 3 | 8 | 16 | 0 | 31 | 31 | 15 | 25 | 54 | 23 | 41 | 59 | 58 | 59 | 59 |
| AST7 | 24 | 15 | 30 | 23 | 15 | 31 | 0 | 4 | 20 | 12 | 27 | 8 | 16 | 32 | 35 | 32 | 34 |
| AST8 | 24 | 15 | 30 | 23 | 15 | 31 | 4 | 0 | 20 | 14 | 27 | 10 | 14 | 32 | 35 | 32 | 34 |
| AST13 | 10 | 27 | 14 | 9 | 27 | 15 | 20 | 20 | 0 | 14 | 43 | 24 | 30 | 46 | 45 | 46 | 46 |
| AST14 | 18 | 25 | 24 | 17 | 25 | 25 | 12 | 14 | 14 | 0 | 33 | 18 | 24 | 40 | 43 | 40 | 40 |
| VIR5 | 51 | 42 | 55 | 50 | 42 | 54 | 27 | 27 | 43 | 33 | 0 | 35 | 13 | 27 | 28 | 25 | 27 |
| VIR6 | 18 | 9 | 22 | 17 | 9 | 23 | 8 | 10 | 24 | 18 | 35 | 0 | 24 | 40 | 43 | 40 | 42 |
| VIR7 | 38 | 29 | 42 | 37 | 29 | 41 | 16 | 14 | 30 | 24 | 13 | 24 | 0 | 34 | 37 | 34 | 36 |
| ID7 | 52 | 43 | 58 | 51 | 43 | 59 | 32 | 32 | 46 | 40 | 27 | 40 | 34 | — | — | — | — |
| AST2 | 51 | 46 | 57 | 50 | 46 | 58 | 35 | 35 | 45 | 43 | 28 | 43 | 37 | — | — | — | — |
| VIR21 | 52 | 43 | 58 | 51 | 43 | 59 | 32 | 32 | 46 | 40 | 25 | 40 | 34 | — | — | — | — |
| VIR26 | 52 | 43 | 58 | 51 | 43 | 59 | 34 | 34 | 46 | 40 | 27 | 42 | 36 | — | — | — | — |

The strains which have a score less than or equal to 4 are of the same type, the strains which have a score strictly above 4 are of different type.

Thus, the ID2 and ID2a, ID3 and ID3a, ID4 and ID4a and AST7 and AST8 strains are of the same type. All the other strains taken in pairs are of different type. The high sums obtained between the ID7, AST2, VIR21 and VIR26 strains, which are not S. aureus, and all the other strains which are S. aureus, should be noted. These results confirm the specificity of the method.

The ID7, AST2, VIR21 and VIR26 strains are not of course of the same type; this would be absurd, they are of different species. These strains cannot therefore be compared with one another and no value is reported in TABLE 6.

Extremely advantageously, scores above 25, for instance between ID2 and VR7, reflect a great divergence between strains. Scores between 15 and 25, as between ID2 and AST14, reflect a moderate divergence and scores between 5 and 15, as between ID2 and ID4a, a weak divergence.

The method thus implemented therefore makes it possible not only to establish whether two strains are of the same type, which is important for identifying a common seat of infection, but also to estimate the proximity of two strains, which is extremely important for epidemiological studies.

This example shows that, very advantageously, the present invention makes it possible, in a time of less than one hour, which is very short, to confirm the identity of a species such as *S. aureus* and to determine, simultaneously within the same analysis, the properties of typing and potential resistance to at least one antibiotic and to establish the existence of a virulence factor. These properties were established with the same instrument, which greatly facilitates the analysis and the reporting of the results. Finally, the characteristics of the bacteria are established using bacterial proteins, which reflects the existence of live and viable microorganisms, unlike characterizations using bacterial DNA which can be distorted by the existence of dead bacteria.

EXAMPLE 6: PROTOCOL FOR DIGESTION OF MICROORGANISMS WITH A DESALIFYING STEP

Conventionally, the following protocol is implemented in 17 steps:
Steps 1 to 10: idem example 4.
11. The sample volume is made up to 1 ml with water/0.1% (v/v) formic acid.
12. Equilibration of Waters Oasis HLB columns with 1 ml of methanol then 1 ml of H$_2$O/0.1% (v/v) formic acid.
13. Loading of the sample which flows by gravity.
14. Washing with 1 ml of H$_2$O/0.1% (v/v) formic acid.
15. Elution with 1 ml of a mixture of 80% methanol and 20% water/0.1% (v/v) formic acid.
16. The eluate is evaporated with a SpeedVac® SPD2010 evaporator (Thermo Electron Corporation, Waltham, Mass., United States of America), for two hours, in order to obtain a volume of approximately 100 µl.
17. The eluate is then taken up in a water/0.5% (v/v) formic acid solution, quantity sufficient for (QS) 250 µl.

EXAMPLE 7: CHARACTERIZATION OF *E COLI* SAMPLES

After having established the one or more species of the samples according to any one of the methods described in examples 1 to 3, the species listed below are analyzed. Fifteen *E. coli* strains are analyzed in order to confirm their identification and to establish their characteristics:

| | |
|---|---|
| AST1 | AST2 |
| AST3 | AST4 |
| AST5 | VIR41 |
| VIR42 | VIR43 |
| VIR44 | VIR45 |
| ID6 | ID7 |

-continued

| | |
|---|---|
| ID8 | ID9 |
| ID10 | |

The same method of analysis is applied to species not belonging to the *E. coli* species in order to serve as a negative control:
*S. aureus*
VIR10
*S. pneumoniae*
VIR19
*C. difficile*
VIR28
Each sample is treated according to example 6, then a volume of 5 µl of digested proteins is injected and analyzed according to the following conditions:
  Agilent 1100 series chromatographic system from the company Agilent Technologies (Massy, France).
  Waters Symmetry C18 column, 2.1 mm internal diameter, 100 mm long, particle size 3.5 µm.
  Solvent A: H$_2$O+0.1% formic acid.
  Solvent B: ACN+0.1% formic acid.
  HPLC gradient defined in TABLE 7 hereinafter:

TABLE 7

| Time (min) | Flow rate (µl) | Solvent A (%) | Solvent B (%) |
|---|---|---|---|
| 0 | 300 | 95 | 5 |
| 3 | 300 | 95 | 5 |
| 28 | 300 | 60 | 40 |
| 30 | 300 | 0 | 100 |
| 38 | 300 | 0 | 100 |
| 38.1 | 300 | 95 | 5 |
| 45 | 300 | 95 | 5 |

The eluate at the output of the chromatographic column is directly injected into the ionization source of the QTRAP® 5500 mass spectrometer from the company Applied Biosystems (Foster City, United States of America).
The peptides, resulting from the digestion of the proteins of the microorganism, are analyzed using the mass spectrometer in MRM mode. Only the peptides indicated in TABLE 8 are detected. For this, the first-generation fragment(s) indicated in TABLE 8 is (are) detected. The application, to which each transition, i.e. each peptide associated with its first-generation fragment, makes it possible to respond, is specified in the clinical interest column of TABLE 8 with the letters I, T, R and V. I denotes the confirmation of the identification of the microorganism, T the typing, R the resistance to at least one antibiotic and V the detection of virulence factors.

TABLE 8

| Transition number | Protein | Peptide (SEQ. ID NO.) | first-generation fragment ion | Clinical interest |
|---|---|---|---|---|
| 1 | ACON2 | ILEIEGLPDLK (46) | y7 singly charged | I + T |
| 2 | ACON2 | ILEIEGLPDLK (46) | y8 singly charged | I + T |
| 3 | ACON2 | ILEIEGLPDLK (46) | y9 singly charged | I + T |
| 4 | ACON2 | VADGATVVSTSTR (47) | y7 singly charged | I + T |
| 5 | ACON2 | VADGATVVSTSTR (47) | y8 singly charged | I + T |
| 6 | ACON2 | VADGATVVSTSTR (47) | y9 singly charged | I + T |
| 7 | ASPG2 | TNTTDVATFK (48) | y6 singly charged | I + T |
| 8 | ASPG2 | TNTTDVATFK (48) | y7 singly charged | I + T |
| 9 | ASPG2 | TNTTDVATFK (48) | y8 singly charged | I + T |
| 10 | FABB | LDTTGLIDR (49) | y6 singly charged | I + T |
| 11 | FABB | LDTTGLIDR (46) | y7 singly charged | I + T |

TABLE 8-continued

| Transition number | Protein | Peptide (SEQ. ID NO.) | first-generation fragment ion | Clinical interest |
|---|---|---|---|---|
| 12 | FABB | LDTTGLIDR (46) | y8 singly charged | I + T |
| 13 | FABB | VGLIAGSGGGSPR (50) | y8 singly charged | I + T |
| 14 | FABB | VGLIAGSGGGSPR (50) | y9 singly charged | I + T |
| 15 | FABB | VGLIAGSGGGSPR (50) | y10 singly charged | I + T |
| 16 | GLNH | AIDFSDGYYK (51) | y6 singly charged | I + T |
| 17 | GLNH | AIDFSDGYYK (51) | y7 singly charged | I + T |
| 18 | GLNH | AIDFSDGYYK (51) | y8 singly charged | I + T |
| 19 | MODA | LGAWDTLSPK (52) | y7 singly charged | I + T |
| 20 | MODA | LGAWDTLSPK (52) | y8 singly charged | I + T |
| 21 | MODA | LGAWDTLSPK (52) | y9 singly charged | I + T |
| 22 | ODP2 | FGEIEEVELGR (53) | y7 singly charged | I + T |
| 23 | ODP2 | FGEIEEVELGR (53) | y8 singly charged | I + T |
| 24 | ODP2 | FGEIEEVELGR (53) | y9 singly charged | I + T |
| 25 | OMPC | INLLDDNQFTR (54) | y7 singly charged | I + T |
| 26 | OMPC | INLLDDNQFTR (54) | y8 singly charged | I + T |
| 27 | OMPC | INLLDDNQFTR (54) | y9 singly charged | I + T |
| 28 | PFLB | LATAWEGFTK (55) | y6 singly charged | I + T |
| 29 | PFLB | LATAWEGFTK (55) | y7 singly charged | I + T |
| 30 | PFLB | LATAWEGFTK (55) | y8 singly charged | I + T |
| 31 | SUCD | DSILEAIDAGIK (56) | y8 singly charged | I + T |
| 32 | SUCD | DSILEAIDAGIK (56) | y9 singly charged | I + T |
| 33 | SUCD | DSILEAIDAGIK (56) | y10 singly charged | I + T |
| 34 | SUCD | FAALEAAGVK (57) | y7 singly charged | I + T |
| 35 | SUCD | FAALEAAGVK (57) | y8 singly charged | I + T |
| 36 | SUCD | FAALEAAGVK (57) | y9 singly charged | I + T |
| 37 | SUCD | SLADIGEALK (58) | y6 singly charged | I + T |
| 38 | SUCD | SLADIGEALK (58) | y7 singly charged | I + T |
| 39 | SUCD | SLADIGEALK (58) | y8 singly charged | I + T |
| 40 | TKT1 | TEEQLANIAR (59) | y7 singly charged | I + T |
| 41 | TKT1 | TEEQLANIAR (59) | y8 singly charged | I + T |
| 42 | TKT1 | TEEQLANIAR (59) | y9 singly charged | I + T |
| 43 | YFCZ | AEAEQTLAALTEK (60) | y8 singly charged | I + T |
| 44 | YFCZ | AEAEQTLAALTEK (60) | y9 singly charged | I + T |
| 45 | YFCZ | AEAEQTLAALTEK (60) | y10 singly charged | I + T |
| 46 | YGAU | SGDTLSAISK (61) | y6 singly charged | I + T |
| 47 | YGAU | SGDTLSAISK (61) | y7 singly charged | I + T |
| 48 | YGAU | SGDTLSAISK (61) | y8 singly charged | I + T |
| 49 | TEM-2 | LLTGELLTLASR (62) | y7 singly charged | R + T |
| 50 | TEM-2 | LLTGELLTLASR (62) | y8 singly charged | R + T |
| 51 | TEM-2 | LLTGELLTLASR (62) | y9 singly charged | R + T |
| 52 | TEM-2 | SALPAGWFIADK (63) | y7 singly charged | R + T |
| 53 | TEM-2 | SALPAGWFIADK (63) | y8 singly charged | R + T |
| 54 | TEM-2 | SALPAGWFIADK (63) | y9 singly charged | R + T |
| 55 | TEM-2 | VAGPLLR (64) | y4 singly charged | R + T |
| 56 | TEM-2 | VAGPLLR (64) | y5 singly charged | R + T |
| 57 | TEM-2 | VAGPLLR (64) | y6 singly charged | R + T |
| 58 | TEM-2 | VGYIELDLNSGK (65) | y8 singly charged | R + T |
| 59 | TEM-2 | VGYIELDLNSGK (65) | y9 singly charged | R + T |
| 60 | TEM-2 | VGYIELDLNSGK (65) | y10 singly charged | R + T |
| 61 | TEM-2 | VLLCGAVLSR (66) | y7 singly charged | R + T |
| 62 | TEM-2 | VLLCGAVLSR (66) | y8 singly charged | R + T |
| 63 | TEM-2 | VLLCGAVLSR (66) | y9 singly charged | R + T |
| 64 | ASPA | ISDIPEFVR (67) | y5 singly charged | T |
| 65 | ASPA | ISDIPEFVR (67) | y6 singly charged | T |
| 66 | ASPA | ISDIPEFVR (67) | y7 singly charged | T |
| 67 | ASPA | IEEDLLGTR (68) | y6 singly charged | T |
| 68 | ASPA | IEEDLLGTR (68) | y7 singly charged | T |
| 69 | ASPA | IEEDLLGTR (68) | y8 singly charged | T |
| 70 | ASPA | LVDAINQLR (69) | y6 singly charged | T |
| 71 | ASPA | LVDAINQLR (69) | y7 singly charged | T |
| 72 | ASPA | LVDAINQLR (69) | y8 singly charged | T |
| 73 | ATPA | TALAIDAIINQR (70) | y7 singly charged | T |
| 74 | ATPA | TALAIDAIINQR (70) | y8 singly charged | T |
| 75 | ATPA | TALAIDAIINQR (70) | y9 singly charged | T |
| 76 | ATPA | VVNTLGAPIDGK (71) | y7 singly charged | T |
| 77 | ATPA | VVNTLGAPIDGK (71) | y8 singly charged | T |
| 78 | ATPA | VVNTLGAPIDGK (71) | y9 singly charged | T |
| 79 | CH10 | SAGGIVLTGSAAAK (72) | y9 singly charged | T |
| 80 | CH10 | SAGGIVLTGSAAAK (72) | y10 singly charged | T |
| 81 | CH10 | SAGGIVLTGSAAAK (72) | y11 singly charged | T |
| 82 | CH60 | AVTAAVEELK (73) | y6 singly charged | T |
| 83 | CH60 | AVTAAVEELK (73) | y7 singly charged | T |
| 84 | CH60 | AVTAAVEELK (73) | y8 singly charged | T |
| 85 | DBHB | ALDAIIASVTESLK (74) | y8 singly charged | T |
| 86 | DBHB | ALDAIIASVTESLK (74) | y9 singly charged | T |
| 87 | DBHB | ALDAIIASVTESLK (74) | y10 singly charged | T |
| 88 | DCEB | YWDVELR (75) | y5 singly charged | T |

TABLE 8-continued

| Transition number | Protein | Peptide (SEQ. ID NO.) | first-generation fragment ion | Clinical interest |
|---|---|---|---|---|
| 89 | DCEB | YWDVELR (75) | y6 singly charged | T |
| 90 | DCEB | YWDVELR (75) | y4 singly charged | T |
| 91 | DHSA | LPGILELSR (76) | y6 singly charged | T |
| 92 | DHSA | LPGILELSR (76) | y7 singly charged | T |
| 93 | DHSA | LPGILELSR (76) | y8 singly charged | T |
| 94 | DPS | SKATNLLYTR (77) | y6 singly charged | T |
| 95 | DPS | SKATNLLYTR (77) | y7 singly charged | T |
| 96 | DPS | SKATNLLYTR (77) | y8 singly charged | T |
| 97 | HNS | SEALKILNNIR (78) | y7 singly charged | T |
| 98 | HNS | SEALKILNNIR (78) | y8 singly charged | T |
| 99 | HNS | SEALKILNNIR (78) | y9 singly charged | T |
| 100 | MDH | LFGVTTLDIIR (79) | y6 singly charged | T |
| 101 | MDH | LFGVTTLDIIR (79) | y7 singly charged | T |
| 102 | MDH | LFGVTTLDIIR (79) | y8 singly charged | T |
| 103 | PGK | ASLPTIELALK (80) | y7 singly charged | T |
| 104 | PGK | ASLPTIELALK (80) | y8 singly charged | T |
| 105 | PGK | ASLPTIELALK (80) | y9 singly charged | T |
| 106 | PUR7 | LLSDTECLVK (81) | y6 singly charged | T |
| 107 | PUR7 | LLSDTECLVK (81) | y7 singly charged | T |
| 108 | PUR7 | LLSDTECLVK (81) | y8 singly charged | T |
| 109 | RL4 | SILSELVR (82) | y5 singly charged | T |
| 110 | RL4 | SILSELVR (82) | y6 singly charged | T |
| 111 | RL4 | SILSELVR (82) | y7 singly charged | T |
| 112 | RS1 | GGFTVELNGIR (83) | y7 singly charged | T |
| 113 | RS1 | GGFTVELNGIR (83) | y8 singly charged | T |
| 114 | RS1 | GGFTVELNGIR (83) | y9 singly charged | T |
| 115 | YJGF | TGEVPADVAAQAR (84) | y8 singly charged | T |
| 116 | YJGF | TGEVPADVAAQAR (84) | y9 singly charged | T |
| 117 | YJGF | TGEVPADVAAQAR (84) | y10 singly charged | T |
| 118 | stx1A | TYVDSLNVIR (85) | y6 singly charged | V + T |
| 119 | stx1A | TYVDSLNVIR (85) | y7 singly charged | V + T |
| 120 | stx1A | TYVDSLNVIR (85) | y8 singly charged | V + T |
| 121 | stx1A-2A | FVTVTAEALR (86) | y7 singly charged | V + T |
| 122 | stx1A-2A | FVTVTAEALR (86) | y8 singly charged | V + T |
| 123 | stx2A | ISNVLPEYR (87) | y6 singly charged | V + T |
| 124 | stx2A | ISNVLPEYR (87) | y7 singly charged | V + T |
| 125 | stx2A | ISNVLPEYR (87) | y8 singly charged | V + T |

The charge state of the precursor peptide, its retention time and the transitions, i.e. the ratios $(m/z)_1$ in Q1 and $(m/z)_2$ in Q3, are indicated in TABLE 9. The collision energy used to fragment the precursor ion is also indicated in TABLE 9.

TABLE 9

| Transition number | Precursor charge state | Retention time | (m/z) filtered in Q1 | (m/z) filtered in Q3 | Collision energy |
|---|---|---|---|---|---|
| 1 | 2 | 19.04 | 620.36 | 771.42 | 36 |
| 2 | 2 | 19.04 | 620.36 | 884.51 | 36 |
| 3 | 2 | 19.04 | 620.36 | 1013.55 | 36 |
| 4 | 2 | 8.93 | 632.33 | 749.42 | 37 |
| 5 | 2 | 8.93 | 632.33 | 850.46 | 37 |
| 6 | 2 | 8.93 | 632.33 | 921.5 | 37 |
| 7 | 2 | 9.99 | 549.28 | 680.36 | 32 |
| 8 | 2 | 9.99 | 549.28 | 781.41 | 32 |
| 9 | 2 | 9.99 | 549.28 | 882.46 | 32 |
| 10 | 2 | 12.89 | 502.27 | 674.38 | 30 |
| 11 | 2 | 12.89 | 502.27 | 775.43 | 30 |
| 12 | 2 | 12.89 | 502.27 | 890.46 | 30 |
| 13 | 2 | 10.63 | 564.31 | 674.32 | 33 |
| 14 | 2 | 10.63 | 564.31 | 745.36 | 33 |
| 15 | 2 | 10.63 | 564.31 | 858.44 | 33 |
| 16 | 2 | 14.12 | 589.77 | 732.32 | 34 |
| 17 | 2 | 14.12 | 589.77 | 879.39 | 34 |
| 18 | 2 | 14.12 | 589.77 | 994.42 | 34 |
| 19 | 2 | 15.09 | 544.29 | 846.44 | 32 |
| 20 | 2 | 15.09 | 544.29 | 917.47 | 32 |
| 21 | 2 | 15.09 | 544.29 | 974.49 | 32 |
| 22 | 2 | 15.61 | 639.32 | 831.42 | 37 |
| 23 | 2 | 15.61 | 639.32 | 944.5 | 37 |
| 24 | 2 | 15.61 | 639.32 | 1073.55 | 37 |
| 25 | 2 | 16.42 | 674.85 | 895.39 | 39 |
| 26 | 2 | 16.42 | 674.85 | 1008.47 | 39 |
| 27 | 2 | 16.42 | 674.85 | 1121.56 | 39 |
| 28 | 2 | 15.49 | 562.29 | 767.37 | 33 |
| 29 | 2 | 15.49 | 562.29 | 838.41 | 33 |
| 30 | 2 | 15.49 | 562.29 | 939.46 | 33 |
| 31 | 2 | 19.84 | 622.84 | 816.45 | 36 |
| 32 | 2 | 19.84 | 622.84 | 929.53 | 36 |
| 33 | 2 | 19.84 | 622.84 | 1042.61 | 36 |
| 34 | 2 | 13.35 | 488.78 | 687.4 | 29 |
| 35 | 2 | 13.35 | 488.78 | 758.44 | 29 |
| 36 | 2 | 13.35 | 488.78 | 829.48 | 29 |
| 37 | 2 | 15.56 | 508.78 | 630.38 | 30 |
| 38 | 2 | 15.56 | 508.78 | 745.41 | 30 |
| 39 | 2 | 15.56 | 508.78 | 816.45 | 30 |
| 40 | 2 | 11.4 | 572.8 | 785.46 | 34 |
| 41 | 2 | 11.4 | 572.8 | 914.51 | 34 |
| 42 | 2 | 11.4 | 572.8 | 1043.55 | 34 |
| 43 | 2 | 14.85 | 687.86 | 846.49 | 39 |
| 44 | 2 | 14.85 | 687.86 | 974.55 | 39 |
| 45 | 2 | 14.85 | 687.86 | 1103.59 | 39 |
| 46 | 2 | 9.8 | 489.76 | 618.38 | 29 |
| 47 | 2 | 9.8 | 489.76 | 719.43 | 29 |
| 48 | 2 | 9.8 | 489.76 | 834.46 | 29 |
| 49 | 2 | 19.38 | 643.89 | 773.49 | 33 |
| 50 | 2 | 19.38 | 643.89 | 902.53 | 33 |
| 51 | 2 | 19.38 | 643.89 | 959.55 | 33 |
| 52 | 2 | 18.43 | 638.34 | 836.43 | 33 |
| 53 | 2 | 18.43 | 638.34 | 907.47 | 33 |
| 54 | 2 | 18.43 | 638.34 | 1004.52 | 33 |

TABLE 9-continued

| Transition number | Precursor charge state | Retention time | (m/z) filtered in Q1 | (m/z) filtered in Q3 | Collision energy |
|---|---|---|---|---|---|
| 55 | 2 | 10.79 | 363.24 | 498.34 | 21 |
| 56 | 2 | 10.79 | 363.24 | 555.36 | 21 |
| 57 | 2 | 10.79 | 363.24 | 626.4 | 21 |
| 58 | 2 | 15.94 | 654.35 | 875.45 | 34 |
| 59 | 2 | 15.94 | 654.35 | 988.53 | 34 |
| 60 | 2 | 15.94 | 654.35 | 1151.59 | 34 |
| 61 | 2 | 14.8 | 544.32 | 762.39 | 29 |
| 62 | 2 | 14.8 | 544.32 | 875.48 | 29 |
| 63 | 2 | 14.8 | 544.32 | 988.56 | 29 |
| 64 | 2 | 12.8 | 538.29 | 647.35 | 29 |
| 65 | 2 | 12.8 | 538.29 | 760.44 | 29 |
| 66 | 2 | 12.8 | 538.29 | 875.46 | 29 |
| 67 | 2 | 12.9 | 523.28 | 674.38 | 28 |
| 68 | 2 | 12.9 | 523.28 | 803.43 | 28 |
| 69 | 2 | 12.9 | 523.28 | 932.47 | 28 |
| 70 | 2 | 15.31 | 521.31 | 714.43 | 28 |
| 71 | 2 | 15.31 | 521.31 | 829.45 | 28 |
| 72 | 2 | 15.31 | 521.31 | 928.52 | 28 |
| 73 | 2 | 17.37 | 649.87 | 829.45 | 34 |
| 74 | 2 | 17.37 | 649.87 | 942.54 | 34 |
| 75 | 2 | 17.37 | 649.87 | 1013.57 | 34 |
| 76 | 2 | 11.94 | 592.34 | 657.36 | 31 |
| 77 | 2 | 11.94 | 592.34 | 770.44 | 31 |
| 78 | 2 | 11.94 | 592.34 | 871.49 | 31 |
| 79 | 2 | 11.08 | 601.84 | 817.48 | 31 |
| 80 | 2 | 11.08 | 601.84 | 930.56 | 31 |
| 81 | 2 | 11.08 | 601.84 | 987.58 | 31 |
| 82 | 2 | 11.86 | 515.79 | 688.39 | 28 |
| 83 | 2 | 11.86 | 515.79 | 759.42 | 28 |
| 84 | 2 | 11.86 | 515.79 | 860.47 | 28 |
| 85 | 2 | 22.24 | 715.91 | 834.46 | 36 |
| 86 | 2 | 22.24 | 715.91 | 947.54 | 36 |
| 87 | 2 | 22.24 | 715.91 | 1060.62 | 36 |
| 88 | 2 | 15.35 | 490.75 | 631.34 | 27 |
| 89 | 2 | 15.35 | 490.75 | 817.42 | 27 |
| 90 | 2 | 15.35 | 490.75 | 516.31 | 27 |
| 91 | 2 | 17.1 | 499.31 | 730.45 | 27 |
| 92 | 2 | 17.1 | 499.31 | 787.47 | 27 |
| 93 | 2 | 17.1 | 499.31 | 884.52 | 27 |
| 94 | 2 | 10.02 | 583.83 | 779.44 | 31 |
| 95 | 2 | 10.02 | 583.83 | 880.49 | 31 |
| 96 | 2 | 10.02 | 583.83 | 951.53 | 31 |
| 97 | 2 | 14.94 | 635.88 | 870.55 | 33 |
| 98 | 2 | 14.94 | 635.88 | 983.64 | 33 |
| 99 | 2 | 14.94 | 635.88 | 1054.67 | 33 |
| 100 | 2 | 20.34 | 624.37 | 730.45 | 32 |
| 101 | 2 | 20.34 | 624.37 | 831.49 | 32 |
| 102 | 2 | 20.34 | 624.37 | 930.56 | 32 |
| 103 | 2 | 18.16 | 578.35 | 787.49 | 30 |
| 104 | 2 | 18.16 | 578.35 | 884.55 | 30 |
| 105 | 2 | 18.16 | 578.35 | 997.63 | 30 |
| 106 | 2 | 13.11 | 589.31 | 749.39 | 31 |
| 107 | 2 | 13.11 | 589.31 | 864.41 | 31 |
| 108 | 2 | 13.11 | 589.31 | 951.45 | 31 |
| 109 | 2 | 17.68 | 458.78 | 603.35 | 25 |
| 110 | 2 | 17.68 | 458.78 | 716.43 | 25 |
| 111 | 2 | 17.68 | 458.78 | 829.51 | 25 |
| 112 | 2 | 15.99 | 581.81 | 800.46 | 31 |
| 113 | 2 | 15.99 | 581.81 | 901.51 | 31 |
| 114 | 2 | 15.99 | 581.81 | 1048.58 | 31 |
| 115 | 2 | 10.34 | 642.83 | 801.42 | 33 |
| 116 | 2 | 10.34 | 642.83 | 898.47 | 33 |
| 117 | 2 | 10.34 | 642.83 | 997.54 | 33 |
| 118 | 2 | 14.85 | 590.32 | 701.43 | 31 |
| 119 | 2 | 14.85 | 590.32 | 816.46 | 31 |
| 120 | 2 | 14.85 | 590.32 | 915.53 | 31 |
| 121 | 2 | 14.15 | 553.81 | 759.44 | 29 |
| 122 | 2 | 14.15 | 553.81 | 860.48 | 29 |
| 123 | 2 | 12.9 | 545.8 | 776.43 | 29 |
| 124 | 2 | 12.9 | 545.8 | 890.47 | 29 |
| 125 | 2 | 12.9 | 545.8 | 977.51 | 29 |

The other machine parameters used are the following:
Scan type: MRM
Scheduled MRM: yes
Polarity: Positive
Ionization source: Turbo V™ (Applied BioSystems)
Q1 setting: Filtering with unit resolution
Q3 setting: Filtering with unit resolution
Inter-scan pause: 5.00 msec
Scan speed: 10 Da/s
Curtain gas: 50.00 psi
Cone voltage: 5500.00 V
Source temperature: 550.00° C.
Nebulizing gas: 50.00 psi
Heating gas: 40.00 psi
Dynamic filling: activated
Declustering potential (DP): 100.00 V
Entry potential before Q0 (EP): 9.00 V
Collision cell exit potential (CXP): 35 V
Total cycle time: 1.2 sec
Detection window 80 sec The areas obtained for each of the transitions and for each of the microorganisms studied were measured. All the transitions with an area greater than or equal to 2500 (arbitrary units) are considered to be positive and have been denoted "1" in tables 10A and 10B. All the transitions with an area less than 2500 are considered to be negative and have been denoted 0 in tables 10A and 10B. When no signal peak was observed, the transition was noted as negative.

The positive-transition number is then summed for the I, R and V applications and reported in TABLE 11:

TABLE 10A

| Transition number | AST1 | AST2 | AST3 | AST4 | AST5 | VIR41 | VIR42 | VIR43 | VIR44 |
|---|---|---|---|---|---|---|---|---|---|
| 1 | 1 | 1 | 1 | 1 | 1 | 1 | 1 | 1 | 1 |
| 2 | 1 | 1 | 1 | 1 | 1 | 1 | 1 | 1 | 1 |
| 3 | 1 | 1 | 1 | 1 | 1 | 1 | 1 | 1 | 1 |
| 4 | 1 | 1 | 1 | 1 | 1 | 1 | 1 | 1 | 1 |
| 5 | 1 | 1 | 1 | 1 | 1 | 1 | 1 | 1 | 1 |
| 6 | 1 | 1 | 1 | 1 | 1 | 1 | 1 | 1 | 1 |
| 7 | 1 | 1 | 1 | 1 | 1 | 1 | 1 | 1 | 1 |
| 8 | 1 | 1 | 1 | 1 | 1 | 1 | 1 | 1 | 1 |
| 9 | 1 | 1 | 1 | 1 | 1 | 1 | 1 | 1 | 1 |
| 10 | 1 | 1 | 1 | 1 | 1 | 1 | 1 | 1 | 1 |
| 11 | 1 | 1 | 1 | 1 | 1 | 1 | 1 | 1 | 1 |
| 12 | 1 | 1 | 1 | 1 | 1 | 1 | 1 | 1 | 1 |
| 13 | 1 | 1 | 1 | 1 | 1 | 1 | 1 | 1 | 1 |
| 14 | 1 | 1 | 1 | 1 | 1 | 1 | 1 | 1 | 1 |

TABLE 10A-continued

| Transition number | AST1 | AST2 | AST3 | AST4 | AST5 | VIR41 | VIR42 | VIR43 | VIR44 |
|---|---|---|---|---|---|---|---|---|---|
| 15 | 1 | 1 | 1 | 1 | 1 | 1 | 1 | 1 | 1 |
| 16 | 1 | 1 | 1 | 1 | 1 | 1 | 1 | 1 | 1 |
| 17 | 1 | 1 | 1 | 1 | 1 | 1 | 1 | 1 | 1 |
| 18 | 1 | 1 | 1 | 1 | 1 | 1 | 1 | 1 | 1 |
| 19 | 1 | 1 | 1 | 1 | 1 | 1 | 1 | 1 | 1 |
| 20 | 1 | 1 | 1 | 1 | 1 | 1 | 1 | 1 | 1 |
| 21 | 1 | 1 | 1 | 1 | 1 | 1 | 1 | 1 | 1 |
| 22 | 1 | 1 | 1 | 1 | 1 | 1 | 1 | 1 | 1 |
| 23 | 1 | 1 | 1 | 1 | 1 | 1 | 1 | 1 | 1 |
| 24 | 1 | 1 | 1 | 1 | 1 | 1 | 1 | 1 | 1 |
| 25 | 1 | 1 | 1 | 1 | 1 | 1 | 1 | 1 | 1 |
| 26 | 1 | 1 | 1 | 1 | 1 | 1 | 1 | 1 | 1 |
| 27 | 1 | 1 | 1 | 1 | 1 | 0 | 0 | 0 | 0 |
| 28 | 1 | 1 | 1 | 1 | 1 | 1 | 1 | 1 | 1 |
| 29 | 1 | 1 | 1 | 1 | 1 | 1 | 1 | 1 | 1 |
| 30 | 1 | 1 | 1 | 1 | 1 | 1 | 1 | 1 | 1 |
| 31 | 1 | 1 | 1 | 1 | 1 | 1 | 1 | 1 | 1 |
| 32 | 1 | 1 | 1 | 1 | 1 | 1 | 1 | 1 | 1 |
| 33 | 1 | 1 | 1 | 1 | 1 | 1 | 1 | 1 | 1 |
| 34 | 1 | 1 | 1 | 1 | 1 | 1 | 1 | 1 | 1 |
| 35 | 1 | 1 | 1 | 1 | 1 | 1 | 1 | 1 | 1 |
| 36 | 1 | 1 | 1 | 1 | 1 | 1 | 1 | 1 | 1 |
| 37 | 1 | 1 | 1 | 1 | 1 | 1 | 1 | 1 | 1 |
| 38 | 1 | 1 | 1 | 1 | 1 | 1 | 1 | 1 | 1 |
| 39 | 1 | 1 | 1 | 1 | 1 | 1 | 1 | 1 | 1 |
| 40 | 1 | 1 | 1 | 1 | 1 | 1 | 1 | 1 | 1 |
| 41 | 1 | 1 | 1 | 1 | 1 | 1 | 1 | 1 | 1 |
| 42 | 1 | 1 | 0 | 0 | 0 | 1 | 1 | 1 | 1 |
| 43 | 1 | 1 | 1 | 1 | 1 | 1 | 1 | 1 | 1 |
| 44 | 1 | 1 | 1 | 1 | 1 | 1 | 1 | 1 | 1 |
| 45 | 1 | 1 | 1 | 1 | 1 | 1 | 1 | 1 | 1 |
| 46 | 1 | 1 | 1 | 1 | 1 | 1 | 1 | 1 | 1 |
| 47 | 1 | 1 | 1 | 1 | 1 | 1 | 1 | 1 | 1 |
| 48 | 1 | 1 | 1 | 1 | 1 | 1 | 1 | 1 | 1 |
| 49 | 0 | 1 | 1 | 1 | 1 | 1 | 1 | 1 | 1 |
| 50 | 0 | 1 | 1 | 1 | 1 | 0 | 0 | 0 | 0 |
| 51 | 0 | 1 | 1 | 1 | 1 | 1 | 1 | 1 | 1 |
| 52 | 0 | 1 | 1 | 1 | 1 | 0 | 0 | 1 | 1 |
| 53 | 0 | 1 | 1 | 1 | 1 | 0 | 0 | 0 | 0 |
| 54 | 0 | 1 | 1 | 1 | 1 | 0 | 0 | 0 | 0 |
| 55 | 0 | 1 | 1 | 1 | 1 | 1 | 1 | 1 | 1 |
| 56 | 1 | 1 | 1 | 1 | 1 | 0 | 0 | 0 | 1 |
| 57 | 0 | 1 | 1 | 1 | 1 | 0 | 0 | 0 | 0 |
| 58 | 0 | 1 | 1 | 1 | 1 | 0 | 0 | 0 | 0 |
| 59 | 0 | 1 | 1 | 1 | 1 | 0 | 0 | 0 | 0 |
| 60 | 0 | 1 | 1 | 1 | 1 | 0 | 0 | 0 | 0 |
| 61 | 0 | 1 | 1 | 1 | 1 | 0 | 0 | 0 | 0 |
| 62 | 0 | 1 | 1 | 1 | 1 | 0 | 1 | 1 | 1 |
| 63 | 0 | 1 | 1 | 1 | 1 | 0 | 0 | 0 | 0 |
| 64 | 0 | 0 | 0 | 0 | 0 | 0 | 0 | 0 | 1 |
| 65 | 0 | 0 | 0 | 0 | 0 | 0 | 0 | 0 | 1 |
| 66 | 0 | 0 | 0 | 0 | 0 | 1 | 1 | 1 | 1 |
| 67 | 1 | 1 | 1 | 1 | 1 | 1 | 1 | 1 | 1 |
| 68 | 1 | 1 | 1 | 1 | 1 | 1 | 1 | 1 | 1 |
| 69 | 1 | 1 | 1 | 1 | 1 | 1 | 1 | 1 | 1 |
| 70 | 1 | 1 | 1 | 1 | 1 | 1 | 1 | 1 | 1 |
| 71 | 1 | 1 | 1 | 1 | 1 | 1 | 1 | 1 | 1 |
| 72 | 1 | 1 | 1 | 1 | 1 | 1 | 1 | 1 | 1 |
| 73 | 1 | 1 | 1 | 1 | 1 | 1 | 1 | 1 | 1 |
| 74 | 1 | 1 | 1 | 1 | 1 | 1 | 1 | 1 | 1 |
| 75 | 1 | 1 | 1 | 1 | 1 | 1 | 1 | 1 | 1 |
| 76 | 1 | 1 | 1 | 1 | 1 | 1 | 1 | 1 | 1 |
| 77 | 1 | 1 | 1 | 1 | 1 | 1 | 1 | 1 | 1 |
| 78 | 1 | 1 | 1 | 1 | 1 | 1 | 1 | 1 | 1 |
| 79 | 1 | 1 | 1 | 1 | 1 | 1 | 1 | 1 | 1 |
| 80 | 1 | 1 | 1 | 1 | 1 | 1 | 1 | 1 | 1 |
| 81 | 1 | 1 | 1 | 1 | 1 | 1 | 1 | 1 | 1 |
| 82 | 1 | 1 | 1 | 1 | 1 | 1 | 1 | 1 | 1 |
| 83 | 1 | 1 | 1 | 1 | 1 | 1 | 1 | 1 | 1 |
| 84 | 1 | 1 | 1 | 1 | 1 | 1 | 1 | 1 | 1 |
| 85 | 1 | 1 | 1 | 1 | 1 | 1 | 1 | 1 | 1 |
| 86 | 1 | 1 | 1 | 1 | 1 | 1 | 1 | 1 | 1 |
| 87 | 1 | 1 | 1 | 1 | 1 | 1 | 1 | 1 | 1 |
| 88 | 1 | 1 | 1 | 1 | 1 | 1 | 1 | 1 | 1 |
| 89 | 0 | 1 | 1 | 1 | 1 | 1 | 1 | 1 | 1 |
| 90 | 1 | 1 | 1 | 1 | 1 | 1 | 1 | 1 | 1 |
| 91 | 1 | 1 | 1 | 1 | 1 | 1 | 1 | 1 | 1 |

TABLE 10A-continued

| Transition number | AST1 | AST2 | AST3 | AST4 | AST5 | VIR41 | VIR42 | VIR43 | VIR44 |
|---|---|---|---|---|---|---|---|---|---|
| 92 | 1 | 1 | 1 | 1 | 1 | 1 | 1 | 1 | 1 |
| 93 | 1 | 1 | 1 | 1 | 1 | 1 | 1 | 1 | 1 |
| 94 | 1 | 1 | 1 | 1 | 1 | 1 | 1 | 1 | 0 |
| 95 | 1 | 1 | 1 | 1 | 1 | 1 | 1 | 1 | 0 |
| 96 | 1 | 1 | 1 | 1 | 1 | 1 | 1 | 1 | 1 |
| 97 | 0 | 0 | 0 | 0 | 0 | 1 | 1 | 1 | 1 |
| 98 | 0 | 0 | 0 | 0 | 0 | 1 | 1 | 1 | 0 |
| 99 | 0 | 0 | 0 | 0 | 0 | 1 | 0 | 0 | 0 |
| 100 | 1 | 1 | 1 | 1 | 1 | 1 | 1 | 1 | 1 |
| 101 | 1 | 1 | 1 | 1 | 1 | 1 | 1 | 1 | 1 |
| 102 | 1 | 1 | 1 | 1 | 1 | 1 | 1 | 1 | 1 |
| 103 | 1 | 1 | 1 | 1 | 1 | 1 | 1 | 1 | 1 |
| 104 | 1 | 1 | 1 | 1 | 1 | 1 | 1 | 1 | 1 |
| 105 | 1 | 1 | 1 | 1 | 1 | 1 | 1 | 1 | 1 |
| 106 | 1 | 1 | 1 | 1 | 1 | 1 | 1 | 1 | 1 |
| 107 | 1 | 1 | 1 | 1 | 1 | 1 | 1 | 1 | 1 |
| 108 | 1 | 1 | 1 | 1 | 1 | 1 | 1 | 1 | 1 |
| 109 | 1 | 1 | 1 | 1 | 1 | 1 | 1 | 1 | 1 |
| 110 | 1 | 1 | 1 | 1 | 1 | 1 | 1 | 1 | 1 |
| 111 | 1 | 1 | 1 | 1 | 1 | 1 | 1 | 1 | 1 |
| 112 | 1 | 1 | 1 | 1 | 1 | 1 | 1 | 1 | 1 |
| 113 | 1 | 1 | 1 | 1 | 1 | 1 | 1 | 1 | 1 |
| 114 | 0 | 0 | 0 | 0 | 0 | 0 | 0 | 0 | 1 |
| 115 | 1 | 1 | 1 | 1 | 1 | 1 | 1 | 1 | 1 |
| 116 | 1 | 1 | 1 | 1 | 1 | 1 | 1 | 1 | 1 |
| 117 | 1 | 1 | 1 | 1 | 1 | 1 | 1 | 1 | 1 |
| 118 | 0 | 0 | 0 | 0 | 0 | 1 | 0 | 1 | 0 |
| 119 | 1 | 0 | 0 | 0 | 0 | 1 | 0 | 1 | 0 |
| 120 | 0 | 1 | 1 | 0 | 1 | 1 | 0 | 1 | 0 |
| 121 | 0 | 0 | 0 | 0 | 0 | 1 | 1 | 1 | 1 |
| 122 | 1 | 0 | 0 | 0 | 0 | 1 | 1 | 1 | 1 |
| 123 | 0 | 0 | 0 | 0 | 0 | 1 | 1 | 0 | 1 |
| 124 | 0 | 1 | 0 | 0 | 1 | 1 | 1 | 1 | 1 |
| 125 | 0 | 0 | 0 | 0 | 0 | 1 | 1 | 0 | 1 |

TABLE 10B

| Transition number | VIR45 | ID6 | ID7 | ID8 | ID9 | ID10 | VIR10 | VIR19 | VIR28 |
|---|---|---|---|---|---|---|---|---|---|
| 1 | 1 | 1 | 1 | 1 | 1 | 1 | 0 | 0 | 0 |
| 2 | 1 | 1 | 1 | 1 | 1 | 1 | 0 | 0 | 0 |
| 3 | 1 | 1 | 1 | 1 | 1 | 1 | 0 | 0 | 0 |
| 4 | 1 | 1 | 1 | 1 | 1 | 1 | 0 | 0 | 0 |
| 5 | 1 | 1 | 1 | 1 | 1 | 1 | 0 | 0 | 0 |
| 6 | 1 | 1 | 1 | 1 | 1 | 1 | 0 | 0 | 0 |
| 7 | 1 | 1 | 1 | 1 | 1 | 1 | 0 | 0 | 0 |
| 8 | 1 | 1 | 1 | 1 | 1 | 1 | 0 | 0 | 0 |
| 9 | 1 | 1 | 1 | 1 | 1 | 1 | 0 | 0 | 0 |
| 10 | 1 | 1 | 1 | 1 | 1 | 1 | 0 | 0 | 0 |
| 11 | 1 | 1 | 1 | 1 | 1 | 1 | 0 | 0 | 1 |
| 12 | 1 | 1 | 1 | 1 | 1 | 1 | 0 | 0 | 0 |
| 13 | 1 | 1 | 1 | 1 | 1 | 1 | 0 | 0 | 0 |
| 14 | 1 | 1 | 1 | 1 | 1 | 1 | 0 | 0 | 1 |
| 15 | 1 | 1 | 1 | 1 | 1 | 1 | 0 | 0 | 0 |
| 16 | 1 | 1 | 1 | 1 | 1 | 1 | 0 | 0 | 0 |
| 17 | 1 | 1 | 1 | 1 | 1 | 1 | 0 | 0 | 0 |
| 18 | 1 | 1 | 1 | 1 | 1 | 1 | 0 | 0 | 0 |
| 19 | 1 | 1 | 1 | 1 | 1 | 1 | 0 | 0 | 0 |
| 20 | 1 | 1 | 1 | 1 | 1 | 1 | 0 | 0 | 0 |
| 21 | 1 | 1 | 1 | 1 | 1 | 1 | 0 | 0 | 0 |
| 22 | 1 | 1 | 1 | 1 | 1 | 1 | 0 | 0 | 0 |
| 23 | 1 | 1 | 1 | 1 | 1 | 1 | 0 | 0 | 0 |
| 24 | 1 | 1 | 1 | 1 | 1 | 1 | 0 | 0 | 0 |
| 25 | 1 | 1 | 1 | 1 | 1 | 1 | 0 | 0 | 0 |
| 26 | 1 | 1 | 1 | 1 | 1 | 1 | 0 | 0 | 0 |
| 27 | 1 | 1 | 1 | 1 | 1 | 1 | 0 | 0 | 0 |
| 28 | 1 | 1 | 1 | 1 | 1 | 1 | 0 | 0 | 0 |
| 29 | 1 | 1 | 1 | 1 | 1 | 1 | 0 | 0 | 0 |
| 30 | 1 | 1 | 1 | 1 | 1 | 1 | 0 | 0 | 0 |
| 31 | 1 | 1 | 1 | 1 | 1 | 1 | 0 | 0 | 0 |
| 32 | 1 | 1 | 1 | 1 | 1 | 1 | 0 | 0 | 0 |
| 33 | 1 | 1 | 0 | 0 | 0 | 0 | 0 | 0 | 0 |
| 34 | 1 | 1 | 1 | 1 | 1 | 1 | 1 | 0 | 0 |

TABLE 10B-continued

| Transition number | VIR45 | ID6 | ID7 | ID8 | ID9 | ID10 | VIR10 | VIR19 | VIR28 |
|---|---|---|---|---|---|---|---|---|---|
| 35 | 1 | 1 | 1 | 1 | 1 | 1 | 0 | 1 | 0 |
| 36 | 1 | 1 | 1 | 1 | 1 | 1 | 0 | 0 | 0 |
| 37 | 1 | 1 | 1 | 1 | 1 | 1 | 0 | 0 | 0 |
| 38 | 1 | 1 | 1 | 1 | 1 | 1 | 0 | 0 | 0 |
| 39 | 1 | 1 | 1 | 1 | 1 | 1 | 0 | 0 | 0 |
| 40 | 1 | 1 | 1 | 1 | 1 | 1 | 0 | 0 | 0 |
| 41 | 1 | 1 | 1 | 1 | 1 | 1 | 0 | 0 | 0 |
| 42 | 1 | 1 | 0 | 0 | 0 | 0 | 0 | 0 | 0 |
| 43 | 1 | 1 | 1 | 1 | 1 | 1 | 0 | 0 | 0 |
| 44 | 1 | 1 | 1 | 1 | 1 | 1 | 0 | 0 | 0 |
| 45 | 1 | 1 | 0 | 0 | 0 | 0 | 0 | 0 | 0 |
| 46 | 1 | 1 | 1 | 1 | 1 | 1 | 0 | 0 | 0 |
| 47 | 1 | 1 | 1 | 1 | 1 | 1 | 0 | 0 | 0 |
| 48 | 1 | 1 | 1 | 1 | 1 | 1 | 0 | 0 | 0 |
| 49 | 1 | 0 | 0 | 0 | 0 | 0 | 0 | 0 | 0 |
| 50 | 0 | 0 | 0 | 0 | 0 | 0 | 0 | 0 | 0 |
| 51 | 1 | 0 | 0 | 0 | 0 | 0 | 0 | 0 | 0 |
| 52 | 1 | 0 | 0 | 0 | 0 | 0 | 0 | 0 | 0 |
| 53 | 0 | 0 | 0 | 0 | 0 | 0 | 0 | 1 | 0 |
| 54 | 0 | 0 | 0 | 0 | 0 | 0 | 0 | 0 | 0 |
| 55 | 1 | 0 | 0 | 0 | 0 | 0 | 0 | 0 | 0 |
| 56 | 0 | 0 | 0 | 0 | 0 | 0 | 0 | 0 | 0 |
| 57 | 0 | 0 | 0 | 0 | 0 | 0 | 0 | 0 | 0 |
| 58 | 0 | 0 | 0 | 0 | 1 | 1 | 1 | 0 | 0 |
| 59 | 0 | 0 | 0 | 0 | 0 | 0 | 0 | 0 | 0 |
| 60 | 0 | 0 | 0 | 0 | 0 | 0 | 0 | 0 | 0 |
| 61 | 0 | 0 | 1 | 1 | 1 | 0 | 0 | 0 | 0 |
| 62 | 1 | 0 | 1 | 1 | 1 | 0 | 0 | 0 | 0 |
| 63 | 0 | 0 | 0 | 0 | 0 | 0 | 0 | 0 | 0 |
| 64 | 1 | 0 | 0 | 0 | 0 | 0 | 0 | 0 | 0 |
| 65 | 1 | 0 | 0 | 0 | 0 | 0 | 0 | 0 | 0 |
| 66 | 1 | 0 | 0 | 0 | 0 | 0 | 0 | 0 | 0 |
| 67 | 1 | 1 | 1 | 1 | 1 | 1 | 0 | 0 | 0 |
| 68 | 1 | 1 | 1 | 1 | 1 | 1 | 1 | 0 | 0 |
| 69 | 1 | 1 | 1 | 1 | 1 | 1 | 0 | 1 | 0 |
| 70 | 1 | 1 | 1 | 1 | 1 | 1 | 0 | 0 | 0 |
| 71 | 1 | 1 | 1 | 1 | 1 | 1 | 0 | 0 | 0 |
| 72 | 1 | 1 | 0 | 0 | 0 | 0 | 0 | 0 | 0 |
| 73 | 1 | 1 | 1 | 1 | 1 | 1 | 0 | 0 | 0 |
| 74 | 1 | 1 | 1 | 1 | 1 | 1 | 0 | 0 | 0 |
| 75 | 1 | 1 | 1 | 1 | 1 | 1 | 0 | 0 | 0 |
| 76 | 1 | 1 | 1 | 1 | 1 | 1 | 0 | 0 | 0 |
| 77 | 1 | 1 | 1 | 1 | 1 | 1 | 0 | 0 | 0 |
| 78 | 1 | 1 | 1 | 1 | 1 | 1 | 0 | 0 | 0 |
| 79 | 1 | 1 | 1 | 1 | 1 | 1 | 1 | 1 | 0 |
| 80 | 1 | 1 | 1 | 1 | 1 | 1 | 0 | 0 | 0 |
| 81 | 1 | 1 | 1 | 1 | 1 | 1 | 0 | 0 | 0 |
| 82 | 1 | 1 | 1 | 1 | 1 | 1 | 0 | 0 | 0 |
| 83 | 1 | 1 | 1 | 1 | 1 | 1 | 0 | 0 | 0 |
| 84 | 1 | 1 | 1 | 1 | 1 | 1 | 0 | 0 | 0 |
| 85 | 1 | 1 | 1 | 1 | 1 | 1 | 0 | 0 | 0 |
| 86 | 1 | 1 | 1 | 1 | 1 | 1 | 0 | 0 | 0 |
| 87 | 1 | 1 | 0 | 0 | 0 | 0 | 0 | 0 | 0 |
| 88 | 1 | 0 | 1 | 1 | 1 | 1 | 0 | 0 | 0 |
| 89 | 1 | 0 | 1 | 1 | 1 | 1 | 0 | 0 | 0 |
| 90 | 1 | 1 | 1 | 1 | 1 | 1 | 0 | 0 | 0 |
| 91 | 1 | 1 | 1 | 1 | 1 | 1 | 1 | 0 | 0 |
| 92 | 1 | 1 | 1 | 1 | 1 | 1 | 0 | 0 | 0 |
| 93 | 1 | 1 | 1 | 1 | 1 | 1 | 0 | 0 | 0 |
| 94 | 0 | 1 | 1 | 1 | 1 | 1 | 0 | 0 | 0 |
| 95 | 1 | 1 | 1 | 1 | 1 | 1 | 0 | 0 | 0 |
| 96 | 1 | 1 | 1 | 1 | 1 | 1 | 0 | 0 | 0 |
| 97 | 1 | 1 | 1 | 1 | 1 | 1 | 0 | 0 | 0 |
| 98 | 1 | 0 | 1 | 0 | 1 | 0 | 0 | 0 | 0 |
| 99 | 0 | 0 | 0 | 0 | 0 | 0 | 0 | 0 | 0 |
| 100 | 1 | 1 | 1 | 1 | 1 | 1 | 0 | 0 | 0 |
| 101 | 1 | 1 | 1 | 1 | 1 | 1 | 1 | 0 | 0 |
| 102 | 1 | 1 | 1 | 1 | 1 | 1 | 0 | 0 | 0 |
| 103 | 1 | 1 | 1 | 1 | 1 | 1 | 0 | 0 | 0 |
| 104 | 1 | 1 | 1 | 1 | 1 | 1 | 0 | 0 | 0 |
| 105 | 1 | 1 | 1 | 1 | 1 | 1 | 0 | 0 | 0 |
| 106 | 1 | 1 | 1 | 1 | 1 | 1 | 0 | 0 | 0 |
| 107 | 1 | 1 | 1 | 1 | 1 | 1 | 0 | 0 | 0 |
| 108 | 1 | 1 | 1 | 1 | 1 | 1 | 0 | 0 | 0 |
| 109 | 1 | 1 | 1 | 1 | 1 | 1 | 0 | 0 | 0 |
| 110 | 1 | 1 | 1 | 1 | 1 | 1 | 0 | 0 | 0 |
| 111 | 1 | 1 | 1 | 1 | 1 | 1 | 0 | 0 | 0 |

TABLE 10B-continued

| Transition number | VIR45 | ID6 | ID7 | ID8 | ID9 | ID10 | VIR10 | VIR19 | VIR28 |
|---|---|---|---|---|---|---|---|---|---|
| 112 | 1 | 1 | 1 | 1 | 1 | 1 | 0 | 0 | 0 |
| 113 | 1 | 1 | 1 | 1 | 1 | 1 | 0 | 0 | 0 |
| 114 | 1 | 0 | 0 | 0 | 0 | 0 | 0 | 0 | 0 |
| 115 | 1 | 1 | 1 | 1 | 1 | 1 | 0 | 0 | 0 |
| 116 | 1 | 1 | 1 | 1 | 1 | 1 | 0 | 0 | 0 |
| 117 | 1 | 1 | 1 | 1 | 1 | 1 | 0 | 0 | 0 |
| 118 | 0 | 0 | 0 | 0 | 0 | 0 | 0 | 0 | 0 |
| 119 | 0 | 0 | 0 | 0 | 0 | 0 | 0 | 0 | 0 |
| 120 | 0 | 0 | 0 | 0 | 0 | 0 | 0 | 0 | 0 |
| 121 | 0 | 0 | 0 | 0 | 0 | 0 | 0 | 0 | 0 |
| 122 | 0 | 1 | 0 | 1 | 1 | 1 | 0 | 0 | 0 |
| 123 | 1 | 0 | 0 | 0 | 0 | 0 | 0 | 0 | 0 |
| 124 | 1 | 0 | 0 | 0 | 0 | 0 | 0 | 0 | 0 |
| 125 | 0 | 0 | 0 | 0 | 0 | 0 | 0 | 0 | 0 |

TABLE 11

| Strains | Species | Transitions I | Transitions R | Transitions V |
|---|---|---|---|---|
| AST1 | E. coli | 48 | 1 | 2 |
| AST2 | E. coli | 48 | 15 | 2 |
| AST3 | E. coli | 47 | 15 | 1 |
| AST4 | E. coli | 47 | 15 | 0 |
| AST5 | E. coli | 47 | 15 | 2 |
| VIR41 | E. coli | 47 | 3 | 8 |
| VIR42 | E. coli | 47 | 4 | 5 |
| VIR43 | E. coli | 47 | 5 | 6 |
| VIR44 | E. coli | 47 | 6 | 5 |
| VIR45 | E. coli | 48 | 5 | 2 |
| ID6 | E. coli | 48 | 0 | 1 |
| ID7 | E. coli | 45 | 2 | 0 |
| ID8 | E. coli | 45 | 2 | 1 |
| ID9 | E. coli | 45 | 3 | 1 |
| ID10 | E. coli | 45 | 1 | 1 |
| VIR10 | S. aureus | 1 | 1 | 0 |
| VIR19 | S. pneumoniae | 1 | 1 | 0 |
| VIR28 | C. difficile | 2 | 0 | 0 |

All the E. coli samples exhibit more than 44 positive transitions in the I category. All these samples are therefore confirmed as indeed belonging to the E. coli species.

On the other hand, the VIR10, VIR19 and VIR28 samples exhibit less than 3 positive transitions in the I category, these samples are therefore confirmed as not belonging to the E. coli species.

The AST2, AST3, AST4 and AST5 strains of E. coli exhibit more than 14 positive transitions for the R category, they therefore express the plasmid-mediated penicillinase TEM-2, this being synonymous with a mechanism of resistance to penicillins.

On the other hand, the AST1, VIR41, VIR42, VIR43, VIR44, VIR45, ID6, ID7, ID8, ID9 and ID10 strains of E. coli exhibit less than 7 positive transitions for the R category, they do not therefore express the plasmid-mediated penicillinase TEM-2. These strains are therefore sensitive to penicillins, in particular aminopenicillins or A penicillins (ampicillin), carboxypenicillins or C penicillins (ticarcillin) and ureidopenicillin or penicillin U (piperacillin).

The VIR10, VIR19 and VIR28 strains which do not belong to the E. coli species exhibit less than two transitions for the R category, they do not therefore express TEM-2, thereby confirming the specificity of the method.

The VIR41, VIR42, VIR43 and VIR44 samples of E. coli exhibit more than four positive transitions in the V category, they therefore express the shigatoxin 1 or 2 (STX1 or STX2) toxins. More specifically, for VIR41, transitions 118 to 125 are positive, VIR41 therefore simultaneously expresses shigatoxin 1 and shigatoxin 2. VIR42 and VIR44 are positive for transitions 121 to 125, they therefore express shigatoxin 2. The same is true for VIR45, which exhibits transitions 123 and 124. VIR43, which exhibits transitions 118 to 122, expresses shigatoxin 2. On the other hand, the AST1, AST2, AST3, AST4, AST5, VIR45, ID6, ID7, ID8, ID9 and ID10 strains of E. coli exhibit less than three positive transitions, they do not therefore express shigatoxin. These strains do not therefore have the properties of virulence related to shigatoxins.

The VIR10, VIR19 and VIR28 strains which do not belong to the E. coli species also exhibit less than three transitions for the V category, they do not therefore express stx1 or stx2, thereby confirming the specificity of the method.

For the typing, the T-category transitions of each strain are compared with the transitions of the other strains considered as reference strains. In practice, a value 0 is assigned when the transitions between the two strains are classified in the same category (positive or negative) and a value of 1 is assigned when the transitions between the two strains are classified in different categories (a positive transition and a negative transition). The values are summed for all the T-category transitions of each strain pair in order to establish a score. The scores are given in TABLE 12:

TABLE 12

| | AST1 | AST2 | AST3 | AST4 | AST5 | VIR41 | VIR42 | VIR43 | VIR44 | VIR45 |
|---|---|---|---|---|---|---|---|---|---|---|
| AST1 | 0 | 19 | 18 | 18 | 19 | 17 | 12 | 15 | 17 | 16 |
| AST2 | 19 | 0 | 3 | 3 | 2 | 24 | 21 | 18 | 22 | 19 |
| AST3 | 18 | 3 | 0 | 0 | 1 | 25 | 22 | 21 | 23 | 20 |
| AST4 | 18 | 3 | 0 | 0 | 1 | 25 | 22 | 21 | 23 | 20 |
| AST5 | 19 | 2 | 1 | 1 | 0 | 24 | 23 | 20 | 24 | 21 |
| VIR41 | 17 | 24 | 25 | 25 | 24 | 0 | 5 | 6 | 12 | 13 |
| VIR42 | 12 | 21 | 22 | 22 | 23 | 5 | 0 | 7 | 7 | 8 |
| VIR43 | 15 | 18 | 21 | 21 | 20 | 6 | 7 | 0 | 10 | 9 |

TABLE 12-continued

| | | | | | | | | | |
|---|---|---|---|---|---|---|---|---|---|
| VIR44 | 17 | 22 | 23 | 23 | 24 | 12 | 7 | 10 | 0 | 5 |
| VIR45 | 16 | 19 | 20 | 20 | 21 | 13 | 8 | 9 | 5 | 0 |
| ID6 | 3 | 22 | 19 | 19 | 20 | 16 | 13 | 16 | 18 | 17 |
| ID7 | 11 | 22 | 19 | 19 | 20 | 22 | 19 | 20 | 22 | 19 |
| ID8 | 12 | 23 | 20 | 20 | 21 | 23 | 20 | 21 | 23 | 20 |
| ID9 | 11 | 22 | 19 | 19 | 20 | 20 | 17 | 18 | 22 | 19 |
| ID10 | 9 | 22 | 19 | 19 | 20 | 20 | 17 | 20 | 22 | 19 |
| VIR10 | 92 | 109 | 106 | 106 | 107 | 105 | 102 | 105 | 103 | 102 |
| VIR19 | 92 | 109 | 106 | 106 | 107 | 105 | 102 | 105 | 103 | 102 |
| VIR28 | 95 | 112 | 109 | 109 | 110 | 108 | 105 | 108 | 106 | 105 |

| | ID6 | ID7 | ID8 | ID9 | ID10 | VIR10 | VIR19 | VIR28 |
|---|---|---|---|---|---|---|---|---|
| AST1 | 3 | 11 | 12 | 11 | 9 | 92 | 92 | 95 |
| AST2 | 22 | 22 | 23 | 22 | 22 | 109 | 109 | 112 |
| AST3 | 19 | 19 | 20 | 19 | 19 | 106 | 106 | 109 |
| AST4 | 19 | 19 | 20 | 19 | 19 | 106 | 106 | 109 |
| AST5 | 20 | 20 | 21 | 20 | 20 | 107 | 107 | 110 |
| VIR41 | 16 | 22 | 23 | 20 | 20 | 105 | 105 | 108 |
| VIR42 | 13 | 19 | 20 | 17 | 17 | 102 | 102 | 105 |
| VIR43 | 16 | 20 | 21 | 18 | 20 | 105 | 105 | 108 |
| VIR44 | 18 | 22 | 23 | 22 | 22 | 103 | 103 | 106 |
| VIR45 | 17 | 19 | 20 | 19 | 19 | 102 | 102 | 105 |
| ID6 | 0 | 10 | 11 | 10 | 8 | 91 | 91 | 94 |
| ID7 | 10 | 0 | 1 | 4 | 4 | 89 | 89 | 92 |
| ID8 | 11 | 1 | 0 | 2 | 3 | 90 | 92 | 92 |
| ID9 | 10 | 4 | 2 | 0 | 3 | 90 | 94 | 94 |
| ID10 | 8 | 4 | 3 | 3 | 0 | 87 | 91 | 91 |
| VIR10 | 91 | 89 | 90 | 90 | 87 | ~ | ~ | ~ |
| VIR19 | 91 | 89 | 92 | 94 | 91 | ~ | ~ | ~ |
| VIR28 | 94 | 92 | 92 | 94 | 91 | ~ | ~ | ~ |

The strains which have a score less than or equal to 4 are of the same type, the strains which have a score strictly greater than 4 are of different type.

Thus, the AST2, AST3, AST4 and AST5 strains are of the same type. The same is true, respectively, for the AST1 and ID6 strains and for the ID7, ID8, ID9 and ID10 strains. All the other strains taken in pairs are of different types. The high sums obtained between the VIR10, VIR19 and VIR28 strains, which are not *S. aureus*, and all the other strains which are *S. aureus*, should be noted. These results confirm the specificity of the method.

The VIR10, VIR19 and VIR28 strains are of different species. These strains cannot therefore be compared with one another and no value is reported in TABLE 12. Extremely advantageously, scores greater than 20, for instance between AST4 and VIR41, reflect a great divergence between strains. Scores between 12 and 20, as between ID7 and VIR42, reflect a moderate divergence and scores between 4 and 12, as between ID10 and AST1, a weak divergence.

The method thus implemented therefore makes it possible not only to establish whether two strains are of the same type, which is important for identifying a common seat of infection, but also to estimate the proximity of two strains, which is extremely important for epidemiological studies.

This example shows that, very advantageously, the present invention makes it possible, in a time of less than one hour, which is very short, to confirm the identity of a species such as *E. coli* and to determine, simultaneously within the same analysis, the properties of typing and potential resistance to at least one antibiotic and to establish the existence of a virulence factor. These properties were established with the same instrument, which greatly facilitates the analysis and the reporting of the results. Finally, the characteristics of the bacteria are established using bacterial proteins, which reflects the existence of live and viable microorganisms, unlike characterizations using bacterial DNA which can be distorted by the existence of dead bacteria.

EXAMPLE 8: PROTOCOL FOR DIGESTION OF MICROORGANISMS IN THE PRESENCE OF METHANOL

Conventionally, the following protocol is implemented in 17 steps:
1. Sampling of a microorganism colony, obtained according to example 1, and suspension in 400 µl of a 50 mM ammonium bicarbonate solution, pH=8.0.
2. Addition of 600 µl of methanol.
Steps 3 to 7: idem steps 2 to 6 of example 4.
Steps 8 to 17: idem steps 8 to 17 of example 6.

EXAMPLE 9: CHARACTERIZATION OF *C. ALBICANS* SAMPLES

After having established the one or more species of the samples according to any one of the methods described in examples 1 to 3, the species listed below are analyzed. Seventeen *C. albicans* strains are analyzed in order to confirm their identification and to establish their characteristics:

| | |
|---|---|
| ATF1 | ATF2 |
| ATF3 | ATF4 |
| ATF5 | ATF6 |
| ATF7 | VIR31 |
| VIR32 | VIR33 |
| VIR34 | VIR35 |
| VIR36 | VIR37 |
| VIR38 | VIR39 |
| CA16 | |

The same method of analysis is applied to species not belonging to the *C. albicans* species in order to serve as a negative control:
*E. coli*
VIR43

*S. aureus*
VIR5
*E. faecium*
AST-VAN8

Each sample is treated according to example 8, then a volume of 5 µl of digested proteins is injected and analyzed according to the same conditions as in example 7.

The peptides, resulting from the digestion of the proteins of the microorganism, are analyzed using the mass spectrometer in MRM mode. Only the peptides indicated in TABLE 13 are detected. For this, the first-generation fragment(s) indicated in TABLE 13 is (are) detected. The application, to which each transition, i.e. each peptide associated with its first-generation fragment, makes it possible to respond, is specified in the clinical interest column of TABLE 14 with the letters I, T, R and V. I denotes the confirmation of the identification of the microorganism, T the typing, R the resistance to at least one antibiotic and V the detection of virulence factors.

TABLE 13

| Transition number | Protein | Peptide (SEQ ID NO.) | First-generation fragment ion | Clinical interest |
|---|---|---|---|---|
| 1 | ALF | ADEEFFAK (88) | y5 singly charged | I + T |
| 2 | ALF | ADEEFFAK (88) | y6 singly charged | I + T |
| 3 | ALF | ADEEFFAK (88) | y7 singly charged | I + T |
| 4 | HSP75 | AFDDESVQK (89) | y6 singly charged | I + T |
| 5 | HSP75 | AFDDESVQK (89) | y7 singly charged | I + T |
| 6 | HSP75 | AFDDESVQK (89) | y8 singly charged | I + T |
| 7 | ENO1 | AKIDVVDQAK (90) | y6 singly charged | I + T |
| 8 | ENO1 | AKIDVVDQAK (90) | y7 singly charged | I + T |
| 9 | ENO1 | AKIDVVDQAK (90) | y8 singly charged | I + T |
| 10 | RL13 | AVEVPEQTAYR (91) | y6 singly charged | I + T |
| 11 | RL13 | AVEVPEQTAYR (91) | y7 singly charged | I + T |
| 12 | RL13 | AVEVPEQTAYR (91) | y8 singly charged | I + T |
| 13 | RS22 | CGVIQPR (92) | y5 singly charged | I + T |
| 14 | RS22 | CGVIQPR (92) | y6 singly charged | I + T |
| 15 | RS22 | CGVIQPR (92) | y4 singly charged | I + T |
| 16 | RLA4 | DLQELIAEGNTK (93) | y8 singly charged | I + T |
| 17 | RLA4 | DLQELIAEGNTK (93) | y9 singly charged | I + T |
| 18 | RLA4 | DLQELIAEGNTK (93) | y7 singly charged | I + T |
| 19 | PPIA | FADENFVKR (94) | y6 singly charged | I + T |
| 20 | PPIA | FADENFVKR (94) | y7 singly charged | I + T |
| 21 | PPIA | FADENFVKR (94) | y8 singly charged | I + T |
| 22 | TPIS | FALDTGVK (95) | y6 singly charged | I + T |
| 23 | TPIS | FALDTGVK (95) | y7 singly charged | I + T |
| 24 | TPIS | FALDTGVK (95) | y5 singly charged | I + T |
| 25 | RL28 | GRLPEVPVIVK (96) | y8 singly charged | I + T |
| 26 | RL28 | GRLPEVPVIVK (96) | y5 singly charged | I + T |
| 27 | ALF | IAEALDIFHTK (97) | y6 singly charged | I + T |
| 28 | ALF | IAEALDIFHTK (97) | y7 singly charged | I + T |
| 29 | ALF | IAEALDIFHTK (97) | y8 singly charged | I + T |
| 30 | ENO1 | IDVVDQAK (98) | y5 singly charged | I + T |
| 31 | ENO1 | IDVVDQAK (98) | y6 singly charged | I + T |
| 32 | ENO1 | IDVVDQAK (98) | y7 singly charged | I + T |
| 33 | ENO1 | IEEELGSEAIYAGKDFQK (99) | y8 singly charged | I + T |
| 34 | ENO1 | IEEELGSEAIYAGKDFQK (99) | y9 singly charged | I + T |
| 35 | PPIA | IESFGSGSGATSK (100) | y9 singly charged | I + T |
| 36 | PPIA | IESFGSGSGATSK (100) | y10 singly charged | I + T |
| 37 | PPIA | IESFGSGSGATSK (100) | y11 singly charged | I + T |
| 38 | NTF2 | LASLPFQK (101) | y5 singly charged | I + T |
| 39 | NTF2 | LASLPFQK (101) | y6 singly charged | I + T |
| 40 | NTF2 | LASLPFQK (101) | y7 singly charged | I + T |
| 41 | MBF1 | LDATDDVVAVK (102) | y7 singly charged | I + T |
| 42 | MBF1 | LDATDDVVAVK (102) | y8 singly charged | I + T |
| 43 | MBF1 | LDATDDVVAVK (102) | y9 singly charged | I + T |
| 44 | PGK | NVEHLVEK (103) | y6 singly charged | I + T |
| 45 | PGK | NVEHLVEK (103) | y7 singly charged | I + T |
| 46 | PGK | NVEHLVEK (103) | y5 singly charged | I + T |
| 47 | RL36 | SGIAAGVNK (104) | y5 singly charged | I + T |
| 48 | RL36 | SGIAAGVNK (104) | y6 singly charged | I + T |
| 49 | RL36 | SGIAAGVNK (104) | y7 singly charged | I + T |
| 50 | G3P | SGVDYVIESTGVFTK (105) | y9 singly charged | I + T |
| 51 | G3P | SGVDYVIESTGVFTK (105) | y10 singly charged | I + T |
| 52 | G3P | SGVDYVIESTGVFTK (105) | y8 singly charged | I + T |
| 53 | EF1B | SLNEFLADK (106) | y6 singly charged | I + T |
| 54 | EF1B | SLNEFLADK (106) | y7 singly charged | I + T |
| 55 | RL13 | SQETFDANVAR (107) | y7 singly charged | I + T |
| 56 | RL13 | SQETFDANVAR (107) | b8 singly charged | I + T |
| 57 | RL13 | SQETFDANVAR (107) | y9 singly charged | I + T |
| 58 | CS111 | SSSSTTKK (108) | y6 singly charged | I + T |
| 59 | CS111 | SSSSTTKK (108) | y7 singly charged | I + T |
| 60 | HSP71 | STLDPVGK (109) | y6 singly charged | I + T |
| 61 | HSP71 | STLDPVGK (109) | y7 singly charged | I + T |
| 62 | HSP71 | STLDPVGK (109) | y5 singly charged | I + T |
| 63 | PGK | SVELFQQAVAK (110) | y7 singly charged | I + T |
| 64 | PGK | SVELFQQAVAK (110) | y8 singly charged | I + T |

TABLE 13-continued

| Transition number | Protein | Peptide (SEQ ID NO.) | First-generation fragment ion | Clinical interest |
|---|---|---|---|---|
| 65 | PGK | SVELFQQAVAK (110) | y6 singly charged | I + T |
| 66 | KPYK | TANDVLELR (111) | y5 singly charged | I + T |
| 67 | KPYK | TANDVLELR (111) | y6 singly charged | I + T |
| 68 | KPYK | TANDVLELR (111) | y7 singly charged | I + T |
| 69 | ENO1 | VGDKIQIVGDDLTVTNPTR (112) | y7 singly charged | I + T |
| 70 | ENO1 | VGDKIQIVGDDLTVTNPTR (112) | y8 singly charged | I + T |
| 71 | ENO1 | VGDKIQIVGDDLTVTNPTR (112) | y9 singly charged | I + T |
| 72 | ADH1 | VVAIDGGDEK (113) | y7 singly charged | I + T |
| 73 | ADH1 | VVAIDGGDEK (113) | y8 singly charged | I + T |
| 74 | ADH1 | VVAIDGGDEK (113) | y9 singly charged | I + T |
| 75 | RS22 | WTDNLLPAR (114) | y6 singly charged | I + T |
| 76 | RS22 | WTDNLLPAR (114) | y7 singly charged | I + T |
| 77 | RS22 | WTDNLLPAR (114) | y8 singly charged | I + T |
| 78 | G3P | YKGEVTASGDDLVIDGHK (115) | y10 singly charged | I + T |
| 79 | G3P | YKGEVTASGDDLVIDGHK (115) | y11 singly charged | I + T |
| 80 | G3P | YKGEVTASGDDLVIDGHK (115) | y9 singly charged | I + T |
| 81 | ADH1 | YVLDTSK (116) | y5 singly charged | I + T |
| 82 | ADH1 | YVLDTSK (116) | y6 singly charged | I + T |
| 83 | ADH1 | YVLDTSK (116) | y4 singly charged | I + T |
| 84 | CP51 | AVIYDCPNSR (117) | y6 singly charged | R + T |
| 85 | CP51 | AVIYDCPNSR (117) | y7 singly charged | R + T |
| 86 | CP51 | GHYVLVFPGYAHTSER (177) | 10 singly charged | R + T |
| 87 | CP51 | GHYVLVFPGYAHTSER (177) | y9 singly charged | R + T |
| 88 | CP51 | GHYVLVSPGYAHTSER (118) | y9 singly charged | R + T |
| 89 | CP51 | GHYVLVSPGYAHTSER (118) | 10 singly charged | R + T |
| 90 | CP51 | GVIYDCPNSR (119) | y6 singly charged | R + T |
| 91 | CP51 | GVIYDCPNSR (119) | y7 singly charged | R + T |
| 92 | CP51 | GVIYDCPNSR (119) | y8 singly charged | R + T |
| 93 | CP51 | GVSSPYLPFGGGR (120) | y9 singly charged | R + T |
| 94 | CP51 | GVSSPYLPFGGGR (120) | y6 singly charged | R + T |
| 95 | CP51 | GVSSPYLPFSGGK (121) | y9 doubly charged | R + T |
| 96 | CP51 | GVSSPYLPFSGGK (121) | y9 singly charged | R + T |
| 97 | CP51 | GVSSPYLPFSGGK (121) | y6 singly charged | R + T |
| 98 | CP51 | GVSSPYLPFSGGR (122) | y9 doubly charged | R + T |
| 99 | CP51 | GVSSPYLPFSGGR (122) | y9 singly charged | R + T |
| 100 | CP51 | GVSSPYLPFSGGR (122) | y6 singly charged | R + T |
| 101 | LIPASE8 | AAVGDILQSR (123) | y7 singly charged | V + T |
| 102 | LIPASE8 | AAVGDILQSR (123) | y8 singly charged | V + T |
| 103 | LIPASE8 | ITPDDLR (124) | y5 singly charged | V + T |
| 104 | LIPASE8 | ITPDDLR (124) | y6 singly charged | V + T |
| 105 | LIPASE8 | ITPDDLR (124) | y4 singly charged | V + T |
| 106 | LIPASE8 | TGWDILK (125) | y5 singly charged | V + T |
| 107 | LIPASE8 | TGWDILK (125) | y6 singly charged | V + T |
| 108 | LIPASE8 | TGWDILK (125) | y4 singly charged | V + T |

The charge state of the precursor peptide, its retention time and the transitions, i.e. the ratios $(m/z)_1$ in Q1 and $(m/z)_2$ in Q3, are indicated in TABLE 14. The collision energy used to fragment the precursor ion is also indicated in TABLE 14.

TABLE 14

| Transition number | Precursor charge state | Retention time | (m/z) filtered in Q1 | (m/z) filtered in Q3 | Collision energy |
|---|---|---|---|---|---|
| 1 | 2 | 11.9 | 478.72 | 641.33 | 26 |
| 2 | 2 | 11.9 | 478.72 | 770.37 | 26 |
| 3 | 2 | 11.9 | 478.72 | 885.4 | 26 |
| 4 | 2 | 7.8 | 519.74 | 705.34 | 28 |
| 5 | 2 | 7.8 | 519.74 | 820.37 | 28 |
| 6 | 2 | 7.8 | 519.74 | 967.44 | 28 |
| 7 | 2 | 8.5 | 543.81 | 659.37 | 29 |
| 8 | 2 | 8.5 | 543.81 | 774.4 | 29 |
| 9 | 2 | 8.5 | 543.81 | 887.48 | 29 |
| 10 | 2 | 11 | 631.82 | 767.37 | 33 |
| 11 | 2 | 11 | 631.82 | 864.42 | 33 |
| 12 | 2 | 11 | 631.82 | 963.49 | 33 |
| 13 | 2 | 6.4 | 415.22 | 612.38 | 23 |
| 14 | 2 | 6.4 | 415.22 | 669.4 | 23 |
| 15 | 2 | 6.4 | 415.22 | 513.31 | 23.3 |
| 16 | 2 | 15.5 | 665.85 | 845.47 | 34 |
| 17 | 2 | 15.5 | 665.85 | 974.52 | 34 |
| 18 | 2 | 15.5 | 665.85 | 732.39 | 34.3 |
| 19 | 2 | 10.5 | 563.29 | 792.44 | 30 |
| 20 | 2 | 10.5 | 563.29 | 907.46 | 30 |
| 21 | 2 | 10.5 | 563.29 | 978.5 | 30 |
| 22 | 2 | 12.5 | 425.74 | 632.36 | 24 |
| 23 | 2 | 12.5 | 425.74 | 703.4 | 24 |
| 24 | 2 | 12.5 | 425.74 | 519.28 | 23.7 |
| 25 | 2 | 14.8 | 603.88 | 880.55 | 32 |
| 26 | 2 | 14.8 | 603.88 | 555.39 | 31.6 |
| 27 | 2 | 17.8 | 629.35 | 760.4 | 33 |
| 28 | 2 | 17.8 | 629.35 | 873.48 | 33 |
| 29 | 2 | 17.8 | 629.35 | 944.52 | 33 |
| 30 | 2 | 9 | 444.25 | 560.3 | 25 |
| 31 | 2 | 9 | 444.25 | 659.37 | 25 |
| 32 | 2 | 9 | 444.25 | 774.4 | 25 |
| 33 | 3 | 18.6 | 676.34 | 956.48 | 38 |
| 34 | 3 | 18.6 | 676.34 | 1069.57 | 38 |
| 35 | 2 | 8.4 | 614.3 | 751.36 | 32 |
| 36 | 2 | 8.4 | 614.3 | 898.43 | 32 |
| 37 | 2 | 8.4 | 614.3 | 985.46 | 32 |
| 38 | 2 | 14.1 | 452.27 | 632.38 | 25 |
| 39 | 2 | 14.1 | 452.27 | 719.41 | 25 |
| 40 | 2 | 14.1 | 452.27 | 790.45 | 25 |

TABLE 14-continued

| Transition number | Precursor charge state | Retention time | (m/z) filtered in Q1 | (m/z) filtered in Q3 | Collision energy |
|---|---|---|---|---|---|
| 41 | 2 | 12.1 | 573.31 | 745.41 | 30 |
| 42 | 2 | 12.1 | 573.31 | 846.46 | 30 |
| 43 | 2 | 12.1 | 573.31 | 917.49 | 30 |
| 44 | 2 | 7 | 484.26 | 754.41 | 26 |
| 45 | 2 | 7 | 484.26 | 853.48 | 26 |
| 46 | 2 | 7 | 484.26 | 625.37 | 26.3 |
| 47 | 2 | 4.5 | 408.73 | 488.28 | 23 |
| 48 | 2 | 4.5 | 408.73 | 559.32 | 23 |
| 49 | 2 | 4.5 | 408.73 | 672.4 | 23 |
| 50 | 2 | 18 | 801.41 | 981.53 | 40 |
| 51 | 2 | 18 | 801.41 | 1080.59 | 40 |
| 52 | 2 | 18 | 801.41 | 868.44 | 40.3 |
| 53 | 2 | 14.3 | 518.77 | 722.37 | 28 |
| 54 | 2 | 14.3 | 518.77 | 836.41 | 28 |
| 55 | 2 | 10.1 | 619.29 | 792.4 | 32 |
| 56 | 2 | 10.1 | 619.29 | 893.36 | 32 |
| 57 | 2 | 10.1 | 619.29 | 1022.49 | 32 |
| 58 | 2 | 10.6 | 413.22 | 651.37 | 23 |
| 59 | 2 | 10.6 | 413.22 | 738.4 | 23 |
| 60 | 2 | 8.7 | 408.73 | 628.37 | 23 |
| 61 | 2 | 8.7 | 408.73 | 729.41 | 23 |
| 62 | 2 | 8.7 | 408.73 | 515.28 | 23 |
| 63 | 2 | 14.6 | 610.34 | 791.44 | 32 |
| 64 | 2 | 14.6 | 610.34 | 904.53 | 32 |
| 65 | 2 | 14.6 | 610.34 | 644.37 | 31.9 |
| 66 | 2 | 12.9 | 515.78 | 629.4 | 28 |
| 67 | 2 | 12.9 | 515.78 | 744.43 | 28 |
| 68 | 2 | 12.9 | 515.78 | 858.47 | 28 |
| 69 | 3 | 15.3 | 681.04 | 788.43 | 38 |
| 70 | 3 | 15.3 | 681.04 | 901.51 | 38 |
| 71 | 3 | 15.3 | 681.04 | 1016.54 | 38 |
| 72 | 2 | 7.7 | 501.76 | 733.34 | 27 |
| 73 | 2 | 7.7 | 501.76 | 804.37 | 27 |
| 74 | 2 | 7.7 | 501.76 | 903.44 | 27 |
| 75 | 2 | 14.9 | 543.29 | 683.42 | 29 |
| 76 | 2 | 14.9 | 543.29 | 798.45 | 29 |
| 77 | 2 | 14.9 | 543.29 | 899.49 | 29 |
| 78 | 2 | 11.4 | 952.47 | 1068.53 | 47 |
| 79 | 2 | 11.4 | 952.47 | 1155.56 | 47 |
| 80 | 2 | 11.4 | 952.47 | 1011.51 | 46.9 |
| 81 | 2 | 8.5 | 413.22 | 563.3 | 23 |
| 82 | 2 | 8.5 | 413.22 | 662.37 | 23 |
| 83 | 2 | 8.5 | 413.22 | 450.22 | 23.2 |
| 84 | 2 | 9.3 | 597.78 | 748.3 | 31 |
| 85 | 2 | 9.3 | 597.78 | 911.37 | 31 |
| 86 | 2 | 14.3 | 916.96 | 1164.54 | 45 |
| 87 | 2 | 14.3 | 916.96 | 1017.47 | 45.3 |
| 88 | 2 | 11 | 886.94 | 1017.47 | 44 |
| 89 | 2 | 11 | 886.94 | 1104.51 | 44 |
| 90 | 2 | 9.4 | 590.77 | 748.3 | 31 |
| 91 | 2 | 9.4 | 590.77 | 911.37 | 31 |
| 92 | 2 | 9.4 | 590.77 | 1024.45 | 31 |
| 93 | 2 | 16.1 | 647.33 | 963.5 | 33 |
| 94 | 2 | 16.1 | 647.33 | 590.3 | 33.5 |
| 95 | 2 | 15.8 | 648.34 | 483.26 | 34 |
| 96 | 2 | 15.8 | 648.34 | 965.51 | 34 |
| 97 | 2 | 15.8 | 648.34 | 592.31 | 33.5 |
| 98 | 2 | 16 | 662.34 | 497.26 | 34 |
| 99 | 2 | 16 | 662.34 | 993.52 | 34 |
| 100 | 2 | 16 | 662.34 | 620.32 | 34.1 |
| 101 | 2 | 12.75 | 515.29 | 788.43 | 28 |
| 102 | 2 | 12.75 | 515.29 | 887.49 | 28 |
| 103 | 2 | 9.83 | 415.22 | 615.31 | 23 |
| 104 | 2 | 9.83 | 415.22 | 716.36 | 23 |
| 105 | 2 | 9.83 | 415.22 | 518.26 | 23.3 |
| 106 | 2 | 15.81 | 416.73 | 674.39 | 23 |
| 107 | 2 | 15.81 | 416.73 | 731.41 | 23 |
| 108 | 2 | 15.81 | 416.73 | 488.31 | 23.3 |

The other machine parameters used are the same as in example 7. The areas obtained for each of the transitions and for each of the microorganisms studied were measured. All the transitions with an area greater than or equal to 2000 (arbitrary units) are considered to be positive and have been denoted "1" in tables 15A and 15B. All the transitions with an area less than 2000 are considered to be negative and have been denoted 0 in tables 15A and 15B. When no signal peak was observed, the transition was noted as negative.

TABLE 15A

| Transition number | ATF1 | ATF2 | ATF3 | ATF4 | VIR31 | ATF5 | ATF6 | ATF7 | VIR32 | VIR33 |
|---|---|---|---|---|---|---|---|---|---|---|
| 1 | 1 | 1 | 1 | 1 | 1 | 1 | 1 | 1 | 1 | 1 |
| 2 | 1 | 1 | 1 | 1 | 1 | 1 | 1 | 1 | 1 | 1 |
| 3 | 1 | 1 | 1 | 1 | 1 | 1 | 1 | 1 | 1 | 1 |
| 4 | 1 | 1 | 1 | 1 | 1 | 1 | 1 | 1 | 1 | 1 |
| 5 | 1 | 1 | 1 | 1 | 1 | 1 | 1 | 1 | 1 | 1 |
| 6 | 1 | 1 | 1 | 1 | 1 | 1 | 1 | 1 | 1 | 1 |
| 7 | 1 | 1 | 1 | 1 | 1 | 1 | 1 | 1 | 1 | 1 |
| 8 | 1 | 1 | 1 | 1 | 1 | 1 | 1 | 1 | 1 | 1 |
| 9 | 1 | 1 | 1 | 1 | 1 | 1 | 1 | 1 | 1 | 1 |
| 10 | 1 | 1 | 1 | 1 | 0 | 1 | 1 | 1 | 0 | 0 |
| 11 | 1 | 1 | 1 | 1 | 0 | 1 | 1 | 1 | 0 | 1 |
| 12 | 1 | 1 | 1 | 1 | 0 | 1 | 1 | 1 | 0 | 0 |
| 13 | 1 | 1 | 1 | 1 | 0 | 1 | 1 | 1 | 1 | 1 |
| 14 | 1 | 1 | 1 | 1 | 0 | 1 | 1 | 1 | 1 | 1 |
| 15 | 1 | 1 | 1 | 1 | 1 | 1 | 1 | 1 | 1 | 1 |
| 16 | 1 | 1 | 1 | 1 | 1 | 1 | 1 | 1 | 1 | 1 |
| 17 | 1 | 1 | 1 | 1 | 1 | 1 | 1 | 1 | 1 | 1 |
| 18 | 1 | 1 | 1 | 1 | 1 | 1 | 1 | 1 | 1 | 1 |
| 19 | 1 | 1 | 1 | 1 | 0 | 1 | 1 | 1 | 0 | 1 |
| 20 | 1 | 1 | 1 | 1 | 0 | 1 | 1 | 1 | 1 | 1 |
| 21 | 1 | 1 | 1 | 1 | 0 | 1 | 1 | 1 | 0 | 1 |
| 22 | 1 | 1 | 1 | 1 | 1 | 1 | 1 | 1 | 1 | 1 |
| 23 | 1 | 1 | 1 | 1 | 1 | 1 | 1 | 1 | 1 | 1 |
| 24 | 1 | 1 | 1 | 1 | 1 | 1 | 1 | 1 | 1 | 1 |
| 25 | 1 | 1 | 1 | 1 | 1 | 1 | 1 | 1 | 1 | 1 |
| 26 | 1 | 1 | 1 | 1 | 1 | 1 | 1 | 1 | 1 | 1 |
| 27 | 0 | 0 | 0 | 0 | 1 | 0 | 0 | 0 | 1 | 1 |
| 28 | 0 | 0 | 0 | 0 | 1 | 0 | 0 | 0 | 1 | 1 |

TABLE 15A-continued

| Transition number | ATF1 | ATF2 | ATF3 | ATF4 | VIR31 | ATF5 | ATF6 | ATF7 | VIR32 | VIR33 |
|---|---|---|---|---|---|---|---|---|---|---|
| 29 | 0 | 0 | 0 | 0 | 0 | 0 | 0 | 0 | 0 | 1 |
| 30 | 1 | 1 | 1 | 1 | 1 | 1 | 1 | 1 | 1 | 1 |
| 31 | 1 | 1 | 1 | 1 | 1 | 1 | 1 | 1 | 1 | 1 |
| 32 | 1 | 1 | 1 | 1 | 1 | 1 | 1 | 1 | 1 | 1 |
| 33 | 0 | 0 | 0 | 0 | 1 | 0 | 0 | 0 | 1 | 1 |
| 34 | 0 | 0 | 0 | 0 | 0 | 0 | 0 | 0 | 0 | 1 |
| 35 | 1 | 1 | 1 | 1 | 1 | 1 | 1 | 1 | 1 | 1 |
| 36 | 1 | 1 | 1 | 1 | 1 | 1 | 1 | 1 | 1 | 1 |
| 37 | 1 | 1 | 1 | 1 | 1 | 1 | 1 | 1 | 1 | 1 |
| 38 | 1 | 1 | 1 | 1 | 0 | 1 | 1 | 1 | 0 | 0 |
| 39 | 1 | 1 | 1 | 1 | 0 | 1 | 1 | 1 | 0 | 1 |
| 40 | 1 | 1 | 1 | 1 | 0 | 1 | 1 | 1 | 0 | 0 |
| 41 | 1 | 1 | 1 | 1 | 1 | 1 | 1 | 1 | 1 | 1 |
| 42 | 1 | 1 | 1 | 1 | 1 | 1 | 1 | 1 | 1 | 1 |
| 43 | 1 | 1 | 1 | 1 | 1 | 1 | 1 | 1 | 1 | 1 |
| 44 | 1 | 1 | 1 | 1 | 1 | 1 | 1 | 1 | 1 | 1 |
| 45 | 1 | 1 | 1 | 1 | 1 | 1 | 1 | 1 | 1 | 1 |
| 46 | 1 | 1 | 1 | 1 | 1 | 1 | 1 | 1 | 1 | 1 |
| 47 | 1 | 1 | 1 | 1 | 1 | 1 | 1 | 1 | 1 | 1 |
| 48 | 1 | 1 | 1 | 1 | 1 | 1 | 1 | 1 | 1 | 1 |
| 49 | 0 | 0 | 0 | 0 | 1 | 0 | 0 | 0 | 1 | 1 |
| 50 | 1 | 1 | 1 | 1 | 1 | 1 | 1 | 1 | 1 | 1 |
| 51 | 1 | 1 | 1 | 1 | 1 | 1 | 1 | 1 | 1 | 1 |
| 52 | 1 | 1 | 1 | 1 | 1 | 1 | 1 | 1 | 1 | 1 |
| 53 | 1 | 1 | 1 | 1 | 0 | 1 | 1 | 1 | 1 | 1 |
| 54 | 1 | 1 | 1 | 1 | 1 | 1 | 1 | 1 | 1 | 1 |
| 55 | 1 | 1 | 1 | 1 | 0 | 1 | 1 | 1 | 0 | 0 |
| 56 | 1 | 1 | 1 | 1 | 0 | 1 | 1 | 1 | 0 | 0 |
| 57 | 1 | 1 | 1 | 1 | 0 | 1 | 1 | 1 | 0 | 0 |
| 58 | 0 | 0 | 0 | 0 | 1 | 0 | 0 | 0 | 1 | 1 |
| 59 | 0 | 0 | 0 | 0 | 1 | 0 | 0 | 0 | 1 | 1 |
| 60 | 1 | 1 | 1 | 1 | 1 | 1 | 1 | 1 | 1 | 1 |
| 61 | 1 | 1 | 1 | 1 | 0 | 1 | 1 | 1 | 0 | 1 |
| 62 | 1 | 1 | 1 | 1 | 1 | 1 | 1 | 1 | 1 | 1 |
| 63 | 1 | 1 | 1 | 1 | 1 | 1 | 1 | 1 | 1 | 1 |
| 64 | 1 | 1 | 1 | 1 | 0 | 1 | 1 | 1 | 0 | 0 |
| 65 | 1 | 1 | 1 | 1 | 0 | 1 | 1 | 1 | 1 | 1 |
| 66 | 1 | 1 | 1 | 1 | 1 | 1 | 1 | 1 | 1 | 1 |
| 67 | 1 | 1 | 1 | 1 | 1 | 1 | 1 | 1 | 1 | 1 |
| 68 | 1 | 1 | 1 | 1 | 1 | 1 | 1 | 1 | 1 | 1 |
| 69 | 1 | 1 | 1 | 1 | 1 | 1 | 1 | 1 | 1 | 1 |
| 70 | 1 | 1 | 1 | 1 | 1 | 1 | 1 | 1 | 1 | 1 |
| 71 | 1 | 1 | 1 | 1 | 0 | 1 | 1 | 1 | 1 | 1 |
| 72 | 1 | 1 | 1 | 1 | 1 | 1 | 1 | 1 | 1 | 1 |
| 73 | 1 | 1 | 1 | 1 | 1 | 1 | 1 | 1 | 1 | 1 |
| 74 | 1 | 1 | 1 | 1 | 1 | 1 | 1 | 1 | 1 | 1 |
| 75 | 1 | 1 | 1 | 1 | 1 | 1 | 1 | 1 | 1 | 1 |
| 76 | 1 | 1 | 1 | 1 | 1 | 1 | 1 | 1 | 1 | 1 |
| 77 | 1 | 1 | 1 | 1 | 1 | 1 | 1 | 1 | 1 | 1 |
| 78 | 1 | 1 | 1 | 1 | 1 | 1 | 1 | 1 | 1 | 1 |
| 79 | 1 | 1 | 1 | 1 | 1 | 1 | 1 | 1 | 1 | 1 |
| 80 | 1 | 1 | 1 | 1 | 0 | 1 | 1 | 1 | 1 | 1 |
| 81 | 1 | 1 | 1 | 1 | 1 | 1 | 1 | 1 | 1 | 1 |
| 82 | 1 | 1 | 1 | 1 | 1 | 1 | 1 | 1 | 1 | 1 |
| 83 | 1 | 1 | 1 | 1 | 1 | 1 | 1 | 1 | 1 | 1 |
| 84 | 0 | 0 | 0 | 0 | 0 | 0 | 1 | 1 | 0 | 0 |
| 85 | 0 | 0 | 0 | 0 | 0 | 0 | 1 | 1 | 0 | 0 |
| 86 | 0 | 0 | 1 | 0 | 0 | 0 | 0 | 0 | 0 | 0 |
| 87 | 0 | 1 | 1 | 0 | 0 | 0 | 0 | 0 | 0 | 0 |
| 88 | 0 | 0 | 0 | 1 | 0 | 0 | 0 | 0 | 0 | 0 |
| 89 | 0 | 0 | 0 | 1 | 0 | 0 | 0 | 0 | 0 | 0 |
| 90 | 1 | 1 | 0 | 1 | 0 | 1 | 1 | 0 | 0 | 1 |
| 91 | 1 | 1 | 0 | 1 | 0 | 1 | 1 | 0 | 0 | 0 |
| 92 | 0 | 0 | 0 | 1 | 0 | 0 | 0 | 0 | 0 | 0 |
| 93 | 1 | 1 | 1 | 1 | 0 | 0 | 1 | 0 | 0 | 0 |
| 94 | 1 | 1 | 1 | 1 | 0 | 0 | 1 | 1 | 0 | 0 |
| 95 | 0 | 0 | 0 | 0 | 1 | 1 | 0 | 0 | 1 | 1 |
| 96 | 0 | 0 | 0 | 0 | 0 | 1 | 0 | 0 | 0 | 0 |
| 97 | 1 | 0 | 0 | 1 | 1 | 1 | 0 | 1 | 1 | 1 |
| 98 | 0 | 0 | 0 | 0 | 0 | 0 | 1 | 0 | 0 | 1 |
| 99 | 0 | 0 | 0 | 0 | 0 | 0 | 1 | 0 | 0 | 0 |
| 100 | 0 | 0 | 0 | 0 | 0 | 0 | 1 | 0 | 0 | 0 |
| 101 | 0 | 0 | 0 | 0 | 1 | 0 | 0 | 0 | 0 | 0 |
| 102 | 0 | 0 | 0 | 0 | 1 | 0 | 0 | 0 | 0 | 0 |
| 103 | 0 | 0 | 0 | 0 | 1 | 0 | 0 | 0 | 1 | 1 |
| 104 | 0 | 0 | 0 | 1 | 1 | 0 | 0 | 0 | 1 | 1 |
| 105 | 0 | 0 | 0 | 0 | 1 | 0 | 0 | 0 | 1 | 0 |

TABLE 15A-continued

| Transition number | ATF1 | ATF2 | ATF3 | ATF4 | VIR31 | ATF5 | ATF6 | ATF7 | VIR32 | VIR33 |
|---|---|---|---|---|---|---|---|---|---|---|
| 106 | 0 | 0 | 0 | 0 | 1 | 0 | 0 | 0 | 1 | 0 |
| 107 | 0 | 0 | 0 | 0 | 1 | 0 | 0 | 0 | 1 | 0 |
| 108 | 0 | 0 | 0 | 0 | 1 | 0 | 0 | 0 | 1 | 0 |

TABLE 15B

| Transition number | VIR34 | VIR35 | VIR36 | VIR37 | VIR38 | VIR39 | CA16 | VIR43 | VIR5 | AST-VAN8 |
|---|---|---|---|---|---|---|---|---|---|---|
| 1 | 1 | 1 | 1 | 1 | 1 | 1 | 1 | 0 | 0 | 0 |
| 2 | 1 | 1 | 1 | 1 | 1 | 1 | 1 | 0 | 0 | 0 |
| 3 | 1 | 1 | 1 | 1 | 1 | 1 | 1 | 0 | 0 | 0 |
| 4 | 1 | 1 | 1 | 1 | 1 | 1 | 1 | 0 | 0 | 0 |
| 5 | 1 | 1 | 1 | 1 | 1 | 1 | 1 | 0 | 0 | 0 |
| 6 | 1 | 1 | 1 | 1 | 1 | 1 | 1 | 0 | 0 | 0 |
| 7 | 1 | 1 | 1 | 1 | 1 | 1 | 1 | 1 | 0 | 0 |
| 8 | 1 | 1 | 1 | 1 | 1 | 1 | 1 | 0 | 0 | 0 |
| 9 | 1 | 1 | 1 | 1 | 1 | 1 | 1 | 0 | 0 | 0 |
| 10 | 0 | 0 | 0 | 0 | 0 | 0 | 1 | 0 | 0 | 0 |
| 11 | 1 | 1 | 1 | 1 | 1 | 1 | 1 | 0 | 0 | 0 |
| 12 | 0 | 0 | 0 | 0 | 0 | 0 | 1 | 1 | 0 | 0 |
| 13 | 1 | 1 | 1 | 1 | 1 | 0 | 1 | 0 | 0 | 0 |
| 14 | 1 | 1 | 0 | 1 | 1 | 1 | 1 | 0 | 0 | 0 |
| 15 | 1 | 1 | 1 | 1 | 1 | 1 | 1 | 0 | 0 | 0 |
| 16 | 1 | 1 | 1 | 1 | 1 | 1 | 1 | 0 | 0 | 0 |
| 17 | 1 | 1 | 1 | 1 | 1 | 1 | 1 | 0 | 0 | 0 |
| 18 | 1 | 1 | 1 | 1 | 1 | 1 | 1 | 0 | 0 | 0 |
| 19 | 1 | 1 | 1 | 1 | 1 | 1 | 1 | 0 | 0 | 0 |
| 20 | 1 | 1 | 1 | 1 | 1 | 1 | 1 | 1 | 0 | 0 |
| 21 | 1 | 1 | 1 | 1 | 1 | 1 | 1 | 0 | 0 | 0 |
| 22 | 1 | 1 | 1 | 1 | 1 | 1 | 1 | 0 | 0 | 0 |
| 23 | 1 | 1 | 1 | 1 | 1 | 1 | 1 | 1 | 0 | 0 |
| 24 | 1 | 1 | 1 | 1 | 1 | 1 | 1 | 1 | 0 | 0 |
| 25 | 1 | 1 | 1 | 1 | 1 | 1 | 1 | 0 | 0 | 0 |
| 26 | 1 | 1 | 1 | 1 | 1 | 1 | 1 | 0 | 0 | 0 |
| 27 | 1 | 1 | 1 | 1 | 1 | 1 | 1 | 0 | 0 | 0 |
| 28 | 1 | 1 | 1 | 1 | 1 | 1 | 1 | 0 | 0 | 0 |
| 29 | 1 | 1 | 1 | 1 | 1 | 1 | 1 | 0 | 0 | 0 |
| 30 | 1 | 1 | 1 | 1 | 1 | 1 | 1 | 0 | 0 | 0 |
| 31 | 1 | 1 | 1 | 1 | 1 | 1 | 1 | 0 | 0 | 0 |
| 32 | 1 | 1 | 1 | 1 | 1 | 1 | 1 | 1 | 1 | 1 |
| 33 | 1 | 1 | 1 | 1 | 1 | 1 | 1 | 0 | 0 | 0 |
| 34 | 1 | 1 | 0 | 1 | 1 | 1 | 1 | 0 | 0 | 0 |
| 35 | 1 | 1 | 1 | 1 | 1 | 1 | 1 | 0 | 0 | 0 |
| 36 | 1 | 1 | 1 | 1 | 1 | 1 | 1 | 0 | 0 | 0 |
| 37 | 1 | 1 | 1 | 1 | 1 | 1 | 1 | 0 | 0 | 0 |
| 38 | 0 | 0 | 0 | 0 | 0 | 0 | 1 | 0 | 0 | 0 |
| 39 | 1 | 1 | 1 | 0 | 0 | 1 | 1 | 0 | 0 | 0 |
| 40 | 0 | 0 | 0 | 0 | 0 | 0 | 1 | 0 | 0 | 0 |
| 41 | 1 | 1 | 1 | 1 | 1 | 1 | 1 | 0 | 0 | 0 |
| 42 | 1 | 1 | 1 | 1 | 1 | 1 | 1 | 0 | 0 | 0 |
| 43 | 1 | 1 | 1 | 1 | 1 | 1 | 1 | 0 | 0 | 0 |
| 44 | 1 | 1 | 1 | 1 | 1 | 1 | 1 | 0 | 0 | 0 |
| 45 | 1 | 1 | 1 | 1 | 1 | 1 | 1 | 0 | 0 | 0 |
| 46 | 1 | 1 | 1 | 1 | 1 | 1 | 1 | 0 | 0 | 0 |
| 47 | 1 | 1 | 1 | 1 | 1 | 1 | 1 | 0 | 0 | 0 |
| 48 | 1 | 1 | 1 | 1 | 1 | 1 | 1 | 0 | 0 | 0 |
| 49 | 1 | 1 | 1 | 1 | 1 | 1 | 0 | 0 | 0 | 0 |
| 50 | 1 | 1 | 1 | 1 | 1 | 1 | 1 | 0 | 0 | 0 |
| 51 | 0 | 1 | 1 | 1 | 1 | 1 | 1 | 0 | 0 | 0 |
| 52 | 1 | 1 | 1 | 1 | 1 | 1 | 1 | 0 | 0 | 0 |
| 53 | 1 | 1 | 1 | 1 | 1 | 1 | 1 | 0 | 0 | 0 |
| 54 | 1 | 1 | 1 | 1 | 1 | 1 | 1 | 0 | 0 | 0 |
| 55 | 0 | 0 | 0 | 0 | 0 | 0 | 1 | 0 | 0 | 0 |
| 56 | 0 | 0 | 0 | 0 | 0 | 0 | 1 | 0 | 0 | 0 |
| 57 | 0 | 0 | 0 | 0 | 0 | 0 | 1 | 0 | 0 | 0 |
| 58 | 1 | 1 | 1 | 1 | 1 | 1 | 1 | 0 | 0 | 0 |
| 59 | 1 | 1 | 1 | 1 | 1 | 1 | 1 | 0 | 0 | 0 |
| 60 | 1 | 1 | 1 | 1 | 1 | 1 | 1 | 0 | 0 | 0 |
| 61 | 1 | 0 | 0 | 0 | 1 | 1 | 0 | 0 | 0 | 0 |
| 62 | 1 | 1 | 1 | 1 | 1 | 1 | 1 | 0 | 0 | 0 |
| 63 | 0 | 1 | 1 | 1 | 1 | 1 | 1 | 1 | 0 | 0 |
| 64 | 0 | 1 | 1 | 1 | 1 | 1 | 1 | 0 | 0 | 0 |
| 65 | 0 | 1 | 1 | 1 | 1 | 1 | 1 | 1 | 0 | 0 |

TABLE 15B-continued

| Transition number | VIR34 | VIR35 | VIR36 | VIR37 | VIR38 | VIR39 | CA16 | VIR43 | VIR5 | AST-VAN8 |
|---|---|---|---|---|---|---|---|---|---|---|
| 66 | 1 | 1 | 1 | 1 | 1 | 1 | 1 | 0 | 0 | 0 |
| 67 | 1 | 1 | 1 | 1 | 1 | 1 | 1 | 0 | 0 | 0 |
| 68 | 1 | 1 | 1 | 1 | 1 | 1 | 1 | 0 | 0 | 0 |
| 69 | 1 | 1 | 1 | 1 | 1 | 1 | 1 | 0 | 0 | 0 |
| 70 | 1 | 1 | 1 | 1 | 1 | 1 | 1 | 1 | 0 | 0 |
| 71 | 1 | 1 | 1 | 1 | 1 | 1 | 1 | 0 | 0 | 0 |
| 72 | 1 | 1 | 1 | 1 | 1 | 1 | 1 | 0 | 0 | 0 |
| 73 | 1 | 1 | 1 | 1 | 1 | 1 | 1 | 0 | 0 | 0 |
| 74 | 1 | 1 | 1 | 1 | 1 | 1 | 1 | 0 | 0 | 0 |
| 75 | 1 | 1 | 1 | 1 | 1 | 1 | 1 | 0 | 0 | 0 |
| 76 | 1 | 1 | 1 | 1 | 1 | 1 | 1 | 1 | 0 | 0 |
| 77 | 1 | 1 | 1 | 1 | 1 | 1 | 1 | 0 | 0 | 0 |
| 78 | 1 | 1 | 1 | 1 | 1 | 1 | 1 | 0 | 0 | 0 |
| 79 | 1 | 1 | 1 | 1 | 1 | 1 | 1 | 0 | 0 | 0 |
| 80 | 1 | 1 | 1 | 1 | 1 | 1 | 0 | 0 | 0 | 0 |
| 81 | 1 | 1 | 1 | 1 | 1 | 1 | 1 | 0 | 1 | 0 |
| 82 | 1 | 1 | 1 | 1 | 1 | 1 | 1 | 1 | 0 | 0 |
| 83 | 1 | 1 | 1 | 1 | 1 | 1 | 1 | 0 | 0 | 0 |
| 84 | 0 | 0 | 0 | 0 | 0 | 0 | 0 | 0 | 0 | 0 |
| 85 | 0 | 0 | 0 | 0 | 0 | 0 | 0 | 0 | 0 | 0 |
| 86 | 0 | 0 | 0 | 0 | 0 | 0 | 0 | 0 | 0 | 0 |
| 87 | 0 | 0 | 0 | 0 | 0 | 0 | 0 | 0 | 0 | 0 |
| 88 | 0 | 0 | 0 | 0 | 0 | 0 | 0 | 0 | 0 | 0 |
| 89 | 0 | 0 | 0 | 0 | 0 | 0 | 0 | 0 | 0 | 0 |
| 90 | 0 | 0 | 0 | 0 | 0 | 0 | 0 | 0 | 0 | 0 |
| 91 | 0 | 0 | 0 | 0 | 0 | 0 | 0 | 0 | 0 | 0 |
| 92 | 0 | 0 | 0 | 0 | 0 | 0 | 0 | 1 | 0 | 0 |
| 93 | 0 | 0 | 0 | 0 | 0 | 0 | 0 | 0 | 0 | 0 |
| 94 | 1 | 0 | 0 | 0 | 0 | 0 | 0 | 0 | 0 | 0 |
| 95 | 0 | 1 | 1 | 1 | 1 | 1 | 1 | 0 | 0 | 0 |
| 96 | 0 | 0 | 0 | 0 | 0 | 0 | 0 | 0 | 0 | 0 |
| 97 | 1 | 0 | 0 | 1 | 1 | 1 | 0 | 0 | 0 | 0 |
| 98 | 1 | 1 | 1 | 1 | 1 | 0 | 0 | 0 | 0 | 0 |
| 99 | 0 | 0 | 0 | 0 | 0 | 0 | 0 | 0 | 0 | 0 |
| 100 | 0 | 0 | 0 | 0 | 0 | 0 | 0 | 0 | 0 | 0 |
| 101 | 0 | 0 | 0 | 0 | 0 | 0 | 0 | 0 | 0 | 0 |
| 102 | 0 | 0 | 0 | 0 | 0 | 0 | 0 | 0 | 0 | 0 |
| 103 | 0 | 1 | 1 | 0 | 0 | 1 | 0 | 1 | 0 | 0 |
| 104 | 0 | 1 | 1 | 1 | 1 | 0 | 1 | 0 | 0 | 0 |
| 105 | 0 | 0 | 0 | 0 | 0 | 0 | 0 | 0 | 0 | 0 |
| 106 | 0 | 0 | 0 | 0 | 0 | 0 | 0 | 0 | 0 | 0 |
| 107 | 0 | 0 | 0 | 0 | 0 | 0 | 0 | 0 | 0 | 0 |
| 108 | 0 | 0 | 0 | 0 | 0 | 0 | 0 | 0 | 0 | 0 |

The positive-transition number is then summed for the I, R and V applications and reported in TABLE 16:

TABLE 16

| Strains | Species | Transitions I |
|---|---|---|
| ATF1 | C. albicans | 75 |
| ATF2 | C. albicans | 75 |
| ATF3 | C. albicans | 75 |
| ATF4 | C. albicans | 75 |
| VIR31 | C. albicans | 61 |
| ATF5 | C. albicans | 75 |
| ATF6 | C. albicans | 75 |
| ATF7 | C. albicans | 75 |
| VIR32 | C. albicans | 68 |
| VIR33 | C. albicans | 75 |
| VIR34 | C. albicans | 72 |
| VIR35 | C. albicans | 75 |
| VIR36 | C. albicans | 73 |
| VIR37 | C. albicans | 74 |
| VIR38 | C. albicans | 75 |
| VIR39 | C. albicans | 75 |
| CA16 | C. albicans | 80 |
| VIR43 | E coli | 12 |
| VIR5 | S. aureus | 2 |
| AST-VAN8 | E. faecium | 1 |

All the *C. albicans* samples exhibit more than 60 positive transitions in the I category. All these samples are therefore confirmed as indeed belonging to the *C. albicans* species.

On the other hand, the VIR43, VIR5 and AST-VANS samples exhibit less than 13 positive transitions in the I category, these samples are therefore confirmed as not belonging to the *C. albicans* species.

The observation of transitions 84 and 85 indicates the presence of the mutated peptide and reflects the resistance of the ATF6 and ATF7 strains.

The observation of transitions 86 and 87 indicates the presence of the mutated peptide and reflects the resistance of the ATF2 and ATF3 strains.

The observation of transition 96 indicates the presence of the mutated peptide and reflects the resistance of the ATF5 strain.

The observation of transitions 99 and 100 indicates the presence of the mutated peptide and reflects the resistance of the ATF7 strain.

The observation of transitions 88 and 89 indicates the presence of the native peptide and reflects the sensitivity of the ATF4 strain.

The observation of transitions 93 and 94 indicates the presence of the native peptide and reflects the sensitivity of the ATF1 and ATF4 strains.

All the areas of the I transitions are summed to give the sum SI. All the areas of the V transitions are summed to give the sum SV. The SV/SI ratio is then calculated and multiplied by a multiplication factor MF. The results obtained are given in TABLE 17. TABLE 17:

TABLE 17

| Strains | Sum (SI) of the areas of the I transitions | Sum (SV) of the areas of the V transitions | Ratio of the sums SV/SI multipled by the multiplication factor (MF) | Multiplication factor (MF) |
|---|---|---|---|---|
| ATF1 | 1.8E+07 | 1.6E+03 | 1.9E+03 | 2.0E+07 |
| ATF2 | 1.3E+07 | 1.6E+03 | 2.4E+03 | |
| ATF3 | 2.0E+07 | 2.3E+03 | 2.3E+03 | |
| ATF4 | 2.9E+07 | 3.3E+03 | 2.3E+03 | |
| VIR31 | 1.6E+07 | 1.4E+06 | 1.8E+06 | |
| ATF5 | 1.7E+07 | 2.3E+03 | 2.6E+03 | |
| ATF6 | 2.4E+07 | 4.8E+03 | 4.0E+03 | |
| ATF7 | 2.9E+07 | 2.4E+03 | 1.7E+03 | |
| VIR32 | 2.9E+07 | 5.3E+05 | 3.6E+05 | |
| VIR33 | 1.9E+07 | 4.2E+04 | 4.4E+04 | |
| VIR34 | 4.2E+07 | 1.8E+03 | 8.9E+02 | |
| VIR35 | 1.1E+07 | 8.8E+03 | 1.5E+04 | |
| VIR36 | 8.3E+06 | 3.5E+04 | 8.5E+04 | |
| VIR37 | 2.3E+07 | 3.9E+03 | 3.4E+03 | |
| VIR38 | 2.4E+07 | 3.4E+03 | 2.8E+03 | |

TABLE 17-continued

| Strains | Sum (SI) of the areas of the I transitions | Sum (SV) of the areas of the V transitions | Ratio of the sums SV/SI multipled by the multiplication factor (MF) | Multiplication factor (MF) |
|---|---|---|---|---|
| VIR39 | 1.6E+07 | 9.2E+03 | 1.1E+04 | |
| CA16 | 1.2E+07 | 5.4E+03 | 9.1E+03 | |

The VIR31 and VIR32 strains, which have a (SV/SI) ratio×MF greater than $9 \times 10^4$, overexpress lipase 8, these strains are therefore virulent. All the other strains have a ratio less than $9 \times 10^4$, they do not overexpress lipase 8 and are not therefore virulent. Interestingly, since the (SV/SI) ratio×MF is higher for the VIR31 strain than for the VIR32 strain, the VIR31 strain is characterized as more virulent than the VIR32 strain.

For the typing, the T-category transitions of each strain are compared with the transitions of the other strains considered as reference strains. In practice, a value 0 is assigned when the transitions between the two strains are classified in the same category (positive or negative) and a value of 1 is assigned when the transitions between the two strains are classified in different categories (a positive transition and a negative transition). The values are summed for all the T-category transitions of each strain pair in order to establish a score. The scores are given in TABLE 18:

TABLE 18

| Strain | ATF1 | ATF2 | ATF3 | ATF4 | ATF5 | ATF6 | ATF7 | VIR31 | VIR32 | VIR33 | VIR34 |
|---|---|---|---|---|---|---|---|---|---|---|---|
| ATF1 | 0 | 2 | 5 | 4 | 4 | 3 | 8 | 39 | 30 | 23 | 23 |
| ATF2 | 2 | 0 | 3 | 6 | 6 | 3 | 10 | 41 | 32 | 25 | 25 |
| ATF3 | 5 | 3 | 0 | 9 | 9 | 6 | 9 | 40 | 31 | 26 | 24 |
| ATF4 | 4 | 6 | 9 | 0 | 8 | 7 | 12 | 41 | 32 | 25 | 27 |
| ATF5 | 4 | 6 | 9 | 8 | 0 | 7 | 10 | 37 | 28 | 21 | 25 |
| ATF6 | 3 | 3 | 6 | 7 | 7 | 0 | 7 | 42 | 33 | 26 | 26 |
| ATF7 | 8 | 10 | 9 | 12 | 10 | 7 | 0 | 41 | 32 | 25 | 23 |
| VIR31 | 39 | 41 | 40 | 41 | 37 | 42 | 41 | 0 | 9 | 22 | 26 |
| VIR32 | 30 | 32 | 31 | 32 | 28 | 33 | 32 | 9 | 0 | 13 | 19 |
| VIR33 | 23 | 25 | 26 | 25 | 21 | 26 | 25 | 22 | 13 | 0 | 8 |
| VIR34 | 23 | 25 | 24 | 27 | 25 | 26 | 23 | 26 | 19 | 8 | 0 |
| VIR35 | 25 | 25 | 24 | 27 | 23 | 26 | 25 | 22 | 13 | 4 | 10 |
| VIR36 | 25 | 25 | 24 | 27 | 23 | 26 | 25 | 20 | 13 | 6 | 12 |
| VIR37 | 24 | 26 | 25 | 26 | 22 | 27 | 24 | 21 | 12 | 5 | 9 |
| VIR38 | 23 | 25 | 24 | 25 | 21 | 26 | 23 | 22 | 13 | 4 | 8 |
| VIR39 | 22 | 24 | 23 | 26 | 20 | 25 | 24 | 21 | 14 | 5 | 9 |
| CA16 | 16 | 16 | 15 | 18 | 14 | 17 | 18 | 29 | 22 | 15 | 19 |
| VIR43 | 70 | 70 | 69 | 72 | 70 | 71 | 72 | 65 | 66 | 71 | 71 |
| VIR5 | 78 | 78 | 77 | 82 | 78 | 79 | 80 | 69 | 74 | 79 | 73 |
| AST-VAN8 | 79 | 79 | 78 | 83 | 79 | 80 | 81 | 70 | 75 | 80 | 74 |

| Strain | VIR35 | VIR36 | VIR37 | VIR38 | VIR39 | CA16 | VIR43 | VIR5 | AST-VAN8 |
|---|---|---|---|---|---|---|---|---|---|
| ATF1 | 25 | 25 | 24 | 23 | 22 | 16 | 70 | 78 | 79 |
| ATF2 | 25 | 25 | 26 | 25 | 24 | 16 | 70 | 78 | 79 |
| ATF3 | 24 | 24 | 25 | 24 | 23 | 15 | 69 | 77 | 78 |
| ATF4 | 27 | 27 | 26 | 25 | 26 | 18 | 72 | 82 | 83 |
| ATF5 | 23 | 23 | 22 | 21 | 20 | 14 | 70 | 78 | 79 |
| ATF6 | 26 | 26 | 27 | 26 | 25 | 17 | 71 | 79 | 80 |
| ATF7 | 25 | 25 | 24 | 23 | 24 | 18 | 72 | 80 | 81 |
| VIR31 | 22 | 20 | 21 | 22 | 21 | 29 | 65 | 69 | 70 |
| VIR32 | 13 | 13 | 12 | 13 | 14 | 22 | 66 | 74 | 75 |
| VIR33 | 4 | 6 | 5 | 4 | 5 | 15 | 71 | 79 | 80 |

TABLE 18-continued

| | | | | | | | | | |
|---|---|---|---|---|---|---|---|---|---|
| VIR34 | 10 | 12 | 9 | 8 | 9 | 19 | 71 | 73 | 74 |
| VIR35 | 0 | 2 | 3 | 4 | 5 | 11 | 69 | 77 | 78 |
| VIR36 | 2 | 0 | 5 | 6 | 7 | 13 | 67 | 75 | 76 |
| VIR37 | 3 | 5 | 0 | 1 | 6 | 12 | 70 | 76 | 77 |
| VIR38 | 4 | 6 | 1 | 0 | 5 | 13 | 71 | 77 | 78 |
| VIR39 | 5 | 7 | 6 | 5 | 0 | 14 | 68 | 76 | 77 |
| CA16 | 11 | 13 | 12 | 13 | 14 | 0 | 72 | 80 | 81 |
| VIR43 | 69 | 67 | 70 | 71 | 68 | 72 | ~ | ~ | ~ |
| VIR5 | 77 | 75 | 76 | 77 | 76 | 80 | ~ | ~ | ~ |
| AST-VAN8 | 78 | 76 | 77 | 78 | 77 | 81 | ~ | ~ | ~ |

The strains which have a score less than or equal to 2 are of the same type, the strains which have a score strictly greater than 2 are of different type. Thus, the ATF1 and ATF2, VIR35 and VIR36, and VIR37 and VIR38 strains are respectively of the same type. All the other strains taken in pairs are of different types.
The high sums obtained between the VIR43, VIR5 and AST-VANS strains, which are not *S. aureus*, and all the other strains, which are *S. aureus*, should be noted. These results confirm the specificity of the method.
The VIR43, VIR5 and AST-VANS strains are of different species. These strains cannot therefore be compared with one another and no value is reported in TABLE 18. Extremely advantageously, scores greater than 20, for instance between ATF1 and VIR39, reflect a great divergence between strains. Scores between 14 and 20, as between CA16 and ATF1, reflect a moderate divergence and scores between 4 and 14, as between ATF1 and ATF7, a weak divergence.
The method thus implemented therefore makes it possible not only to establish whether two strains are of the same type, which is important for identifying a common seat of infection, but also to estimate the proximity of two strains, which is extremely important for epidemiological studies.
This example shows that, very advantageously, the present invention makes it possible, in a time of less than one hour, which is very short, to confirm the identity of a species such as *C. albicans* and to determine, simultaneously within the same analysis, the properties of typing and potential resistance to at least one antibiotic and to establish the existence of a virulence factor. The present invention also allows quantitative assaying, which is particularly advantageous when the properties of resistance to at least one antibiotic, or virulence, are linked to the level of expression of a protein or of a metabolite. This is what we illustrate here with the quantitative assaying of lipase 8. These properties were established with the same instrument, which greatly facilitates the analysis and the reporting of the results. Finally, the characteristics of yeasts are established using fungal proteins, which reflects the existence of live and viable microorganisms, unlike characterizations using fungal DNA which can be distorted by the existence of dead yeasts.

EXAMPLE 10: PROTOCOL FOR DIGESTION OF MICROORGANISMS IN THE PRESENCE OF METHANOL, SUITABLE FOR ASSAYING AT LEAST ONE METABOLITE

Conventionally, the following protocol is implemented in 19 steps:
1. Sampling of five microorganism colonies, obtained according to example 1, and suspension in 100 µl of a 6M guanidine hydrochloride, 50 mM Tris-HCl solution, pH=8.0.
2. Centrifugation at 15000 g for 5 minutes.
3. Pellet taken up in 400 µl of a 50 mM ammonium bicarbonate solution, pH=8.0.
4. Addition of 600 µl of methanol.

Steps 5 to 9: idem steps 2 to 6 of example 4.
Steps 10 to 19: idem steps 8 to 17 of example 6.

EXAMPLE 11: CHARACTERIZATION OF *C. ALBICANS* SAMPLES BY SIMULTANEOUS ANALYSIS OF PROTEINS AND OF METABOLITES

After having established the one or more species of the samples according to any one of the methods described in examples 1 to 3, the species listed below are analyzed.
Five strains of *C. albicans* are analyzed in order to confirm their identification and to establish their characteristics:

| | |
|---|---|
| ATF1 | ATF2 |
| ATF3 | ATF4 |
| ATF6 | |

Each sample is treated according to example 10, then a volume of 20 µl of digested proteins is injected and analyzed according to the same conditions as in example 7. Tables 13 and 14 are identical, with one exception. The transition number 109 is added to the method. It corresponds to the molecule, ergosterol, with clinical interest I and R. The charge state of the precursor is 1, the retention time is 36.3 minutes, the m/z filtered in Q1 is 379.4, the m/z filtered in Q3 is 69.2, and the collision energy is 47. The mass parameters are identical to those of example 7, with the exception of those below:

Curtain gas: 25.00 psi
Source temperature: 450.00° C.
Heating gas: 50.00 psi
Entry potential before Q0 (EP): 4.00 V
For transition 109, parameters differ:
Declustering potential (DP): 200.00 V
Entry potential before Q0 (EP): 10.00 V
Collision cell exit potential (CXP): 8 V All the transitions 1 to 108 are analyzed in a manner identical to example 9. All the areas of the I transitions are summed to give the sum SI. The area of transition 109 is called A109. The A109/SI ratio is then calculated and multiplied by a multiplication factor MF. The results obtained are given in table 19.

TABLE 19

| Strains | Area of transition 109 (A109) | Sum (SI) of the areas of the I transitions | A109/SI ratio multiplied by the multiplication factor (MF) | Multiplification factor (MF) |
|---|---|---|---|---|
| ATF1 | 1.7E+03 | 9.3E+07 | 1.6E+03 | 9.0E+07 |
| ATF2 | 7.9E+03 | 1.1E+08 | 6.4E+03 | |
| ATF3 | 3.9E+03 | 5.7E+07 | 6.3E+03 | |
| ATF4 | 5.7E+03 | 2.9E+08 | 1.8E+03 | |
| ATF6 | 6.4E+03 | 6.8E+07 | 8.5E+03 | |

The ATF2, ATF3 and ATF6 strains, which have a (A109/SI) ratio×MF greater than $2\times10^3$, overexpress ergosterol; these strains are therefore resistant. All the other strains have a ratio less than $2\times10^3$, they do not express ergosterol and are therefore not resistant.

This example shows that, very advantageously, the present invention makes it possible to simultaneously assay, within the same analysis, in a time of less than one hour, which is very short, and quantitatively, various compounds such as proteins, peptides or metabolites. Even more advantageously than the assaying of a protein, the quantitative assaying of a metabolite resulting from the action of this protein characterizes the presence of a functional protein and more broadly of a functional synthesis pathway. Thus, the quantification of ergosterol makes it possible in this case to establish the existence of a mechanism of resistance to fluconazole linked to the existence of functional and strongly active lanosterol demethylase.

EXAMPLE 12: CHARACTERIZATION OF MICROORGANISMS PRESENT IN URINE SAMPLES

After having established the one or more species of the samples according to any one of the methods described in examples 1 to 3, five urine samples contaminated with *E. coli* (Urine 1 to 5) are analyzed. A noncontaminated sixth urine (Urine 6) is also analyzed in order to serve as a negative control.

The following protocol is implemented in 29 steps (steps 5 to 12 are optional and could be omitted without significantly altering the results):

1. Centrifugation of 5 ml of contaminated urine at 2000 g for 30 seconds.
2. Recovery of the supernatant.
3. Centrifugation at 15000 g for 5 minutes.
4. Removal of the supernatant.
5. Washing of the pellet with 3 ml of distilled water by resuspension.
6. Centrifugation at 15000 g for 5 minutes.
7. Removal of the supernatant.
8. Bringing the pellet into contact with solvent in a dilution to 1/10.
9. Leaving for one hour at −20° C.
10. Centrifugation at 15000 g for 5 minutes.
11. Removal of the supernatant.
12. Bringing the pellet into contact with solvent in a dilution to 1/10.
13. Leaving for one hour at −20° C.
14. Centrifugation at 15000 g for 5 minutes.
15. Removal of the supernatant.
12. Suspension of the pellet in 10 to 100 µl of a 6M guanidine hydrochloride, 50 mM Tris-HCl solution, pH=8.0.
13. Steps 14 to 18: idem steps 2 to 6 of example 4.
19. Steps 19 to 28: idem steps 8 to 17 of example 6.
29. Injection of 100 µl of acidified eluate onto the chromatographic system and mass spectrometer, according to the protocol described in example 7.

The areas obtained for each of the transitions and for each of the microorganisms studied were measured. Since the urine samples have a bacterial load that is very different from one sample to another, the threshold used in example 7 for declaring a positive transition cannot be used here. It must be adjusted to the amount of bacteria present. In the previous example, the sampling of a colony resulted in a comparable amount of microorganisms. This is no longer the case in this example. Thus, the amount of bacteria is estimated by summing the area of all the I transitions. The sum of the areas of the I transitions is reported in TABLE 20.

TABLE 20

| Urine 1 | Urine 2 | Urine 3 | Urine 4 | Urine 5 | Urine 6 |
|---|---|---|---|---|---|
| 1 509 251.3 | 828 079.5 | 5 349 271.0 | 11 918 946.9 | 1 054 480.6 | 0.0 |

Thus, sample 4 comprises a bacterial load that is higher than sample 3, which itself has a higher load than examples 1 and 5, which themselves have higher loads than sample 2. Samples 1 and 5 have a comparable bacterial load. Sample 6 does not comprise an *E. coli* and exhibits a zero load, thereby demonstrating the specificity of the technique.

The area of each transition is then standardized by dividing it by the area of all the I transitions. All the transitions of which the ratio is greater than or equal to 0.00015 (non-dimensional ratio) are considered to be positive and have been denoted "1" in TABLE 21. All the transitions of which the ratio is less than 0.00015 are considered to be negative and have been denoted 0 in TABLE 21. When no signal peak was observed, the transition was noted as negative.

TABLE 21

| Transition number | Urine 1 | Urine 2 | Urine 3 | Urine 4 | Urine 5 | Urine 6 |
|---|---|---|---|---|---|---|
| 1 | 1 | 1 | 1 | 1 | 1 | 0 |
| 2 | 1 | 1 | 1 | 1 | 1 | 0 |
| 3 | 1 | 1 | 1 | 1 | 1 | 0 |
| 4 | 0 | 0 | 1 | 1 | 1 | 0 |
| 5 | 0 | 0 | 1 | 1 | 1 | 0 |
| 6 | 0 | 0 | 0 | 1 | 1 | 0 |
| 7 | 0 | 0 | 0 | 0 | 0 | 0 |
| 8 | 0 | 0 | 0 | 0 | 0 | 0 |
| 9 | 0 | 0 | 0 | 0 | 0 | 0 |
| 10 | 1 | 1 | 1 | 1 | 1 | 0 |
| 11 | 1 | 1 | 1 | 1 | 1 | 0 |
| 12 | 1 | 1 | 1 | 1 | 1 | 0 |
| 13 | 1 | 1 | 1 | 1 | 1 | 0 |
| 14 | 1 | 1 | 1 | 1 | 1 | 0 |
| 15 | 1 | 1 | 1 | 1 | 1 | 0 |
| 16 | 1 | 1 | 1 | 1 | 1 | 0 |
| 17 | 1 | 1 | 1 | 1 | 1 | 0 |
| 18 | 1 | 1 | 1 | 1 | 0 | 0 |
| 19 | 1 | 1 | 1 | 1 | 0 | 0 |
| 20 | 1 | 0 | 1 | 0 | 0 | 0 |
| 21 | 1 | 1 | 1 | 1 | 1 | 0 |

TABLE 21-continued

| Transition number | Urine 1 | Urine 2 | Urine 3 | Urine 4 | Urine 5 | Urine 6 |
|---|---|---|---|---|---|---|
| 22 | 1 | 1 | 1 | 1 | 1 | 0 |
| 23 | 1 | 1 | 1 | 1 | 1 | 0 |
| 24 | 1 | 1 | 1 | 1 | 1 | 0 |
| 25 | 1 | 1 | 0 | 1 | 1 | 0 |
| 26 | 1 | 1 | 0 | 1 | 1 | 0 |
| 27 | 1 | 1 | 0 | 1 | 1 | 0 |
| 28 | 1 | 1 | 1 | 1 | 1 | 0 |
| 29 | 1 | 1 | 1 | 1 | 1 | 0 |
| 30 | 1 | 1 | 1 | 1 | 1 | 0 |
| 31 | 0 | 1 | 1 | 1 | 1 | 0 |
| 32 | 0 | 0 | 1 | 1 | 1 | 0 |
| 33 | 0 | 0 | 0 | 1 | 0 | 0 |
| 34 | 1 | 1 | 1 | 1 | 1 | 0 |
| 35 | 1 | 1 | 1 | 1 | 1 | 0 |
| 36 | 1 | 1 | 1 | 1 | 1 | 0 |
| 37 | 1 | 1 | 1 | 1 | 1 | 0 |
| 38 | 1 | 1 | 1 | 1 | 1 | 0 |
| 39 | 1 | 1 | 1 | 1 | 1 | 0 |
| 40 | 1 | 1 | 1 | 1 | 1 | 0 |
| 41 | 1 | 1 | 1 | 1 | 1 | 0 |
| 42 | 1 | 1 | 1 | 1 | 1 | 0 |
| 43 | 1 | 1 | 1 | 1 | 1 | 0 |
| 44 | 1 | 1 | 1 | 1 | 1 | 0 |
| 45 | 1 | 1 | 1 | 1 | 1 | 0 |
| 46 | 0 | 0 | 1 | 1 | 1 | 0 |
| 47 | 0 | 0 | 1 | 1 | 1 | 0 |
| 48 | 0 | 0 | 1 | 1 | 1 | 0 |
| 49 | 0 | 0 | 0 | 0 | 0 | 0 |
| 50 | 0 | 0 | 0 | 0 | 0 | 0 |
| 51 | 0 | 0 | 0 | 0 | 0 | 0 |
| 52 | 0 | 0 | 0 | 0 | 0 | 0 |
| 53 | 0 | 0 | 0 | 0 | 0 | 0 |
| 54 | 0 | 0 | 0 | 0 | 0 | 0 |
| 55 | 1 | 1 | 1 | 0 | 1 | 0 |
| 56 | 1 | 1 | 1 | 0 | 1 | 0 |
| 57 | 1 | 1 | 1 | 0 | 1 | 0 |
| 58 | 1 | 1 | 1 | 0 | 1 | 0 |
| 59 | 1 | 1 | 1 | 0 | 1 | 0 |
| 60 | 1 | 1 | 1 | 0 | 0 | 0 |
| 61 | 0 | 0 | 0 | 0 | 0 | 0 |
| 62 | 0 | 0 | 0 | 0 | 0 | 0 |
| 63 | 0 | 0 | 0 | 0 | 0 | 0 |
| 64 | 0 | 0 | 0 | 0 | 0 | 0 |
| 65 | 0 | 0 | 0 | 0 | 0 | 0 |
| 66 | 1 | 0 | 0 | 0 | 0 | 0 |
| 67 | 1 | 1 | 1 | 1 | 1 | 0 |
| 68 | 1 | 1 | 1 | 1 | 1 | 0 |
| 69 | 1 | 1 | 1 | 1 | 1 | 0 |
| 70 | 1 | 0 | 0 | 1 | 1 | 0 |
| 71 | 1 | 0 | 0 | 1 | 1 | 0 |
| 72 | 0 | 0 | 0 | 0 | 0 | 0 |
| 73 | 1 | 0 | 1 | 1 | 1 | 0 |
| 74 | 1 | 0 | 1 | 1 | 1 | 0 |
| 75 | 1 | 0 | 1 | 1 | 1 | 0 |
| 76 | 1 | 1 | 1 | 1 | 1 | 0 |
| 77 | 1 | 1 | 1 | 1 | 1 | 0 |
| 78 | 1 | 1 | 1 | 1 | 1 | 0 |
| 79 | 1 | 1 | 1 | 1 | 1 | 0 |
| 80 | 1 | 1 | 1 | 1 | 1 | 0 |
| 81 | 1 | 1 | 1 | 1 | 1 | 0 |
| 82 | 1 | 1 | 1 | 1 | 1 | 0 |
| 83 | 1 | 1 | 1 | 1 | 1 | 0 |
| 84 | 1 | 1 | 1 | 1 | 1 | 0 |
| 85 | 1 | 1 | 1 | 1 | 1 | 0 |
| 86 | 1 | 1 | 1 | 1 | 1 | 0 |
| 87 | 1 | 1 | 1 | 1 | 1 | 0 |
| 88 | 1 | 1 | 1 | 1 | 1 | 0 |
| 89 | 1 | 1 | 1 | 1 | 1 | 0 |
| 90 | 1 | 1 | 1 | 1 | 1 | 0 |
| 91 | 1 | 0 | 1 | 1 | 1 | 0 |
| 92 | 1 | 1 | 1 | 1 | 1 | 0 |
| 93 | 1 | 0 | 1 | 1 | 1 | 0 |
| 94 | 0 | 0 | 0 | 0 | 0 | 0 |
| 95 | 0 | 0 | 0 | 0 | 0 | 0 |
| 96 | 0 | 0 | 0 | 0 | 0 | 0 |
| 97 | 0 | 0 | 0 | 0 | 0 | 0 |
| 98 | 0 | 0 | 0 | 0 | 0 | 0 |
| 99 | 0 | 0 | 0 | 0 | 0 | 0 |
| 100 | 0 | 0 | 0 | 0 | 0 | 0 |
| 101 | 0 | 0 | 0 | 0 | 0 | 0 |
| 102 | 0 | 1 | 0 | 0 | 0 | 0 |
| 103 | 1 | 1 | 1 | 1 | 1 | 0 |
| 104 | 1 | 1 | 1 | 1 | 1 | 0 |
| 105 | 1 | 1 | 1 | 1 | 1 | 0 |
| 106 | 1 | 1 | 1 | 1 | 1 | 0 |
| 107 | 1 | 1 | 1 | 1 | 1 | 0 |
| 108 | 1 | 1 | 1 | 1 | 1 | 0 |
| 109 | 1 | 1 | 1 | 1 | 1 | 0 |
| 110 | 1 | 1 | 1 | 1 | 1 | 0 |
| 111 | 1 | 1 | 1 | 1 | 1 | 0 |
| 112 | 1 | 1 | 1 | 1 | 1 | 0 |
| 113 | 1 | 1 | 1 | 1 | 1 | 0 |
| 114 | 0 | 0 | 0 | 1 | 1 | 0 |
| 115 | 1 | 1 | 1 | 1 | 1 | 0 |
| 116 | 1 | 1 | 1 | 1 | 1 | 0 |
| 117 | 1 | 1 | 1 | 1 | 1 | 0 |
| 118 | 0 | 0 | 0 | 0 | 0 | 0 |
| 119 | 0 | 0 | 0 | 0 | 0 | 0 |
| 120 | 0 | 0 | 0 | 0 | 0 | 0 |
| 121 | 1 | 1 | 1 | 0 | 0 | 0 |
| 122 | 0 | 0 | 0 | 0 | 0 | 0 |
| 123 | 0 | 0 | 0 | 0 | 0 | 0 |
| 124 | 0 | 0 | 0 | 0 | 0 | 0 |
| 125 | 0 | 0 | 0 | 0 | 0 | 0 |

The positive-transition number is then summed for the I, R and V applications and reported in TABLE 22:

TABLE 22

|  | Urine 1 | Urine 2 | Urine 3 | Urine 4 | Urine 5 | Urine 6 |
|---|---|---|---|---|---|---|
| I | 36 | 36 | 40 | 44 | 41 | 0 |
| R | 6 | 6 | 6 | 0 | 5 | 0 |
| V | 1 | 1 | 1 | 0 | 0 | 0 |

In the same way as the transition positivity threshold had to be modified in order to take into account the concentration of the samples, the number of peptides necessary for characterizing a strain must be adjusted to the total concentration of bacteria. Certain weakly detected peptides in example 7 may be under the limit of detection if the amount of bacteria is less than one colony.

Urines 1 to 5 exhibit more than 30 positive transitions in the I category. All these samples are therefore confirmed as contaminated with the *E. coli* species.

On the other hand, urine 6 exhibits no positive transition in the I category. It is therefore confirmed as not being contaminated with the *E. coli* species.

Urines 1, 2, 3 and 5 exhibit at least five positive transitions for the R category, they therefore express the plasmid-mediated penicillinase TEM-2, which is synonymous with a mechanism of resistance to penicillins, in particular aminopenicillins or A penicillins (ampicillin), carboxypenicillins or C penicillins (ticarcillin) and uréidopénicillin or penicillin U (piperacillin).

On the other hand, urines 4 and 6 do not exhibit positive transitions for the R category, they do not therefore express the plasmid-mediated penicillinase TEM-2. These strains are therefore sensitive to penicillins These results of resistance to ampicillin, ticarcillin and piperacillin were confirmed with the VITEK®2 automated device sold by the applicant and the AST-EXN and AST-N103 cards. The confirmation took a time of 6 to 8 hours on the VITEK®2 automated device, which is slower than for the present invention.

Urines 1 to 6 do not exhibit more than one positive transition for the V category. These urines are not therefore contaminated with toxins of shigatoxin type.

For the typing, the T-category transitions of each strain are compared with the transitions of the other strains considered as reference strains. In practice, a value 0 is assigned when the transitions between the two strains are classified in the same category (positive or negative) and a value of 1 is assigned when the transitions between the two strains are classified in different categories (a positive transition and a negative transition). The values are summed for all the T-category transitions of each strain pair in order to establish a score. The scores are given in TABLE 23:

TABLE 23

|        | Urine 1 | Urine 2 | Urine 3 | Urine 4 | Urine 5 |
|--------|---------|---------|---------|---------|---------|
| Urine 1 | 0  | 11 | 13 | 19 | 15 |
| Urine 2 | 11 | 0  | 16 | 24 | 20 |
| Urine 3 | 13 | 16 | 0  | 16 | 12 |
| Urine 4 | 19 | 24 | 16 | 0  | 8  |
| Urine 5 | 15 | 20 | 12 | 8  | 0  |

No urine has a score less than or equal to 4. The strains infecting urines 1 to 5 are therefore of different types. These urine samples were collected in a local medical test laboratory where infections often occur in different environments. Under these conditions, it is uncommon to observe urine infections linked to the same strain.

This example shows that, very advantageously, the present invention makes it possible, directly from the primary sample, which is very advantageous, to confirm the identity of a species such as *E. coli* and to determine, simultaneously within the same analysis, the properties of typing and potential resistance to at least one antibiotic.

LITERATURE REFERENCES

[1] J. Anhalt & C. Fenselau, 1975, Anal. Chem., 47(2):219-225.
[2] A. Fox et al., ed., 1990, Analytical microbiology methods: chromatography and mass spectrometry, Plenum Press, New York, N.Y.
[3] M. Claydon et al., 1996, Nature Biotech. 14:1584-1586.
[4] T. Krishnamurthy & P. Ross, 1996, Rapid Com. Mass Spec., 10:1992-1996.
[5] P. Seng et al. 2009, Clin. Infect. Dis., 49:543-551.
[6] C. Fenselau et al., 2008, Appl. Environ. Microbiol., 904-906.
[7] D. Ding et al. 2009, J. Pharm. Biomed. Anal. 50:79-85.
[8] R. Everley et al., 2009, J. Microbiol. Methods, 77:152-158.
[9] S. Hofstadler et al., 2005, Int. J. Mass Spectrom., 242:23-41.
[10] D. Ecker, 2008, Nat. Rev. Microbiol., 6(7):553-558.
[11] W.-J. Chen et al., 2008, Anal. Chem., 80: 9612-9621.
[12] D. Lopez-Ferrer et al., 2008, Anal. Chem., 80:8930-8936.
[13] D. Lopez-Ferrer et al., 2005, J. Proteome res., 4(5): 1569-1574.
[14] T. Fortin et al., 2009, Mol. Cell Proteomics, 8(5): 1006-1015.
[15] H. Keshishian et al., 2007, Mol. Cell Proteomics, 2212-2229.
[16] J. Stal-Zeng et al., 2007, Mol. Cell Proteomics, 1809-1817.
[17] Gaskell, Electrospray: principles and practise, 1997, J. Mass Spectrom., 32, 677-688).
[18] V. Fusaro et al., 2009, Nature Biotech. 27, 190-198.
[19] J. Mead et al., 15 Nov. 2008, Mol. Cell Proteomics, E-pub.
[20] F. Desiere et al., 2006, Nucleic Acids Res., 34 (database issue): D655-8.
[21] L. Anderson & C. Hunter, 2006, Mol. Cell Proteomics, 573-588.
[22] B. Han & R. Higgs, 2008, Brief Funct Genomic Proteomic., 7(5):340-54.
[23] K.-Y. Wang et al., 2008, Anal Chem, 80(16) 6159-6167.
[24] J. Bundy & C. Fenselau, 1999, Anal. Chem. 71: 1460-1463.
[25] K-C Ho et al., 2004, Anal. Chem. 76: 7162-7268.
[26] Y. S. Lin et al., 2005, Anal. Chem., 77: 1753-1760.
[27] S. Vaidyanathan et al., 2001, Anal. Chem., 73:4134-4144.
[28] P. Seng et al., 2009, Clin. Infect. Dis., 49:543-551.
[29] Manes N. et al., 2007, Mol. & Cell. Proteomics, 6(4): 717-727.
[30] R. Nandakumar et al., 2009, Oral Microbiology Immunology, 24:347-352.
[31] L. Hernychova et al., 2008, Anal. Chem., 80:7097-7104.
[32] J.-M. Pratt et al., 2006, Nat. Protoc., 1:1029-1043.
[33] V. Brun et al., 2007, Mol. Cell Proteomics, 2139-2149.

The invention claimed is:

1. A method for characterizing a microorganism, comprising:
   identifying the microorganism; and
   subjecting the microorganism identified to mass spectrometry with a spectrometer in MS/MS mode using multiple reaction monitoring (MRM) to identify markers of properties of typing, potential resistance to at least one antimicrobial, and virulence factor, of the microorganism,
   wherein:
   the markers are selected from the group consisting of proteins, peptides, and metabolites, and
   the microorganism is a bacterium, a virus, a protozoan, or a yeast.

2. The method for characterizing a microorganism of claim 1, wherein the microorganism is *Staphylococcus aureus*.

3. The method for characterizing a microorganism of claim 2, wherein the markers identified comprise at least one peptide that has an amino acid sequence selected from the group consisting of SEQ ID NOs: 2, 13, 15, 21, and 24.

4. The method for characterizing a microorganism of claim 2, wherein the markers identified comprise at least one peptide that has an amino acid sequence selected from the group consisting of SEQ ID NOs: 13 and 15.

5. The method for characterizing a microorganism of claim 2, wherein the markers identified comprise at least one peptide that has an amino acid sequence selected from the group consisting of SEQ ID NOs: 21 and 24.

6. The method for characterizing a microorganism of claim 1, wherein the microorganism is *Escherichia coli*.

7. The method for characterizing a microorganism of claim 6, wherein the markers identified comprise at least one peptide that has an amino acid sequence selected from the group consisting of SEQ ID NOs: 64, 66, and 85 to 87.

8. The method for characterizing a microorganism of claim 6, wherein the markers identified comprise at least one peptide that has an amino acid sequence selected from the group consisting of SEQ ID NOs: 64 and 66.

9. The method for characterizing a microorganism of claim 6, wherein the markers identified comprise at least one peptide that has an amino acid sequence selected from the group consisting of SEQ ID NOs: 85, 86, and 87.

10. The method for characterizing a microorganism of claim 1, wherein the microorganism is *Candida albicans*.

11. The method for characterizing a microorganism of claim 1, wherein the markers are identified simultaneously.

12. The method for characterizing a microorganism of claim 1, wherein the markers are identified in the same mass spectrometry apparatus.

13. The method for characterizing a microorganism of claim 1, wherein the microorganism is identified by mass spectrometry.

14. The method for characterizing a microorganism of claim 13, wherein the mass spectrometry for identifying the microorganism is selected from the group consisting of MS type, MS/MS type, and MS type followed by MS/MS type.

15. The method for characterizing a microorganism of claim 1, further comprising:
    confirming, by mass spectrometry, the identification of the microorganism.

16. The method for characterizing a microorganism of claim 15, wherein the mass spectrometry for confirming the identification of the microorganism is MS/MS type.

17. The method for characterizing a microorganism of claim 16, wherein the mass spectrometry for confirming the identification of the microorganism is MRM type.

18. The method for characterizing a microorganism of claim 1, wherein:

the markers are peptides, and the microorganism is a bacterium or a yeast.

19. A method for characterizing a microorganism, comprising:

identifying the microorganism; and subjecting the microorganism identified to mass spectrometry with a spectrometer in MS/MS mode using multiple reaction monitoring (MRM) to identify at least one marker of a property of typing, potential resistance to at least one antimicrobial, or virulence factor, of the microorganism, wherein:

the marker is a protein or a peptide, and the microorganism is a bacterium, a virus, a protozoan, or a yeast.

20. A method for characterizing a microorganism, comprising:

identifying the microorganism; and subjecting the microorganism identified to mass spectrometry with a spectrometer in MS/MS mode using multiple reaction monitoring (MRM) to identify at least one marker of a property of typing, potential resistance to at least one antimicrobial, or virulence factor, of the microorganism, wherein:

the marker is selected from the group consisting of proteins, peptides, and metabolites, and the microorganism is a virus, a protozoan, or a yeast.

* * * * *

```
                        SEQUENCE LISTING

<160> NUMBER OF SEQ ID NOS: 177

<210> SEQ ID NO 1
<211> LENGTH: 508
<212> TYPE: PRT
<213> ORGANISM: Staphylococcus aureus

<400> SEQUENCE: 1

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
```

```
                50                  55                  60
Ile Gln Ser Leu Lys Asp Asp Pro Ser Gln Ser Ala Asn Val Leu Gly
 65                  70                  75                  80

Glu Ala Gln Lys Leu Asn Asp Ser Gln Ala Pro Lys Ala Asp Ala Gln
                 85                  90                  95

Gln Asn Lys Phe Asn Lys Asp Gln Gln Ser Ala Phe Tyr Glu Ile Leu
                100                 105                 110

Asn Met Pro Asn Leu Asn Glu Glu Gln Arg Asn Gly Phe Ile Gln Ser
            115                 120                 125

Leu Lys Asp Asp Pro Ser Gln Ser Thr Asn Val Leu Gly Glu Ala Lys
            130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Glu Ser Gln
            195                 200                 205

Ala Pro Lys Ala Asp Asn Lys Phe Asn Lys Glu Gln Gln Asn Ala Phe
210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
                260                 265                 270

Lys Phe Asn Lys Glu Gln Gln Asn Ala Phe Tyr Glu Ile Leu His Leu
            275                 280                 285

Pro Asn Leu Thr Glu Glu Gln Arg Asn Gly Phe Ile Gln Ser Leu Lys
            290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Gly Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
            355                 360                 365

Glu Asp Asn Lys Lys Pro Gly Lys Glu Asp Gly Asn Lys Pro Gly Lys
            370                 375                 380

Glu Asp Gly Asn Lys Pro Gly Lys Glu Asp Gly Asn Lys Pro Gly Lys
385                 390                 395                 400

Glu Asp Gly Asn Lys Pro Gly Lys Glu Asp Gly Asn Gly Val His Val
                405                 410                 415

Val Lys Pro Gly Asp Thr Val Asn Asp Ile Ala Lys Ala Asn Gly Thr
                420                 425                 430

Thr Ala Asp Lys Ile Ala Ala Asp Asn Lys Leu Ala Asp Lys Asn Met
            435                 440                 445

Ile Lys Pro Gly Gln Glu Leu Val Val Asp Lys Lys Gln Pro Ala Asn
            450                 455                 460

His Ala Asp Ala Asn Lys Ala Gln Ala Leu Pro Glu Thr Gly Glu Glu
465                 470                 475                 480
```

```
Asn Pro Phe Ile Gly Thr Thr Val Phe Gly Gly Leu Ser Leu Ala Leu
                485                 490                 495

Gly Ala Ala Leu Leu Ala Gly Arg Arg Arg Glu Leu
            500                 505

<210> SEQ ID NO 2
<211> LENGTH: 15
<212> TYPE: PRT
<213> ORGANISM: Staphylococcus aureus

<400> SEQUENCE: 2

Asp Asp Pro Ser Gln Ser Ala Asn Val Leu Gly Glu Ala Gln Lys
1               5                   10                  15

<210> SEQ ID NO 3
<211> LENGTH: 20
<212> TYPE: PRT
<213> ORGANISM: Staphylococcus aureus

<400> SEQUENCE: 3

Asp Gln Gln Ser Ala Phe Tyr Glu Ile Leu Asn Met Pro Asn Leu Asn
1               5                   10                  15

Glu Glu Gln Arg
            20

<210> SEQ ID NO 4
<211> LENGTH: 14
<212> TYPE: PRT
<213> ORGANISM: Staphylococcus aureus

<400> SEQUENCE: 4

Asp Asp Pro Ser Gln Ser Thr Asn Val Leu Gly Glu Ala Lys
1               5                   10

<210> SEQ ID NO 5
<211> LENGTH: 20
<212> TYPE: PRT
<213> ORGANISM: Staphylococcus aureus

<400> SEQUENCE: 5

Glu Gln Gln Asn Ala Phe Tyr Glu Ile Leu Asn Met Pro Asn Leu Asn
1               5                   10                  15

Glu Glu Gln Arg
            20

<210> SEQ ID NO 6
<211> LENGTH: 14
<212> TYPE: PRT
<213> ORGANISM: Staphylococcus aureus

<400> SEQUENCE: 6

Asp Asp Pro Ser Gln Ser Ala Asn Leu Leu Ala Glu Ala Lys
1               5                   10

<210> SEQ ID NO 7
<211> LENGTH: 7
<212> TYPE: PRT
<213> ORGANISM: Staphylococcus aureus

<400> SEQUENCE: 7

Asp Asp Pro Ser Val Ser Lys
1               5
```

<210> SEQ ID NO 8
<211> LENGTH: 6
<212> TYPE: PRT
<213> ORGANISM: Staphylococcus aureus

<400> SEQUENCE: 8

Ile Ala Ala Asp Asn Lys
1               5

<210> SEQ ID NO 9
<211> LENGTH: 668
<212> TYPE: PRT
<213> ORGANISM: Staphylococcus aureus

<400> SEQUENCE: 9

Met Lys Lys Ile Lys Ile Val Pro Leu Ile Leu Ile Val Val Val Val
1               5                   10                  15

Gly Phe Gly Ile Tyr Phe Tyr Ala Ser Lys Asp Lys Glu Ile Asn Asn
                20                  25                  30

Thr Ile Asp Ala Ile Glu Asp Lys Asn Phe Lys Gln Val Tyr Lys Asp
            35                  40                  45

Ser Ser Tyr Ile Ser Lys Ser Asp Asn Gly Glu Val Glu Met Thr Glu
50                  55                  60

Arg Pro Ile Lys Ile Tyr Asn Ser Leu Gly Val Lys Asp Ile Asn Ile
65                  70                  75                  80

Gln Asp Arg Lys Ile Lys Val Ser Lys Asn Lys Arg Val Asp
                85                  90                  95

Ala Gln Tyr Lys Ile Lys Thr Asn Tyr Gly Asn Ile Arg Asn Val
                100                 105                 110

Gln Phe Asn Phe Val Lys Glu Asp Gly Met Trp Lys Leu Asp Trp Asp
            115                 120                 125

His Ser Val Ile Ile Pro Gly Met Gln Lys Asp Gln Ser Ile His Ile
        130                 135                 140

Glu Asn Leu Lys Ser Glu Arg Gly Lys Ile Leu Asp Arg Asn Asn Val
145                 150                 155                 160

Glu Leu Ala Asn Thr Gly Thr Ala Tyr Glu Ile Gly Ile Val Pro Lys
                165                 170                 175

Asn Val Ser Lys Lys Asp Tyr Lys Ala Ile Ala Lys Glu Leu Ser Ile
            180                 185                 190

Ser Glu Asp Tyr Ile Lys Gln Gln Met Asp Gln Asn Trp Val Gln Asp
        195                 200                 205

Asp Thr Phe Val Pro Leu Lys Thr Val Lys Lys Met Asp Glu Tyr Leu
210                 215                 220

Ser Asp Phe Ala Lys Lys Phe His Leu Thr Thr Asn Glu Thr Glu Ser
225                 230                 235                 240

Arg Asn Tyr Pro Leu Glu Lys Ala Thr Ser His Leu Leu Gly Tyr Val
                245                 250                 255

Gly Pro Ile Asn Ser Glu Glu Leu Lys Gln Lys Glu Tyr Lys Gly Tyr
            260                 265                 270

Lys Asp Asp Ala Val Ile Gly Lys Lys Gly Leu Glu Lys Leu Tyr Asp
        275                 280                 285

Lys Lys Leu Gln His Glu Asp Gly Tyr Arg Val Thr Ile Val Asp Asp
290                 295                 300

Asn Ser Asn Thr Ile Ala His Thr Leu Ile Glu Lys Lys Lys Lys Asp
305                 310                 315                 320

```
Gly Lys Asp Ile Gln Leu Thr Ile Asp Ala Lys Val Gln Lys Ser Ile
            325                 330                 335

Tyr Asn Asn Met Lys Asn Asp Tyr Gly Ser Gly Thr Ala Ile His Pro
        340                 345                 350

Gln Thr Gly Glu Leu Leu Ala Leu Val Ser Thr Pro Ser Tyr Asp Val
    355                 360                 365

Tyr Pro Phe Met Tyr Gly Met Ser Asn Glu Glu Tyr Asn Lys Leu Thr
370                 375                 380

Glu Asp Lys Lys Glu Pro Leu Leu Asn Lys Phe Gln Ile Thr Thr Ser
385                 390                 395                 400

Pro Gly Ser Thr Gln Lys Ile Leu Thr Ala Met Ile Gly Leu Asn Asn
            405                 410                 415

Lys Thr Leu Asp Asp Lys Thr Ser Tyr Lys Ile Asp Gly Lys Gly Trp
        420                 425                 430

Gln Lys Asp Lys Ser Trp Gly Gly Tyr Asn Val Thr Arg Tyr Glu Val
    435                 440                 445

Val Asn Gly Asn Ile Asp Leu Lys Gln Ala Ile Glu Ser Ser Asp Asn
450                 455                 460

Ile Phe Phe Ala Arg Val Ala Leu Glu Leu Gly Ser Lys Lys Phe Glu
465                 470                 475                 480

Lys Gly Met Lys Lys Leu Gly Val Gly Glu Asp Ile Pro Ser Asp Tyr
            485                 490                 495

Pro Phe Tyr Asn Ala Gln Ile Ser Asn Lys Asn Leu Asp Asn Glu Ile
        500                 505                 510

Leu Leu Ala Asp Ser Gly Tyr Gly Gln Gly Glu Ile Leu Ile Asn Pro
    515                 520                 525

Val Gln Ile Leu Ser Ile Tyr Ser Ala Leu Glu Asn Asn Gly Asn Ile
530                 535                 540

Asn Ala Pro His Leu Leu Lys Asp Thr Lys Asn Lys Val Trp Lys Lys
545                 550                 555                 560

Asn Ile Ile Ser Lys Glu Asn Ile Asn Leu Leu Thr Asp Gly Met Gln
            565                 570                 575

Gln Val Val Asn Lys Thr His Lys Glu Asp Ile Tyr Arg Ser Tyr Ala
        580                 585                 590

Asn Leu Ile Gly Lys Ser Gly Thr Ala Glu Leu Lys Met Lys Gln Gly
    595                 600                 605

Glu Thr Gly Arg Gln Ile Gly Trp Phe Ile Ser Tyr Asp Lys Asp Asn
610                 615                 620

Pro Asn Met Met Met Ala Ile Asn Val Lys Asp Val Gln Asp Lys Gly
625                 630                 635                 640

Met Ala Ser Tyr Asn Ala Lys Ile Ser Gly Lys Val Tyr Asp Glu Leu
            645                 650                 655

Tyr Glu Asn Gly Asn Lys Lys Tyr Asp Ile Asp Glu
        660                 665

<210> SEQ ID NO 10
<211> LENGTH: 8
<212> TYPE: PRT
<213> ORGANISM: Staphylococcus aureus

<400> SEQUENCE: 10

Ile Tyr Asn Ser Leu Gly Val Lys
1               5

<210> SEQ ID NO 11
```

```
<211> LENGTH: 7
<212> TYPE: PRT
<213> ORGANISM: Staphylococcus aureus

<400> SEQUENCE: 11

Asp Ile Asn Ile Gln Asp Arg
1               5

<210> SEQ ID NO 12
<211> LENGTH: 10
<212> TYPE: PRT
<213> ORGANISM: Staphylococcus aureus

<400> SEQUENCE: 12

Glu Leu Ser Ile Ser Glu Asp Tyr Ile Lys
1               5                   10

<210> SEQ ID NO 13
<211> LENGTH: 12
<212> TYPE: PRT
<213> ORGANISM: Staphylococcus aureus

<400> SEQUENCE: 13

Phe Gln Ile Thr Thr Ser Pro Gly Ser Thr Gln Lys
1               5                   10

<210> SEQ ID NO 14
<211> LENGTH: 11
<212> TYPE: PRT
<213> ORGANISM: Staphylococcus aureus

<400> SEQUENCE: 14

Ile Leu Thr Ala Met Ile Gly Leu Asn Asn Lys
1               5                   10

<210> SEQ ID NO 15
<211> LENGTH: 11
<212> TYPE: PRT
<213> ORGANISM: Staphylococcus aureus

<400> SEQUENCE: 15

Tyr Glu Val Val Asn Gly Asn Ile Asp Leu Lys
1               5                   10

<210> SEQ ID NO 16
<211> LENGTH: 8
<212> TYPE: PRT
<213> ORGANISM: Staphylococcus aureus

<400> SEQUENCE: 16

Val Ala Leu Glu Leu Gly Ser Lys
1               5

<210> SEQ ID NO 17
<211> LENGTH: 8
<212> TYPE: PRT
<213> ORGANISM: Staphylococcus aureus

<400> SEQUENCE: 17

Ser Tyr Ala Asn Leu Ile Gly Lys
1               5

<210> SEQ ID NO 18
<211> LENGTH: 315
<212> TYPE: PRT
```

<213> ORGANISM: Staphylococcus aureus

<400> SEQUENCE: 18

Met Ile Phe Met Val Lys Lys Arg Leu Leu Ala Ala Thr Leu Ser Leu
1               5                   10                  15

Gly Ile Ile Thr Pro Ile Ala Thr Ser Phe His Glu Ser Lys Ala Asp
            20                  25                  30

Asn Asn Ile Glu Asn Ile Gly Asp Gly Ala Glu Val Val Lys Arg Thr
        35                  40                  45

Glu Asp Thr Ser Ser Asp Lys Trp Gly Val Thr Gln Asn Ile Gln Val
    50                  55                  60

Asp Phe Val Lys Asp Lys Lys Tyr Asn Lys Asp Ala Leu Ile Leu Lys
65                  70                  75                  80

Met Gln Gly Phe Ile Asn Ser Lys Thr Thr Tyr Tyr Asn Tyr Lys Asn
                85                  90                  95

Thr Asp His Ile Lys Ala Met Arg Trp Pro Phe Gln Tyr Asn Ile Gly
            100                 105                 110

Leu Lys Thr Asn Asp Pro Asn Val Asp Leu Ile Asn Tyr Leu Pro Lys
        115                 120                 125

Asn Lys Ile Asp Ser Val Asn Val Ser Gln Thr Leu Gly Tyr Asn Ile
    130                 135                 140

Gly Gly Asn Phe Asn Ser Gly Pro Ser Thr Gly Asn Gly Ser Phe
145                 150                 155                 160

Asn Tyr Ser Lys Thr Ile Ser Tyr Asn Gln Gln Asn Tyr Ile Ser Glu
                165                 170                 175

Val Glu Arg Gln Asn Ser Lys Ser Val Gln Trp Gly Ile Lys Ala Asn
            180                 185                 190

Ser Phe Ile Thr Ser Leu Gly Lys Met Ser Gly His Asp Pro Asn Leu
        195                 200                 205

Phe Val Gly Tyr Lys Pro Tyr Ser Gln Asn Pro Arg Asp Tyr Phe Val
    210                 215                 220

Pro Asp Asn Glu Leu Pro Pro Leu Val His Ser Gly Phe Asn Pro Ser
225                 230                 235                 240

Phe Ile Ala Thr Val Ser His Glu Lys Gly Ser Gly Asp Thr Ser Glu
                245                 250                 255

Phe Glu Ile Thr Tyr Gly Arg Asn Met Asp Val Thr His Ala Thr Arg
            260                 265                 270

Arg Thr Thr His Tyr Gly Asn Ser Tyr Leu Glu Gly Ser Arg Ile His
        275                 280                 285

Asn Ala Phe Val Asn Arg Asn Tyr Thr Val Lys Tyr Glu Val Asn Trp
290                 295                 300

Lys Thr His Glu Ile Lys Val Lys Gly His Asn
305                 310                 315

<210> SEQ ID NO 19
<211> LENGTH: 14
<212> TYPE: PRT
<213> ORGANISM: Staphylococcus aureus

<400> SEQUENCE: 19

Thr Asn Asp Pro Asn Val Asp Leu Ile Asn Tyr Leu Pro Lys
1               5                   10

<210> SEQ ID NO 20
<211> LENGTH: 7
<212> TYPE: PRT

<213> ORGANISM: Staphylococcus aureus

<400> SEQUENCE: 20

Ser Val Gln Trp Gly Ile Lys
1               5

<210> SEQ ID NO 21
<211> LENGTH: 10
<212> TYPE: PRT
<213> ORGANISM: Staphylococcus aureus

<400> SEQUENCE: 21

Ala Asn Ser Phe Ile Thr Ser Leu Gly Lys
1               5                   10

<210> SEQ ID NO 22
<211> LENGTH: 325
<212> TYPE: PRT
<213> ORGANISM: Staphylococcus aureus

<400> SEQUENCE: 22

Met Lys Lys Ile Val Lys Ser Ser Val Val Thr Ser Ile Ala Leu Leu
1               5                   10                  15

Leu Leu Ser Asn Thr Val Asp Ala Ala Gln His Ile Thr Pro Val Ser
                20                  25                  30

Glu Lys Lys Val Asp Asp Lys Ile Thr Leu Tyr Lys Thr Thr Ala Thr
            35                  40                  45

Ser Asp Ser Asp Lys Leu Lys Ile Ser Gln Ile Leu Thr Phe Asn Phe
        50                  55                  60

Ile Lys Asp Lys Ser Tyr Asp Lys Asp Thr Leu Ile Leu Lys Ala Ala
65                  70                  75                  80

Gly Asn Ile Tyr Ser Gly Tyr Thr Lys Pro Asn Pro Lys Asp Thr Ile
                85                  90                  95

Ser Ser Gln Phe Tyr Trp Gly Ser Lys Tyr Asn Ile Ser Ile Asn Ser
            100                 105                 110

Asp Ser Asn Asp Ser Val Asn Val Asp Tyr Ala Pro Lys Asn Gln
        115                 120                 125

Asn Glu Glu Phe Gln Val Gln Gln Thr Val Gly Tyr Ser Tyr Gly Gly
    130                 135                 140

Asp Ile Asn Ile Ser Asn Gly Leu Ser Gly Gly Asn Gly Ser Lys
145                 150                 155                 160

Ser Phe Ser Glu Thr Ile Asn Tyr Lys Gln Glu Ser Tyr Arg Thr Ser
                165                 170                 175

Leu Asp Lys Arg Thr Asn Phe Lys Lys Ile Gly Trp Asp Val Glu Ala
            180                 185                 190

His Lys Ile Met Asn Asn Gly Trp Gly Pro Tyr Gly Arg Asp Ser Tyr
        195                 200                 205

His Ser Thr Tyr Gly Asn Glu Met Phe Leu Gly Ser Arg Gln Ser Asn
    210                 215                 220

Leu Asn Ala Gly Gln Asn Phe Leu Glu Tyr His Lys Met Pro Val Leu
225                 230                 235                 240

Ser Arg Gly Asn Phe Asn Pro Glu Phe Ile Gly Val Leu Ser Arg Lys
                245                 250                 255

Gln Asn Ala Ala Lys Lys Ser Lys Ile Thr Val Thr Tyr Gln Arg Glu
            260                 265                 270

Met Asp Arg Tyr Thr Asn Phe Trp Asn Gln Leu His Trp Ile Gly Asn
        275                 280                 285

```
Asn Tyr Lys Asp Glu Asn Arg Ala Thr His Thr Ser Ile Tyr Glu Val
        290                 295                 300

Asp Trp Glu Asn His Thr Val Lys Leu Ile Asp Thr Gln Ser Lys Glu
305                 310                 315                 320

Lys Asn Pro Met Ser
                325

<210> SEQ ID NO 23
<211> LENGTH: 6
<212> TYPE: PRT
<213> ORGANISM: Staphylococcus aureus

<400> SEQUENCE: 23

Met Pro Val Leu Ser Arg
1               5

<210> SEQ ID NO 24
<211> LENGTH: 13
<212> TYPE: PRT
<213> ORGANISM: Staphylococcus aureus

<400> SEQUENCE: 24

Gly Asn Phe Asn Pro Glu Phe Ile Gly Val Leu Ser Arg
1               5                   10

<210> SEQ ID NO 25
<211> LENGTH: 59
<212> TYPE: PRT
<213> ORGANISM: Staphylococcus aureus

<400> SEQUENCE: 25

Met Ala Lys Leu Gln Ile Thr Leu Thr Arg Ser Val Ile Gly Arg Pro
1               5                   10                  15

Glu Thr Gln Arg Lys Thr Val Glu Ala Leu Gly Leu Lys Lys Thr Asn
            20                  25                  30

Ser Ser Val Val Val Glu Asp Asn Pro Ala Ile Arg Gly Gln Ile Asn
        35                  40                  45

Lys Val Lys His Leu Val Thr Val Glu Glu Lys
    50                  55

<210> SEQ ID NO 26
<211> LENGTH: 7
<212> TYPE: PRT
<213> ORGANISM: Staphylococcus aureus

<400> SEQUENCE: 26

Leu Gln Ile Thr Leu Thr Arg
1               5

<210> SEQ ID NO 27
<211> LENGTH: 14
<212> TYPE: PRT
<213> ORGANISM: Staphylococcus aureus

<400> SEQUENCE: 27

Thr Asn Ser Ser Val Val Val Glu Asp Asn Pro Ala Ile Arg
1               5                   10

<210> SEQ ID NO 28
<211> LENGTH: 49
<212> TYPE: PRT
<213> ORGANISM: Staphylococcus aureus
```

<400> SEQUENCE: 28

Met Arg Val Asn Val Thr Leu Ala Cys Thr Glu Cys Gly Asp Arg Asn
1               5                   10                  15

Tyr Ile Thr Thr Lys Asn Lys Arg Asn Asn Pro Glu Arg Val Glu Met
            20                  25                  30

Lys Lys Phe Cys Ser Arg Glu Asn Lys Gln Thr Leu His Arg Glu Thr
        35                  40                  45

Lys

<210> SEQ ID NO 29
<211> LENGTH: 13
<212> TYPE: PRT
<213> ORGANISM: Staphylococcus aureus

<400> SEQUENCE: 29

Val Asn Val Thr Leu Ala Cys Thr Glu Cys Gly Asp Arg
1               5                   10

<210> SEQ ID NO 30
<211> LENGTH: 6
<212> TYPE: PRT
<213> ORGANISM: Staphylococcus aureus

<400> SEQUENCE: 30

Asn Tyr Ile Thr Thr Lys
1               5

<210> SEQ ID NO 31
<211> LENGTH: 267
<212> TYPE: PRT
<213> ORGANISM: Staphylococcus aureus

<400> SEQUENCE: 31

Met Lys Lys Ile Ala Thr Ala Thr Ile Ala Thr Ala Gly Phe Ala Thr
1               5                   10                  15

Ile Ala Ile Ala Ser Gly Asn Gln Ala His Ala Ser Glu Gln Asp Asn
            20                  25                  30

Tyr Gly Tyr Asn Pro Asn Asp Pro Thr Ser Tyr Ser Tyr Thr Tyr Thr
        35                  40                  45

Ile Asp Ala Gln Gly Asn Tyr His Tyr Thr Trp Lys Gly Asn Trp His
    50                  55                  60

Pro Ser Gln Leu Asn Gln Asp Asn Gly Tyr Tyr Ser Tyr Tyr Tyr Tyr
65                  70                  75                  80

Asn Gly Tyr Asn Asn Tyr Asn Asn Tyr Asn Asn Gly Tyr Ser Tyr Asn
                85                  90                  95

Asn Tyr Ser Arg Tyr Asn Asn Tyr Ser Asn Asn Gln Ser Tyr Asn
            100                 105                 110

Tyr Asn Asn Tyr Asn Ser Tyr Asn Thr Asn Ser Tyr Arg Thr Gly Gly
        115                 120                 125

Leu Gly Ala Ser Tyr Ser Thr Ser Ser Asn Asn Val Gln Val Thr Thr
    130                 135                 140

Thr Met Ala Pro Ser Ser Asn Gly Arg Ser Ile Ser Ser Gly Tyr Thr
145                 150                 155                 160

Ser Gly Arg Asn Leu Tyr Thr Ser Gly Gln Cys Thr Tyr Tyr Val Phe
                165                 170                 175

Asp Arg Val Gly Gly Lys Ile Gly Ser Thr Trp Gly Asn Ala Ser Asn
            180                 185                 190

```
Trp Ala Asn Ala Ala Arg Ala Gly Tyr Thr Val Asn Asn Thr Pro
        195                 200                 205

Lys Ala Gly Ala Ile Met Gln Thr Thr Gln Gly Ala Tyr Gly His Val
    210                 215                 220

Ala Tyr Val Glu Ser Val Asn Ser Asn Gly Ser Val Arg Val Ser Glu
225                 230                 235                 240

Met Asn Tyr Gly Tyr Gly Pro Gly Val Val Thr Ser Arg Thr Ile Ser
                245                 250                 255

Ala Ser Gln Ala Ala Gly Tyr Asn Phe Ile His
            260                 265

<210> SEQ ID NO 32
<211> LENGTH: 10
<212> TYPE: PRT
<213> ORGANISM: Staphylococcus aureus

<400> SEQUENCE: 32

Ala Gly Tyr Thr Val Asn Asn Thr Pro Lys
1               5                   10

<210> SEQ ID NO 33
<211> LENGTH: 64
<212> TYPE: PRT
<213> ORGANISM: Staphylococcus aureus

<400> SEQUENCE: 33

Met Ala Asp Glu Ser Lys Phe Glu Gln Ala Lys Gly Asn Val Lys Glu
1               5                   10                  15

Thr Val Gly Asn Val Thr Asp Asn Lys Asn Leu Glu Asn Glu Gly Lys
            20                  25                  30

Glu Asp Lys Ala Ser Gly Lys Ala Lys Glu Phe Val Glu Asn Ala Lys
        35                  40                  45

Glu Lys Ala Thr Asp Phe Ile Asp Lys Val Lys Gly Asn Lys Gly Glu
    50                  55                  60

<210> SEQ ID NO 34
<211> LENGTH: 9
<212> TYPE: PRT
<213> ORGANISM: Staphylococcus aureus

<400> SEQUENCE: 34

Glu Phe Val Glu Asn Ala Lys Glu Lys
1               5

<210> SEQ ID NO 35
<211> LENGTH: 9
<212> TYPE: PRT
<213> ORGANISM: Staphylococcus aureus

<400> SEQUENCE: 35

Ala Thr Asp Phe Ile Asp Lys Val Lys
1               5

<210> SEQ ID NO 36
<211> LENGTH: 1248
<212> TYPE: PRT
<213> ORGANISM: Staphylococcus aureus

<400> SEQUENCE: 36

Met Ala Lys Lys Phe Asn Tyr Lys Leu Pro Ser Met Val Ala Leu Thr
1               5                   10                  15
```

-continued

```
Leu Val Gly Ser Ala Val Thr Ala His Gln Val Gln Ala Ala Glu Thr
         20                  25                  30
Thr Gln Asp Gln Thr Thr Asn Lys Asn Val Leu Asp Ser Asn Lys Val
     35                  40                  45
Lys Ala Thr Thr Glu Gln Ala Lys Ala Glu Val Lys Asn Pro Thr Gln
 50                  55                  60
Asn Ile Ser Gly Thr Gln Val Tyr Gln Asp Pro Ala Ile Val Gln Pro
 65                  70                  75                  80
Lys Thr Ala Asn Asn Lys Thr Gly Asn Ala Gln Val Ser Gln Lys Val
             85                  90                  95
Asp Thr Ala Gln Val Asn Gly Asp Thr Arg Ala Asn Gln Ser Ala Thr
             100                 105                 110
Thr Asn Asn Thr Gln Pro Val Ala Lys Ser Thr Ser Thr Thr Ala Pro
             115                 120                 125
Lys Thr Asn Thr Asn Val Thr Asn Ala Gly Tyr Ser Leu Val Asp Asp
     130                 135                 140
Glu Asp Asp Asn Ser Glu His Gln Ile Asn Pro Glu Leu Ile Lys Ser
145                 150                 155                 160
Ala Ala Lys Pro Ala Ala Leu Glu Thr Gln Tyr Lys Ala Ala Ala Pro
                 165                 170                 175
Lys Ala Lys Thr Glu Ala Thr Pro Lys Val Thr Thr Phe Ser Ala Ser
             180                 185                 190
Ala Gln Pro Arg Ser Val Ala Ala Thr Pro Lys Thr Ser Leu Pro Lys
         195                 200                 205
Tyr Lys Pro Gln Val Asn Ser Ser Ile Asn Asp Tyr Ile Arg Lys Asn
     210                 215                 220
Asn Leu Lys Ala Pro Lys Ile Glu Glu Asp Tyr Thr Ser Tyr Phe Pro
225                 230                 235                 240
Lys Tyr Ala Tyr Arg Asn Gly Val Gly Arg Pro Glu Gly Ile Val Val
                 245                 250                 255
His Asp Thr Ala Asn Asp Arg Ser Thr Ile Asn Gly Glu Ile Ser Tyr
             260                 265                 270
Met Lys Asn Asn Tyr Gln Asn Ala Phe Val His Ala Phe Val Asp Gly
         275                 280                 285
Asp Arg Ile Ile Glu Thr Ala Pro Thr Asp Tyr Leu Ser Trp Gly Val
     290                 295                 300
Gly Ala Val Gly Asn Pro Arg Phe Ile Asn Val Glu Ile Val His Thr
305                 310                 315                 320
His Asp Tyr Ala Ser Phe Ala Arg Ser Met Asn Asn Tyr Ala Asp Tyr
                 325                 330                 335
Ala Ala Thr Gln Leu Gln Tyr Tyr Gly Leu Lys Pro Asp Ser Ala Glu
             340                 345                 350
Tyr Asp Gly Asn Gly Thr Val Trp Thr His Tyr Ala Val Ser Lys Tyr
         355                 360                 365
Leu Gly Gly Thr Asp His Ala Asp Pro His Gly Tyr Leu Arg Ser His
     370                 375                 380
Asn Tyr Ser Tyr Asp Gln Leu Tyr Asp Leu Ile Asn Glu Lys Tyr Leu
385                 390                 395                 400
Ile Lys Met Gly Lys Val Ala Pro Trp Gly Thr Gln Phe Thr Thr Thr
                 405                 410                 415
Pro Thr Thr Pro Ser Lys Pro Thr Thr Pro Ser Lys Pro Ser Thr Gly
             420                 425                 430
```

```
Lys Leu Thr Val Ala Ala Asn Asn Gly Val Ala Gln Ile Lys Pro Thr
            435                 440                 445

Asn Ser Gly Leu Tyr Thr Thr Val Tyr Asp Lys Thr Gly Lys Ala Thr
450                 455                 460

Asn Glu Val Gln Lys Thr Phe Ala Val Ser Lys Thr Ala Thr Leu Gly
465                 470                 475                 480

Asn Gln Lys Phe Tyr Leu Val Gln Asp Tyr Asn Ser Gly Asn Lys Phe
                485                 490                 495

Gly Trp Val Lys Glu Gly Asp Val Val Tyr Asn Thr Ala Lys Ser Pro
                500                 505                 510

Val Asn Val Asn Gln Ser Tyr Ser Ile Lys Ser Gly Thr Lys Leu Tyr
                515                 520                 525

Thr Val Pro Trp Gly Thr Ser Lys Gln Val Ala Gly Ser Val Ser Gly
530                 535                 540

Ser Gly Asn Gln Thr Phe Lys Ala Ser Lys Gln Gln Ile Asp Lys
545                 550                 555                 560

Ser Ile Tyr Leu Tyr Gly Ser Val Asn Gly Lys Ser Gly Trp Val Ser
                565                 570                 575

Lys Ala Tyr Leu Val Asp Thr Ala Lys Pro Thr Pro Thr Pro Ile Pro
                580                 585                 590

Lys Pro Ser Thr Pro Thr Thr Asn Asn Lys Leu Thr Val Ser Ser Leu
            595                 600                 605

Asn Gly Val Ala Gln Ile Asn Ala Lys Asn Asn Gly Leu Phe Thr Thr
            610                 615                 620

Val Tyr Asp Lys Thr Gly Lys Pro Thr Lys Glu Val Gln Lys Thr Phe
625                 630                 635                 640

Ala Val Thr Lys Glu Ala Ser Leu Gly Gly Asn Lys Phe Tyr Leu Val
                645                 650                 655

Lys Asp Tyr Asn Ser Pro Thr Leu Ile Gly Trp Val Lys Gln Gly Asp
                660                 665                 670

Val Ile Tyr Asn Asn Ala Lys Ser Pro Val Asn Val Met Gln Thr Tyr
                675                 680                 685

Thr Val Lys Pro Gly Thr Lys Leu Tyr Ser Val Pro Trp Gly Thr Tyr
            690                 695                 700

Lys Gln Glu Ala Gly Ala Val Ser Gly Thr Gly Asn Gln Thr Phe Lys
705                 710                 715                 720

Ala Thr Lys Gln Gln Gln Ile Asp Lys Ser Ile Tyr Leu Phe Gly Thr
                725                 730                 735

Val Asn Gly Lys Ser Gly Trp Val Ser Lys Ala Tyr Leu Ala Val Pro
                740                 745                 750

Ala Ala Pro Lys Lys Ala Val Ala Gln Pro Lys Thr Ala Val Lys Ala
                755                 760                 765

Tyr Thr Val Thr Lys Pro Gln Thr Thr Gln Thr Val Ser Lys Ile Ala
770                 775                 780

Gln Val Lys Pro Asn Asn Thr Gly Ile Arg Ala Ser Val Tyr Glu Lys
785                 790                 795                 800

Thr Ala Lys Asn Gly Ala Lys Tyr Ala Asp Arg Thr Phe Tyr Val Thr
                805                 810                 815

Lys Glu Arg Ala His Gly Asn Glu Thr Tyr Val Leu Leu Asn Asn Thr
            820                 825                 830

Ser His Asn Ile Pro Leu Gly Trp Phe Asn Val Lys Asp Leu Asn Val
            835                 840                 845

Gln Asn Leu Gly Lys Glu Val Lys Thr Thr Gln Lys Tyr Thr Val Asn
```

850                 855                 860
Lys Ser Asn Asn Gly Leu Ser Met Val Pro Trp Gly Thr Lys Asn Gln
865                 870                 875                 880

Val Ile Leu Thr Gly Asn Asn Ile Ala Gln Gly Thr Phe Asn Ala Thr
                885                 890                 895

Lys Gln Val Ser Val Gly Lys Asp Val Tyr Leu Tyr Gly Thr Ile Asn
                900                 905                 910

Asn Arg Thr Gly Trp Val Asn Ala Lys Asp Leu Thr Ala Pro Thr Ala
        915                 920                 925

Val Lys Pro Thr Thr Ser Ala Ala Lys Asp Tyr Asn Tyr Thr Tyr Val
        930                 935                 940

Ile Lys Asn Gly Asn Gly Tyr Tyr Tyr Val Thr Pro Asn Ser Asp Thr
945                 950                 955                 960

Ala Lys Tyr Ser Leu Lys Ala Phe Asn Glu Gln Pro Phe Ala Val Val
                965                 970                 975

Lys Glu Gln Val Ile Asn Gly Gln Thr Trp Tyr Tyr Gly Lys Leu Ser
                980                 985                 990

Asn Gly Lys Leu Ala Trp Ile Lys Ser Thr Asp Leu Ala Lys Glu Leu
        995                 1000                1005

Ile Lys Tyr Asn Gln Thr Gly Met Thr Leu Asn Gln Val Ala Gln
        1010                1015                1020

Ile Gln Ala Gly Leu Gln Tyr Lys Pro Gln Val Gln Arg Val Pro
        1025                1030                1035

Gly Lys Trp Thr Asp Ala Asn Phe Asn Asp Val Lys His Ala Met
        1040                1045                1050

Asp Thr Lys Arg Leu Ala Gln Asp Pro Ala Leu Lys Tyr Gln Phe
        1055                1060                1065

Leu Arg Leu Asp Gln Pro Gln Asn Ile Ser Ile Asp Lys Ile Asn
        1070                1075                1080

Gln Phe Leu Lys Gly Lys Gly Val Leu Glu Asn Gln Gly Ala Ala
        1085                1090                1095

Phe Asn Lys Ala Ala Gln Met Tyr Gly Ile Asn Glu Val Tyr Leu
        1100                1105                1110

Ile Ser His Ala Leu Leu Glu Thr Gly Asn Gly Thr Ser Gln Leu
        1115                1120                1125

Ala Lys Gly Ala Asp Val Val Asn Asn Lys Val Val Thr Asn Ser
        1130                1135                1140

Asn Thr Lys Tyr His Asn Val Phe Gly Ile Ala Ala Tyr Asp Asn
        1145                1150                1155

Asp Pro Leu Arg Glu Gly Ile Lys Tyr Ala Lys Gln Ala Gly Trp
        1160                1165                1170

Asp Thr Val Ser Lys Ala Ile Val Gly Gly Ala Lys Phe Ile Gly
        1175                1180                1185

Asn Ser Tyr Val Lys Ala Gly Gln Asn Thr Leu Tyr Lys Met Arg
        1190                1195                1200

Trp Asn Pro Ala His Pro Gly Thr His Gln Tyr Ala Thr Asp Val
        1205                1210                1215

Asp Trp Ala Asn Ile Asn Ala Lys Ile Ile Lys Gly Tyr Tyr Asp
        1220                1225                1230

Lys Ile Gly Glu Val Gly Lys Tyr Phe Asp Ile Pro Gln Tyr Lys
        1235                1240                1245

<210> SEQ ID NO 37

```
<211> LENGTH: 10
<212> TYPE: PRT
<213> ORGANISM: Staphylococcus aureus

<400> SEQUENCE: 37

Leu Tyr Ser Val Pro Trp Gly Thr Tyr Lys
1               5                   10

<210> SEQ ID NO 38
<211> LENGTH: 10
<212> TYPE: PRT
<213> ORGANISM: Staphylococcus aureus

<400> SEQUENCE: 38

Ala Tyr Leu Ala Val Pro Ala Ala Pro Lys
1               5                   10

<210> SEQ ID NO 39
<211> LENGTH: 394
<212> TYPE: PRT
<213> ORGANISM: Staphylococcus aureus

<400> SEQUENCE: 39

Met Ala Lys Glu Lys Phe Asp Arg Ser Lys Glu His Ala Asn Ile Gly
1               5                   10                  15

Thr Ile Gly His Val Asp His Gly Lys Thr Thr Leu Thr Ala Ala Ile
                20                  25                  30

Ala Thr Val Leu Ala Lys Asn Gly Asp Ser Val Ala Gln Ser Tyr Asp
            35                  40                  45

Met Ile Asp Asn Ala Pro Glu Lys Glu Arg Gly Ile Thr Ile Asn
    50                  55                  60

Thr Ser His Ile Glu Tyr Gln Thr Asp Lys Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Gly Ile Leu Val Val Ser Ala Ala Asp Gly Pro
            100                 105                 110

Met Pro Gln Thr Arg Glu His Ile Leu Leu Ser Arg Asn Val Gly Val
        115                 120                 125

Pro Ala Leu Val Val Phe Leu Asn Lys Val Asp Met Val Asp Asp Glu
    130                 135                 140

Glu Leu Leu Glu Leu Val Glu Met Glu Val Arg Asp Leu Leu Ser Glu
145                 150                 155                 160

Tyr Asp Phe Pro Gly Asp Asp Val Pro Val Ile Ala Gly Ser Ala Leu
                165                 170                 175

Lys Ala Leu Glu Gly Asp Ala Gln Tyr Glu Glu Lys Ile Leu Glu Leu
            180                 185                 190

Met Glu Ala Val Asp Thr Tyr Ile Pro Thr Pro Glu Arg Asp Ser Asp
        195                 200                 205

Lys Pro Phe Met Met Pro Val Glu Asp Val Phe Ser Ile Thr Gly Arg
    210                 215                 220

Gly Thr Val Ala Thr Gly Arg Val Glu Arg Gly Gln Ile Lys Val Gly
225                 230                 235                 240

Glu Glu Val Glu Ile Ile Gly Leu His Asp Thr Ser Lys Thr Thr Val
                245                 250                 255

Thr Gly Val Glu Met Phe Arg Lys Leu Leu Asp Tyr Ala Glu Ala Gly
            260                 265                 270
```

```
Asp Asn Ile Gly Ala Leu Leu Arg Gly Val Ala Arg Glu Asp Val Gln
            275                 280                 285

Arg Gly Gln Val Leu Ala Ala Pro Gly Ser Ile Thr Pro His Thr Glu
        290                 295                 300

Phe Lys Ala Glu Val Tyr Val Leu Ser Lys Asp Glu Gly Gly Arg His
305                 310                 315                 320

Thr Pro Phe Phe Ser Asn Tyr Arg Pro Gln Phe Tyr Phe Arg Thr Thr
                325                 330                 335

Asp Val Thr Gly Val Val His Leu Pro Glu Gly Thr Glu Met Val Met
            340                 345                 350

Pro Gly Asp Asn Val Glu Met Thr Val Glu Leu Ile Ala Pro Ile Ala
        355                 360                 365

Ile Glu Asp Gly Thr Arg Phe Ser Ile Arg Glu Gly Arg Thr Val
370                 375                 380

Gly Ser Gly Val Val Thr Glu Ile Ile Lys
385                 390

<210> SEQ ID NO 40
<211> LENGTH: 12
<212> TYPE: PRT
<213> ORGANISM: Staphylococcus aureus

<400> SEQUENCE: 40

Thr Val Gly Ser Gly Val Val Thr Glu Ile Ile Lys
1               5                   10

<210> SEQ ID NO 41
<211> LENGTH: 233
<212> TYPE: PRT
<213> ORGANISM: Staphylococcus aureus

<400> SEQUENCE: 41

Met Lys Lys Thr Ile Met Ala Ser Ser Leu Ala Val Ala Leu Gly Val
1               5                   10                  15

Thr Gly Tyr Ala Ala Gly Thr Gly His Gln Ala His Ala Ala Glu Val
            20                  25                  30

Asn Val Asp Gln Ala His Leu Val Asp Leu Ala His Asn His Gln Asp
        35                  40                  45

Gln Leu Asn Ala Ala Pro Ile Lys Asp Gly Ala Tyr Asp Ile His Phe
    50                  55                  60

Val Lys Asp Gly Phe Gln Tyr Asn Phe Thr Ser Asn Gly Thr Thr Trp
65                  70                  75                  80

Ser Trp Ser Tyr Glu Ala Ala Asn Gly Gln Thr Ala Gly Phe Ser Asn
                85                  90                  95

Val Ala Gly Ala Asp Tyr Thr Ser Tyr Asn Gln Gly Ser Asn Val
            100                 105                 110

Gln Ser Val Ser Tyr Asn Ala Gln Ser Ser Asn Ser Asn Val Glu Ala
        115                 120                 125

Val Ser Ala Pro Thr Tyr His Asn Tyr Ser Thr Ser Thr Ser Ser
    130                 135                 140

Ser Val Arg Leu Ser Asn Gly Asn Thr Ala Gly Ala Thr Gly Ser Ser
145                 150                 155                 160

Ala Ala Gln Ile Met Ala Gln Arg Thr Gly Val Ser Ala Ser Thr Trp
                165                 170                 175

Ala Ala Ile Ile Ala Arg Glu Ser Asn Gly Gln Val Asn Ala Tyr Asn
            180                 185                 190
```

Pro Ser Gly Ala Ser Gly Leu Phe Gln Thr Met Pro Gly Trp Pro
            195                 200                 205

Thr Asn Thr Val Asp Gln Gln Ile Asn Ala Ala Val Lys Ala Tyr Lys
    210                 215                 220

Ala Gln Gly Leu Gly Ala Trp Gly Phe
225                 230

<210> SEQ ID NO 42
<211> LENGTH: 21
<212> TYPE: PRT
<213> ORGANISM: Staphylococcus aureus

<400> SEQUENCE: 42

Leu Ser Asn Gly Asn Thr Ala Gly Ala Thr Gly Ser Ser Ala Ala Gln
1               5                   10                  15

Ile Met Ala Gln Arg
            20

<210> SEQ ID NO 43
<211> LENGTH: 86
<212> TYPE: PRT
<213> ORGANISM: Staphylococcus aureus

<400> SEQUENCE: 43

Met Ala Met Thr Val Lys Lys Asp Asn Asn Glu Val Arg Ile Gln Trp
1               5                   10                  15

Arg Val Ala Asp Ile Lys Ile Pro Thr Ser Glu Ile Lys Asn Ile Thr
            20                  25                  30

Gln Asp Gln Asp Ile His Ala Val Pro Lys Leu Asp Ser Lys Asp Val
        35                  40                  45

Ser Arg Ile Gly Ser Thr Phe Gly Lys Thr Asn Arg Val Ile Ile Asp
    50                  55                  60

Thr Glu Asp His Glu Tyr Ile Ile Tyr Thr Gln Asn Asp Gln Lys Val
65                  70                  75                  80

Tyr Asn Glu Leu Thr Lys
                85

<210> SEQ ID NO 44
<211> LENGTH: 13
<212> TYPE: PRT
<213> ORGANISM: Staphylococcus aureus

<400> SEQUENCE: 44

Asn Ile Thr Gln Asp Gln Asp Ile His Ala Val Pro Lys
1               5                   10

<210> SEQ ID NO 45
<211> LENGTH: 8
<212> TYPE: PRT
<213> ORGANISM: Staphylococcus aureus

<400> SEQUENCE: 45

Leu Asp Ser Lys Asp Val Ser Arg
1               5

<210> SEQ ID NO 46
<211> LENGTH: 11
<212> TYPE: PRT
<213> ORGANISM: Escherichia coli

<400> SEQUENCE: 46

```
Ile Leu Glu Ile Glu Gly Leu Pro Asp Leu Lys
1               5                   10

<210> SEQ ID NO 47
<211> LENGTH: 13
<212> TYPE: PRT
<213> ORGANISM: Escherichia coli

<400> SEQUENCE: 47

Val Ala Asp Gly Ala Thr Val Val Ser Thr Ser Thr Arg
1               5                   10

<210> SEQ ID NO 48
<211> LENGTH: 10
<212> TYPE: PRT
<213> ORGANISM: Escherichia coli

<400> SEQUENCE: 48

Thr Asn Thr Thr Asp Val Ala Thr Phe Lys
1               5                   10

<210> SEQ ID NO 49
<211> LENGTH: 9
<212> TYPE: PRT
<213> ORGANISM: Escherichia coli

<400> SEQUENCE: 49

Leu Asp Thr Thr Gly Leu Ile Asp Arg
1               5

<210> SEQ ID NO 50
<211> LENGTH: 13
<212> TYPE: PRT
<213> ORGANISM: Escherichia coli

<400> SEQUENCE: 50

Val Gly Leu Ile Ala Gly Ser Gly Gly Ser Pro Arg
1               5                   10

<210> SEQ ID NO 51
<211> LENGTH: 10
<212> TYPE: PRT
<213> ORGANISM: Escherichia coli

<400> SEQUENCE: 51

Ala Ile Asp Phe Ser Asp Gly Tyr Tyr Lys
1               5                   10

<210> SEQ ID NO 52
<211> LENGTH: 10
<212> TYPE: PRT
<213> ORGANISM: Escherichia coli

<400> SEQUENCE: 52

Leu Gly Ala Trp Asp Thr Leu Ser Pro Lys
1               5                   10

<210> SEQ ID NO 53
<211> LENGTH: 11
<212> TYPE: PRT
<213> ORGANISM: Escherichia coli

<400> SEQUENCE: 53

Phe Gly Glu Ile Glu Glu Val Glu Leu Gly Arg
1               5                   10
```

```
<210> SEQ ID NO 54
<211> LENGTH: 11
<212> TYPE: PRT
<213> ORGANISM: Escherichia coli

<400> SEQUENCE: 54

Ile Asn Leu Leu Asp Asp Asn Gln Phe Thr Arg
1               5                   10

<210> SEQ ID NO 55
<211> LENGTH: 10
<212> TYPE: PRT
<213> ORGANISM: Escherichia coli

<400> SEQUENCE: 55

Leu Ala Thr Ala Trp Glu Gly Phe Thr Lys
1               5                   10

<210> SEQ ID NO 56
<211> LENGTH: 12
<212> TYPE: PRT
<213> ORGANISM: Escherichia coli

<400> SEQUENCE: 56

Asp Ser Ile Leu Glu Ala Ile Asp Ala Gly Ile Lys
1               5                   10

<210> SEQ ID NO 57
<211> LENGTH: 10
<212> TYPE: PRT
<213> ORGANISM: Escherichia coli

<400> SEQUENCE: 57

Phe Ala Ala Leu Glu Ala Ala Gly Val Lys
1               5                   10

<210> SEQ ID NO 58
<211> LENGTH: 10
<212> TYPE: PRT
<213> ORGANISM: Escherichia coli

<400> SEQUENCE: 58

Ser Leu Ala Asp Ile Gly Glu Ala Leu Lys
1               5                   10

<210> SEQ ID NO 59
<211> LENGTH: 10
<212> TYPE: PRT
<213> ORGANISM: Escherichia coli

<400> SEQUENCE: 59

Thr Glu Glu Gln Leu Ala Asn Ile Ala Arg
1               5                   10

<210> SEQ ID NO 60
<211> LENGTH: 13
<212> TYPE: PRT
<213> ORGANISM: Escherichia coli

<400> SEQUENCE: 60

Ala Glu Ala Glu Gln Thr Leu Ala Ala Leu Thr Glu Lys
1               5                   10
```

```
<210> SEQ ID NO 61
<211> LENGTH: 10
<212> TYPE: PRT
<213> ORGANISM: Escherichia coli

<400> SEQUENCE: 61

Ser Gly Asp Thr Leu Ser Ala Ile Ser Lys
1               5                   10

<210> SEQ ID NO 62
<211> LENGTH: 12
<212> TYPE: PRT
<213> ORGANISM: Escherichia coli

<400> SEQUENCE: 62

Leu Leu Thr Gly Glu Leu Leu Thr Leu Ala Ser Arg
1               5                   10

<210> SEQ ID NO 63
<211> LENGTH: 12
<212> TYPE: PRT
<213> ORGANISM: Escherichia coli

<400> SEQUENCE: 63

Ser Ala Leu Pro Ala Gly Trp Phe Ile Ala Asp Lys
1               5                   10

<210> SEQ ID NO 64
<211> LENGTH: 7
<212> TYPE: PRT
<213> ORGANISM: Escherichia coli

<400> SEQUENCE: 64

Val Ala Gly Pro Leu Leu Arg
1               5

<210> SEQ ID NO 65
<211> LENGTH: 12
<212> TYPE: PRT
<213> ORGANISM: Escherichia coli

<400> SEQUENCE: 65

Val Gly Tyr Ile Glu Leu Asp Leu Asn Ser Gly Lys
1               5                   10

<210> SEQ ID NO 66
<211> LENGTH: 10
<212> TYPE: PRT
<213> ORGANISM: Escherichia coli

<400> SEQUENCE: 66

Val Leu Leu Cys Gly Ala Val Leu Ser Arg
1               5                   10

<210> SEQ ID NO 67
<211> LENGTH: 9
<212> TYPE: PRT
<213> ORGANISM: Escherichia coli

<400> SEQUENCE: 67

Ile Ser Asp Ile Pro Glu Phe Val Arg
1               5

<210> SEQ ID NO 68
<211> LENGTH: 9
```

<212> TYPE: PRT
<213> ORGANISM: Escherichia coli

<400> SEQUENCE: 68

Ile Glu Glu Asp Leu Leu Gly Thr Arg
1               5

<210> SEQ ID NO 69
<211> LENGTH: 9
<212> TYPE: PRT
<213> ORGANISM: Escherichia coli

<400> SEQUENCE: 69

Leu Val Asp Ala Ile Asn Gln Leu Arg
1               5

<210> SEQ ID NO 70
<211> LENGTH: 12
<212> TYPE: PRT
<213> ORGANISM: Escherichia coli

<400> SEQUENCE: 70

Thr Ala Leu Ala Ile Asp Ala Ile Ile Asn Gln Arg
1               5                   10

<210> SEQ ID NO 71
<211> LENGTH: 12
<212> TYPE: PRT
<213> ORGANISM: Escherichia coli

<400> SEQUENCE: 71

Val Val Asn Thr Leu Gly Ala Pro Ile Asp Gly Lys
1               5                   10

<210> SEQ ID NO 72
<211> LENGTH: 14
<212> TYPE: PRT
<213> ORGANISM: Escherichia coli

<400> SEQUENCE: 72

Ser Ala Gly Gly Ile Val Leu Thr Gly Ser Ala Ala Ala Lys
1               5                   10

<210> SEQ ID NO 73
<211> LENGTH: 10
<212> TYPE: PRT
<213> ORGANISM: Escherichia coli

<400> SEQUENCE: 73

Ala Val Thr Ala Ala Val Glu Glu Leu Lys
1               5                   10

<210> SEQ ID NO 74
<211> LENGTH: 14
<212> TYPE: PRT
<213> ORGANISM: Escherichia coli

<400> SEQUENCE: 74

Ala Leu Asp Ala Ile Ile Ala Ser Val Thr Glu Ser Leu Lys
1               5                   10

<210> SEQ ID NO 75
<211> LENGTH: 7
<212> TYPE: PRT
<213> ORGANISM: Escherichia coli

<400> SEQUENCE: 75

Tyr Trp Asp Val Glu Leu Arg
1               5

<210> SEQ ID NO 76
<211> LENGTH: 9
<212> TYPE: PRT
<213> ORGANISM: Escherichia coli

<400> SEQUENCE: 76

Leu Pro Gly Ile Leu Glu Leu Ser Arg
1               5

<210> SEQ ID NO 77
<211> LENGTH: 10
<212> TYPE: PRT
<213> ORGANISM: Escherichia coli

<400> SEQUENCE: 77

Ser Lys Ala Thr Asn Leu Leu Tyr Thr Arg
1               5                   10

<210> SEQ ID NO 78
<211> LENGTH: 11
<212> TYPE: PRT
<213> ORGANISM: Escherichia coli

<400> SEQUENCE: 78

Ser Glu Ala Leu Lys Ile Leu Asn Asn Ile Arg
1               5                   10

<210> SEQ ID NO 79
<211> LENGTH: 11
<212> TYPE: PRT
<213> ORGANISM: Escherichia coli

<400> SEQUENCE: 79

Leu Phe Gly Val Thr Thr Leu Asp Ile Ile Arg
1               5                   10

<210> SEQ ID NO 80
<211> LENGTH: 11
<212> TYPE: PRT
<213> ORGANISM: Escherichia coli

<400> SEQUENCE: 80

Ala Ser Leu Pro Thr Ile Glu Leu Ala Leu Lys
1               5                   10

<210> SEQ ID NO 81
<211> LENGTH: 10
<212> TYPE: PRT
<213> ORGANISM: Escherichia coli

<400> SEQUENCE: 81

Leu Leu Ser Asp Thr Glu Cys Leu Val Lys
1               5                   10

<210> SEQ ID NO 82
<211> LENGTH: 8
<212> TYPE: PRT
<213> ORGANISM: Escherichia coli

<400> SEQUENCE: 82

Ser Ile Leu Ser Glu Leu Val Arg
1               5

<210> SEQ ID NO 83
<211> LENGTH: 11
<212> TYPE: PRT
<213> ORGANISM: Escherichia coli

<400> SEQUENCE: 83

Gly Gly Phe Thr Val Glu Leu Asn Gly Ile Arg
1               5                   10

<210> SEQ ID NO 84
<211> LENGTH: 13
<212> TYPE: PRT
<213> ORGANISM: Escherichia coli

<400> SEQUENCE: 84

Thr Gly Glu Val Pro Ala Asp Val Ala Ala Gln Ala Arg
1               5                   10

<210> SEQ ID NO 85
<211> LENGTH: 10
<212> TYPE: PRT
<213> ORGANISM: Escherichia coli

<400> SEQUENCE: 85

Thr Tyr Val Asp Ser Leu Asn Val Ile Arg
1               5                   10

<210> SEQ ID NO 86
<211> LENGTH: 10
<212> TYPE: PRT
<213> ORGANISM: Escherichia coli

<400> SEQUENCE: 86

Phe Val Thr Val Thr Ala Glu Ala Leu Arg
1               5                   10

<210> SEQ ID NO 87
<211> LENGTH: 9
<212> TYPE: PRT
<213> ORGANISM: Escherichia coli

<400> SEQUENCE: 87

Ile Ser Asn Val Leu Pro Glu Tyr Arg
1               5

<210> SEQ ID NO 88
<211> LENGTH: 8
<212> TYPE: PRT
<213> ORGANISM: Candida albicans

<400> SEQUENCE: 88

Ala Asp Glu Glu Phe Phe Ala Lys
1               5

<210> SEQ ID NO 89
<211> LENGTH: 9
<212> TYPE: PRT
<213> ORGANISM: Candida albicans

<400> SEQUENCE: 89

Ala Phe Asp Asp Glu Ser Val Gln Lys

```
1               5
```

<210> SEQ ID NO 90
<211> LENGTH: 10
<212> TYPE: PRT
<213> ORGANISM: Candida albicans

<400> SEQUENCE: 90

```
Ala Lys Ile Asp Val Val Asp Gln Ala Lys
1               5                  10
```

<210> SEQ ID NO 91
<211> LENGTH: 11
<212> TYPE: PRT
<213> ORGANISM: Candida albicans

<400> SEQUENCE: 91

```
Ala Val Glu Val Pro Glu Gln Thr Ala Tyr Arg
1               5                  10
```

<210> SEQ ID NO 92
<211> LENGTH: 7
<212> TYPE: PRT
<213> ORGANISM: Candida albicans

<400> SEQUENCE: 92

```
Cys Gly Val Ile Gln Pro Arg
1               5
```

<210> SEQ ID NO 93
<211> LENGTH: 12
<212> TYPE: PRT
<213> ORGANISM: Candida albicans

<400> SEQUENCE: 93

```
Asp Leu Gln Glu Leu Ile Ala Glu Gly Asn Thr Lys
1               5                  10
```

<210> SEQ ID NO 94
<211> LENGTH: 9
<212> TYPE: PRT
<213> ORGANISM: Candida albicans

<400> SEQUENCE: 94

```
Phe Ala Asp Glu Asn Phe Val Lys Arg
1               5
```

<210> SEQ ID NO 95
<211> LENGTH: 8
<212> TYPE: PRT
<213> ORGANISM: Candida albicans

<400> SEQUENCE: 95

```
Phe Ala Leu Asp Thr Gly Val Lys
1               5
```

<210> SEQ ID NO 96
<211> LENGTH: 11
<212> TYPE: PRT
<213> ORGANISM: Candida albicans

<400> SEQUENCE: 96

```
Gly Arg Leu Pro Glu Val Pro Val Ile Val Lys
1               5                  10
```

```
<210> SEQ ID NO 97
<211> LENGTH: 11
<212> TYPE: PRT
<213> ORGANISM: Candida albicans

<400> SEQUENCE: 97

Ile Ala Glu Ala Leu Asp Ile Phe His Thr Lys
1               5                   10

<210> SEQ ID NO 98
<211> LENGTH: 8
<212> TYPE: PRT
<213> ORGANISM: Candida albicans

<400> SEQUENCE: 98

Ile Asp Val Val Asp Gln Ala Lys
1               5

<210> SEQ ID NO 99
<211> LENGTH: 18
<212> TYPE: PRT
<213> ORGANISM: Candida albicans

<400> SEQUENCE: 99

Ile Glu Glu Glu Leu Gly Ser Glu Ala Ile Tyr Ala Gly Lys Asp Phe
1               5                   10                  15

Gln Lys

<210> SEQ ID NO 100
<211> LENGTH: 13
<212> TYPE: PRT
<213> ORGANISM: Candida albicans

<400> SEQUENCE: 100

Ile Glu Ser Phe Gly Ser Gly Ser Gly Ala Thr Ser Lys
1               5                   10

<210> SEQ ID NO 101
<211> LENGTH: 8
<212> TYPE: PRT
<213> ORGANISM: Candida albicans

<400> SEQUENCE: 101

Leu Ala Ser Leu Pro Phe Gln Lys
1               5

<210> SEQ ID NO 102
<211> LENGTH: 11
<212> TYPE: PRT
<213> ORGANISM: Candida albicans

<400> SEQUENCE: 102

Leu Asp Ala Thr Asp Asp Val Val Ala Val Lys
1               5                   10

<210> SEQ ID NO 103
<211> LENGTH: 8
<212> TYPE: PRT
<213> ORGANISM: Candida albicans

<400> SEQUENCE: 103

Asn Val Glu His Leu Val Glu Lys
1               5
```

<210> SEQ ID NO 104
<211> LENGTH: 9
<212> TYPE: PRT
<213> ORGANISM: Candida albicans

<400> SEQUENCE: 104

Ser Gly Ile Ala Ala Gly Val Asn Lys
1               5

<210> SEQ ID NO 105
<211> LENGTH: 15
<212> TYPE: PRT
<213> ORGANISM: Candida albicans

<400> SEQUENCE: 105

Ser Gly Val Asp Tyr Val Ile Glu Ser Thr Gly Val Phe Thr Lys
1               5                   10                  15

<210> SEQ ID NO 106
<211> LENGTH: 9
<212> TYPE: PRT
<213> ORGANISM: Candida albicans

<400> SEQUENCE: 106

Ser Leu Asn Glu Phe Leu Ala Asp Lys
1               5

<210> SEQ ID NO 107
<211> LENGTH: 11
<212> TYPE: PRT
<213> ORGANISM: Candida albicans

<400> SEQUENCE: 107

Ser Gln Glu Thr Phe Asp Ala Asn Val Ala Arg
1               5                   10

<210> SEQ ID NO 108
<211> LENGTH: 8
<212> TYPE: PRT
<213> ORGANISM: Candida albicans

<400> SEQUENCE: 108

Ser Ser Ser Ser Thr Thr Lys Lys
1               5

<210> SEQ ID NO 109
<211> LENGTH: 8
<212> TYPE: PRT
<213> ORGANISM: Candida albicans

<400> SEQUENCE: 109

Ser Thr Leu Asp Pro Val Gly Lys
1               5

<210> SEQ ID NO 110
<211> LENGTH: 11
<212> TYPE: PRT
<213> ORGANISM: Candida albicans

<400> SEQUENCE: 110

Ser Val Glu Leu Phe Gln Gln Ala Val Ala Lys
1               5                   10

<210> SEQ ID NO 111

```
<211> LENGTH: 9
<212> TYPE: PRT
<213> ORGANISM: Candida albicans

<400> SEQUENCE: 111

Thr Ala Asn Asp Val Leu Glu Leu Arg
1               5

<210> SEQ ID NO 112
<211> LENGTH: 19
<212> TYPE: PRT
<213> ORGANISM: Candida albicans

<400> SEQUENCE: 112

Val Gly Asp Lys Ile Gln Ile Val Gly Asp Asp Leu Thr Val Thr Asn
1               5                   10                  15

Pro Thr Arg

<210> SEQ ID NO 113
<211> LENGTH: 10
<212> TYPE: PRT
<213> ORGANISM: Candida albicans

<400> SEQUENCE: 113

Val Val Ala Ile Asp Gly Gly Asp Glu Lys
1               5                   10

<210> SEQ ID NO 114
<211> LENGTH: 9
<212> TYPE: PRT
<213> ORGANISM: Candida albicans

<400> SEQUENCE: 114

Trp Thr Asp Asn Leu Leu Pro Ala Arg
1               5

<210> SEQ ID NO 115
<211> LENGTH: 18
<212> TYPE: PRT
<213> ORGANISM: Candida albicans

<400> SEQUENCE: 115

Tyr Lys Gly Glu Val Thr Ala Ser Gly Asp Asp Leu Val Ile Asp Gly
1               5                   10                  15

His Lys

<210> SEQ ID NO 116
<211> LENGTH: 7
<212> TYPE: PRT
<213> ORGANISM: Candida albicans

<400> SEQUENCE: 116

Tyr Val Leu Asp Thr Ser Lys
1               5

<210> SEQ ID NO 117
<211> LENGTH: 10
<212> TYPE: PRT
<213> ORGANISM: Candida albicans

<400> SEQUENCE: 117

Ala Val Ile Tyr Asp Cys Pro Asn Ser Arg
1               5                   10
```

<210> SEQ ID NO 118
<211> LENGTH: 16
<212> TYPE: PRT
<213> ORGANISM: Candida albicans

<400> SEQUENCE: 118

Gly His Tyr Val Leu Val Ser Pro Gly Tyr Ala His Thr Ser Glu Arg
1               5                   10                  15

<210> SEQ ID NO 119
<211> LENGTH: 10
<212> TYPE: PRT
<213> ORGANISM: Candida albicans

<400> SEQUENCE: 119

Gly Val Ile Tyr Asp Cys Pro Asn Ser Arg
1               5                   10

<210> SEQ ID NO 120
<211> LENGTH: 13
<212> TYPE: PRT
<213> ORGANISM: Candida albicans

<400> SEQUENCE: 120

Gly Val Ser Ser Pro Tyr Leu Pro Phe Gly Gly Gly Arg
1               5                   10

<210> SEQ ID NO 121
<211> LENGTH: 13
<212> TYPE: PRT
<213> ORGANISM: Candida albicans

<400> SEQUENCE: 121

Gly Val Ser Ser Pro Tyr Leu Pro Phe Ser Gly Gly Lys
1               5                   10

<210> SEQ ID NO 122
<211> LENGTH: 13
<212> TYPE: PRT
<213> ORGANISM: Candida albicans

<400> SEQUENCE: 122

Gly Val Ser Ser Pro Tyr Leu Pro Phe Ser Gly Gly Arg
1               5                   10

<210> SEQ ID NO 123
<211> LENGTH: 10
<212> TYPE: PRT
<213> ORGANISM: Candida albicans

<400> SEQUENCE: 123

Ala Ala Val Gly Asp Ile Leu Gln Ser Arg
1               5                   10

<210> SEQ ID NO 124
<211> LENGTH: 7
<212> TYPE: PRT
<213> ORGANISM: Candida albicans

<400> SEQUENCE: 124

Ile Thr Pro Asp Asp Leu Arg
1               5

<210> SEQ ID NO 125

```
<211> LENGTH: 7
<212> TYPE: PRT
<213> ORGANISM: Candida albicans

<400> SEQUENCE: 125

Thr Gly Trp Asp Ile Leu Lys
1               5

<210> SEQ ID NO 126
<211> LENGTH: 263
<212> TYPE: PRT
<213> ORGANISM: Escherichia coli

<400> SEQUENCE: 126

His Pro Glu Thr Leu Val Lys Val Lys Asp Ala Glu Asp Lys Leu Gly
1               5                   10                  15

Ala Arg Val Gly Tyr Ile Glu Leu Asp Leu Asn Ser Gly Lys Ile Leu
            20                  25                  30

Glu Ser Phe Arg Pro Glu Glu Arg Phe Pro Met Met Ser Thr Phe Lys
        35                  40                  45

Val Leu Leu Cys Gly Ala Val Leu Ser Arg Val Asp Ala Gly Gln Glu
    50                  55                  60

Gln Leu Gly Arg Arg Ile His Tyr Ser Gln Asn Asp Leu Val Glu Tyr
65                  70                  75                  80

Ser Pro Val Thr Glu Lys His Leu Thr Asp Gly Met Thr Val Arg Glu
                85                  90                  95

Leu Cys Ser Ala Ala Ile Thr Met Ser Asp Asn Thr Ala Ala Asn Leu
            100                 105                 110

Leu Leu Thr Thr Ile Gly Gly Pro Lys Glu Leu Thr Ala Phe Leu His
        115                 120                 125

Asn Met Gly Asp His Val Thr Arg Leu Asp Arg Trp Glu Pro Glu Leu
    130                 135                 140

Asn Glu Ala Ile Pro Asn Asp Glu Arg Asp Thr Thr Met Pro Ala Ala
145                 150                 155                 160

Met Ala Thr Thr Leu Arg Lys Leu Leu Thr Gly Glu Leu Leu Thr Leu
                165                 170                 175

Ala Ser Arg Gln Gln Leu Ile Asp Trp Met Glu Ala Asp Lys Val Ala
            180                 185                 190

Gly Pro Leu Leu Arg Ser Ala Leu Pro Ala Gly Trp Phe Ile Ala Asp
        195                 200                 205

Lys Ser Gly Val Gly Glu Arg Gly Ser Arg Gly Ile Ile Ala Ala Leu
    210                 215                 220

Gly Pro Asp Gly Lys Pro Ser Arg Ile Val Val Ile Tyr Thr Thr Gly
225                 230                 235                 240

Ser Gln Ala Thr Met Asp Glu Arg Asn Arg Gln Ile Ala Glu Ile Gly
                245                 250                 255

Ala Ser Leu Ile Lys His Trp
            260

<210> SEQ ID NO 127
<211> LENGTH: 865
<212> TYPE: PRT
<213> ORGANISM: Escherichia coli

<400> SEQUENCE: 127

Met Leu Glu Glu Tyr Arg Lys His Val Ala Arg Ala Ala Glu Gly
1               5                   10                  15
```

-continued

```
Ile Ala Pro Lys Pro Leu Asp Ala Asn Gln Met Ala Ala Leu Val Glu
             20                  25                  30
Leu Leu Lys Asn Pro Pro Ala Gly Glu Glu Phe Leu Leu Asp Leu
         35                  40                  45
Leu Thr Asn Arg Val Pro Pro Gly Val Asp Glu Ala Ala Tyr Val Lys
 50                  55                  60
Ala Gly Phe Leu Ala Ala Ile Ala Lys Gly Glu Ala Lys Ser Pro Leu
 65                  70                  75                  80
Leu Thr Pro Glu Lys Ala Ile Glu Leu Leu Gly Thr Met Gln Gly Gly
             85                  90                  95
Tyr Asn Ile His Pro Leu Ile Asp Ala Leu Asp Asp Ala Lys Leu Ala
             100                 105                 110
Pro Ile Ala Ala Lys Ala Leu Ser His Thr Leu Leu Met Phe Asp Asn
             115                 120                 125
Phe Tyr Asp Val Glu Glu Lys Ala Lys Ala Gly Asn Glu Tyr Ala Lys
 130                 135                 140
Gln Val Met Gln Ser Trp Ala Asp Ala Glu Trp Phe Leu Asn Arg Pro
145                 150                 155                 160
Ala Leu Ala Glu Lys Leu Thr Val Thr Val Phe Lys Val Thr Gly Glu
                 165                 170                 175
Thr Asn Thr Asp Asp Leu Ser Pro Ala Pro Asp Ala Trp Ser Arg Pro
             180                 185                 190
Asp Ile Pro Leu His Ala Leu Ala Met Leu Lys Asn Ala Arg Glu Gly
             195                 200                 205
Ile Glu Pro Asp Gln Pro Gly Val Val Gly Pro Ile Lys Gln Ile Glu
210                 215                 220
Ala Leu Gln Gln Lys Gly Phe Pro Leu Ala Tyr Val Gly Asp Val Val
225                 230                 235                 240
Gly Thr Gly Ser Ser Arg Lys Ser Ala Thr Asn Ser Val Leu Trp Phe
                 245                 250                 255
Met Gly Asp Asp Ile Pro His Val Pro Asn Lys Arg Gly Gly Gly Leu
             260                 265                 270
Cys Leu Gly Gly Lys Ile Ala Pro Ile Phe Phe Asn Thr Met Glu Asp
         275                 280                 285
Ala Gly Ala Leu Pro Ile Glu Val Asp Val Ser Asn Leu Asn Met Gly
 290                 295                 300
Asp Val Ile Asp Val Tyr Pro Tyr Lys Gly Glu Val Arg Asn His Glu
305                 310                 315                 320
Thr Gly Glu Leu Leu Ala Thr Phe Glu Leu Lys Thr Asp Val Leu Ile
                 325                 330                 335
Asp Glu Val Arg Ala Gly Gly Arg Ile Pro Leu Ile Ile Gly Arg Gly
             340                 345                 350
Leu Thr Thr Lys Ala Arg Glu Ala Leu Gly Leu Pro His Ser Asp Val
         355                 360                 365
Phe Arg Gln Ala Lys Asp Val Ala Glu Ser Asp Arg Gly Phe Ser Leu
 370                 375                 380
Ala Gln Lys Met Val Gly Arg Ala Cys Gly Val Lys Gly Ile Arg Pro
385                 390                 395                 400
Gly Ala Tyr Cys Glu Pro Lys Met Thr Ser Val Gly Ser Gln Asp Thr
                 405                 410                 415
Thr Gly Pro Met Thr Arg Asp Glu Leu Lys Asp Leu Ala Cys Leu Gly
             420                 425                 430
Phe Ser Ala Asp Leu Val Met Gln Ser Phe Cys His Thr Ala Ala Tyr
```

```
            435                 440                 445
Pro Lys Pro Val Asp Val Asn Thr His His Thr Leu Pro Asp Phe Ile
450                 455                 460

Met Asn Arg Gly Gly Val Ser Leu Arg Pro Gly Asp Gly Val Ile His
465                 470                 475                 480

Ser Trp Leu Asn Arg Met Leu Leu Pro Asp Thr Val Gly Thr Gly Gly
                    485                 490                 495

Asp Ser His Thr Arg Phe Pro Ile Gly Ile Ser Phe Pro Ala Gly Ser
                500                 505                 510

Gly Leu Val Ala Phe Ala Ala Thr Gly Val Met Pro Leu Asp Met
            515                 520                 525

Pro Glu Ser Val Leu Val Arg Phe Lys Gly Lys Met Gln Pro Gly Ile
530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Lys Asn Ile Phe Ser Gly
                565                 570                 575

Arg Ile Leu Glu Ile Glu Gly Leu Pro Asp Leu Lys Val Glu Gln Ala
                580                 585                 590

Phe Glu Leu Thr Asp Ala Ser Ala Glu Arg Ser Ala Ala Gly Cys Thr
            595                 600                 605

Ile Lys Leu Asn Lys Glu Pro Ile Ile Glu Tyr Leu Asn Ser Asn Ile
610                 615                 620

Val Leu Leu Lys Trp Met Ile Ala Glu Gly Tyr Gly Asp Arg Arg Thr
625                 630                 635                 640

Leu Glu Arg Arg Ile Gln Gly Met Glu Lys Trp Leu Ala Asn Pro Glu
                645                 650                 655

Leu Leu Glu Ala Asp Ala Asp Ala Glu Tyr Ala Ala Val Ile Asp Ile
                660                 665                 670

Asp Leu Ala Asp Ile Lys Glu Pro Ile Leu Cys Ala Pro Asn Asp Pro
            675                 680                 685

Asp Asp Ala Arg Pro Leu Ser Ala Val Gln Gly Glu Lys Ile Asp Glu
        690                 695                 700

Val Phe Ile Gly Ser Cys Met Thr Asn Ile Gly His Phe Arg Ala Ala
705                 710                 715                 720

Gly Lys Leu Leu Asp Ala His Lys Gly Gln Leu Pro Thr Arg Leu Trp
                725                 730                 735

Val Ala Pro Pro Thr Arg Met Asp Ala Ala Gln Leu Thr Glu Glu Gly
                740                 745                 750

Tyr Tyr Ser Val Phe Gly Lys Ser Gly Ala Arg Ile Glu Ile Pro Gly
            755                 760                 765

Cys Ser Leu Cys Met Gly Asn Gln Ala Arg Val Ala Asp Gly Ala Thr
770                 775                 780

Val Val Ser Thr Ser Thr Arg Asn Phe Pro Asn Arg Leu Gly Thr Gly
785                 790                 795                 800

Ala Asn Val Phe Leu Ala Ser Ala Glu Leu Ala Ala Val Ala Ala Leu
                805                 810                 815

Ile Gly Lys Leu Pro Thr Pro Glu Glu Tyr Gln Thr Tyr Val Ala Gln
                820                 825                 830

Val Asp Lys Thr Ala Val Asp Thr Tyr Arg Tyr Leu Asn Phe Asn Gln
            835                 840                 845

Leu Ser Gln Tyr Thr Glu Lys Ala Asp Gly Val Ile Phe Gln Thr Ala
850                 855                 860
```

Val
865

<210> SEQ ID NO 128
<211> LENGTH: 348
<212> TYPE: PRT
<213> ORGANISM: Escherichia coli

<400> SEQUENCE: 128

```
Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
            20                  25                  30

Gly Thr Ile Ala Gly Gly Gly Asp Ser Ala Thr Lys Ser Asn Tyr Thr
        35                  40                  45

Val Gly Lys Val Gly Val Glu Asn Leu Val Asn Ala Val Pro Gln Leu
    50                  55                  60

Lys Asp Ile Ala Asn Val Lys Gly Glu Gln Val Val Asn Ile Gly Ser
65                  70                  75                  80

Gln Asp Met Asn Asp Asn Val Trp Leu Thr Leu Ala Lys Lys Ile Asn
                85                  90                  95

Thr Asp Cys Asp Lys Thr Asp Gly Phe Val Ile Thr His Gly Thr Asp
            100                 105                 110

Thr Met Glu Glu Thr Ala Tyr Phe Leu Asp Leu Thr Val Lys Cys Asp
        115                 120                 125

Lys Pro Val Val Met Val Gly Ala Met Arg Pro Ser Thr Ser Met Ser
130                 135                 140

Ala Asp Gly Pro Phe Asn Leu Tyr Asn Ala Val Val Thr Ala Ala Asp
145                 150                 155                 160

Lys Ala Ser Ala Asn Arg Gly Val Leu Val Val Met Asn Asp Thr Val
                165                 170                 175

Leu Asp Gly Arg Asp Val Thr Lys Thr Asn Thr Thr Asp Val Ala Thr
            180                 185                 190

Phe Lys Ser Val Asn Tyr Gly Pro Leu Gly Tyr Ile His Asn Gly Lys
        195                 200                 205

Ile Asp Tyr Gln Arg Thr Pro Ala Arg Lys His Thr Ser Asp Thr Pro
    210                 215                 220

Phe Asp Val Ser Lys Leu Asn Glu Leu Pro Lys Val Gly Ile Val Tyr
225                 230                 235                 240

Asn Tyr Ala Asn Ala Ser Asp Leu Pro Ala Lys Ala Leu Val Asp Ala
                245                 250                 255

Gly Tyr Asp Gly Ile Val Ser Ala Gly Val Gly Asn Gly Asn Leu Tyr
            260                 265                 270

Lys Ser Val Phe Asp Thr Leu Ala Thr Ala Ala Lys Thr Gly Thr Ala
        275                 280                 285

Val Val Arg Ser Ser Arg Val Pro Thr Gly Ala Thr Thr Gln Asp Ala
    290                 295                 300

Glu Val Asp Asp Ala Lys Tyr Gly Phe Val Ala Ser Gly Thr Leu Asn
305                 310                 315                 320

Pro Gln Lys Ala Arg Val Leu Leu Gln Leu Ala Leu Thr Gln Thr Lys
                325                 330                 335

Asp Pro Gln Gln Ile Gln Gln Ile Phe Asn Gln Tyr
            340                 345
```

```
<210> SEQ ID NO 129
<211> LENGTH: 406
<212> TYPE: PRT
<213> ORGANISM: Escherichia coli

<400> SEQUENCE: 129

Met Lys Arg Ala Val Ile Thr Gly Leu Gly Ile Val Ser Ser Ile Gly
  1               5                  10                  15

Asn Asn Gln Gln Glu Val Leu Ala Ser Leu Arg Glu Gly Arg Ser Gly
                 20                  25                  30

Ile Thr Phe Ser Gln Glu Leu Lys Asp Ser Gly Met Arg Ser His Val
             35                  40                  45

Trp Gly Asn Val Lys Leu Asp Thr Thr Gly Leu Ile Asp Arg Lys Val
         50                  55                  60

Val Arg Phe Met Ser Asp Ala Ser Ile Tyr Ala Phe Leu Ser Met Glu
 65                  70                  75                  80

Gln Ala Ile Ala Asp Ala Gly Leu Ser Pro Glu Ala Tyr Gln Asn Asn
                 85                  90                  95

Pro Arg Val Gly Leu Ile Ala Gly Ser Gly Gly Gly Ser Pro Arg Phe
                100                 105                 110

Gln Val Phe Gly Ala Asp Ala Met Arg Gly Pro Arg Gly Leu Lys Ala
            115                 120                 125

Val Gly Pro Tyr Val Val Thr Lys Ala Met Ala Ser Gly Val Ser Ala
130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
210                 215                 220

His Arg Asp Gly Phe Val Ile Ala Gly Gly Gly Met Val Val Val
225                 230                 235                 240

Glu Glu Leu Glu His Ala Leu Ala Arg Gly Ala His Ile Tyr Ala Glu
                245                 250                 255

Ile Val Gly Tyr Gly Ala Thr Ser Asp Gly Ala Asp Met Val Ala Pro
            260                 265                 270

Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Ala Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
370                 375                 380
```

```
Val Met Ser Asn Ser Phe Gly Phe Gly Gly Thr Asn Ala Thr Leu Val
385                 390                 395                 400

Met Arg Lys Leu Lys Asp
                405

<210> SEQ ID NO 130
<211> LENGTH: 248
<212> TYPE: PRT
<213> ORGANISM: Escherichia coli

<400> SEQUENCE: 130

Met Lys Ser Val Leu Lys Val Ser Leu Ala Ala Leu Thr Leu Ala Phe
1               5                   10                  15

Ala Val Ser Ser His Ala Ala Asp Lys Lys Leu Val Val Ala Thr Asp
                20                  25                  30

Thr Ala Phe Val Pro Phe Glu Phe Lys Gln Gly Asp Lys Tyr Val Gly
            35                  40                  45

Phe Asp Val Asp Leu Trp Ala Ala Ile Ala Lys Glu Leu Lys Leu Asp
50                  55                  60

Tyr Glu Leu Lys Pro Met Asp Phe Ser Gly Ile Ile Pro Ala Leu Gln
65                  70                  75                  80

Thr Lys Asn Val Asp Leu Ala Leu Ala Gly Ile Thr Ile Thr Asp Glu
                85                  90                  95

Arg Lys Lys Ala Ile Asp Phe Ser Asp Gly Tyr Tyr Lys Ser Gly Leu
            100                 105                 110

Leu Val Met Val Lys Ala Asn Asn Asn Asp Val Lys Ser Val Lys Asp
        115                 120                 125

Leu Asp Gly Lys Val Val Ala Val Lys Ser Gly Thr Gly Ser Val Asp
130                 135                 140

Tyr Ala Lys Ala Asn Ile Lys Thr Lys Asp Leu Arg Gln Phe Pro Asn
145                 150                 155                 160

Ile Asp Asn Ala Tyr Met Glu Leu Gly Thr Asn Arg Ala Asp Ala Val
                165                 170                 175

Leu His Asp Thr Pro Asn Ile Leu Tyr Phe Ile Lys Thr Ala Gly Asn
            180                 185                 190

Gly Gln Phe Lys Ala Val Gly Asp Ser Leu Glu Ala Gln Gln Tyr Gly
        195                 200                 205

Ile Ala Phe Pro Lys Gly Ser Asp Glu Leu Arg Asp Lys Val Asn Gly
210                 215                 220

Ala Leu Lys Thr Leu Arg Glu Asn Gly Thr Tyr Asn Glu Ile Tyr Lys
225                 230                 235                 240

Lys Trp Phe Gly Thr Glu Pro Lys
                245

<210> SEQ ID NO 131
<211> LENGTH: 257
<212> TYPE: PRT
<213> ORGANISM: Escherichia coli

<400> SEQUENCE: 131

Met Ala Arg Lys Trp Leu Asn Leu Phe Ala Gly Ala Ala Leu Ser Phe
1               5                   10                  15

Ala Val Ala Gly Asn Ala Leu Ala Asp Glu Gly Lys Ile Thr Val Phe
                20                  25                  30

Ala Ala Ala Ser Leu Thr Asn Ala Met Gln Asp Ile Ala Thr Gln Phe
            35                  40                  45
```

```
Lys Lys Glu Lys Gly Val Asp Val Ser Ser Phe Ala Ser Ser Ser
 50                  55                  60

Thr Leu Ala Arg Gln Ile Glu Ala Gly Ala Pro Ala Asp Leu Phe Ile
 65                  70                  75                  80

Ser Ala Asp Gln Lys Trp Met Asp Tyr Ala Val Asp Lys Lys Ala Ile
                 85                  90                  95

Asp Thr Ala Thr Arg Gln Thr Leu Leu Gly Asn Ser Leu Val Val Val
             100                 105                 110

Ala Pro Lys Ala Ser Val Gln Lys Asp Phe Thr Ile Asp Ser Lys Thr
         115                 120                 125

Asn Trp Thr Ser Leu Leu Asn Gly Gly Arg Leu Ala Val Gly Asp Pro
130                 135                 140

Glu His Val Pro Ala Gly Ile Tyr Ala Lys Glu Ala Leu Gln Lys Leu
145                 150                 155                 160

Gly Ala Trp Asp Thr Leu Ser Pro Lys Leu Ala Pro Ala Glu Asp Val
                165                 170                 175

Arg Gly Ala Leu Ala Leu Val Glu Arg Asn Glu Ala Pro Leu Gly Ile
            180                 185                 190

Val Tyr Gly Ser Asp Ala Val Ala Ser Lys Gly Val Lys Val Val Ala
        195                 200                 205

Thr Phe Pro Glu Asp Ser His Lys Lys Val Glu Tyr Pro Val Ala Val
    210                 215                 220

Val Glu Gly His Asn Asn Ala Thr Val Lys Ala Phe Tyr Asp Tyr Leu
225                 230                 235                 240

Lys Gly Pro Gln Ala Ala Glu Ile Phe Lys Arg Tyr Gly Phe Thr Ile
                245                 250                 255

Lys

<210> SEQ ID NO 132
<211> LENGTH: 630
<212> TYPE: PRT
<213> ORGANISM: Escherichia coli

<400> SEQUENCE: 132

Met Ala Ile Glu Ile Lys Val Pro Asp Ile Gly Ala Asp Glu Val Glu
 1               5                  10                  15

Ile Thr Glu Ile Leu Val Lys Val Gly Asp Lys Val Glu Ala Glu Gln
                 20                  25                  30

Ser Leu Ile Thr Val Glu Gly Asp Lys Ala Ser Met Glu Val Pro Ser
             35                  40                  45

Pro Gln Ala Gly Ile Val Lys Glu Ile Lys Val Ser Val Gly Asp Lys
         50                  55                  60

Thr Gln Thr Gly Ala Leu Ile Met Ile Phe Asp Ser Ala Asp Gly Ala
 65                  70                  75                  80

Ala Asp Ala Ala Pro Ala Gln Ala Glu Glu Lys Lys Glu Ala Ala Pro
                 85                  90                  95

Ala Ala Ala Pro Ala Ala Ala Ala Lys Asp Val Asn Val Pro Asp
             100                 105                 110

Ile Gly Ser Asp Glu Val Glu Val Thr Glu Ile Leu Val Lys Val Gly
         115                 120                 125

Asp Lys Val Glu Ala Glu Gln Ser Leu Ile Thr Val Glu Gly Asp Lys
130                 135                 140

Ala Ser Met Glu Val Pro Ala Pro Phe Ala Gly Thr Val Lys Glu Ile
145                 150                 155                 160
```

```
Lys Val Asn Val Gly Asp Lys Val Ser Thr Gly Ser Leu Ile Met Val
                165                 170                 175
Phe Glu Val Ala Gly Glu Ala Gly Ala Ala Pro Ala Ala Lys Gln
        180                 185                 190
Glu Ala Ala Pro Ala Ala Ala Pro Ala Pro Ala Ala Gly Val Lys Glu
            195                 200                 205
Val Asn Val Pro Asp Ile Gly Gly Asp Glu Val Glu Val Thr Glu Val
    210                 215                 220
Met Val Lys Val Gly Asp Lys Val Ala Ala Glu Gln Ser Leu Ile Thr
225                 230                 235                 240
Val Glu Gly Asp Lys Ala Ser Met Glu Val Pro Ala Pro Phe Ala Gly
                245                 250                 255
Val Val Lys Glu Leu Lys Val Asn Val Gly Asp Lys Val Lys Thr Gly
                260                 265                 270
Ser Leu Ile Met Ile Phe Glu Val Glu Gly Ala Ala Pro Ala Ala Ala
            275                 280                 285
Pro Ala Lys Gln Glu Ala Ala Ala Pro Ala Pro Ala Ala Lys Ala Glu
        290                 295                 300
Ala Pro Ala Ala Ala Pro Ala Ala Lys Ala Glu Gly Lys Ser Glu Phe
305                 310                 315                 320
Ala Glu Asn Asp Ala Tyr Val His Ala Thr Pro Leu Ile Arg Arg Leu
                325                 330                 335
Ala Arg Glu Phe Gly Val Asn Leu Ala Lys Val Lys Gly Thr Gly Arg
                340                 345                 350
Lys Gly Arg Ile Leu Arg Glu Asp Val Gln Ala Tyr Val Lys Glu Ala
            355                 360                 365
Ile Lys Arg Ala Glu Ala Ala Pro Ala Ala Thr Gly Gly Gly Ile Pro
        370                 375                 380
Gly Met Leu Pro Trp Pro Lys Val Asp Phe Ser Lys Phe Gly Glu Ile
385                 390                 395                 400
Glu Glu Val Glu Leu Gly Arg Ile Gln Lys Ile Ser Gly Ala Asn Leu
                405                 410                 415
Ser Arg Asn Trp Val Met Ile Pro His Val Thr His Phe Asp Lys Thr
                420                 425                 430
Asp Ile Thr Glu Leu Glu Ala Phe Arg Lys Gln Gln Asn Glu Glu Ala
            435                 440                 445
Ala Lys Arg Lys Leu Asp Val Lys Ile Thr Pro Val Val Phe Ile Met
        450                 455                 460
Lys Ala Val Ala Ala Ala Leu Glu Gln Met Pro Arg Phe Asn Ser Ser
465                 470                 475                 480
Leu Ser Glu Asp Gly Gln Arg Leu Thr Leu Lys Lys Tyr Ile Asn Ile
                485                 490                 495
Gly Val Ala Val Asp Thr Pro Asn Gly Leu Val Val Pro Val Phe Lys
                500                 505                 510
Asp Val Asn Lys Lys Gly Ile Ile Glu Leu Ser Arg Glu Leu Met Thr
            515                 520                 525
Ile Ser Lys Lys Ala Arg Asp Gly Lys Leu Thr Ala Gly Glu Met Gln
        530                 535                 540
Gly Gly Cys Phe Thr Ile Ser Ser Ile Gly Gly Leu Gly Thr Thr His
545                 550                 555                 560
Phe Ala Pro Ile Val Asn Ala Pro Glu Val Ala Ile Leu Gly Val Ser
                565                 570                 575
Lys Ser Ala Met Glu Pro Val Trp Asn Gly Lys Glu Phe Val Pro Arg
```

Leu Met Leu Pro Ile Ser Leu Ser Phe Asp His Arg Val Ile Asp Gly
                595                 600                 605

Ala Asp Gly Ala Arg Phe Ile Thr Ile Ile Asn Asn Thr Leu Ser Asp
            610                 615                 620

Ile Arg Arg Leu Val Met
625                 630

<210> SEQ ID NO 133
<211> LENGTH: 367
<212> TYPE: PRT
<213> ORGANISM: Escherichia coli

<400> SEQUENCE: 133

Met Lys Val Lys Val Leu Ser Leu Leu Val Pro Ala Leu Leu Val Ala
1               5                   10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asp Lys
        35                  40                  45

Ser Val Asp Gly Asp Gln Thr Tyr Met Arg Leu Gly Phe Lys Gly Glu
50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
130                 135                 140

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Ser
                165                 170                 175

Val Ser Gly Glu Gly Met Thr Asn Asn Gly Arg Glu Ala Leu Arg Gln
            180                 185                 190

Asn Gly Asp Gly Val Gly Gly Ser Ile Thr Tyr Asp Tyr Glu Gly Phe
        195                 200                 205

Gly Ile Gly Ala Ala Val Ser Ser Ser Lys Arg Thr Asp Asp Gln Asn
210                 215                 220

Ser Pro Leu Tyr Ile Gly Asn Gly Asp Arg Ala Glu Thr Tyr Thr Gly
225                 230                 235                 240

Gly Leu Lys Tyr Asp Ala Asn Asn Ile Tyr Leu Ala Ala Gln Tyr Thr
                245                 250                 255

Gln Thr Tyr Asn Ala Thr Arg Val Gly Ser Leu Gly Trp Ala Asn Lys
            260                 265                 270

Ala Gln Asn Phe Glu Ala Val Ala Gln Tyr Gln Phe Asp Phe Gly Leu
        275                 280                 285

Arg Pro Ser Leu Ala Tyr Leu Gln Ser Lys Gly Lys Asn Leu Gly Val
290                 295                 300

Ile Asn Gly Arg Asn Tyr Asp Asp Glu Asp Ile Leu Lys Tyr Val Asp
305                 310                 315                 320

```
Val Gly Ala Thr Tyr Tyr Phe Asn Lys Asn Met Ser Thr Tyr Val Asp
                    325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
            355                 360                 365
```

<210> SEQ ID NO 134
<211> LENGTH: 760
<212> TYPE: PRT
<213> ORGANISM: Escherichia coli

<400> SEQUENCE: 134

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335
```

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
                420                 425                 430

Phe Gly Ala Arg Ala Asn Leu Ala Lys Thr Met Leu Tyr Ala Ile Asn
                435                 440                 445

Gly Gly Val Asp Glu Lys Leu Lys Met Gln Val Gly Pro Lys Ser Glu
            450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
                500                 505                 510

Ala Leu His Asp Arg Asp Val Ile Arg Thr Met Ala Cys Gly Ile Ala
                515                 520                 525

Gly Leu Ser Val Ala Ala Asp Ser Leu Ser Ala Ile Lys Tyr Ala Lys
            530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
                580                 585                 590

His Thr Tyr Arg Asp Ala Ile Pro Thr Gln Ser Val Leu Thr Ile Thr
            595                 600                 605

Ser Asn Val Val Tyr Gly Lys Lys Thr Gly Asn Thr Pro Asp Gly Arg
610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
                660                 665                 670

Asn Ala Leu Gly Lys Asp Asp Glu Val Arg Lys Thr Asn Leu Ala Gly
                675                 680                 685

Leu Met Asp Gly Tyr Phe His His Glu Ala Ser Ile Glu Gly Gly Gln
            690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
          755                 760

<210> SEQ ID NO 135
<211> LENGTH: 289
<212> TYPE: PRT
<213> ORGANISM: Escherichia coli

<400> SEQUENCE: 135

Met Ser Ile Leu Ile Asp Lys Asn Thr Lys Val Ile Cys Gln Gly Phe
1               5                   10                  15

Thr Gly Ser Gln Gly Thr Phe His Ser Glu Gln Ala Ile Ala Tyr Gly
            20                  25                  30

Thr Lys Met Val Gly Val Thr Pro Gly Lys Gly Gly Thr Thr His
        35                  40                  45

Leu Gly Leu Pro Val Phe Asn Thr Val Arg Glu Ala Val Ala Ala Thr
    50                  55                  60

Gly Ala Thr Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
        115                 120                 125

Thr Pro Gly Glu Cys Lys Ile Gly Ile Gln Pro Gly His Ile His Lys
    130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Ala Ala Ala Tyr Ile Lys Glu
    210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
        275                 280                 285

Lys

<210> SEQ ID NO 136
<211> LENGTH: 94
<212> TYPE: PRT
<213> ORGANISM: Escherichia coli

<400> SEQUENCE: 136

Met Ser Lys Cys Ser Ala Asp Glu Thr Pro Val Cys Cys Cys Met Asp
1               5                   10                  15

Val Gly Thr Ile Met Asp Asn Ser Asp Cys Thr Ala Ser Tyr Ser Arg

```
                20                  25                  30

Val Phe Ala Asn Arg Ala Glu Ala Glu Gln Thr Leu Ala Ala Leu Thr
             35                  40                  45

Glu Lys Ala Arg Ser Val Glu Ser Glu Pro Cys Lys Ile Thr Pro Thr
 50                  55                  60

Phe Thr Glu Glu Ser Asp Gly Val Arg Leu Asp Ile Asp Phe Thr Phe
 65                  70                  75                  80

Ala Cys Glu Ala Glu Met Leu Ile Phe Gln Leu Gly Leu Arg
                 85                  90

<210> SEQ ID NO 137
<211> LENGTH: 149
<212> TYPE: PRT
<213> ORGANISM: Escherichia coli

<400> SEQUENCE: 137

Met Gly Leu Phe Asn Phe Val Lys Asp Ala Gly Glu Lys Leu Trp Asp
 1               5                  10                  15

Ala Val Thr Gly Gln His Asp Lys Asp Gln Ala Lys Lys Val Gln
                 20                  25                  30

Glu His Leu Asn Lys Thr Gly Ile Pro Asp Ala Asp Lys Val Asn Ile
             35                  40                  45

Gln Ile Ala Asp Gly Lys Ala Thr Val Thr Gly Asp Gly Leu Ser Gln
 50                  55                  60

Glu Ala Lys Glu Lys Ile Leu Val Ala Val Gly Asn Ile Ser Gly Ile
 65                  70                  75                  80

Ala Ser Val Asp Asp Gln Val Lys Thr Ala Thr Pro Ala Thr Ala Ser
                 85                  90                  95

Gln Phe Tyr Thr Val Lys Ser Gly Asp Thr Leu Ser Ala Ile Ser Lys
                100                 105                 110

Gln Val Tyr Gly Asn Ala Asn Leu Tyr Asn Lys Ile Phe Glu Ala Asn
             115                 120                 125

Lys Pro Met Leu Lys Ser Pro Asp Lys Ile Tyr Pro Gly Gln Val Leu
 130                 135                 140

Arg Ile Pro Glu Glu
 145

<210> SEQ ID NO 138
<211> LENGTH: 478
<212> TYPE: PRT
<213> ORGANISM: Escherichia coli

<400> SEQUENCE: 138

Met Ser Asn Asn Ile Arg Ile Glu Glu Asp Leu Leu Gly Thr Arg Glu
 1               5                  10                  15

Val Pro Ala Asp Ala Tyr Tyr Gly Val His Thr Leu Arg Ala Ile Glu
                 20                  25                  30

Asn Phe Tyr Ile Ser Asn Asn Lys Ile Ser Asp Ile Pro Glu Phe Val
             35                  40                  45

Arg Gly Met Val Met Val Lys Lys Ala Ala Ala Met Ala Asn Lys Glu
 50                  55                  60

Leu Gln Thr Ile Pro Lys Ser Val Ala Asn Ala Ile Ile Ala Ala Cys
 65                  70                  75                  80

Asp Glu Val Leu Asn Asn Gly Lys Cys Met Asp Gln Phe Pro Val Asp
                 85                  90                  95

Val Tyr Gln Gly Gly Ala Gly Thr Ser Val Asn Met Asn Thr Asn Glu
```

100                 105                 110
Val Leu Ala Asn Ile Gly Leu Glu Leu Met Gly His Gln Lys Gly Glu
            115                 120                 125

Tyr Gln Tyr Leu Asn Pro Asn Asp His Val Asn Lys Cys Gln Ser Thr
130                 135                 140

Asn Asp Ala Tyr Pro Thr Gly Phe Arg Ile Ala Val Tyr Ser Ser Leu
145                 150                 155                 160

Ile Lys Leu Val Asp Ala Ile Asn Gln Leu Arg Glu Gly Phe Glu Arg
            165                 170                 175

Lys Ala Val Glu Phe Gln Asp Ile Leu Lys Met Gly Arg Thr Gln Leu
            180                 185                 190

Gln Asp Ala Val Pro Met Thr Leu Gly Gln Glu Phe Arg Ala Phe Ser
            195                 200                 205

Ile Leu Leu Lys Glu Val Lys Asn Ile Gln Arg Thr Ala Glu Leu
            210                 215                 220

Leu Leu Glu Val Asn Leu Gly Ala Thr Ala Ile Gly Thr Gly Leu Asn
225                 230                 235                 240

Thr Pro Lys Glu Tyr Ser Pro Leu Ala Val Lys Lys Leu Ala Glu Val
                245                 250                 255

Thr Gly Phe Pro Cys Val Pro Ala Glu Asp Leu Ile Glu Ala Thr Ser
                260                 265                 270

Asp Cys Gly Ala Tyr Val Met Val His Gly Ala Leu Lys Arg Leu Ala
            275                 280                 285

Val Lys Met Ser Lys Ile Cys Asn Asp Leu Arg Leu Leu Ser Ser Gly
            290                 295                 300

Pro Arg Ala Gly Leu Asn Glu Ile Asn Leu Pro Glu Leu Gln Ala Gly
305                 310                 315                 320

Ser Ser Ile Met Pro Ala Lys Val Asn Pro Val Pro Glu Val Val
                325                 330                 335

Asn Gln Val Cys Phe Lys Val Ile Gly Asn Asp Thr Thr Val Thr Met
            340                 345                 350

Ala Ala Glu Ala Gly Gln Leu Gln Leu Asn Val Met Glu Pro Val Ile
            355                 360                 365

Gly Gln Ala Met Phe Glu Ser Val His Ile Leu Thr Asn Ala Cys Tyr
            370                 375                 380

Asn Leu Leu Glu Lys Cys Ile Asn Gly Ile Thr Ala Asn Lys Glu Val
385                 390                 395                 400

Cys Glu Gly Tyr Val Tyr Asn Ser Ile Gly Ile Val Thr Tyr Leu Asn
                405                 410                 415

Pro Phe Ile Gly His His Asn Gly Asp Ile Val Gly Lys Ile Cys Ala
            420                 425                 430

Glu Thr Gly Lys Ser Val Arg Glu Val Val Leu Glu Arg Gly Leu Leu
            435                 440                 445

Thr Glu Ala Glu Leu Asp Asp Ile Phe Ser Val Gln Asn Leu Met His
450                 455                 460

Pro Ala Tyr Lys Ala Lys Arg Tyr Thr Asp Glu Ser Glu Gln
465                 470                 475

<210> SEQ ID NO 139
<211> LENGTH: 513
<212> TYPE: PRT
<213> ORGANISM: Escherichia coli

<400> SEQUENCE: 139

-continued

```
Met Gln Leu Asn Ser Thr Glu Ile Ser Glu Leu Ile Lys Gln Arg Ile
1               5                   10                  15

Ala Gln Phe Asn Val Val Ser Glu Ala His Asn Glu Gly Thr Ile Val
            20                  25                  30

Ser Val Ser Asp Gly Val Ile Arg Ile His Gly Leu Ala Asp Cys Met
        35                  40                  45

Gln Gly Glu Met Ile Ser Leu Pro Gly Asn Arg Tyr Ala Ile Ala Leu
50                  55                  60

Asn Leu Glu Arg Asp Ser Val Gly Ala Val Val Met Gly Pro Tyr Ala
65                  70                  75                  80

Asp Leu Ala Glu Gly Met Lys Val Lys Cys Thr Gly Arg Ile Leu Glu
                85                  90                  95

Val Pro Val Gly Arg Gly Leu Leu Gly Arg Val Val Asn Thr Leu Gly
            100                 105                 110

Ala Pro Ile Asp Gly Lys Gly Pro Leu Asp His Asp Gly Phe Ser Ala
        115                 120                 125

Val Glu Ala Ile Ala Pro Gly Val Ile Glu Arg Gln Ser Val Asp Gln
130                 135                 140

Pro Val Gln Thr Gly Tyr Lys Ala Val Asp Ser Met Ile Pro Ile Gly
145                 150                 155                 160

Arg Gly Gln Arg Glu Leu Ile Ile Gly Asp Arg Gln Thr Gly Lys Thr
                165                 170                 175

Ala Leu Ala Ile Asp Ala Ile Ile Asn Gln Arg Asp Ser Gly Ile Lys
            180                 185                 190

Cys Ile Tyr Val Ala Ile Gly Gln Lys Ala Ser Thr Ile Ser Asn Val
        195                 200                 205

Val Arg Lys Leu Glu Glu His Gly Ala Leu Ala Asn Thr Ile Val Val
210                 215                 220

Val Ala Thr Ala Ser Glu Ser Ala Ala Leu Gln Tyr Leu Ala Pro Tyr
225                 230                 235                 240

Ala Gly Cys Ala Met Gly Glu Tyr Phe Arg Asp Arg Gly Glu Asp Ala
                245                 250                 255

Leu Ile Ile Tyr Asp Asp Leu Ser Lys Gln Ala Val Ala Tyr Arg Gln
            260                 265                 270

Ile Ser Leu Leu Leu Arg Arg Pro Gly Arg Glu Ala Phe Pro Gly
        275                 280                 285

Asp Val Phe Tyr Leu His Ser Arg Leu Leu Glu Arg Ala Ala Arg Val
        290                 295                 300

Asn Ala Glu Tyr Val Glu Ala Phe Thr Lys Gly Glu Val Lys Gly Lys
305                 310                 315                 320

Thr Gly Ser Leu Thr Ala Leu Pro Ile Ile Glu Thr Gln Ala Gly Asp
                325                 330                 335

Val Ser Ala Phe Val Pro Thr Asn Val Ile Ser Ile Thr Asp Gly Gln
            340                 345                 350

Ile Phe Leu Glu Thr Asn Leu Phe Asn Ala Gly Ile Arg Pro Ala Val
        355                 360                 365

Asn Pro Gly Ile Ser Val Ser Arg Val Gly Ala Ala Gln Thr Lys
        370                 375                 380

Ile Met Lys Lys Leu Ser Gly Gly Ile Arg Thr Ala Leu Ala Gln Tyr
385                 390                 395                 400

Arg Glu Leu Ala Ala Phe Ser Gln Phe Ala Ser Asp Leu Asp Asp Ala
                405                 410                 415

Thr Arg Lys Gln Leu Asp His Gly Gln Lys Val Thr Glu Leu Leu Lys
```

```
                420             425             430
Gln Lys Gln Tyr Ala Pro Met Ser Val Ala Gln Gln Ser Leu Val Leu
            435                 440                 445

Phe Ala Ala Glu Arg Gly Tyr Leu Ala Asp Val Glu Leu Ser Lys Ile
    450                 455                 460

Gly Ser Phe Glu Ala Ala Leu Leu Ala Tyr Val Asp Arg Asp His Ala
465                 470                 475                 480

Pro Leu Met Gln Glu Ile Asn Gln Thr Gly Gly Tyr Asn Asp Glu Ile
                485                 490                 495

Glu Gly Lys Leu Lys Gly Ile Leu Asp Ser Phe Lys Ala Thr Gln Ser
            500                 505                 510

Trp

<210> SEQ ID NO 140
<211> LENGTH: 97
<212> TYPE: PRT
<213> ORGANISM: Escherichia coli

<400> SEQUENCE: 140

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 141
<211> LENGTH: 548
<212> TYPE: PRT
<213> ORGANISM: Escherichia coli

<400> SEQUENCE: 141

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125
```

-continued

```
Glu Glu Leu Lys Ala Leu Ser Val Pro Cys Ser Asp Ser Lys Ala Ile
    130                 135                 140
Ala Gln Val Gly Thr Ile Ser Ala Asn Ser Asp Glu Thr Val Gly Lys
145                 150                 155                 160
Leu Ile Ala Glu Ala Met Asp Lys Val Gly Lys Glu Gly Val Ile Thr
                165                 170                 175
Val Glu Asp Gly Thr Gly Leu Gln Asp Glu Leu Asp Val Val Glu Gly
            180                 185                 190
Met Gln Phe Asp Arg Gly Tyr Leu Ser Pro Tyr Phe Ile Asn Lys Pro
        195                 200                 205
Glu Thr Gly Ala Val Glu Leu Glu Ser Pro Phe Ile Leu Leu Ala Asp
    210                 215                 220
Lys Lys Ile Ser Asn Ile Arg Glu Met Leu Pro Val Leu Glu Ala Val
225                 230                 235                 240
Ala Lys Ala Gly Lys Pro Leu Leu Ile Ile Ala Glu Asp Val Glu Gly
                245                 250                 255
Glu Ala Leu Ala Thr Leu Val Val Asn Thr Met Arg Gly Ile Val Lys
            260                 265                 270
Val Ala Ala Val Lys Ala Pro Gly Phe Gly Asp Arg Arg Lys Ala Met
        275                 280                 285
Leu Gln Asp Ile Ala Thr Leu Thr Gly Gly Thr Val Ile Ser Glu Glu
    290                 295                 300
Ile Gly Met Glu Leu Glu Lys Ala Thr Leu Glu Asp Leu Gly Gln Ala
305                 310                 315                 320
Lys Arg Val Val Ile Asn Lys Asp Thr Thr Thr Ile Ile Asp Gly Val
                325                 330                 335
Gly Glu Glu Ala Ala Ile Gln Gly Arg Val Ala Gln Ile Arg Gln Gln
            340                 345                 350
Ile Glu Glu Ala Thr Ser Asp Tyr Asp Arg Glu Lys Leu Gln Glu Arg
        355                 360                 365
Val Ala Lys Leu Ala Gly Gly Val Ala Val Ile Lys Val Gly Ala Ala
    370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Val Val Ala Gly Gly Gly
                405                 410                 415
Val Ala Leu Ile Arg Val Ala Ser Lys Leu Ala Asp Leu Arg Gly Gln
            420                 425                 430
Asn Glu Asp Gln Asn Val Gly Ile Lys Val Ala Leu Arg Ala Met Glu
        435                 440                 445
Ala Pro Leu Arg Gln Ile Val Leu Asn Cys Gly Glu Glu Pro Ser Val
    450                 455                 460
Val Ala Asn Thr Val Lys Gly Gly Asp Gly Asn Tyr Gly Tyr Asn Ala
465                 470                 475                 480
Ala Thr Glu Glu Tyr Gly Asn Met Ile Asp Met Gly Ile Leu Asp Pro
                485                 490                 495
Thr Lys Val Thr Arg Ser Ala Leu Gln Tyr Ala Ala Ser Val Ala Gly
            500                 505                 510
Leu Met Ile Thr Thr Glu Cys Met Val Thr Asp Leu Pro Lys Asn Asp
        515                 520                 525
Ala Ala Asp Leu Gly Ala Ala Gly Gly Met Gly Gly Met Gly Gly Met
    530                 535                 540
Gly Gly Met Met
```

545

<210> SEQ ID NO 142
<211> LENGTH: 90
<212> TYPE: PRT
<213> ORGANISM: Escherichia coli

<400> SEQUENCE: 142

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
            35                  40                  45

Thr Phe Ala Val Lys Glu Arg Ala Ala Arg Thr Gly Arg Asn Pro Gln
        50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90

<210> SEQ ID NO 143
<211> LENGTH: 466
<212> TYPE: PRT
<213> ORGANISM: Escherichia coli

<400> SEQUENCE: 143

Met Asp Lys Lys Gln Val Thr Asp Leu Arg Ser Glu Leu Leu Asp Ser
1               5                   10                  15

Arg Phe Gly Ala Lys Ser Ile Ser Thr Ile Ala Glu Ser Lys Arg Phe
                20                  25                  30

Pro Leu His Glu Met Arg Asp Asp Val Ala Phe Gln Ile Ile Asn Asp
            35                  40                  45

Glu Leu Tyr Leu Asp Gly Asn Ala Arg Gln Asn Leu Ala Thr Phe Cys
        50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110

Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met

```
                225                 230                 235                 240
        His Ile Asp Ala Ala Ser Gly Gly Phe Leu Ala Pro Phe Val Ala Pro
                            245                 250                 255

Asp Ile Val Trp Asp Phe Arg Leu Pro Arg Val Lys Ser Ile Ser Ala
                            260                 265                 270

Ser Gly His Lys Phe Gly Leu Ala Pro Leu Gly Cys Gly Trp Val Ile
                            275                 280                 285

Trp Arg Asp Glu Glu Ala Leu Pro Gln Glu Leu Val Phe Asn Val Asp
                290                 295                 300

Tyr Leu Gly Gly Gln Ile Gly Thr Phe Ala Ile Asn Phe Ser Arg Pro
        305                 310                 315                 320

Ala Gly Gln Val Ile Ala Gln Tyr Tyr Glu Phe Leu Arg Leu Gly Arg
                            325                 330                 335

Glu Gly Tyr Thr Lys Val Gln Asn Ala Ser Tyr Gln Val Ala Ala Tyr
                            340                 345                 350

Leu Ala Asp Glu Ile Ala Lys Leu Gly Pro Tyr Glu Phe Ile Cys Thr
                            355                 360                 365

Gly Arg Pro Asp Glu Gly Ile Pro Ala Val Cys Phe Lys Leu Lys Asp
                370                 375                 380

Gly Glu Asp Pro Gly Tyr Thr Leu Tyr Asp Leu Ser Glu Arg Leu Arg
        385                 390                 395                 400

Leu Arg Gly Trp Gln Val Pro Ala Phe Thr Leu Gly Gly Glu Ala Thr
                            405                 410                 415

Asp Ile Val Val Met Arg Ile Met Cys Arg Arg Gly Phe Glu Met Asp
                            420                 425                 430

Phe Ala Glu Leu Leu Leu Glu Asp Tyr Lys Ala Ser Leu Lys Tyr Leu
                            435                 440                 445

Ser Asp His Pro Lys Leu Gln Gly Ile Ala Gln Gln Asn Ser Phe Lys
                450                 455                 460

His Thr
        465

<210> SEQ ID NO 144
        <211> LENGTH: 588
        <212> TYPE: PRT
        <213> ORGANISM: Escherichia coli

<400> SEQUENCE: 144

Met Lys Leu Pro Val Arg Glu Phe Asp Ala Val Ile Gly Ala Gly
        1               5                   10                  15

Gly Ala Gly Met Arg Ala Ala Leu Gln Ile Ser Gln Ser Gly Gln Thr
                        20                  25                  30

Cys Ala Leu Leu Ser Lys Val Phe Pro Thr Arg Ser His Thr Val Ser
                    35                  40                  45

Ala Gln Gly Gly Ile Thr Val Ala Leu Gly Asn Thr His Glu Asp Asn
                    50                  55                  60

Trp Glu Trp His Met Tyr Asp Thr Val Lys Gly Ser Asp Tyr Ile Gly
        65                  70                  75                  80

Asp Gln Asp Ala Ile Glu Tyr Met Cys Lys Thr Gly Pro Glu Ala Ile
                            85                  90                  95

Leu Glu Leu Glu His Met Gly Leu Pro Phe Ser Arg Leu Asp Asp Gly
                        100                 105                 110

Arg Ile Tyr Gln Arg Pro Phe Gly Gly Gln Ser Lys Asn Phe Gly Gly
                    115                 120                 125
```

```
Glu Gln Ala Ala Arg Thr Ala Ala Ala Asp Arg Thr Gly His Ala
    130                 135                 140
Leu Leu His Thr Leu Tyr Gln Gln Asn Leu Lys Asn His Thr Thr Ile
145                 150                 155                 160
Phe Ser Glu Trp Tyr Ala Leu Asp Leu Val Lys Asn Gln Asp Gly Ala
                165                 170                 175
Val Val Gly Cys Thr Ala Leu Cys Ile Glu Thr Gly Glu Val Val Tyr
            180                 185                 190
Phe Lys Ala Arg Ala Thr Val Leu Ala Thr Gly Gly Ala Gly Arg Ile
            195                 200                 205
Tyr Gln Ser Thr Thr Asn Ala His Ile Asn Thr Gly Asp Gly Val Gly
    210                 215                 220
Met Ala Ile Arg Ala Gly Val Pro Val Gln Asp Met Glu Met Trp Gln
225                 230                 235                 240
Phe His Pro Thr Gly Ile Ala Gly Ala Gly Val Leu Val Thr Glu Gly
                245                 250                 255
Cys Arg Gly Glu Gly Gly Tyr Leu Leu Asn Lys His Gly Glu Arg Phe
            260                 265                 270
Met Glu Arg Tyr Ala Pro Asn Ala Lys Asp Leu Ala Gly Arg Asp Val
            275                 280                 285
Val Ala Arg Ser Ile Met Ile Glu Ile Arg Glu Gly Arg Gly Cys Asp
    290                 295                 300
Gly Pro Trp Gly Pro His Ala Lys Leu Lys Leu Asp His Leu Gly Lys
305                 310                 315                 320
Glu Val Leu Glu Ser Arg Leu Pro Gly Ile Leu Glu Leu Ser Arg Thr
                325                 330                 335
Phe Ala His Val Asp Pro Val Lys Glu Pro Ile Pro Val Ile Pro Thr
                340                 345                 350
Cys His Tyr Met Met Gly Gly Ile Pro Thr Lys Val Thr Gly Gln Ala
            355                 360                 365
Leu Thr Val Asn Glu Lys Gly Glu Asp Val Val Pro Gly Leu Phe
    370                 375                 380
Ala Val Gly Glu Ile Ala Cys Val Ser Val His Gly Ala Asn Arg Leu
385                 390                 395                 400
Gly Gly Asn Ser Leu Leu Asp Leu Val Val Phe Gly Arg Ala Ala Gly
                405                 410                 415
Leu His Leu Gln Glu Ser Ile Ala Glu Gln Gly Ala Leu Arg Asp Ala
            420                 425                 430
Ser Glu Ser Asp Val Glu Ala Ser Leu Asp Arg Leu Asn Arg Trp Asn
            435                 440                 445
Asn Asn Arg Asn Gly Glu Asp Pro Val Ala Ile Arg Lys Ala Leu Gln
    450                 455                 460
Glu Cys Met Gln His Asn Phe Ser Val Phe Arg Gly Asp Ala Met
465                 470                 475                 480
Ala Lys Gly Leu Glu Gln Leu Lys Val Ile Arg Glu Arg Leu Lys Asn
                485                 490                 495
Ala Arg Leu Asp Asp Thr Ser Ser Glu Phe Asn Thr Gln Arg Val Glu
            500                 505                 510
Cys Leu Glu Leu Asp Asn Leu Met Glu Thr Ala Tyr Ala Thr Ala Val
            515                 520                 525
Ser Ala Asn Phe Arg Thr Glu Ser Arg Gly Ala His Ser Arg Phe Asp
    530                 535                 540
Phe Pro Asp Arg Asp Asp Glu Asn Trp Leu Cys His Ser Leu Tyr Leu
```

Pro Glu Ser Glu Ser Met Thr Arg Arg Ser Val Asn Met Glu Pro Lys
545                 550                 555                 560

Leu Arg Pro Ala Phe Pro Pro Lys Ile Arg Thr Tyr
            565                 570                 575

<210> SEQ ID NO 145
<211> LENGTH: 167
<212> TYPE: PRT
<213> ORGANISM: Escherichia coli

<400> SEQUENCE: 145

Met Ser Thr Ala Lys Leu Val Lys Ser Lys Ala Thr Asn Leu Leu Tyr
1               5                   10                  15

Thr Arg Asn Asp Val Ser Asp Ser Glu Lys Lys Ala Thr Val Glu Leu
            20                  25                  30

Leu Asn Arg Gln Val Ile Gln Phe Ile Asp Leu Ser Leu Ile Thr Lys
        35                  40                  45

Gln Ala His Trp Asn Met Arg Gly Ala Asn Phe Ile Ala Val His Glu
    50                  55                  60

Met Leu Asp Gly Phe Arg Thr Ala Leu Ile Asp His Leu Asp Thr Met
65                  70                  75                  80

Ala Glu Arg Ala Val Gln Leu Gly Gly Val Ala Leu Gly Thr Thr Gln
                85                  90                  95

Val Ile Asn Ser Lys Thr Pro Leu Lys Ser Tyr Pro Leu Asp Ile His
            100                 105                 110

Asn Val Gln Asp His Leu Lys Glu Leu Ala Asp Arg Tyr Ala Ile Val
        115                 120                 125

Ala Asn Asp Val Arg Lys Ala Ile Gly Glu Ala Lys Asp Asp Thr
    130                 135                 140

Ala Asp Ile Leu Thr Ala Ala Ser Arg Asp Leu Asp Lys Phe Leu Trp
145                 150                 155                 160

Phe Ile Glu Ser Asn Ile Glu
                165

<210> SEQ ID NO 146
<211> LENGTH: 137
<212> TYPE: PRT
<213> ORGANISM: Escherichia coli

<400> SEQUENCE: 146

Met Ser Glu Ala Leu Lys Ile Leu Asn Asn Ile Arg Thr Leu Arg Ala
1               5                   10                  15

Gln Ala Arg Glu Cys Thr Leu Glu Thr Leu Glu Glu Met Leu Glu Lys
            20                  25                  30

Leu Glu Val Val Val Asn Glu Arg Arg Glu Glu Ser Ala Ala Ala
        35                  40                  45

Ala Glu Val Glu Glu Arg Thr Arg Lys Leu Gln Gln Tyr Arg Glu Met
    50                  55                  60

Leu Ile Ala Asp Gly Ile Asp Pro Asn Glu Leu Leu Asn Ser Leu Ala
65                  70                  75                  80

Ala Val Lys Ser Gly Thr Lys Ala Lys Arg Ala Gln Arg Pro Ala Lys
                85                  90                  95

Tyr Ser Tyr Val Asp Glu Asn Gly Glu Thr Lys Thr Trp Thr Gly Gln
            100                 105                 110

Gly Arg Thr Pro Ala Val Ile Lys Lys Ala Met Asp Glu Gln Gly Lys

Ser Leu Asp Asp Phe Leu Ile Lys Gln
    130                 135

<210> SEQ ID NO 147
<211> LENGTH: 312
<212> TYPE: PRT
<213> ORGANISM: Escherichia coli

<400> SEQUENCE: 147

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asn Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
            260                 265                 270

Asn Gly Val Glu Glu Arg Lys Ser Ile Gly Thr Leu Ser Ala Phe Glu
        275                 280                 285

Lys Asn Ala Leu Glu Gly Met Leu Asp Thr Leu Lys Lys Asp Ile Ala
    290                 295                 300

Leu Gly Glu Glu Phe Val Asn Lys
305                 310

<210> SEQ ID NO 148
<211> LENGTH: 387
<212> TYPE: PRT
<213> ORGANISM: Escherichia coli

```
<400> SEQUENCE: 148

Met Ser Val Ile Lys Met Thr Asp Leu Asp Leu Ala Gly Lys Arg Val
1               5                   10                  15

Phe Ile Arg Ala Asp Leu Asn Val Pro Val Lys Asp Gly Lys Val Thr
                20                  25                  30

Ser Asp Ala Arg Ile Arg Ala Ser Leu Pro Thr Ile Glu Leu Ala Leu
            35                  40                  45

Lys Gln Gly Ala Lys Val Met Val Thr Ser His Leu Gly Arg Pro Thr
50                  55                  60

Glu Gly Glu Tyr Asn Glu Glu Phe Ser Leu Leu Pro Val Val Asn Tyr
65                  70                  75                  80

Leu Lys Asp Lys Leu Ser Asn Pro Val Arg Leu Val Lys Asp Tyr Leu
                85                  90                  95

Asp Gly Val Asp Val Ala Glu Gly Glu Leu Val Val Leu Glu Asn Val
                100                 105                 110

Arg Phe Asn Lys Gly Glu Lys Lys Asp Asp Glu Thr Leu Ser Lys Lys
            115                 120                 125

Tyr Ala Ala Leu Cys Asp Val Phe Val Met Asp Ala Phe Gly Thr Ala
130                 135                 140

His Arg Ala Gln Ala Ser Thr His Gly Ile Gly Lys Phe Ala Asp Val
145                 150                 155                 160

Ala Cys Ala Gly Pro Leu Leu Ala Ala Glu Leu Asp Ala Leu Gly Lys
                165                 170                 175

Ala Leu Lys Glu Pro Ala Arg Pro Met Val Ala Ile Val Gly Gly Ser
            180                 185                 190

Lys Val Ser Thr Lys Leu Thr Val Leu Asp Ser Leu Ser Lys Ile Ala
            195                 200                 205

Asp Gln Leu Ile Val Gly Gly Ile Ala Asn Thr Phe Ile Ala Ala
210                 215                 220

Gln Gly His Asp Val Gly Lys Ser Leu Tyr Glu Ala Asp Leu Val Asp
225                 230                 235                 240

Glu Ala Lys Arg Leu Leu Ser Thr Cys Asn Ile Pro Val Pro Ser Asp
            245                 250                 255

Val Arg Val Ala Thr Glu Phe Ser Glu Thr Ala Pro Ala Thr Leu Lys
            260                 265                 270

Ser Val Asn Asp Val Lys Ala Asp Glu Gln Ile Leu Asp Ile Gly Asp
            275                 280                 285

Ala Ser Ala Gln Glu Leu Ala Glu Ile Leu Lys Asn Ala Lys Thr Ile
290                 295                 300

Leu Trp Asn Gly Pro Val Gly Val Phe Glu Phe Pro Asn Phe Arg Lys
305                 310                 315                 320

Gly Thr Glu Ile Val Ala Asn Ala Ile Ala Asp Ser Glu Ala Phe Ser
                325                 330                 335

Ile Ala Gly Gly Gly Asp Thr Leu Ala Ala Ile Asp Leu Phe Gly Ile
            340                 345                 350

Ala Asp Lys Ile Ser Tyr Ile Ser Thr Gly Gly Gly Ala Phe Leu Glu
            355                 360                 365

Phe Val Glu Gly Lys Val Leu Pro Ala Val Ala Met Leu Glu Glu Arg
370                 375                 380

Ala Lys Lys
385

<210> SEQ ID NO 149
```

<211> LENGTH: 237
<212> TYPE: PRT
<213> ORGANISM: Escherichia coli

<400> SEQUENCE: 149

Met Gln Lys Gln Ala Glu Leu Tyr Arg Gly Lys Ala Lys Thr Val Tyr
1               5                   10                  15

Ser Thr Glu Asn Pro Asp Leu Leu Val Leu Glu Phe Arg Asn Asp Thr
            20                  25                  30

Ser Ala Gly Asp Gly Ala Arg Ile Glu Gln Phe Asp Arg Lys Gly Met
        35                  40                  45

Val Asn Asn Lys Phe Asn Tyr Phe Ile Met Ser Lys Leu Ala Glu Ala
50                  55                  60

Gly Ile Pro Thr Gln Met Glu Arg Leu Leu Ser Asp Thr Glu Cys Leu
65                  70                  75                  80

Val Lys Lys Leu Asp Met Val Pro Val Glu Cys Val Val Arg Asn Arg
                85                  90                  95

Ala Ala Gly Ser Leu Val Lys Arg Leu Gly Ile Glu Glu Gly Ile Glu
            100                 105                 110

Leu Asn Pro Pro Leu Phe Asp Leu Phe Leu Lys Asn Asp Ala Met His
        115                 120                 125

Asp Pro Met Val Asn Glu Ser Tyr Cys Glu Thr Phe Gly Trp Val Ser
    130                 135                 140

Lys Glu Asn Leu Ala Arg Met Lys Glu Leu Thr Tyr Lys Ala Asn Asp
145                 150                 155                 160

Val Leu Lys Lys Leu Phe Asp Asp Ala Gly Leu Ile Leu Val Asp Phe
                165                 170                 175

Lys Leu Glu Phe Gly Leu Tyr Lys Gly Glu Val Val Leu Gly Asp Glu
            180                 185                 190

Phe Ser Pro Asp Gly Ser Arg Leu Trp Asp Lys Glu Thr Leu Glu Lys
        195                 200                 205

Met Asp Lys Asp Arg Phe Arg Gln Ser Leu Gly Gly Leu Ile Glu Ala
    210                 215                 220

Tyr Glu Ala Val Ala Arg Arg Leu Gly Val Gln Leu Asp
225                 230                 235

<210> SEQ ID NO 150
<211> LENGTH: 201
<212> TYPE: PRT
<213> ORGANISM: Escherichia coli

<400> SEQUENCE: 150

Met Glu Leu Val Leu Lys Asp Ala Gln Ser Ala Leu Thr Val Ser Glu
1               5                   10                  15

Thr Thr Phe Gly Arg Asp Phe Asn Glu Ala Leu Val His Gln Val Val
            20                  25                  30

Val Ala Tyr Ala Ala Gly Ala Arg Gln Gly Thr Arg Ala Gln Lys Thr
        35                  40                  45

Arg Ala Glu Val Thr Gly Ser Gly Lys Lys Pro Trp Arg Gln Lys Gly
    50                  55                  60

Thr Gly Arg Ala Arg Ser Gly Ser Ile Lys Ser Pro Ile Trp Arg Ser
65                  70                  75                  80

Gly Gly Val Thr Phe Ala Ala Arg Pro Gln Asp His Ser Gln Lys Val
                85                  90                  95

Asn Lys Lys Met Tyr Arg Gly Ala Leu Lys Ser Ile Leu Ser Glu Leu
            100                 105                 110

```
Val Arg Gln Asp Arg Leu Ile Val Glu Lys Phe Ser Val Glu Ala
            115                 120                 125

Pro Lys Thr Lys Leu Leu Ala Gln Lys Leu Lys Asp Met Ala Leu Glu
    130                 135                 140

Asp Val Leu Ile Ile Thr Gly Glu Leu Asp Glu Asn Leu Phe Leu Ala
145                 150                 155                 160

Ala Arg Asn Leu His Lys Val Asp Val Arg Asp Ala Thr Gly Ile Asp
                165                 170                 175

Pro Val Ser Leu Ile Ala Phe Asp Lys Val Val Met Thr Ala Asp Ala
                180                 185                 190

Val Lys Gln Val Glu Glu Met Leu Ala
                195                 200

<210> SEQ ID NO 151
<211> LENGTH: 557
<212> TYPE: PRT
<213> ORGANISM: Escherichia coli

<400> SEQUENCE: 151

Met Thr Glu Ser Phe Ala Gln Leu Phe Glu Glu Ser Leu Lys Glu Ile
1               5                   10                  15

Glu Thr Arg Pro Gly Ser Ile Val Arg Gly Val Val Ala Ile Asp
            20                  25                  30

Lys Asp Val Val Leu Val Asp Ala Gly Leu Lys Ser Glu Ser Ala Ile
                35                  40                  45

Pro Ala Glu Gln Phe Lys Asn Ala Gln Gly Glu Leu Glu Ile Gln Val
    50                  55                  60

Gly Asp Glu Val Asp Val Ala Leu Asp Ala Val Glu Asp Gly Phe Gly
65                  70                  75                  80

Glu Thr Leu Leu Ser Arg Glu Lys Ala Lys Arg His Glu Ala Trp Ile
                85                  90                  95

Thr Leu Glu Lys Ala Tyr Glu Asp Ala Glu Thr Val Thr Gly Val Ile
                100                 105                 110

Asn Gly Lys Val Lys Gly Gly Phe Thr Val Glu Leu Asn Gly Ile Arg
                115                 120                 125

Ala Phe Leu Pro Gly Ser Leu Val Asp Val Arg Pro Val Arg Asp Thr
    130                 135                 140

Leu His Leu Glu Gly Lys Glu Leu Glu Phe Lys Val Ile Lys Leu Asp
145                 150                 155                 160

Gln Lys Arg Asn Asn Val Val Ser Arg Arg Ala Val Ile Glu Ser
                165                 170                 175

Glu Asn Ser Ala Glu Arg Asp Gln Leu Leu Glu Asn Leu Gln Glu Gly
                180                 185                 190

Met Glu Val Lys Gly Ile Val Lys Asn Leu Thr Asp Tyr Gly Ala Phe
                195                 200                 205

Val Asp Leu Gly Gly Val Asp Gly Leu Leu His Ile Thr Asp Met Ala
    210                 215                 220

Trp Lys Arg Val Lys His Pro Ser Glu Ile Val Asn Val Gly Asp Glu
225                 230                 235                 240

Ile Thr Val Lys Val Leu Lys Phe Asp Arg Glu Arg Thr Arg Val Ser
                245                 250                 255

Leu Gly Leu Lys Gln Leu Gly Glu Asp Pro Trp Val Ala Ile Ala Lys
                260                 265                 270

Arg Tyr Pro Glu Gly Thr Lys Leu Thr Gly Arg Val Thr Asn Leu Thr
```

```
                275                 280                 285
Asp Tyr Gly Cys Phe Val Glu Ile Glu Glu Gly Val Glu Gly Leu Val
            290                 295                 300
His Val Ser Glu Met Asp Trp Thr Asn Lys Asn Ile His Pro Ser Lys
305                 310                 315                 320
Val Val Asn Val Gly Asp Val Val Glu Val Met Val Leu Asp Ile Asp
            325                 330                 335
Glu Glu Arg Arg Arg Ile Ser Leu Gly Leu Lys Gln Cys Lys Ala Asn
            340                 345                 350
Pro Trp Gln Gln Phe Ala Glu Thr His Asn Lys Gly Asp Arg Val Glu
            355                 360                 365
Gly Lys Ile Lys Ser Ile Thr Asp Phe Gly Ile Phe Ile Gly Leu Asp
            370                 375                 380
Gly Gly Ile Asp Gly Leu Val His Leu Ser Asp Ile Ser Trp Asn Val
385                 390                 395                 400
Ala Gly Glu Glu Ala Val Arg Glu Tyr Lys Lys Gly Asp Glu Ile Ala
            405                 410                 415
Ala Val Val Leu Gln Val Asp Ala Glu Arg Glu Arg Ile Ser Leu Gly
            420                 425                 430
Val Lys Gln Leu Ala Glu Asp Pro Phe Asn Asn Trp Val Ala Leu Asn
            435                 440                 445
Lys Lys Gly Ala Ile Val Thr Gly Lys Val Thr Ala Val Asp Ala Lys
            450                 455                 460
Gly Ala Thr Val Glu Leu Ala Asp Gly Val Glu Gly Tyr Leu Arg Ala
465                 470                 475                 480
Ser Glu Ala Ser Arg Asp Arg Val Glu Asp Ala Thr Leu Val Leu Ser
            485                 490                 495
Val Gly Asp Glu Val Glu Ala Lys Phe Thr Gly Val Asp Arg Lys Asn
            500                 505                 510
Arg Ala Ile Ser Leu Ser Val Arg Ala Lys Asp Glu Ala Asp Glu Lys
            515                 520                 525
Asp Ala Ile Ala Thr Val Asn Lys Gln Glu Asp Ala Asn Phe Ser Asn
            530                 535                 540
Asn Ala Met Ala Glu Ala Phe Lys Ala Ala Lys Gly Glu
545                 550                 555

<210> SEQ ID NO 152
<211> LENGTH: 128
<212> TYPE: PRT
<213> ORGANISM: Escherichia coli

<400> SEQUENCE: 152

Met Ser Lys Thr Ile Ala Thr Glu Asn Ala Pro Ala Ala Ile Gly Pro
1               5                   10                  15
Tyr Val Gln Gly Val Asp Leu Gly Asn Met Ile Ile Thr Ser Gly Gln
            20                  25                  30
Ile Pro Val Asn Pro Lys Thr Gly Glu Val Pro Ala Asp Val Ala Ala
            35                  40                  45
Gln Ala Arg Gln Ser Leu Asp Asn Val Lys Ala Ile Val Glu Ala Ala
            50                  55                  60
Gly Leu Lys Val Gly Asp Ile Val Lys Thr Thr Val Phe Val Lys Asp
65                  70                  75                  80
Leu Asn Asp Phe Ala Thr Val Asn Ala Thr Tyr Glu Ala Phe Phe Thr
            85                  90                  95
```

```
Glu His Asn Ala Thr Phe Pro Ala Arg Ser Cys Val Glu Val Ala Arg
            100                 105                 110

Leu Pro Lys Asp Val Lys Ile Glu Ile Glu Ala Ile Ala Val Arg Arg
        115                 120                 125

<210> SEQ ID NO 153
<211> LENGTH: 315
<212> TYPE: PRT
<213> ORGANISM: Escherichia coli

<400> SEQUENCE: 153

Met Lys Ile Ile Ile Phe Arg Val Leu Thr Phe Phe Val Ile Phe
  1               5                  10                  15

Ser Val Asn Val Val Ala Lys Glu Phe Thr Leu Asp Phe Ser Thr Ala
             20                  25                  30

Lys Thr Tyr Val Asp Ser Leu Asn Val Ile Arg Ser Ala Ile Gly Thr
         35                  40                  45

Pro Leu Gln Thr Ile Ser Ser Gly Gly Thr Ser Leu Leu Met Ile Asp
     50                  55                  60

Ser Gly Thr Gly Asp Asn Leu Phe Ala Val Asp Val Arg Gly Ile Asp
 65                  70                  75                  80

Pro Glu Glu Gly Arg Phe Asn Asn Leu Arg Leu Ile Val Glu Arg Asn
             85                  90                  95

Asn Leu Tyr Val Thr Gly Phe Val Asn Arg Thr Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315

<210> SEQ ID NO 154
<211> LENGTH: 319
<212> TYPE: PRT
<213> ORGANISM: Escherichia coli
```

<400> SEQUENCE: 154

Met Lys Cys Ile Leu Phe Lys Trp Val Leu Cys Leu Leu Leu Gly Phe
1               5                   10                  15

Ser Ser Val Ser His Ser Arg Glu Phe Thr Ile Asp Phe Ser Thr Gln
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
50                  55                  60

His Thr Pro Pro Gly Ser Tyr Phe Ala Val Asp Ile Arg Gly Leu Asp
65                  70                  75                  80

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Thr His Ile Ser Val Pro Gly Val Thr Thr Val
        115                 120                 125

Ser Met Thr Thr Asp Ser Ser Tyr Thr Thr Leu Gln Arg Val Ala Ala
130                 135                 140

Leu Glu Arg Ser Gly Met Gln Ile Ser Arg His Ser Leu Val Ser Ser
145                 150                 155                 160

Tyr Leu Ala Leu Val Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Asp Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
290                 295                 300

Ala Phe Leu Asn Arg Lys Ser Gln Phe Leu Tyr Thr Thr Gly Lys
305                 310                 315

<210> SEQ ID NO 155
<211> LENGTH: 350
<212> TYPE: PRT
<213> ORGANISM: Candida albicans

<400> SEQUENCE: 155

Met Ser Glu Gln Ile Pro Lys Thr Gln Lys Ala Val Val Phe Asp Thr
1               5                   10                  15

Asn Gly Gly Gln Leu Val Tyr Lys Asp Tyr Pro Val Pro Thr Pro Lys
            20                  25                  30

Pro Asn Glu Leu Leu Ile His Val Lys Tyr Ser Gly Val Cys His Thr
        35                  40                  45

Asp Leu His Ala Arg Lys Gly Asp Trp Pro Leu Ala Thr Lys Leu Pro
        50                  55                  60

Leu Val Gly Gly His Glu Gly Ala Gly Val Val Gly Met Gly Glu
65                  70                  75                  80

Asn Val Lys Gly Trp Lys Ile Gly Asp Phe Ala Gly Ile Lys Trp Leu
                85                  90                  95

Asn Gly Ser Cys Met Ser Cys Glu Phe Cys Gln Gln Gly Ala Glu Pro
            100                 105                 110

Asn Cys Gly Glu Ala Asp Leu Ser Gly Tyr Thr His Asp Gly Ser Phe
        115                 120                 125

Glu Gln Tyr Ala Thr Ala Asp Ala Val Gln Ala Ala Lys Ile Pro Ala
    130                 135                 140

Gly Thr Asp Leu Ala Asn Val Ala Pro Ile Leu Cys Ala Gly Val Thr
145                 150                 155                 160

Val Tyr Lys Ala Leu Lys Thr Ala Asp Leu Ala Ala Gly Gln Trp Val
                165                 170                 175

Ala Ile Ser Gly Ala Gly Gly Leu Gly Ser Leu Ala Val Gln Tyr
            180                 185                 190

Ala Arg Ala Met Gly Leu Arg Val Val Ala Ile Asp Gly Gly Asp Glu
    195                 200                 205

Lys Gly Glu Phe Val Lys Ser Leu Gly Ala Glu Ala Tyr Val Asp Phe
210                 215                 220

Thr Lys Asp Lys Asp Ile Val Glu Ala Val Lys Lys Ala Thr Asp Gly
225                 230                 235                 240

Gly Pro His Gly Ala Ile Asn Val Ser Val Ser Glu Lys Ala Ile Asp
                245                 250                 255

Gln Ser Val Glu Tyr Val Arg Pro Leu Gly Lys Val Val Leu Val Gly
            260                 265                 270

Leu Pro Ala His Ala Lys Val Thr Ala Pro Val Phe Asp Ala Val Val
        275                 280                 285

Lys Ser Ile Glu Ile Lys Gly Ser Tyr Val Gly Asn Arg Lys Asp Thr
    290                 295                 300

Ala Glu Ala Ile Asp Phe Phe Ser Arg Gly Leu Ile Lys Cys Pro Ile
305                 310                 315                 320

Lys Ile Val Gly Leu Ser Asp Leu Pro Glu Val Phe Lys Leu Met Glu
                325                 330                 335

Glu Gly Lys Ile Leu Gly Arg Tyr Val Leu Asp Thr Ser Lys
            340                 345                 350

<210> SEQ ID NO 156
<211> LENGTH: 359
<212> TYPE: PRT
<213> ORGANISM: Candida albicans

<400> SEQUENCE: 156

Met Ala Pro Pro Ala Val Leu Ser Lys Ser Gly Val Ile Tyr Gly Lys
1               5                   10                  15

Asp Val Lys Asp Leu Phe Asp Tyr Ala Gln Glu Lys Gly Phe Ala Ile
                20                  25                  30

Pro Ala Ile Asn Val Thr Ser Ser Thr Val Val Ala Ala Leu Glu
            35                  40                  45

Ala Ala Arg Asp Asn Lys Ala Pro Ile Ile Leu Gln Thr Ser Gln Gly
    50                  55                  60

Gly Ala Ala Tyr Phe Ala Gly Lys Gly Val Asp Asn Lys Asp Gln Ala

```
            65                  70                  75                  80
Ala Ser Ile Ala Gly Ser Ile Ala Ala His Tyr Ile Arg Ala Ile
                85                  90                  95

Ala Pro Thr Tyr Gly Ile Pro Val Val Leu His Thr Asp His Cys Ala
                100                 105                 110

Lys Lys Leu Leu Pro Trp Phe Asp Gly Met Leu Lys Ala Asp Glu Glu
                115                 120                 125

Phe Phe Ala Lys Thr Gly Thr Pro Leu Phe Ser Ser His Met Leu Asp
        130                 135                 140

Leu Ser Glu Glu Thr Asp Asp Glu Asn Ile Ala Thr Cys Ala Lys Tyr
145                 150                 155                 160

Phe Glu Arg Met Ala Lys Met Gly Gln Trp Leu Glu Met Glu Ile Gly
                165                 170                 175

Ile Thr Gly Gly Glu Glu Asp Gly Val Asn Asn Glu His Val Glu Lys
        180                 185                 190

Asp Ala Leu Tyr Thr Ser Pro Glu Thr Val Phe Ala Val Tyr Glu Ser
                195                 200                 205

Leu His Lys Ile Ser Pro Asn Phe Ser Ile Ala Ala Ala Phe Gly Asn
        210                 215                 220

Val His Gly Val Tyr Lys Pro Gly Asn Val Gln Leu Arg Pro Glu Ile
225                 230                 235                 240

Leu Gly Asp His Gln Val Tyr Ala Lys Lys Gln Ile Gly Thr Asp Ala
                245                 250                 255

Lys His Pro Leu Tyr Leu Val Phe His Gly Gly Ser Gly Ser Thr Gln
                260                 265                 270

Glu Glu Phe Asn Thr Ala Ile Lys Asn Gly Val Val Lys Val Asn Leu
        275                 280                 285

Asp Thr Asp Cys Gln Tyr Ala Tyr Leu Thr Gly Ile Arg Asp Tyr Val
                290                 295                 300

Thr Asn Lys Ile Glu Tyr Leu Lys Ala Pro Val Gly Asn Pro Glu Gly
305                 310                 315                 320

Ala Asp Lys Pro Asn Lys Lys Tyr Phe Asp Pro Arg Val Trp Val Arg
                325                 330                 335

Glu Gly Glu Lys Thr Met Ser Lys Arg Ile Ala Glu Ala Leu Asp Ile
                340                 345                 350

Phe His Thr Lys Gly Gln Leu
        355

<210> SEQ ID NO 157
<211> LENGTH: 528
<212> TYPE: PRT
<213> ORGANISM: Candida albicans

<400> SEQUENCE: 157

Met Ala Ile Val Glu Thr Val Ile Asp Gly Ile Asn Tyr Phe Leu Ser
1               5                   10                  15

Leu Ser Val Thr Gln Gln Ile Ser Leu Leu Gly Val Pro Phe Val
                20                  25                  30

Tyr Asn Leu Val Trp Gln Tyr Leu Tyr Ser Leu Arg Lys Asp Arg Ala
        35                  40                  45

Pro Leu Val Phe Tyr Trp Ile Pro Trp Phe Gly Ser Ala Ala Ser Tyr
        50                  55                  60

Gly Gln Gln Pro Tyr Glu Phe Phe Glu Ser Cys Arg Gln Lys Tyr Gly
65                  70                  75                  80
```

-continued

Asp Val Phe Ser Phe Met Leu Leu Gly Lys Ile Met Thr Val Tyr Leu
              85                  90                  95

Gly Pro Lys Gly His Glu Phe Val Phe Asn Ala Lys Leu Ser Asp Val
          100                 105                 110

Ser Ala Glu Asp Ala Tyr Lys His Leu Thr Thr Pro Val Phe Gly Lys
          115                 120                 125

Gly Val Ile Tyr Asp Cys Pro Asn Ser Arg Leu Met Glu Gln Lys Lys
          130                 135                 140

Phe Ala Lys Phe Ala Leu Thr Thr Asp Ser Phe Lys Arg Tyr Val Pro
145                 150                 155                 160

Lys Ile Arg Glu Glu Ile Leu Asn Tyr Phe Val Thr Asp Glu Ser Phe
              165                 170                 175

Lys Leu Lys Glu Lys Thr His Gly Val Ala Asn Val Met Lys Thr Gln
              180                 185                 190

Pro Glu Ile Thr Ile Phe Thr Ala Ser Arg Ser Leu Phe Gly Asp Glu
              195                 200                 205

Met Arg Arg Ile Phe Asp Arg Ser Phe Ala Gln Leu Tyr Ser Asp Leu
      210                 215                 220

Asp Lys Gly Phe Thr Pro Ile Asn Phe Val Phe Pro Asn Leu Pro Leu
225                 230                 235                 240

Pro His Tyr Trp Arg Arg Asp Ala Ala Gln Lys Lys Ile Ser Ala Thr
              245                 250                 255

Tyr Met Lys Glu Ile Lys Ser Arg Glu Arg Gly Asp Ile Asp Pro
              260                 265                 270

Asn Arg Asp Leu Ile Asp Ser Leu Leu Ile His Ser Thr Tyr Lys Asp
      275                 280                 285

Gly Val Lys Met Thr Asp Gln Glu Ile Ala Asn Leu Leu Ile Gly Ile
      290                 295                 300

Leu Met Gly Gly Gln His Thr Ser Ala Ser Thr Ser Ala Trp Phe Leu
305                 310                 315                 320

Leu His Leu Gly Glu Lys Pro His Leu Gln Asp Val Ile Tyr Gln Glu
              325                 330                 335

Val Val Glu Leu Leu Lys Glu Lys Gly Gly Asp Leu Asn Asp Leu Thr
              340                 345                 350

Tyr Glu Asp Leu Gln Lys Leu Pro Ser Val Asn Asn Thr Ile Lys Glu
      355                 360                 365

Thr Leu Arg Met His Met Pro Leu His Ser Ile Phe Arg Lys Val Thr
      370                 375                 380

Asn Pro Leu Arg Ile Pro Glu Thr Asn Tyr Ile Val Pro Lys Gly His
385                 390                 395                 400

Tyr Val Leu Val Ser Pro Gly Tyr Ala His Thr Ser Glu Arg Tyr Phe
              405                 410                 415

Asp Asn Pro Glu Asp Phe Asp Pro Thr Arg Trp Asp Thr Ala Ala Ala
              420                 425                 430

Lys Ala Asn Ser Val Ser Phe Asn Ser Ser Asp Glu Val Asp Tyr Gly
      435                 440                 445

Phe Gly Lys Val Ser Lys Gly Val Ser Ser Pro Tyr Leu Pro Phe Gly
      450                 455                 460

Gly Gly Arg His Arg Cys Ile Gly Glu Gln Phe Ala Tyr Val Gln Leu
465                 470                 475                 480

Gly Thr Ile Leu Thr Thr Phe Val Tyr Asn Leu Arg Trp Thr Ile Asp
              485                 490                 495

Gly Tyr Lys Val Pro Asp Pro Asp Tyr Ser Ser Met Val Val Leu Pro

```
                    500                 505                 510
Thr Glu Pro Ala Glu Ile Ile Trp Glu Lys Arg Glu Thr Cys Met Phe
            515                 520                 525

<210> SEQ ID NO 158
<211> LENGTH: 743
<212> TYPE: PRT
<213> ORGANISM: Candida albicans

<400> SEQUENCE: 158

Met Leu Lys Thr Asp Ser Leu Asp Phe His Ser Tyr Leu Pro Pro Tyr
1               5                   10                  15

Arg Ser Leu Ile Asn Pro Asn Ala Arg Tyr Asp Tyr Arg Thr His Ser
            20                  25                  30

Leu Ile Pro Leu Thr Gln Asn Asp Leu Asn Leu Leu Arg Ile Ala Phe
        35                  40                  45

Gln Lys Lys Lys Glu Ala Pro Pro Ser Ala Phe Lys Met Lys Tyr Lys
    50                  55                  60

Ser Leu Leu Ser Asp Val Ser Arg Thr Ile Ser Met Arg Leu Ser Asn
65                  70                  75                  80

Ser Asn Leu Leu Ser Ser Ser Ser Ala Asn Asn Asn Val Leu Leu
                85                  90                  95

Ser Pro Pro Pro Ser Ser Ser Ser Thr Leu Ser Thr Pro Cys Gly Asn
            100                 105                 110

Ile Leu Asn Arg Ala Gly Thr Thr Ser Ser Asn Ile Ser Lys Ile Asn
        115                 120                 125

Asn Leu Ser Gln Asn Gln Thr Gln Asn Gln Leu Pro Leu Phe Pro Ala
    130                 135                 140

Glu Leu His Ile Lys Asn Leu Pro Val Glu Ile Leu Asp Tyr Ile Phe
145                 150                 155                 160

Tyr Leu Val Asp Asp Asn Leu Asp Tyr Lys Ser Cys Met Tyr Thr Cys
                165                 170                 175

Lys Leu Phe Tyr Phe Leu Ala Lys Pro Tyr Tyr Tyr Glu Asn Leu Val
            180                 185                 190

Phe Thr Ser Thr Tyr Arg Phe Ala Gln Phe Val Thr Tyr Leu Arg Val
        195                 200                 205

Asn Ser Glu Val Gly Gln Tyr Val Gln Ser Ile Asp Leu Ser Gly Ile
    210                 215                 220

Lys Pro Gly Tyr Asp Glu Asp Glu Gln Glu Glu Gly Gln Glu Glu Asn
225                 230                 235                 240

Ala Glu Asn Gly Glu Glu Asn Gly Gly Ala Arg Asp Pro Gln
                245                 250                 255

Tyr Leu Leu Gly Glu Ile Ala Asp Asn Pro His His Glu Arg Val Asp
            260                 265                 270

Gln Phe Pro Arg Gly Lys Ile Leu Ala Gly Trp Arg Asp Trp Lys Phe
        275                 280                 285

Lys Asn Asn Pro Leu Tyr Thr Ile His Pro Ser Pro Ser Leu Thr Lys
    290                 295                 300

Ile Ala Ser Asn Ser Gln Phe Ser Asn Val Ser Ser Lys Ser Ser Arg
305                 310                 315                 320

Ser Thr Ser Ser Lys Ser Ser Ser Thr Thr Lys Lys Phe Val Lys
                325                 330                 335

Pro Phe Tyr Phe Lys Ser Arg Lys Arg Lys Met Ser Tyr Ser Gly
            340                 345                 350
```

```
Thr Thr Lys Leu Glu Arg Lys Ser Pro Arg Leu Glu Gln Leu Gln Leu
            355                 360                 365

Asp Gln Tyr Ser Ser Asn Trp Asn Lys Arg Val Asn Ser His Pro Leu
        370                 375                 380

Ile Asn Lys Phe Leu Leu His Tyr Ser Thr Ser Lys Asp Leu Pro Ile
385                 390                 395                 400

Gly Tyr Ile Leu His Met Ile Asn Leu Cys Pro Asn Ile Val Ser Leu
                405                 410                 415

Asn Leu Gly Asn Leu Ser Leu Ser Thr Asp Tyr Glu Ile Ser Arg Ser
            420                 425                 430

Thr Ile His Lys Tyr Gln Asn Phe Asp Leu Ile Asn Asn Tyr Pro Lys
        435                 440                 445

Asp Leu Ile Tyr Lys Val Asp Asn Ile Met Arg Leu Asn Asp Val Asp
    450                 455                 460

Asp Val Tyr Ser Ile Asp Gly Ser Ile Leu Arg Phe Gly Asn Ile Asn
465                 470                 475                 480

Ser Gly Ser Ser Gly Ser Asn Trp Glu Arg Asn Gly Ser Ser Ser Asn
                485                 490                 495

Asn Arg Ile Leu Phe Lys Ser Asn Gln Ser Ile Ala Ser Thr Ala Ser
            500                 505                 510

Ser Val Tyr Ser Val Thr Thr Phe Ser Lys Pro Ile Arg Lys Tyr Asn
        515                 520                 525

Ser Leu Leu Pro Pro Leu Pro Gln Thr Val Ala Asp Ile Ser Tyr Leu
    530                 535                 540

Asn Lys Gly Asp Gly Lys Val Tyr Leu Ser Asp Leu Asn Leu Lys Glu
545                 550                 555                 560

Ile Asn Ser Ala Tyr Leu Lys Lys Ile Asn Glu Asp Glu Ile Leu Ser
                565                 570                 575

Ala Ile Ile Asn Val His Gly Lys Arg Leu Ile Glu Tyr Asp Thr Ser
            580                 585                 590

Leu Tyr Gln Ile Pro Lys Pro Leu Asn Val Asp Ile Ala Gly Thr Leu
        595                 600                 605

Lys Tyr Ile Asn Leu Ser Ser Met Ile Trp Leu Asn Arg Lys Leu Ile
    610                 615                 620

Glu Lys Phe Leu Thr Arg Leu Leu Thr Lys Lys Ser Pro Glu Leu Asp
625                 630                 635                 640

Met Tyr Gly Ile Cys Tyr Thr Asp Glu Phe Phe Asp Ser Asp Glu Gln
                645                 650                 655

Glu Ser Asp Asp Asp Tyr Glu Asp Ser Asp Glu Glu Gln Arg Gln
            660                 665                 670

Cys Pro Ile Ile Tyr Lys Gln Asn Leu Val Ile Asp Phe Thr Asp Ser
        675                 680                 685

Gly Met Tyr Lys Ser Leu Pro Trp Ala Lys Arg Ile Asp Leu Asn Ser
    690                 695                 700

Phe Glu Gly Cys Gln Leu Ala Asn Lys Ile Asn Asn Asp Leu Met
705                 710                 715                 720

Thr Pro Gln Glu Gln Ala Leu Arg Arg Glu Arg Arg Arg Gly Ala
                725                 730                 735

Ile Ala Ala Asn Tyr Leu Ala
            740

<210> SEQ ID NO 159
<211> LENGTH: 213
<212> TYPE: PRT
```

<213> ORGANISM: Candida albicans

<400> SEQUENCE: 159

Met Ser Phe Ser Asp Phe Ser Lys Val Glu Ser Ile Lys Ser Leu Asn
1               5                   10                  15

Glu Phe Leu Ala Asp Lys Ser Tyr Ile Asp Gly Thr Thr Ala Thr Gln
            20                  25                  30

Ala Asp Val Thr Val Tyr Lys Ala Phe Gln Lys Glu Phe Pro Gln Phe
        35                  40                  45

Thr Arg Trp Phe Asn His Ile Ala Ser Phe Thr Glu Glu Phe Glu Asp
    50                  55                  60

Leu Pro Ala Gly Lys Ala Pro Ala Ala Ser Gly Ser Ala Ala Ala
65                  70                  75                  80

Ala Glu Glu Glu Asp Glu Asp Val Asp Leu Phe Gly Ser Asp
            85                  90                  95

Glu Val Asp Glu Glu Ala Glu Lys Leu Lys Gln Gln Arg Leu Ala Glu
            100                 105                 110

Tyr Ala Ala Lys Lys Ala Ala Lys Gly Pro Lys Pro Ala Ala Lys Ser
            115                 120                 125

Ile Val Thr Leu Asp Val Lys Pro Trp Asp Asp Glu Thr Asp Leu Asp
    130                 135                 140

Glu Leu Leu Thr Asn Val Lys Ala Ile Glu Met Glu Gly Leu Thr Trp
145                 150                 155                 160

Gly Ala His Gln Trp Ile Pro Val Gly Phe Gly Ile Lys Lys Leu Gln
                165                 170                 175

Ile Asn Leu Val Val Glu Asp Ala Leu Val Ser Leu Asp Leu Gln
            180                 185                 190

Ala Ala Val Glu Glu Asp Glu Asp His Val Gln Ser Thr Asp Ile Ala
            195                 200                 205

Ala Met Gln Lys Leu
        210

<210> SEQ ID NO 160
<211> LENGTH: 440
<212> TYPE: PRT
<213> ORGANISM: Candida albicans

<400> SEQUENCE: 160

Met Ser Tyr Ala Thr Lys Ile His Ala Arg Tyr Val Tyr Asp Ser Arg
1               5                   10                  15

Gly Asn Pro Thr Val Glu Val Asp Phe Thr Thr Asp Lys Gly Leu Phe
            20                  25                  30

Arg Ser Ile Val Pro Ser Gly Ala Ser Thr Gly Val His Glu Ala Leu
        35                  40                  45

Glu Leu Arg Asp Gly Asp Lys Ser Lys Trp Leu Gly Lys Gly Val Leu
    50                  55                  60

Lys Ala Val Ala Asn Val Asn Asp Ile Ile Ala Pro Ala Leu Ile Lys
65                  70                  75                  80

Ala Lys Ile Asp Val Val Asp Gln Ala Lys Ile Asp Glu Phe Leu Leu
            85                  90                  95

Ser Leu Asp Gly Thr Pro Asn Lys Ser Lys Leu Gly Ala Asn Ala Ile
            100                 105                 110

Leu Gly Val Ser Leu Ala Ala Ala Asn Ala Ala Ala Ala Gln Gly
        115                 120                 125

Ile Pro Leu Tyr Lys His Ile Ala Asn Ile Ser Asn Ala Lys Lys Gly

```
                130                 135                 140
Lys Phe Val Leu Pro Val Pro Phe Gln Asn Val Leu Asn Gly Gly Ser
145                 150                 155                 160

His Ala Gly Gly Ala Leu Ala Phe Gln Glu Phe Met Ile Ala Pro Thr
                165                 170                 175

Gly Val Ser Thr Phe Ser Glu Ala Leu Arg Ile Gly Ser Glu Val Tyr
                180                 185                 190

His Asn Leu Lys Ser Leu Thr Lys Lys Tyr Gly Gln Ser Ala Gly
                195                 200                 205

Asn Val Gly Asp Glu Gly Val Ala Pro Asp Ile Lys Thr Pro Lys
    210                 215                 220

Glu Ala Leu Asp Leu Ile Met Asp Ala Ile Asp Lys Ala Gly Tyr Lys
225                 230                 235                 240

Gly Lys Val Gly Ile Ala Met Asp Val Ala Ser Ser Glu Phe Tyr Lys
                245                 250                 255

Asp Gly Lys Tyr Asp Leu Asp Phe Lys Asn Pro Glu Ser Asp Pro Ser
                260                 265                 270

Lys Trp Leu Ser Gly Pro Gln Leu Ala Asp Leu Tyr Glu Gln Leu Ile
                275                 280                 285

Ser Glu Tyr Pro Ile Val Ser Ile Glu Asp Pro Phe Ala Glu Asp Asp
                290                 295                 300

Trp Asp Ala Trp Val His Phe Phe Glu Arg Val Gly Asp Lys Ile Gln
305                 310                 315                 320

Ile Val Gly Asp Asp Leu Thr Val Thr Asn Pro Thr Arg Ile Lys Thr
                325                 330                 335

Ala Ile Glu Lys Lys Ala Ala Asn Ala Leu Leu Leu Lys Val Asn Gln
                340                 345                 350

Ile Gly Thr Leu Thr Glu Ser Ile Gln Ala Ala Asn Asp Ser Tyr Ala
                355                 360                 365

Ala Gly Trp Gly Val Met Val Ser His Arg Ser Gly Glu Thr Glu Asp
                370                 375                 380

Thr Phe Ile Ala Asp Leu Ser Val Gly Leu Arg Ser Gly Gln Ile Lys
385                 390                 395                 400

Thr Gly Ala Pro Ala Arg Ser Glu Arg Leu Ala Lys Leu Asn Gln Ile
                405                 410                 415

Leu Arg Ile Glu Glu Glu Leu Gly Ser Glu Ala Ile Tyr Ala Gly Lys
                420                 425                 430

Asp Phe Gln Lys Ala Ser Gln Leu
                435                 440

<210> SEQ ID NO 161
<211> LENGTH: 331
<212> TYPE: PRT
<213> ORGANISM: Candida albicans

<400> SEQUENCE: 161

Met Ala Ile Lys Ile Gly Ile Asn Gly Phe Gly Arg Ile Gly Arg Leu
1               5                   10                  15

Val Leu Arg Val Ala Leu Gly Arg Lys Asp Ile Glu Val Val Ala Val
                20                  25                  30

Asn Asp Pro Phe Ile Ala Pro Asp Tyr Ala Ala Tyr Met Phe Lys Tyr
                35                  40                  45

Asp Ser Thr His Gly Arg Tyr Lys Gly Glu Val Thr Ala Ser Gly Asp
        50                  55                  60
```

Asp Leu Val Ile Asp Gly His Lys Ile Lys Val Phe Gln Glu Arg Asp
65                  70                  75                  80

Pro Ala Asn Ile Pro Trp Gly Lys Ser Gly Val Asp Tyr Val Ile Glu
            85                  90                  95

Ser Thr Gly Val Phe Thr Lys Val Glu Gly Ala Gln Lys His Ile Asp
        100                 105                 110

Ala Gly Ala Lys Lys Val Ile Ile Thr Ala Pro Ser Ala Asp Ala Pro
    115                 120                 125

Met Phe Val Val Gly Val Asn Glu Asp Lys Tyr Thr Pro Asp Leu Lys
130                 135                 140

Ile Ile Ser Asn Ala Ser Cys Thr Thr Asn Cys Leu Ala Pro Leu Ala
145                 150                 155                 160

Lys Val Val Asn Asp Thr Phe Gly Ile Glu Glu Gly Leu Met Thr Thr
                165                 170                 175

Val His Ser Ile Thr Ala Thr Gln Lys Thr Val Asp Gly Pro Ser His
            180                 185                 190

Lys Asp Trp Arg Gly Gly Arg Thr Ala Ser Gly Asn Ile Ile Pro Ser
        195                 200                 205

Ser Thr Gly Ala Ala Lys Ala Val Gly Lys Val Ile Pro Glu Leu Asn
210                 215                 220

Gly Lys Leu Thr Gly Met Ser Leu Arg Leu Pro Thr Thr Asp Val Ser
225                 230                 235                 240

Val Val Asp Leu Thr Val Arg Leu Lys Lys Ala Ala Ser Tyr Glu Glu
                245                 250                 255

Ile Ala Pro Ala Ile Lys Lys Ala Ser Glu Gly Pro Leu Lys Gly Val
            260                 265                 270

Leu Gly Tyr Thr Glu Asp Ala Val Val Ser Thr Asp Phe Leu Gly Ser
        275                 280                 285

Ser Tyr Ser Ser Ile Phe Asp Glu Lys Ala Gly Ile Leu Leu Ser Pro
290                 295                 300

Thr Phe Val Lys Leu Ile Ser Trp Tyr Asp Asn Glu Tyr Gly Tyr Ser
305                 310                 315                 320

Thr Lys Val Val Asp Leu Leu Glu His Val Ala
                325                 330

<210> SEQ ID NO 162
<211> LENGTH: 656
<212> TYPE: PRT
<213> ORGANISM: Candida albicans

<400> SEQUENCE: 162

Met Ser Lys Ala Val Gly Ile Asp Leu Gly Thr Thr Tyr Ser Cys Val
1               5                   10                  15

Ala His Phe Ala Asn Asp Arg Val Glu Ile Ala Asn Asp Gln Gly
            20                  25                  30

Asn Arg Thr Thr Pro Ser Phe Val Ala Phe Thr Asp Thr Glu Arg Leu
        35                  40                  45

Ile Gly Asp Ala Ala Lys Asn Gln Ala Ala Met Asn Pro Ala Asn Thr
    50                  55                  60

Val Phe Asp Ala Lys Arg Leu Ile Gly Arg Lys Phe Asp Asp Pro Glu
65                  70                  75                  80

Val Ile Asn Asp Ala Lys His Phe Pro Phe Lys Val Ile Asp Lys Ala
                85                  90                  95

Gly Lys Pro Val Ile Gln Val Glu Tyr Lys Gly Glu Thr Lys Thr Phe
            100                 105                 110

-continued

```
Ser Pro Glu Glu Ile Ser Ser Met Val Leu Thr Lys Met Lys Glu Ile
            115                 120                 125
Ala Glu Gly Tyr Leu Gly Ser Thr Val Lys Asp Ala Val Val Thr Val
        130                 135                 140
Pro Ala Tyr Phe Asn Asp Ser Gln Arg Gln Ala Thr Lys Asp Ala Gly
145                 150                 155                 160
Thr Ile Ala Gly Leu Asn Val Leu Arg Ile Ile Asn Glu Pro Thr Ala
                165                 170                 175
Ala Ala Ile Ala Tyr Gly Leu Asp Lys Lys Gly Ser Arg Gly Glu His
            180                 185                 190
Asn Val Leu Ile Phe Asp Leu Gly Gly Gly Thr Phe Asp Val Ser Leu
        195                 200                 205
Leu Ala Ile Asp Glu Gly Ile Phe Glu Val Lys Ala Thr Ala Gly Asp
    210                 215                 220
Thr His Leu Gly Gly Glu Asp Phe Asp Asn Arg Leu Val Asn Phe Phe
225                 230                 235                 240
Ile Gln Glu Phe Lys Arg Lys Asn Lys Lys Asp Ile Ser Thr Asn Gln
                245                 250                 255
Arg Ala Leu Arg Arg Leu Arg Thr Ala Cys Glu Arg Ala Lys Arg Thr
            260                 265                 270
Leu Ser Ser Ser Ala Gln Thr Ser Ile Glu Ile Asp Ser Leu Tyr Glu
        275                 280                 285
Gly Ile Asp Phe Tyr Thr Ser Ile Thr Arg Ala Arg Phe Glu Glu Leu
    290                 295                 300
Cys Ala Asp Leu Phe Arg Ser Thr Leu Asp Pro Val Gly Lys Val Leu
305                 310                 315                 320
Ala Asp Ala Lys Ile Asp Lys Ser Gln Val Glu Glu Ile Val Leu Val
                325                 330                 335
Gly Gly Ser Thr Arg Ile Pro Lys Ile Gln Lys Leu Val Ser Asp Phe
            340                 345                 350
Phe Asn Gly Lys Glu Leu Asn Lys Ser Ile Asn Pro Asp Glu Ala Val
        355                 360                 365
Ala Tyr Gly Ala Ala Val Gln Ala Ala Ile Leu Thr Gly Asp Thr Ser
    370                 375                 380
Ser Lys Thr Gln Asp Ile Leu Leu Leu Asp Val Ala Pro Leu Ser Leu
385                 390                 395                 400
Gly Ile Glu Thr Ala Gly Gly Ile Met Thr Lys Leu Ile Pro Arg Asn
                405                 410                 415
Ser Thr Ile Pro Thr Lys Lys Ser Glu Thr Phe Ser Thr Tyr Ala Asp
            420                 425                 430
Asn Gln Pro Gly Val Leu Ile Gln Val Phe Glu Gly Glu Arg Ala Lys
        435                 440                 445
Thr Lys Asp Asn Asn Leu Leu Gly Lys Phe Glu Leu Ser Gly Ile Pro
    450                 455                 460
Pro Ala Pro Arg Gly Val Pro Gln Ile Glu Val Thr Phe Asp Ile Asp
465                 470                 475                 480
Ala Asn Gly Ile Leu Asn Val Ser Ala Leu Glu Lys Gly Thr Gly Lys
                485                 490                 495
Thr Gln Lys Ile Thr Ile Thr Asn Asp Lys Gly Arg Leu Ser Lys Glu
            500                 505                 510
Glu Ile Asp Lys Met Val Ser Glu Ala Glu Lys Phe Lys Glu Glu Asp
        515                 520                 525
```

Glu Lys Glu Ala Ala Arg Val Gln Ala Lys Asn Gln Leu Glu Ser Tyr
            530                 535                 540

Ala Tyr Ser Leu Lys Asn Thr Ile Asn Asp Gly Glu Met Lys Asp Lys
545                 550                 555                 560

Ile Gly Ala Asp Asp Lys Glu Lys Leu Thr Lys Ala Ile Asp Glu Thr
                565                 570                 575

Ile Ser Trp Leu Asp Ala Ser Gln Ala Ala Ser Thr Glu Glu Tyr Glu
            580                 585                 590

Asp Lys Arg Lys Glu Leu Glu Ser Val Ala Asn Pro Ile Ile Ser Gly
                595                 600                 605

Ala Tyr Gly Ala Ala Gly Gly Ala Pro Gly Gly Ala Gly Gly Phe Pro
            610                 615                 620

Gly Ala Gly Gly Phe Pro Gly Gly Ala Pro Gly Ala Gly Gly Pro Gly
625                 630                 635                 640

Gly Ala Thr Gly Gly Glu Ser Ser Gly Pro Thr Val Glu Glu Val Asp
                645                 650                 655

<210> SEQ ID NO 163
<211> LENGTH: 613
<212> TYPE: PRT
<213> ORGANISM: Candida albicans

<400> SEQUENCE: 163

Met Ala Asp Gly Val Phe Gln Gly Ala Ile Gly Ile Asp Leu Gly Thr
1               5                   10                  15

Thr Tyr Ser Cys Val Ala Thr Tyr Asp Ser Ala Val Glu Ile Ile Ala
                20                  25                  30

Asn Glu Gln Gly Asn Arg Val Thr Pro Ser Phe Val Ala Phe Thr Ser
            35                  40                  45

Glu Glu Arg Leu Ile Gly Asp Ala Ala Lys Asn Gln Ala Ala Leu Asn
50                  55                  60

Pro Lys Asn Thr Val Phe Asp Ala Lys Arg Leu Ile Gly Arg Ala Phe
65                  70                  75                  80

Asp Asp Glu Ser Val Gln Lys Asp Ile Lys Ser Trp Pro Phe Lys Val
                85                  90                  95

Val Glu Ser Asn Gly Gln Pro Leu Ile Glu Val Glu Tyr Leu Asp Glu
            100                 105                 110

Thr Lys Thr Phe Ser Pro Gln Glu Ile Ser Ser Met Val Leu Thr Lys
        115                 120                 125

Met Lys Glu Ile Ala Glu Ala Lys Ile Gly Lys Lys Val Glu Lys Ala
    130                 135                 140

Val Val Thr Val Pro Ala Tyr Phe Asn Asp Ala Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Gly Ala Gly Lys Ser
            180                 185                 190

Glu Lys Glu Arg His Val Leu Ile Phe Asp Leu Gly Gly Gly Thr Phe
        195                 200                 205

Asp Val Ser Leu Leu Asn Ile Thr Gly Gly Val Phe Thr Val Lys Ala
    210                 215                 220

Thr Ala Gly Asp Thr His Leu Gly Gly Gln Asp Phe Asp Thr Asn Leu
225                 230                 235                 240

Leu Glu His Phe Lys Lys Glu Phe Gln Lys Lys Thr Gly Asn Asp Ile
                245                 250                 255

Ser Ser Asp Ala Arg Ala Leu Arg Arg Leu Arg Thr Ala Cys Glu Arg
        260                 265                 270

Ala Lys Arg Ser Leu Ser Ser Gly Thr Gln Thr Thr Val Glu Ile Asp
            275                 280                 285

Ser Leu Phe Asp Gly Glu Asp Phe Ser Ala Asn Ile Thr Arg Ala Arg
290                 295                 300

Phe Glu Asp Ile Asn Ser Ala Leu Phe Lys Ser Thr Leu Glu Pro Val
305                 310                 315                 320

Glu Gln Val Leu Glu Asp Ala Lys Ile Ser Lys Ser Gln Val Asp Glu
                325                 330                 335

Val Val Leu Val Gly Gly Ser Thr Arg Ile Pro Lys Val Gln Lys Leu
            340                 345                 350

Leu Ser Asp Phe Phe Asp Gly Lys Gln Leu Glu Lys Ser Ile Asn Pro
        355                 360                 365

Asp Glu Ala Val Ala Tyr Gly Ala Ala Val Gln Gly Ala Ile Leu Thr
370                 375                 380

Gly Gln Ser Thr Asn Asp Asp Thr Lys Asp Leu Leu Leu Leu Asp Val
385                 390                 395                 400

Ile Pro Leu Ser Leu Gly Val Ala Met Gln Gly Asn Val Leu Ala Pro
                405                 410                 415

Val Val Pro Arg Asn Thr Thr Val Pro Thr Ile Lys Arg Arg Thr Phe
            420                 425                 430

Thr Thr Val Ala Asp His Gln Thr Val Gln Phe Pro Val Tyr Gln
        435                 440                 445

Gly Glu Arg Val Asn Cys Ser Glu Asn Thr Leu Leu Gly Glu Phe Asp
            450                 455                 460

Leu Lys Asn Ile Pro Pro Met Gln Ala Gly Glu Pro Val Leu Glu Ala
465                 470                 475                 480

Ile Phe Glu Val Asp Ala Asn Gly Ile Leu Lys Val Thr Ala Val Glu
                485                 490                 495

Lys Ser Thr Gly Arg Ser Ala Asn Ile Thr Ile Ser Asn Ser Ile Gly
            500                 505                 510

Arg Leu Ser Thr Glu Glu Ile Glu Lys Met Ile Ser Asp Ala Glu Lys
        515                 520                 525

Phe Lys Ser Ser Asp Asp Ala Phe Ala Lys Arg His Glu Gln Lys Gln
530                 535                 540

Lys Leu Glu Ala Tyr Val Ala Ser Val Glu Ser Thr Val Thr Asp Pro
545                 550                 555                 560

Val Leu Ser Ala Lys Leu Lys Ser Ala Lys Asp Lys Ile Glu Ala
                565                 570                 575

Ala Leu Ser Asp Ala Leu Gln Thr Leu Glu Ile Glu Glu Ser Ser Ala
            580                 585                 590

Asp Asp Tyr Arg Lys Ala Glu Leu Ala Leu Lys Arg Ala Val Thr Lys
        595                 600                 605

Gly Met Ala Thr Arg
    610

<210> SEQ ID NO 164
<211> LENGTH: 92
<212> TYPE: PRT
<213> ORGANISM: Candida albicans

<400> SEQUENCE: 164

Phe Thr Ile Pro Pro Asn His Glu Met Ile Phe Thr Thr Asp Asp Ala

```
             1               5                  10                 15
Tyr Lys Thr Lys Cys Asp Asp Lys Val Met Ile Ile Asp Tyr Lys Asn
                    20                 25                 30

Ile Thr Lys Val Ile Ala Pro Gly Lys Ile Ile Tyr Val Asp Asp Gly
                    35                 40                 45

Val Leu Ser Phe Glu Val Ile Ser Val Asp Asp Gln Gln Thr Leu Lys
         50                 55                 60

Val Arg Ser Leu Asn Ala Gly Met Ile Ser Ser His Lys Thr Ala Asn
 65                 70                 75                 80

Asp Val Leu Glu Leu Arg Val Leu Ser Thr Ser Gly
                    85                 90
```

<210> SEQ ID NO 165
<211> LENGTH: 460
<212> TYPE: PRT
<213> ORGANISM: Candida albicans

<400> SEQUENCE: 165

```
Met Leu Phe Leu Leu Phe Leu Leu Ile Thr Pro Ile Tyr Ala Gly Leu
 1               5                  10                 15

Ile Phe Pro Thr Lys Pro Ser Ser Asp Pro Tyr Asn Pro Pro Lys
                    20                 25                 30

Gly Phe Glu Lys Ala Ala Val Gly Asp Ile Leu Gln Ser Arg Glu Thr
                    35                 40                 45

Pro Lys Ser Ile Thr Gly Arg Phe Ala Pro Leu Lys Ile Gln Asn Ser
         50                 55                 60

Trp Gln Leu Leu Val Arg Ser Glu Asp Ser Phe Gly Asn Pro Asn Ala
 65                 70                 75                 80

Ile Val Thr Thr Val Ile Glu Pro Val Asn Ala Asp Pro Ser Lys Ile
                    85                 90                 95

Ala Ser Tyr Gln Val Phe Glu Asp Ala Ala Lys Ala Asp Cys Ala Pro
                    100                105                110

Ser Tyr Ala Leu Gln Phe Gly Ser Asp Leu Thr Thr Phe Val Thr Gln
                    115                120                125

Ala Glu Met Tyr Leu Met Ala Pro Leu Leu Asp Gln Gly Tyr Tyr Val
                    130                135                140

Val Ser Pro Asp Tyr Glu Gly Pro Lys Ser Thr Phe Thr Ile Gly Lys
145                 150                155                160

Gln Ser Gly Gln Ala Val Leu Asn Ser Ile Arg Ala Thr Leu Lys Ser
                    165                170                175

Ser Lys Ile Thr Asn Ile Lys Glu Asp Ala Lys Val Val Met Trp Gly
                    180                185                190

Tyr Ser Gly Gly Ser Leu Ala Ser Gly Trp Ala Ala Leu Gln Pro
                    195                200                205

Ser Tyr Ala Pro Glu Leu Ser Ser Ser Leu Leu Gly Ala Ala Leu Gly
                    210                215                220

Gly Phe Val Thr Asn Ile Thr Ala Thr Ala Gln Ala Ala Asp Gly Thr
225                 230                235                240

Val Phe Ala Gly Ile Val Ala Asn Ala Leu Gly Gly Val Ala Asn Glu
                    245                250                255

Tyr Pro Glu Phe Lys Ser Ile Leu Gln Ser Asp Thr Asp Lys Lys Ser
                    260                265                270

Val Phe Asp Glu Phe Asp Ser His Cys Leu Ala Asp Gly Val Ile Asp
                    275                280                285
```

```
Tyr Ile Asn Thr Ser Phe Leu Thr Gly Asp Asn Lys Ile Phe Lys Thr
        290                 295                 300

Gly Trp Asp Ile Leu Lys Ser Pro Thr Ile Ala Lys Ile Val Glu Asp
305                 310                 315                 320

Asn Gly Leu Val Tyr Gln Lys Gln Leu Val Pro Lys Ile Pro Ile Phe
                325                 330                 335

Val Tyr His Gly Ser Ile Asp Gln Ile Val Pro Ile Val Asn Val Lys
                340                 345                 350

Lys Thr Tyr Gln Asn Trp Cys Glu Gly Ile Ser Ser Leu Glu Phe
                355                 360                 365

Ala Glu Asp Gly Thr Asn Gly His Leu Thr Glu Thr Val Val Gly Ala
        370                 375                 380

Pro Ala Ala Leu Thr Trp Ile Ile Asp Arg Phe Asn Gly Lys Gln Thr
385                 390                 395                 400

Val Ser Gly Cys Gln His Asp Lys Arg Leu Ser Asn Phe Gln Tyr Pro
                405                 410                 415

Asn Ile Ser Ser Ser Ile Leu Lys Tyr Phe Lys Val Ala Leu Asp Thr
                420                 425                 430

Met Met Ser Asn Gly Leu Gly Ser Asp Ile Gln Lys Asp Lys Ile Thr
                435                 440                 445

Pro Asp Asp Leu Arg Lys Phe Leu Leu Gly Gly Trp
450                 455                 460

<210> SEQ ID NO 166
<211> LENGTH: 151
<212> TYPE: PRT
<213> ORGANISM: Candida albicans

<400> SEQUENCE: 166

Met Ser Ser Asp Trp Asp Ser Val Thr Ile Ile Gly Gln Lys Ala Arg
1               5                   10                  15

Val Gly Gly Gly Pro Arg Glu Asn Val Ala Lys Thr Ser Ser Gln
                20                  25                  30

Leu Asn Ala Ala Arg Arg Ala Gly Leu Val Val Gly Thr Glu Lys Lys
            35                  40                  45

Tyr Gly Thr Ala Asn Thr Lys Ser Asn Pro Glu Gly Gln Arg Leu Thr
    50                  55                  60

Lys Leu Asp Ala Thr Asp Asp Val Val Ala Val Lys Lys Val Asp Val
65                  70                  75                  80

Ser Val Gly Lys Ala Ile Gln Gln Ala Arg Gln Glu Lys Lys Leu Thr
                85                  90                  95

Gln Lys Glu Leu Ala Thr Lys Val Asn Glu Lys Pro Asn Val Ile Asn
                100                 105                 110

Asp Tyr Glu Ala Gly Arg Ala Ile Pro Asn Gln Gln Leu Leu Ala Lys
            115                 120                 125

Leu Glu Arg Ala Leu Gly Val Lys Leu Arg Gly Lys Asn Ile Gly Glu
        130                 135                 140

Pro Leu Phe Ala Lys Lys Lys
145                 150

<210> SEQ ID NO 167
<211> LENGTH: 124
<212> TYPE: PRT
<213> ORGANISM: Candida albicans

<400> SEQUENCE: 167
```

```
Met Ser Val Asp Phe Asn Ala Val Ala Thr Glu Phe Cys Asn Phe Tyr
1               5                   10                  15

Tyr Asn Gln Phe Asp Ser Asp Arg Ser Gln Leu Gly Asn Leu Tyr Arg
            20                  25                  30

Asn Glu Ser Met Leu Thr Phe Glu Thr Ser Gln Leu Gln Gly Ala Arg
            35                  40                  45

Asp Ile Val Glu Lys Leu Ala Ser Leu Pro Phe Gln Lys Val Ala His
50                  55                  60

Arg Ile Ser Thr Leu Asp Ala Gln Pro Ala Ser Ala Asn Gly Asp Ile
65                  70                  75                  80

Leu Val Met Val Thr Gly Glu Leu Leu Ile Asp Glu Glu Gln Asn Ala
                85                  90                  95

Gln Arg Tyr Ser Gln Val Phe His Leu Ile Pro Asp Asn Gly Ser Tyr
            100                 105                 110

Tyr Val Phe Asn Asp Ile Phe Arg Leu Asn Tyr Ser
            115                 120
```

<210> SEQ ID NO 168
<211> LENGTH: 417
<212> TYPE: PRT
<213> ORGANISM: Candida albicans

<400> SEQUENCE: 168

```
Met Ser Leu Ser Asn Lys Leu Ser Val Lys Asp Leu Asp Val Ala Gly
1               5                   10                  15

Lys Arg Val Phe Ile Arg Val Asp Phe Asn Val Pro Leu Asp Gly Lys
            20                  25                  30

Thr Ile Thr Asn Asn Gln Arg Ile Val Ala Ala Leu Pro Thr Ile Lys
            35                  40                  45

Tyr Val Glu Glu His Lys Pro Lys Tyr Ile Val Leu Ala Ser His Leu
50                  55                  60

Gly Arg Pro Asn Gly Glu Arg Asn Asp Lys Tyr Ser Leu Ala Pro Val
65                  70                  75                  80

Ala Thr Glu Leu Glu Lys Leu Leu Gly Gln Lys Val Thr Phe Leu Asn
                85                  90                  95

Asp Cys Val Gly Pro Glu Val Thr Lys Ala Val Glu Asn Ala Lys Asp
            100                 105                 110

Gly Glu Ile Phe Leu Leu Glu Asn Leu Arg Tyr His Ile Glu Glu Glu
            115                 120                 125

Gly Ser Ser Lys Asp Lys Asp Gly Lys Lys Val Lys Ala Asp Pro Glu
            130                 135                 140

Ala Val Lys Lys Phe Arg Gln Glu Leu Thr Ser Leu Ala Asp Val Tyr
145                 150                 155                 160

Ile Asn Asp Ala Phe Gly Thr Ala His Arg Ala His Ser Ser Met Val
                165                 170                 175

Gly Leu Glu Val Pro Gln Arg Ala Ala Gly Phe Leu Met Ser Lys Glu
            180                 185                 190

Leu Glu Tyr Phe Ala Lys Ala Leu Glu Asn Pro Glu Arg Pro Phe Leu
            195                 200                 205

Ala Ile Leu Gly Gly Ala Lys Val Ser Asp Lys Ile Gln Leu Ile Asp
            210                 215                 220

Asn Leu Leu Asp Lys Val Asp Met Leu Ile Val Gly Gly Met Ala
225                 230                 235                 240

Phe Thr Phe Lys Lys Ile Leu Asn Lys Met Pro Ile Gly Asp Ser Leu
                245                 250                 255
```

```
Phe Asp Glu Ala Gly Ala Lys Asn Val Glu His Leu Val Glu Lys Ala
            260                 265                 270
Lys Lys Asn Asn Val Glu Leu Ile Leu Pro Val Asp Phe Val Thr Ala
            275                 280                 285
Asp Lys Phe Asp Lys Asp Ala Lys Thr Ser Ser Ala Thr Asp Ala Glu
    290                 295                 300
Gly Ile Pro Asp Asn Trp Met Gly Leu Asp Cys Gly Pro Lys Ser Val
305                 310                 315                 320
Glu Leu Phe Gln Gln Ala Val Ala Lys Ala Lys Thr Ile Val Trp Asn
            325                 330                 335
Gly Pro Pro Gly Val Phe Glu Phe Glu Lys Phe Ala Asn Gly Thr Lys
            340                 345                 350
Ser Leu Leu Asp Ala Ala Val Lys Ser Ala Glu Asn Gly Asn Ile Val
            355                 360                 365
Ile Ile Gly Gly Gly Asp Thr Ala Thr Val Ala Lys Lys Tyr Gly Val
            370                 375                 380
Val Glu Lys Leu Ser His Val Ser Thr Gly Gly Ala Ser Leu Glu
385                 390                 395                 400
Leu Leu Glu Gly Lys Asp Leu Pro Gly Val Val Ala Leu Ser Asn Lys
            405                 410                 415
Asn

<210> SEQ ID NO 169
<211> LENGTH: 162
<212> TYPE: PRT
<213> ORGANISM: Candida albicans

<400> SEQUENCE: 169

Met Ser Thr Val Tyr Phe Asp Val Ser Ala Asp Gly Gln Lys Leu Gly
1               5                   10                  15
Lys Ile Thr Phe Lys Leu Tyr Asp Asp Val Val Pro Lys Thr Ala Glu
            20                  25                  30
Asn Phe Arg Ala Leu Cys Thr Gly Glu Lys Gly Phe Gly Tyr Lys Gly
            35                  40                  45
Ser Ile Phe His Arg Val Ile Pro Gln Phe Met Leu Gln Gly Gly Asp
    50                  55                  60
Phe Thr Asn Phe Asn Gly Thr Gly Gly Lys Ser Ile Tyr Gly Thr Lys
65                  70                  75                  80
Phe Ala Asp Glu Asn Phe Val Lys Arg His Asp Arg Pro Gly Leu Leu
                85                  90                  95
Ser Met Ala Asn Ala Gly Pro Asn Thr Asn Gly Ser Gln Phe Phe Ile
            100                 105                 110
Thr Thr Val Pro Cys Pro Trp Leu Asp Gly Lys His Val Val Phe Gly
            115                 120                 125
Glu Val Thr Asp Gly Leu Asp Ile Val Lys Lys Ile Glu Ser Phe Gly
    130                 135                 140
Ser Gly Ser Gly Ala Thr Ser Lys Lys Ile Val Ile Glu Glu Ser Gly
145                 150                 155                 160
Gln Leu

<210> SEQ ID NO 170
<211> LENGTH: 202
<212> TYPE: PRT
<213> ORGANISM: Candida albicans
```

<400> SEQUENCE: 170

Met Ala Ile Ser Lys Asn Leu Pro Leu Leu Asn Asn His Phe Arg Lys
1               5                   10                  15

His Trp Gln Glu Arg Val Arg Val His Phe Asp Gln Ala Gly Lys Lys
            20                  25                  30

Ala Ser Arg Arg Gln Ser Arg Leu Arg Lys Ala Ala Lys Ile Ala Pro
        35                  40                  45

Arg Pro Ile Asp Ala Leu Arg Pro Val Val Arg Ala Pro Thr Val Lys
    50                  55                  60

Tyr Asn Arg Lys Val Arg Ala Gly Arg Gly Phe Thr Leu Ala Glu Leu
65                  70                  75                  80

Lys Ala Val Gly Ile Ala Pro Lys Tyr Ala Arg Thr Ile Gly Ile Ser
                85                  90                  95

Val Asp His Arg Arg Gln Asn Lys Ser Gln Glu Thr Phe Asp Ala Asn
            100                 105                 110

Val Ala Arg Leu Gln Glu Tyr Lys Ser Lys Leu Val Ile Phe Asp Lys
        115                 120                 125

Lys Thr Lys Ala Ser Glu Val Ala Ser Phe Glu Gln Val Asp Val Ser
    130                 135                 140

Ala Thr Phe Pro Val Glu Gln Pro Ala Pro Glu Ser Gly Leu Arg Ala
145                 150                 155                 160

Val Glu Val Pro Glu Gln Thr Ala Tyr Arg Thr Leu Arg Leu Ala Arg
                165                 170                 175

Asn Glu Lys Lys Tyr Lys Gly Ile Arg Glu Lys Arg Ala Lys Glu Lys
            180                 185                 190

Ala Glu Ala Glu Ala Glu Lys Ala Lys Lys
        195                 200

<210> SEQ ID NO 171
<211> LENGTH: 62
<212> TYPE: PRT
<213> ORGANISM: Candida albicans

<400> SEQUENCE: 171

Glu Lys Lys Asp Glu Tyr Leu Ser Lys Ser Ser Ala Ser Ala Ala Pro
1               5                   10                  15

Val Ile Asp Thr Leu Ala His Gly Tyr Gly Lys Val Leu Gly Lys Gly
            20                  25                  30

Arg Leu Pro Glu Val Pro Val Ile Val Lys Ala Arg Phe Val Ser Lys
        35                  40                  45

Leu Ala Glu Glu Lys Ser Glu Ser Leu Val Val Leu Ser Asn
    50                  55                  60

<210> SEQ ID NO 172
<211> LENGTH: 99
<212> TYPE: PRT
<213> ORGANISM: Candida albicans

<400> SEQUENCE: 172

Met Ala Lys Ser Gly Ile Ala Ala Gly Val Asn Lys Gly Arg Lys Thr
1               5                   10                  15

Thr Ala Lys Glu Val Ala Pro Lys Ile Ser Tyr Arg Lys Gly Ala Ser
            20                  25                  30

Ser Gln Arg Thr Val Phe Val Arg Ser Ile Val Lys Glu Val Ala Gly
        35                  40                  45

Leu Ala Pro Tyr Glu Arg Arg Leu Ile Glu Leu Ile Arg Asn Ala Gly

```
                50                  55                  60
Glu Lys Arg Ala Lys Lys Leu Ala Lys Arg Leu Gly Thr His Lys
 65                  70                  75                  80

Arg Ala Leu Arg Lys Val Glu Met Thr Gln Val Ile Ala Glu Ser
                 85                  90                  95

Arg Arg His

<210> SEQ ID NO 173
<211> LENGTH: 111
<212> TYPE: PRT
<213> ORGANISM: Candida albicans

<400> SEQUENCE: 173

Met Lys Tyr Leu Ala Ala Tyr Leu Leu Leu Val Gln Gly Gly Asn Thr
  1               5                  10                  15

Ser Pro Ser Ala Ser Asp Ile Thr Ala Leu Leu Glu Ser Val Gly Val
                 20                  25                  30

Glu Ala Glu Glu Ser Arg Leu Gln Ala Leu Leu Lys Asp Leu Glu Gly
                 35                  40                  45

Lys Asp Leu Gln Glu Leu Ile Ala Glu Gly Asn Thr Lys Leu Ala Ser
 50                  55                  60

Val Pro Ser Gly Gly Ala Ala Ala Gly Gly Ala Ser Ala Ser Thr Gly
 65                  70                  75                  80

Ala Ala Ala Gly Gly Ala Ala Glu Ala Glu Glu Lys Glu Glu Glu
                 85                  90                  95

Ala Lys Glu Glu Ser Asp Asp Asp Met Gly Phe Gly Leu Phe Asp
                100                 105                 110

<210> SEQ ID NO 174
<211> LENGTH: 130
<212> TYPE: PRT
<213> ORGANISM: Candida albicans

<400> SEQUENCE: 174

Met Thr Arg Thr Ser Val Leu Ala Asp Ala Leu Asn Ala Ile Asn Asn
  1               5                  10                  15

Ala Glu Lys Thr Gly Lys Arg Gln Val Leu Ile Arg Pro Ser Ser Lys
                 20                  25                  30

Val Ile Ile Lys Phe Leu Thr Val Met Gln Lys His Gly Tyr Ile Gly
                 35                  40                  45

Glu Phe Glu Tyr Ile Asp Asp His Arg Ser Gly Lys Ile Val Val Gln
 50                  55                  60

Leu Asn Gly Arg Leu Asn Lys Cys Gly Val Ile Gln Pro Arg Phe Asn
 65                  70                  75                  80

Val Lys Ile Asn Asp Ile Glu Arg Trp Thr Asn Leu Leu Pro Ala
                 85                  90                  95

Arg Gln Phe Gly Tyr Val Ile Leu Thr Thr Ser Ala Gly Ile Met Asp
                100                 105                 110

His Glu Glu Ala Arg Arg Lys His Val Ser Gly Lys Ile Leu Gly Phe
        115                 120                 125

Val Tyr
130

<210> SEQ ID NO 175
<211> LENGTH: 248
<212> TYPE: PRT
<213> ORGANISM: Candida albicans
```

<400> SEQUENCE: 175

Met Ala Arg Gln Phe Phe Val Gly Gly Asn Phe Lys Ala Asn Gly Thr
1               5                   10                  15

Lys Gln Gln Ile Thr Ser Ile Ile Asp Asn Leu Asn Lys Ala Asp Leu
            20                  25                  30

Pro Lys Asp Val Glu Val Val Ile Cys Pro Pro Ala Leu Tyr Leu Gly
        35                  40                  45

Leu Ala Val Glu Gln Asn Lys Gln Pro Thr Val Ala Ile Gly Ala Gln
50                  55                  60

Asn Val Phe Asp Lys Ser Cys Gly Ala Phe Thr Gly Glu Thr Cys Ala
65                  70                  75                  80

Ser Gln Ile Leu Asp Val Gly Ala Ser Trp Thr Leu Thr Gly His Ser
                85                  90                  95

Glu Arg Arg Thr Ile Ile Lys Glu Ser Asp Glu Phe Ile Ala Glu Lys
            100                 105                 110

Thr Lys Phe Ala Leu Asp Thr Gly Val Lys Val Ile Leu Cys Ile Gly
        115                 120                 125

Glu Thr Leu Glu Glu Arg Lys Gly Gly Val Thr Leu Asp Val Cys Ala
130                 135                 140

Arg Gln Leu Asp Ala Val Ser Lys Ile Val Ser Asp Trp Ser Asn Ile
145                 150                 155                 160

Val Val Ala Tyr Glu Pro Val Trp Ala Ile Gly Thr Gly Leu Ala Ala
                165                 170                 175

Thr Pro Glu Asp Ala Glu Glu Thr His Lys Gly Ile Arg Ala His Leu
            180                 185                 190

Ala Lys Ser Ile Gly Ala Glu Gln Ala Glu Lys Thr Arg Ile Leu Tyr
        195                 200                 205

Gly Gly Ser Val Asn Gly Lys Asn Ala Lys Asp Phe Lys Asp Lys Ala
210                 215                 220

Asn Val Asp Gly Phe Leu Val Gly Gly Ala Ser Leu Lys Pro Glu Phe
225                 230                 235                 240

Val Asp Ile Ile Lys Ser Arg Leu
                245

<210> SEQ ID NO 176
<211> LENGTH: 663
<212> TYPE: PRT
<213> ORGANISM: Escherichia coli

<400> SEQUENCE: 176

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
            20                  25                  30

Met Ala Asp Ile Ala Glu Val Leu Trp Arg Asp Phe Leu Lys His Asn
        35                  40                  45

Pro Gln Asn Pro Ser Trp Ala Asp Arg Asp Arg Phe Val Leu Ser Asn
50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
    130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
                180                 185                 190

Val Glu Gly Trp Phe Thr Asp Asp Thr Ala Met Arg Phe Glu Ala Tyr
            195                 200                 205

Gly Trp His Val Ile Arg Asp Ile Asp Gly His Asp Ala Ala Ser Ile
        210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Gln Ala Lys Glu
        290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
                340                 345                 350

Ala Lys Ile Ala Ser Arg Lys Ala Ser Gln Asn Ala Ile Glu Ala Phe
            355                 360                 365

Gly Pro Leu Leu Pro Glu Phe Leu Gly Gly Ser Ala Asp Leu Ala Pro
        370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
                420                 425                 430

Thr Phe Leu Met Phe Val Glu Tyr Ala Arg Asn Ala Val Arg Met Ala
        435                 440                 445

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
        515                 520                 525

```
Thr Glu Glu Gln Leu Ala Asn Ile Ala Arg Gly Gly Tyr Val Leu Lys
    530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
    610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
                645                 650                 655

Ala Lys Ala Lys Glu Leu Leu
            660

<210> SEQ ID NO 177
<211> LENGTH: 16
<212> TYPE: PRT
<213> ORGANISM: Candida albicans

<400> SEQUENCE: 177

Gly His Tyr Val Leu Val Phe Pro Gly Tyr Ala His Thr Ser Glu Arg
1               5                   10                  15
```